United States Patent
Addis et al.

(10) Patent No.: US 11,628,222 B2
(45) Date of Patent: Apr. 18, 2023

(54) CD71 BINDING FIBRONECTIN TYPE III DOMAINS

(71) Applicant: Aro Biotherapeutics Company, Philadelphia, PA (US)

(72) Inventors: Russell C. Addis, Philadelphia, PA (US); Zhanna Druzina, Philadelphia, PA (US); Robert Kolakowski, Philadelphia, PA (US); Swapnil Kulkarni, Philadelphia, PA (US); Steven G. Nadler, Philadelphia, PA (US); Karyn O'Neil, Philadelphia, PA (US); Yao Xin, Philadelphia, PA (US)

(73) Assignee: ARO BIOTHERAPEUTICS COMPANY, Philadelphia, PA (US)

( * ) Notice: Subject to any disclaimer, the term of this patent is extended or adjusted under 35 U.S.C. 154(b) by 121 days.

(21) Appl. No.: 17/070,020

(22) Filed: Oct. 14, 2020

(65) Prior Publication Data
US 2021/0145976 A1    May 20, 2021

Related U.S. Application Data

(60) Provisional application No. 62/949,020, filed on Dec. 17, 2019, provisional application No. 62/914,643, filed on Oct. 14, 2019.

(51) Int. Cl.
*A61K 47/64* (2017.01)
*A61K 31/7088* (2006.01)
*C07K 14/435* (2006.01)
*C12N 15/113* (2010.01)

(52) U.S. Cl.
CPC ...... *A61K 47/6435* (2017.08); *A61K 31/7088* (2013.01); *C07K 14/435* (2013.01); *C12N 15/113* (2013.01); *C12N 2310/11* (2013.01); *C12N 2310/14* (2013.01); *C12N 2310/3513* (2013.01); *C12N 2320/32* (2013.01)

(58) Field of Classification Search
CPC ............ C12N 2320/32; C12N 2310/14; C12N 2310/3513; C12N 2310/11; C12N 15/113; A61K 47/6435; A61K 31/7088; C07K 14/435
See application file for complete search history.

(56) References Cited

U.S. PATENT DOCUMENTS

| | | | |
|---|---|---|---|
| 4,281,061 A | 7/1981 | Zuk et al. |
| 5,223,409 A | 6/1993 | Ladner et al. |
| 5,643,763 A | 7/1997 | Dunn et al. |
| 5,643,768 A | 7/1997 | Kawasaki |
| 5,658,727 A | 8/1997 | Barbas et al. |
| 5,691,157 A | 11/1997 | Gong et al. |
| 5,846,456 A | 12/1998 | Liu |
| 5,856,456 A | 1/1999 | Whitlow et al. |
| 6,018,030 A | 1/2000 | Ferrari et al. |
| 6,162,903 A | 12/2000 | Trowern et al. |
| 6,172,197 B1 | 1/2001 | McCafferty et al. |
| 6,355,776 B1 | 3/2002 | Ferrari et al. |
| 6,462,189 B1 | 10/2002 | Koide |
| 6,472,147 B1 | 10/2002 | Janda et al. |
| 6,521,427 B1 | 2/2003 | Evans |
| 6,582,915 B1 | 6/2003 | Griffiths et al. |
| 6,670,127 B2 | 12/2003 | Evans |
| 6,673,901 B2 | 1/2004 | Koide |
| 6,703,199 B1 | 3/2004 | Koide |
| 6,818,418 B1 | 11/2004 | Lipovsek et al. |
| 6,846,655 B1 | 1/2005 | Wagner et al. |
| 6,969,108 B2 | 11/2005 | Fukumoto et al. |
| 7,078,490 B2 | 7/2006 | Koide |
| 7,115,396 B2 | 10/2006 | Lipovsek et al. |
| 7,119,171 B2 | 10/2006 | Koide |
| 7,153,661 B2 | 12/2006 | Koide |
| 7,288,638 B2 | 10/2007 | Jure-Kunkel et al. |
| 7,427,672 B2 | 9/2008 | Imanishi et al. |
| 7,709,214 B2 | 5/2010 | Freeman et al. |
| 7,794,710 B2 | 9/2010 | Chen et al. |
| 7,842,476 B2 | 11/2010 | McGregor et al. |
| 7,943,743 B2 | 5/2011 | Korman et al. |
| 8,217,149 B2 | 7/2012 | Irving et al. |
| 8,278,419 B2 | 10/2012 | Jacobs et al. |
| 8,293,482 B2 | 10/2012 | Jacobs et al. |
| 8,552,154 B2 | 10/2013 | Freeman et al. |
| 8,569,227 B2 | 10/2013 | Jacobs |
| 8,741,295 B2 | 6/2014 | Olive |
| 8,779,108 B2 | 7/2014 | Queva et al. |

(Continued)

FOREIGN PATENT DOCUMENTS

| CN | 102076713 A | 5/2011 |
|---|---|---|
| CN | 103827361 A | 5/2014 |

(Continued)

OTHER PUBLICATIONS

Tang et al, Anti-transferrin receptor-modified amphotericin B-loaded PLA-PEG nanoparticles cure Candidal meningitis and reduce drug toxicity, International Journal of Nanomedicine, 2015, 10, pp. 6227-6241.*

International Search Report and Written Opinion from PCT/US2022/024846 dated Sep. 12, 2022.

Adjei et al., "Early Clinical Development of ARQ197, a Selective, Non-ADP-Competitive Inhibitor Targeting MET Tyrosine Kinase for the Treatment of Advanced Cancers," The Oncologist, vol. 16, pp. 788-799 (2011).

(Continued)

*Primary Examiner* — Li N Komatsu
(74) *Attorney, Agent, or Firm* — Goodwin Procter LLP

(57) ABSTRACT

The present disclosure relates to polypeptides, such as fibronectin type III (FN3) domains that can bind CD71, their conjugates, isolated nucleotides encoding the molecules, vectors, host-cells, as well as methods of making and using the same.

34 Claims, No Drawings
Specification includes a Sequence Listing.

(56) References Cited

U.S. PATENT DOCUMENTS

| | | |
|---|---|---|
| 8,981,063 B2 | 3/2015 | Chen |
| 9,156,887 B2 | 10/2015 | Jacobs |
| 9,175,082 B2 | 11/2015 | Zhou et al. |
| 9,200,273 B2 | 12/2015 | Diem et al. |
| 9,212,224 B2 | 12/2015 | Cogswell et al. |
| 9,326,941 B2 | 5/2016 | Chae et al. |
| 9,546,368 B2 | 1/2017 | Bennett et al. |
| 9,644,023 B2 | 5/2017 | Torres et al. |
| 9,695,228 B2 | 7/2017 | Mark et al. |
| 9,897,612 B2 | 2/2018 | Diem et al. |
| 10,196,446 B2 | 2/2019 | Goldberg et al. |
| 10,233,448 B2 | 3/2019 | Maier et al. |
| 10,597,438 B2 | 3/2020 | Diem et al. |
| 10,611,823 B2 | 4/2020 | Diem et al. |
| 10,626,165 B2 | 4/2020 | Hawkins et al. |
| 2004/0197332 A1 | 10/2004 | Ullrich et al. |
| 2004/0259781 A1 | 12/2004 | Chiquet-Ehrismann et al. |
| 2005/0004029 A1 | 1/2005 | Garcia |
| 2005/0038229 A1 | 2/2005 | Lipovsek et al. |
| 2005/0255548 A1 | 11/2005 | Lipovsek et al. |
| 2005/0272083 A1 | 12/2005 | Seshagiri |
| 2006/0040278 A1 | 2/2006 | Cojocaru et al. |
| 2006/0246059 A1 | 11/2006 | Lipovsek et al. |
| 2006/0270604 A1 | 11/2006 | Lipovsek et al. |
| 2007/0148126 A1 | 6/2007 | Chen et al. |
| 2007/0160533 A1 | 7/2007 | Chen et al. |
| 2007/0184476 A1 | 8/2007 | Hsieh et al. |
| 2008/0015339 A1 | 1/2008 | Lipovsek et al. |
| 2008/0220049 A1 | 9/2008 | Chen et al. |
| 2008/0241159 A1 | 10/2008 | Gerritsen et al. |
| 2009/0042906 A1 | 2/2009 | Huang et al. |
| 2009/0176654 A1 | 7/2009 | Cappuccilli et al. |
| 2009/0274693 A1 | 11/2009 | Gilmer et al. |
| 2009/0299040 A1 | 12/2009 | Camphausen et al. |
| 2009/0311803 A1 | 12/2009 | Way et al. |
| 2010/0093662 A1 | 4/2010 | Defaye et al. |
| 2010/0136129 A1 | 6/2010 | Agueros Bazo et al. |
| 2010/0144601 A1 | 6/2010 | Jacobs et al. |
| 2010/0179094 A1 | 7/2010 | Emanuel et al. |
| 2010/0203142 A1 | 8/2010 | Zhang et al. |
| 2010/0216708 A1 | 8/2010 | Jacobs et al. |
| 2010/0221248 A1 | 9/2010 | Wittrup et al. |
| 2010/0254989 A1 | 10/2010 | Bossenmaier et al. |
| 2010/0255056 A1 | 10/2010 | Jacobs et al. |
| 2011/0021746 A1 | 1/2011 | Cappuccilli et al. |
| 2011/0038866 A1 | 2/2011 | Hastewell et al. |
| 2011/0053842 A1 | 3/2011 | Camphausen et al. |
| 2011/0081345 A1 | 4/2011 | Moore et al. |
| 2011/0118144 A1 | 5/2011 | Hyun et al. |
| 2011/0124527 A1 | 5/2011 | Cappuccilli et al. |
| 2011/0274623 A1 | 11/2011 | Jacobs |
| 2011/0287009 A1 | 11/2011 | Scheer et al. |
| 2012/0225870 A1 | 9/2012 | Janne et al. |
| 2012/0244164 A1 | 9/2012 | Beste et al. |
| 2012/0263723 A1 | 10/2012 | Davies et al. |
| 2012/0270797 A1 | 10/2012 | Wittrup et al. |
| 2012/0315639 A1 | 12/2012 | Deng et al. |
| 2012/0321666 A1 | 12/2012 | Cooper et al. |
| 2013/0012435 A1 | 1/2013 | Camphausen et al. |
| 2013/0039927 A1 | 2/2013 | Dewhurst et al. |
| 2013/0079243 A1 | 3/2013 | Diem et al. |
| 2013/0123343 A1 | 5/2013 | Croce et al. |
| 2013/0130377 A1 | 5/2013 | Lee et al. |
| 2013/0184212 A1 | 7/2013 | Camphausen et al. |
| 2013/0226834 A1 | 8/2013 | Gannalo, II |
| 2013/0273561 A1 | 10/2013 | Walker et al. |
| 2014/0141000 A1 | 5/2014 | Chiu et al. |
| 2014/0155325 A1 | 6/2014 | Mark et al. |
| 2014/0155326 A1 | 6/2014 | Mark et al. |
| 2014/0255408 A1 | 9/2014 | Chiu et al. |
| 2014/0271467 A1 | 9/2014 | Hackel et al. |
| 2014/0341917 A1 | 11/2014 | Nastri et al. |
| 2014/0349929 A1 | 11/2014 | Camphausen et al. |
| 2014/0371296 A1 | 12/2014 | Bennett et al. |
| 2015/0005364 A1 | 1/2015 | Chae et al. |
| 2015/0104808 A1 | 4/2015 | Goldberg et al. |
| 2015/0118288 A1 | 4/2015 | Lee |
| 2015/0197571 A1 | 7/2015 | Freeman et al. |
| 2015/0203580 A1 | 7/2015 | Papadopoulos et al. |
| 2015/0210756 A1 | 7/2015 | Torres et al. |
| 2015/0252097 A1 | 9/2015 | Camphausen et al. |
| 2015/0274835 A1 | 10/2015 | Marasco et al. |
| 2015/0346208 A1 | 12/2015 | Couto et al. |
| 2015/0355184 A1 | 12/2015 | Pierce et al. |
| 2016/0041182 A1 | 2/2016 | Diem et al. |
| 2016/0303256 A1 | 10/2016 | Liu |
| 2016/0326232 A1 | 11/2016 | Rosa et al. |
| 2016/0355599 A1 | 12/2016 | Sagert et al. |
| 2017/0174748 A1 | 6/2017 | Mitchell et al. |
| 2017/0258948 A1 | 9/2017 | Morin et al. |
| 2017/0281795 A1 | 10/2017 | Geall |
| 2017/0348397 A1 | 12/2017 | Diem et al. |
| 2017/0362301 A1 | 12/2017 | Anderson et al. |
| 2019/0127444 A1 | 5/2019 | Brezski et al. |
| 2019/0175651 A1 | 6/2019 | Lee et al. |
| 2019/0184018 A1 | 6/2019 | Manoharan et al. |
| 2019/0184028 A1 | 6/2019 | Dudkin et al. |
| 2019/0202927 A1 | 7/2019 | Sagert et al. |
| 2019/0256575 A1 | 8/2019 | Chen et al. |
| 2019/0263915 A1 | 8/2019 | Goldberg et al. |
| 2019/0330361 A1 | 10/2019 | Chin et al. |

FOREIGN PATENT DOCUMENTS

| | | |
|---|---|---|
| CN | 105907719 A | 8/2016 |
| EP | 0985039 A2 | 3/2000 |
| EP | 1137941 A1 | 10/2001 |
| EP | 1210428 A1 | 6/2002 |
| EP | 1266025 A1 | 12/2002 |
| EP | 2935329 A1 | 10/2015 |
| JP | 2011507543 A | 3/2011 |
| JP | 2011517314 A | 6/2011 |
| JP | 2011520961 A | 7/2011 |
| JP | 2011522517 A | 8/2011 |
| JP | 2012507295 A | 3/2012 |
| JP | 2014530014 A | 11/2014 |
| JP | 2016504291 A | 2/2016 |
| KR | 10-2016-0067966 A | 6/2016 |
| WO | 9638557 A1 | 12/1996 |
| WO | 2001014557 A1 | 3/2001 |
| WO | 0164942 A1 | 9/2001 |
| WO | 0232925 A2 | 4/2002 |
| WO | 03104418 A2 | 12/2003 |
| WO | 2004029224 A2 | 4/2004 |
| WO | 2004058821 A2 | 7/2004 |
| WO | 2005018534 A2 | 3/2005 |
| WO | 2005042708 A2 | 5/2005 |
| WO | 2007000671 A2 | 1/2007 |
| WO | 2007085815 A2 | 8/2007 |
| WO | 2008066752 A2 | 6/2008 |
| WO | 2008079973 A2 | 7/2008 |
| WO | 2008127710 A2 | 10/2008 |
| WO | 2008156642 A1 | 12/2008 |
| WO | 2009023184 A2 | 2/2009 |
| WO | 2009058379 A2 | 5/2009 |
| WO | 2009083804 A2 | 7/2009 |
| WO | 2009085462 A1 | 7/2009 |
| WO | 2009086116 A2 | 7/2009 |
| WO | 2009102421 A1 | 8/2009 |
| WO | 2009111691 A2 | 9/2009 |
| WO | 2009126834 A2 | 10/2009 |
| WO | 2009133208 A1 | 11/2009 |
| WO | 2009142773 A2 | 11/2009 |
| WO | 2010039248 A1 | 4/2010 |
| WO | 2010051274 A2 | 5/2010 |
| WO | 2010051310 A2 | 5/2010 |
| WO | 2010060095 A1 | 5/2010 |
| WO | 2010093627 A3 | 10/2010 |
| WO | 2010115202 A2 | 10/2010 |
| WO | 2010115551 A1 | 10/2010 |
| WO | 2011005133 A1 | 1/2011 |
| WO | 2011110642 A2 | 9/2011 |
| WO | 2011130324 A1 | 10/2011 |
| WO | 2011131746 A2 | 10/2011 |

(56) References Cited

FOREIGN PATENT DOCUMENTS

| | | |
|---|---|---|
| WO | 2011137319 A2 | 11/2011 |
| WO | 2011151412 A1 | 12/2011 |
| WO | 2012016245 A2 | 2/2012 |
| WO | 2012162418 A1 | 11/2012 |
| WO | 2013049275 A1 | 4/2013 |
| WO | 2014081944 A2 | 5/2014 |
| WO | 2014081954 A1 | 5/2014 |
| WO | 2014100079 A1 | 6/2014 |
| WO | 2014165082 A2 | 10/2014 |
| WO | 2014165093 A2 | 10/2014 |
| WO | 2014189973 A2 | 11/2014 |
| WO | 2014209804 A1 | 12/2014 |
| WO | 2015057545 A2 | 4/2015 |
| WO | 2015061668 A1 | 4/2015 |
| WO | 2015089073 A2 | 6/2015 |
| WO | 2015092393 A2 | 6/2015 |
| WO | 2015109124 A2 | 7/2015 |
| WO | 2015143199 A1 | 9/2015 |
| WO | 2015195163 A1 | 12/2015 |
| WO | 2016000619 A1 | 1/2016 |
| WO | 2016004043 A1 | 1/2016 |
| WO | 2016086021 A1 | 6/2016 |
| WO | 2016086036 | 6/2016 |
| WO | 2016179534 | 11/2016 |
| WO | 2016197071 A1 | 12/2016 |
| WO | 2017011618 A1 | 1/2017 |
| WO | 2017223180 A2 | 12/2017 |
| WO | 2018148501 A1 | 8/2018 |

OTHER PUBLICATIONS

Alderson et al., "Molecular and Biological Characterization of Human 4-1 BB and its Ligand", Eur. J_Immunol., vol. N, pp. 2219-2227, 1994.

Alfthan et al., "Properties of a single-chain antibody containing different linker peptides," Protein Engineering, vol. B, No. 7, pp. 725-731 (1995).

Attwood TK. Genomics. The Babel of bioinformatics. Science. 290(5491):471-473, 2000.

Basel GA et al., "Critical Update and Emerging Trends in Epidermal Growth Factor Receptor Targeting in Cancer," Journal of Clinical Oncology, vol. 23, No. 11, pp. 2445-2459 (2005).

Bass, et al., "Hormone Phage: An Enrichment Method for Variant Proteins with Altered Binding Properties," PROTEINS: Structure, Function, and Genetics, 8: 309-314 (1990).

Batley et al., "Inhibition of FGF-1 Receptor Tyrosine Kinase Activity By PD 161570, a New Protein-Tyrosine Kinase nhibitor," Life Sciences, vol. 62, No. 20, pp. 143-150 (1998).

Bean et al., "MET amplification occurs with or without T790M mutations in EGFR mutant lung tumors with acquired esistance to gefilinib or erlotinib," Proceedings of the National Academy of Science, vol. 104, No. 52, pp. ) 0932-20937 (2007).

Binz et al., "High-affinity binders selected from designed ankyrin repeat protein libraries," Nature Biotechnology, vol. e2, No. 5, pp. 575-582 (May 2004).

Binz, et al., "Engineered proteins as specific binding reagents," Current Opinion in Biotechnology, 16:459-469 (2005).

Birtalan et al., "The Intrinsic Contributions of Tyrosine, Serine, Glycine and Arginine to the Affinity and Specificity of Antibodies," Journal of Molecular Biology, vol. 377, pp. 1518-1528 (2008).

Bork et al., "Proposed acquisition of an animal protein domain by bacteria," Proceedings of the National Academy of Science, USA, vol. 89, pp. 8990-8994 (1992).

Brown et al., "Tolerance of single, but not multiple, amino acid replacements in antibody VH CDR 2: a means of minimizing B cell wastage from somatic hypermutation", J. Immuno. (1996) pp. 3285-3291.

Burgess et al., "Possible dissociation of the heparin-binding and mitogenic activities of heparin-binding (acidic fibroblast) growth factor-1 from its receptor-binding activities by site-directed mutagenesis of a single lysine residue" J Cell Biol (1990) 111:pp. 2129-2138.

Burton Earle Barnett et al.: "Disclosures", Blood, vol. 128, No. 22, Dec. 2, 2016 (Dec. 2, 2016), pp. 4557-4557, XP055711182, US ISSN: 0006-4971, doi: 10.1182/blood.V1 28.22.4557.4557 *abstract*.

C.N. Pace, "Determination and Analysis of Urea and Guanidine Hydrochloride Denaturation Curves," Methods in Enzymology, 131: 266-280 (1986).

Capellas, "Enzymatic Condensation of Cholecystokinin CCK-8 (4-6) and CCK-8 (7-8) Peptide Fragments in Organic Media", Biotechnology and Bioengineering (1997) vol. 56, No. 4, pp. 456-463.

Cappuzzo et al., "Epidermal Growth Factor Receptor Gene and Protein and Gefilinib Sensitivity in Non-small-Cell ung Cancer," Journal of the National Cancer Institute, vol. 97, pp. 643-655 (2005).

Chen et al., "Cell-Surface Display of Heterologous Proteins: From High-Throughput Screening to Environmental Applications", Biotechnology and Bioengineering, (2002) vol. 79, No. 5, pp. 496-503.

Chiba et al., Amyloid Fibril Formation in the Context of Full-length Protein Effects of Praline mutations on the Amyloid fibril formation of b2-Microglobulin, Journal of Biological Chemistry, vol. 278, No. 47, pp. 47016-47024, Nov. 2003.

Chimu RA et al., "Expression of c-mel/HGF Receptor in Human Non-small Cell Lung Carcinomas in vitro and in vivo and Its Prognostic Significance," Japan Journal of Cancer Research, vol. 87 pp. 1063-1069 (1996).

Christensen et al., "c-Met as a target for human cancer and characterization of inhibitors for therapeutic ntervention," Cancer Letters, vol. 225, pp. 1-26 (2005).

Clarke, et al., "Folding and Stability of a Fibronectin Type III Domain of Human Tenascin," Journal of Molecular Biology, 270: 771-778 (1997).

Cooper et al., "4-1 BB (CD 137) controls the clonal expansion and survival of COB T cells in vivo but does not t: ontribute the development of cytotoxicity", Eur. J_Immunol., vol. 32, pp. 521-529, 2002.

Cooper et al., "Molecular cloning of a new transforming gene from a chemically transformed human cell line," Nature, vol. 311, pp. 29-33 (1984).

Cota, et al., "Two Proteins with the Same Structure Respond very Differently to Mutation: The Role of Plasticity in Protein Stability", Journal of Molecular Biology, 302, 713-725 (2000).

DeBenedette et al., "Role of 4-1BB Ligand in Costimulation of T Lymphocyte Growth and its Upregulation on M12 B rymphomas by cAMP," J_Exp_Med., vol. 181, pp. 985-992 (1995).

Dehouck, et al., "Fast and accurate predictions of protein stability changes upon mutations using statistical potentials and neural networks: PoPMuSiC-2.0," Bioinformatics, 25(19): 2537-2543 (2009).

DeRoock et al., "Effects of KRAS, BRAF, NRAS, and PIK3CA mutations on the efficacy of cetuximab plus chemotherapy in chemotherapy-refractory metastatic colorectal cancer: a retrospective consortium analysis," Lancet Oncology, vol. 11, pp. 753-762 (2010).

Diem et al., "Selection of high-affinity Centyrin FN3 domains from a simply library diversified at a combination of strand and loop positions." Protein Engin Design (2014) Selection 27(10): 419-429.

Dineen, et al., "The Adnectin CT-322 is a novel VEGF receptor 2 inhibitor that decreases tumor burden in an orthotopic mouse model of pancreatic cancer," BMC Cancer, 8: 352-361 (2008).

Downward et al., "Autophosphorylation sites on the epidermal growth factor receptor," Nature, vol. 311, pp. 183-485 (1984).

Dutta, et al., "High-affinity fragment complementation of a fibronectin type III domain and its application to stability enhancement," Protein Science, 14: 2838-2848 (2005).

Engelman et al., "MET Amplification Leads to Gefitinib Resistance in Lung Cancer by Activating ERBB3 Signaling," Science, vol. 316, pp. 1039-1043 (2007).

Ferguson, Kathryn M., "Structure-Based View of Epidermal Growth Factor Receptor Regulation," Annual Review of Biophysics, vol. 37, pp. 535-373 (2008).

Final Office Action dated Jul. 10, 2020 in U.S. Appl. No. 15/637,276.
Final Office Action dated Jul. 21, 2020 in U.S. Appl. No. 16/218,990.

(56) References Cited

OTHER PUBLICATIONS

Garcia-Ibilcieta, et al., "Simple method for production of randomized human tenth fibronectin domain III libraries for use in combinatorial screening procedures," Bio Technologies, 44: 559-562 (2008).
Garon et al., "Pembrolizumab for the Treatment of Non-Small-Cell Lung Cancer," The New England Journal of Medicine, vol. 372, No. 21, pp. 2018-2028 (May 21, 2015).
Garrard, et al., "Selection of an anti-IGF-1 Fab from a Fab phage library created by mutagenesis of multiple CDR loops," Gene, 128: 103-109 (1993).
GenBank Accession No. NP 001120972, accessed May 12, 2020.
GenBank Accession No. NP_002151, accessed May 12, 2020.
Getmanova, et al., "Antagonists to Human and Mouse Vascular Endothelial Growth Factor Receptor 2 Generated by Directed Protein Evolution In Vitro," Chemistry & Biology, 13: 549-556 (2006).
Gill et al., "Monoclonal Anti-epidermal Growth Factor Receptor Antibodies Which Are Inhibitors of Epidermal Growth racier Binding and Antagonists of Epidermal Growth Factor-stimulated tyrosine Protein Kinase Activity," The Journal Jf Biological Chemistry, vol. 259, No. 12, pp. 7755-7760 (1984).
Goldberg et al., "Engineering a Targeted Delivery Platform using Centyrins" Protein Engineering, Design & selection, vol. 29, No. 12, pp. 563-572, 2016.
Goldstein et al., "Biological efficacy of a chimeric antibody to the epidermal growth factor receptor in a human umor xenograft model," Clinical Cancer Research, vol. 1, pp. 1311-1318 (1995).
Gramaglia et al., "Co-stimulation of antigen-specific CD4T cells by 4-1BB ligand," Eur. J. Immunol., vol. 30, pp. ô€?¯92-402 (2000).
Grünwald et al., "Developing Inhibitors of the Epidermal Growth Factor Receptor for Cancer Treatment," Journal of he National Cancer Institute, vol. 95, No. 12, pp. 851-867 (2003).
Hackel et al., "Use of 64Cu-Labeled Fibronectin Domain with EGFR-Overexpressing Tumor Xenograft: Molecular Imaging1", Radiology (2012) vol. 263:No. 1 pp. 179-188.
Hackel, et al., "Picomolar Affinity Fibronectin Domains Engineered Utilizing Loop Length Diversity, Recursive Mutagenesis, and Loop Shuffling," Journal of Molecular Biology, 381: 1238-1252 (2008).
Olson, William C. et al, "Antibody-drug Conjugates Targeing Prostate-Specific Membrane Antigen," Frontiers in Bioscience (Landmark Edition) 19: pp. 12-33, Jan. 1, 2014.
Michel et al., "A soluble form of CD 137 (ILA/4-1BB), a member of the TNF receptor family, is released by activated ymphocytes and is detectable in sera of patients with rheumatoid arthritis," Eur. J_Immunol., vol. 28, pp. 290-295 1998).
Michel et al., "CD137-induced apoptosis is independent of CD95," Immunology, vol. 98, pp. 42-46 (1999).
Michel et al., "Expression of soluble CD137 correlates with activation-induced cell death of lymphocytes", Cytokine, vol. 12, No. 6, pp. 742-746, 2000.
Miller et al Ligand binding to proteins: the binding landscape model. Protein Sci. Oct. 1997;6(10):2166-79.
Määttä et al., "Proteolytic Cleavage and Phosphorylation of a Tumor-associated ErbB4 Isoform Promote Ligand-ndependent Survival and Cancer Cell Growth," Molecular Biology, vol. 17, pp. 67-79 (2006).
Natarajan, et al., "A Novel Engineered Anti-CD20 Tracer Enables Early Time PET Imaging in a Humanized Transgenic Mouse Model of B-cell Non-Hodgkins Lymphoma", Clin Cancer Res (2013) 19: pp. 6820-6829.
NCBI Reference Sequence NP _005219.2, "Epidermal Growth Factor Receptor Isoform a Precursor [*Homo sapiens*]," pp. 1-14 (May 18, 2014).
Non-Final Office Action dated Feb. 3, 2021 in U.S. Appl. No. 16/218,990.
Non-Final Office Action dated Jul. 9, 2021 in U.S. Appl. No. 16/821,064.
Non-Final Office Action dated Aug. 18, 2021 in U.S. Appl. No. 16/801,787.
Notice of Allowance dated Mar. 3, 2020 in U.S. Appl. No. 15/840,303.

Odegrip et al., "CIS display: In vitro selection of peptides from libraries of protein-DNA complexes," Proceedings of he National Academy of Science USA, vol. 101, No. 9, pp. 2806-2810 (2004).
Olson et al., "Design, expression, and stability of a diverse protein library based on the human fibronectin type III ô€,?omain," Protein Science, vol. 16, pp. 476-484 (2007).
Pace, "Determination and Analysis of Urea and Guanidine Hydrochloride Denaturation Curves", Methods in Enzymology (1986) vol. 131, pp. 266-280.
Panek et al., "In Vitro Pharmacological Characterization of PD 166285, a New Nanomolar Potent and Broadly Active Protein Tyrosine Kinase Inhibitor," The Journal of Pharmacology and Experimental Therapeutics, vol. 283, No. 3, pp. 1433-1444(1997).
Parker, et al., "Antibody mimics based on human fibronectin type three domain engineered for thermostability and high-affinity binding to vascular endothelial growth factor receptor two," Protein Engineering, Design & Selection, 18(9):435-444 (2005).
Pauly et al., CD137 is expressed by follicular dendritic cells and costimulates B lymphocyte activation in germinal t; enters, Journal of Leukocyte Biology, vol. 72, pp. 35-42, Jul. 2002.
Peters et al., "MET: a promising anticancer therapeutic target," Nature Reviews Clinical Oncology, vol. 9, pp. 314-326 (2012).
Prewett et al., "Mouse-Human chimeric Anti-Epidermal Growth Factor Receptor Antibody C225 Inhibits the Growth Jf Human Renal Cell Carcinoma Xenografts in Nude Mice," Clinical Cancer Research, vol. 4, pp. 2957-2966 (1998).
Reiss et al. Inhibition of platelet aggregation by grafting RGD and KGD sequences on the structural scaffold of small disulfide-rich proteins. Platelets 17(3):153-157, 2006.
Riel Yet al., "Clinical Course of Patients with Non-Small Cell Lung Cancer and Epidermal Growth Factor Receptor Exon 19 and Exon 21 Mutations Treated with Gefitinib or Erlotinib," Clinical Cancer Research, vol. 12, No. 3, pp. g39-844 (2006).
Roberts et al., "RNA-peptide fusions for the in vitro selection of peptides and proteins," Proceedings of the National Academy of Science USA, vol. 94, pp. 12297-12302 (1997).
Robinson et al., "Covalent Attachment of Arc Repressor Subunits by a Peptide Linker Enhances Affinity for Operator DNA," Biochemistry, vol. 35, pp. 109-116 (1996).
Rudikoff el al., "Single amino acid substitution altering antigen-binding specificity", Proc Natl Acad Sci (1982) 79(6): pp. 1979-1983.
Rybalov et al., "PSMA, EpCAM, VEGF and GRPR as Imaging Targets in Locally Recurrent Prostate Cancer after Radiotherapy", Int. J. Mol. Sci. (2014) 15, pp. 6046-6061.
Sakakura et al., "Gains, Losses, and Amplifications of Genomic Materials in Primary Gastric Cancers Analyzed by :; omparative Genomic Hybridization," Genes, Chromosomes & Cancer, vol. 24, pp. 299-305 (1999).
Schmidt et al., "Novel mutations of the MET proto-Oncogene in papillary rental carcinomas," Oncogene, vol. 18, pp. [343-2350 (1999).
Schwarz et al., "ILA, a Member of the Human Nerve Growth FactorfTumor Necrosis Factor Receptor Family, Regulates T-Lymphocyte Proliferation and Survival," Blood, vol. 87, No. 7, pp. 2839-2845 (Apr. 1, 1996).
Shalom D. Goldberg et al: "Engineering a targeted delivery platform using Centyrins", Protein Engineering, Design and Selection, Oct. 13, 2016 (Oct. 13, 2016), XP055384705, GB ISSN: 1741-0126, DOI: 10.1093/protein/gzw054 *abstractp. 564, left-hand column, paragraph 2—right-hand column, line 3 p. 567, right-hand column, paragraph 2p. 568, right-hand column, paragraph 2—p. 569, left-hand column, paragraph 2table l**figure 1a*.
Shuford et al., "4-18B Costimulatory Signals Preferentially Induce COB+ T Cell Proliferation and Lead to the amplification In Vivo of Cytotoxic T Cell Responses," J_Exp_Med., vol. 186, No. 1, pp. 47-55 (Jul. 7, 1997).
Siegfried et al., "The Clinical Significance of Hepatocyte Growth Factor for Non-Small Cell Lung Cancer," Annals of Thoracic Surgery, vol. 66, pp. 1915-1918 (1998).
Sierra et al., "c-MET as a potential therapeutic target and biomarker in cancer," Therapeutic Advances in Medical :: >ncology, vol. 3, No. 51, pp. 521-535 (2011).

(56) References Cited

OTHER PUBLICATIONS

Siggers et al. Conformational dynamics in loop swap mutants of homologous fibronectin type III domains. Biophys J. Oct. 1, 2007 ;93(7):2447-56.

Skerra, et al., "Engineered protein scaffolds for molecular recognition," Journal of Molecular Recognition, 13:167-187 (2000).

Skolnick et al. From genes to protein structure and function: novel applications of computational approaches in the genomic era. Trends Biotechnol. 18(1 ):34-9, 2000.

Slonomics® Technology Website "https://www.morphosys.com/science/drug-development-capabilities/slonomics", accessed May 12, 2020.

Smith, "Filamentous fusion phage: novel expression vectors that display cloned antigens on the virion surface.", Association of Science (1985) vol. 228, pp. 1315(3).

Song et al. Cancer stem cells-an old idea that's new again: implications for the diagnosis and treatment of breast cancer. Expert Opin Biol Ther 7:4):431-438, 2007.

Stamos et al., "Crystal structure of the HGF b-chain in complex with the Sema domain of the Met receptor," The EMBO Journal, vol. 23, pp. 2325-2335 (2004).

Steiner, et al., "Efficient Selection of DARPins with Sub-nonomolar Affinities using SRP Phage Display," Journal of Molecular Biology, 382: 1211-1227 (2008).

Strand et al., "Site-Specific Radioiodination of HER2-Targeting Affibody Molecules using 4-Iodophenethylmaleimide Decreases Renal Uptake of Radioactivity"; Chemitry Open, vol. 4, pp. 174-182, 2015.

Strohl, William R., "Optimization of Fe-mediated effector functions of monoclonal antibodies," Current Opinion in Biotechnology, vol. 20, pp. 685-691 (2009).

SwissProt Accession No. P00533.2, "Epidermal Growth Factor Receptor," pp. 1-49 (Jun. 11, 2014).

Takahashi et al., "Cutting Edge: 4-1 BB Is a Bona Fide COB T Cell Survival Signal," J Immunol., vol. 162, pp. 0037-5040 (1999).

Tannock and Hill. The Basic Science of Oncology. 1998. New York: McGraw-Hill;; pp. 357-358.

Tie et al., "Safety and efficacy of nivolumab in the treatment of cancers: A meta-analysis of 27 prospective clinical rials," International Journal of Cancer, vol. 140, pp. 948-958, (2017).

Turke et al., "Preexistence and Clonal Selection of MET Amplification in EGFR Mutant NSCLC," Cancer Cell, vol. 17, pp. 77-88 (2010).

Ullrich et al., "Human epidermal growth factor receptor cDNA sequence and aberrant expression of the amplified Jene in A431 epidermoid carcinoma cells," Nature, vol. 309, pp. 418-425 (1984).

UniProt Accession No. P10039, accessed May 12, 2020.

Vajdos et al., "Comprehensive funtional maps of the antigen-binding site of an anti-ErbB2 antibody obtained with shotgun scanning mutagenisis", J. Mol. Biol. (2002) 32(2): pp. 415-428.

Van den Burg et al., "Selection of mutations for increased protein stability", Curr. Opin. Biotech. 13:333-337 (2002).

Wang et al., "VISTA, a novel mouse Ig superfamily ligand that negatively regulates T cell responses," Journal of Experimental Medicine, vol. 208, No. 3, pp. 577-592 (Mar. 14, 2011).

Watanabe et al., "Gene Cloning of Chitinase A1 from Bacillus circulans WL-12 Revealed Its Evolutionary Relationship to Serratia Chitinase and to the Type III Homology Units of Fibronectin," Journal of Biological Chemistry, vol. 265, pp. 15659-15665 (1990).

Wattanachaisaereekul, "Production of Polyketides by Saccharomyces cerevisiae", Ph.D. Thesis (2007) Center for Microbial Biotechnology, BioCentrum-DTU Technical University of Denmark, pp. 1-187.

Xu, et al., "Directed Evolution of High-Affinity Antibody Mimics Using mRNA Display," Chemistry & Biology, 9: 933-942 (2002).

Zhang et al., "Complete disulfide bond assignment of a recombinant immunoglobulin G4 monoclonal antibody," Analytical Biochemistry, vol. 311, pp. 1-9 (2002).

Zhou et al., Characterization of human homologue of 4-1 BB and its ligand, Immunology Letters, vol. 45, pp. p7-73, 1995.

Zucali, et al.," Role of cMET expression in non-small-cell lung cancer patients treated with eGFR tyrosine kinase inhibitors", Annals of Anocology (2008) 19:: 1605-1612.

Non-Final Office Action dated Sep. 24, 2021 in U.S. Appl. No. 16/820,844.

Non-Final Office Action dated Feb. 4, 2022 in U.S. Appl. No. 16/801,787.

Non-Final Office Action dated Feb. 10, 2022 in U.S. Appl. No. 16/218,990.

Hackel, et al., "Stability and CDR Composition Biases Enrich Binder Functionality Landscapes," Journal of Molecular Biology, 401: 84-96 (2010).

Hallewell et al., "Genetically Engineered Polymers of Human CuZN Superoxide Dismutase," The Journal of Biological Chemistry, vol. 264, No. 9, pp. 5260-5268 (1989).

Hamill et al., "The Effect of Boundary Selection on the Stability and Folding of the Third Fibronectin Type III Domain from Human Tenascin", Biochemistry, 37: 8071-8079 (1998).

Hanes et al, "In vitro selection and evolution of functional proteins by using ribosome display," Proceedings of the National Academy of Sciences USA, vol. 94, pp. 4937-4942 (1997).

Helms et al. Destabilizing loop swaps in the CDRs of an immunoglobulin VL domain. Protein Science 4:2073-2081, 1995.

Hirsch et al, "Combination of EGFR gene copy number and protein expression predicts outcome for advanced non- ,mall-cell lung cancer patients treated with gefitnib," Annals of Oncology, vol. 18, pp. 752-760 (2007).

Hoogenboom et al., "Natural and designer binding sites made by phage display technology" Immunology Today (2000) vol. 21, No. 8, pp. 371-378.

Hurtado et al., "Potential role of 4-1 BB in T cell Activation Comparison with the Costimulatory Molecule CD28", Journal of Immunology, vol. 155, pp. 3360-3367, 1995.

Hurtado et al., "Signals through 4-1BB are Costimulatory to previously activated splenic T cells and inhibit activation-induced cell death", Journal of Immunology, vol. 158, pp. 2600-2609, 1997.

Hylarides et al., "Preparation and in Vivo Evaluation of an N-9p-[1251]1odophenethyl) maleimide—Antibody Conjugate" Bioconjugate Chem., vol. 2, pp. 435-440, 1991.

Hynes et al., "ERBB Receptors and Cancer: the Complexity of Targeted Inhibitors," Nature Reviews, vol. 5, pp. 341-356 (2005).

Itoh, et al., "Application of Inverse Substrates to Trypsin-Catalyzed Peptide Synthesis", Bioorganic Chemistry (1996) 24, 0007, pp. 59-68.

Jacobs et al., "FN3 Domain Engineering", Protein Engineering, pp. 145-162, 2012.

Jacobs et al., "Fusion to a highly stable consensus albumin binding domain allows for tunable pharmacokinetics", Protein Engineering, Design & Selection, vol. 28, No. 10, pp. 385-393, 2015.

Jänne et al., "Effect of Epidermal Growth Factor Receptor Tyrosine Kinase Domain Mutations on the Outcome of Patients with Non-small Cell Lung Cancer Treated with Epidermal Growth Factor Receptor Tyrosine Kinase Inhibitors," Clinical Cancer Research, vol. 12, No. 14 Suppl, pp. 4416s-4420s (2006).

Karatan, et al., "Molecular Recognition Properties of FN3 Monobodies that Bind the Src SH3 Domain," Chemistry & Biology, 11: 835-844 (2004).

Klein et al. "Abstract LB-312: Bispecific Centyrin Simultaneously targeting EGFR and c-Met demonstrates improved ô€?'ctivity compared to the mixture of single agents", Cancer Research, 73 (8 Supplement), Abstract LB-312, Apr. 2013.

Knappik, et al., "Fully Synthetic Human Combinatorial Antibody Libraries (HuCAL) Based on Modular Consensus Frameworks and CDRs Randomized with Trinucleotides," Journal of Molecular Biology, 296: 57-86 (2002).

Koide et al., "High-affinity single-domain binding proteins with a binary-code interface," PNAS, vol. 104, No. 16, pp. 6632-6637(Apr. 17, 2017).

Koide, et al., "The Fibronectin Type III Domain as a Scaffold for Novel Binding Proteins," Journal of Molecular Biology, 284: 1141-1151 (1998).

Koivunen et al. Identification of Receptor Ligands with Phage Display Peptide Libraries J Nucl Med; 40:883-888, 1999.

(56) References Cited

OTHER PUBLICATIONS

Kumaran et al., "Confrmationally driven protease-catalyzed splicing of peptide segments: V8 protease-mediated syntheses of fragments derived from thermolysin and ribonuclease A", Protein Science, (1997) 6: pp. 2233-2241.
Kunkel et al., "Rapid and Efficient Site-Specific Mutagenesis without Phenotypic Selection", Methods In Enzymology, (1987) vol. 154 pp. 367-375.
Kuntz. Structure-based strategies for drug design and discovery. Science. 1992 257(5073):1078-1082.
Kwon et al., cDNA sequences of two inducible T-cell genes, Proc. Natl. Acad. Sci., vol. 86, pp. 1963-1967, Mar. 1989.
Langstein et al., "CD137 (ILA/4-1 BB), a Member of the TNF Receptor Family, Induces Monocyte Activation via Bidirectional Signaling," The Journal of Immunology, vol. 160, pp. 2488-2494 (1998).
Langstein et al., "CD137 Induces Proliferation and Endomitosis in Monocytes," Blood, vol. 94, No. 9, pp. 3161-3168 1999).
Langstein et al., Identification of CD137 as a potent monocyte survival factor, Journal of Leukocyte Biology, vol. 65, pp. 829-833, Jun. 1999.
Lazar et al., "Transforming growth factor alpha: mutation of aspartic acid 47 and leucie 48 results in different biological activities", Mol Cell Biol. (1988) 8: pp. 1247-1252.
Lee et al., "4-1BB Promotes the Survival of COB+ T Lymphocytes by Increasing Expression of Bcl-xL and Bfl-11," The Journal of Immunol., vol. 169, pp. 4882-4888 (2002).
Lee et al., "A Glu-ruea-Lys Ligand-conjugated Lipid nanoparticle/siRNA System Inhibits Androgen Receptor Expression In Vivo", Molecular Therapy-Nucleic Acids (2016) 5, e348: pp. 1-11.
Lehmann et al., Engineering proteins for thermostability the use of sequence alignments versus rational design and directed evolution, Current Opinion in Biotechnology, vol. 12, pp. 371-375 (2001).
Lejon et al., "Structural basis for the binding of naproxen to human serum albumin in the presence of fatty acids and the GA module", Acta Cryst. (2008) F pp. 64-69.
Lepenies et al., "The Role of Negative Costimulators Dunng Parasitic Infections," Endocrine, Metabolic & Immune Disorders—Drug Targets, vol. 8, pp. 279-288 (2008).
Li et al., "Skin toxicities associated with epidermal growth factor receptor inhibitors," Target Oncology, vol. 4, pp. 107-119 (2009).
Linardou et al., "Somatic EGFR mutations and efficacy of tyrosine kinase inhibitors in NSCLC," National Review of :; linical Oncology, vol. 6, pp. 352-366 (2009).
Lipovsek, et al., "Evolution of an Interloop Disulfide Bond in High-Affinity Antibody Mimics Based on Fibronectin Type III Domain and Selected by Yeast Surface Display: Molecular Convergence with Single-Domain Camelid and Shark Antibodies," Journal of Molecular Biology, 368: 1024-1041 (2007).
Lohse et al., Fluorescein-Conjugated Lysine monomers for Solid Phase Synthesis of Fluorescent Peptides and PNA Pligomers Bioconjugate Chern, vol. 8, pp. 503-509, 1997 .pdf.
Ma et al., "c-Met: Structure, functions and potential for therapeutic inhibition," Cancer and Metastasis Reviews, vol. 22 pp. 309-325 (2003).
Makkouk Amani et al: "Rationale for anti-CD137 cancer immunotherapy", European Journal of Cancer, Elsevier, Amsterdam, NL, vol. 54, Jan. 2, 2016 (Jan. 2, 2016), pp. 112-119, XP029401784, ISSN: 0959-8049, DOI: 10.1016/j.ejca.2015.09.026 *abstractp. 114, right-hand column, paragraph 4—p. 116, right-hand column, paragraph 1table 1*.
Mamluk et al., "Anti-tumor effect of CT-322 as an Adnectin inhibitor of vascular endothelial growth factor receptor-2", mAbs, 2(2), pp. 199-208, 2010.
Mattheakis et al., "An in vitro polysome display system for identifying ligands from very large peptide libraries", Proc. Natl. Acad. Sci (1994) Vo.. 91, pp. 9022-9026.
Maus et al., Ex vivo expansion of polyclonal and antigen-specific cytotoxic T lymphocytes by artificial APCs Expressing ligands for the T-cell receptor, CD28 and 4-1BB Nature Biotechnology, vol. 20, pp. 143-148, Feb. 2002.
McCracken, "Non-invasive monitoring of hematopoietic reconstitution and immune cell function through Positron Emission Tomography" University of California, Los Angeles, Dissertaton ProQuest LLC (2014) pp. 1-202.
McLaughlin et al., "Quantitative Assessmenet of the Heterogeneity of PD-L 1 Expression in Non-small Cell Lung Cancer (NSCLC)," JAMA Oncol., vol. 2, No. 1, pp. 46-54, (Jan. 2016).
Meinke et al., "Cellulose-Binding Polypeptides from Cellulomonas fimi: Endoglucanase D (CenD), a Family A b-1,4-Glucanase," Journal of Bactenology, vol. 175, No. 7, pp. 1910-1918 (1993).
Mendelsohn et al., "Epidermal Growth Factor Receptor Targeting in Cancer," Seminars in Oncology, vol. 33, pp. 369-385 (2006).
Mendelsohn et al., "The EGF receptor family as targets for cancer therapy," Oncogene, vol. 19, pp. 6550-6565 2000).

* cited by examiner

＃ CD71 BINDING FIBRONECTIN TYPE III DOMAINS

CROSS-REFERENCE TO RELATED APPLICATIONS

The present application claims priority to U.S. Provisional Application No. 62/914,643, filed Oct. 14, 2019, and U.S. Provisional Application No. 62/949,020, Dec. 17, 2019, each of which is hereby incorporated by reference in its entirety.

FIELD

The present embodiments relate to fibronectin type III domains (FN3) that specifically bind cluster of differentiation 71 (CD71) and methods of making and using the molecules.

SEQUENCE LISTING

This application contains a Sequence Listing which has been submitted in ASCII format via EFS-Web and is hereby incorporated by reference in its entirety. The ASCII text file was created on Dec. 21, 2020, it is named 145965_02101_SeqList_21_Dec_2020_ST25.TXT, and it is 253 kilobytes in size.

BACKGROUND

CD71, also known as transferrin receptor 1, is transmembrane that is essential for iron transport into cells. It is highly expressed on many tumor types and at the blood brain barrier, and has thus become an important target for drug delivery. Following binding to iron loaded transferrin, CD71 is rapidly endocytosed and efficiently recycled back to the cell surface. Studies with CD71 antibody drug conjugates suggest that targeting CD71 can improve specificity and selectivity of drug delivery and widen the therapeutic index. In addition, studies using anti-CD71 monoclonal antibodies indicate that binding affinity can play an important role in enabling blood brain barrier transcytosis. Antibodies with high affinity for CD71 are rapidly internalized and alter normal receptor trafficking so that instead of recycling, the receptor is targeted to the lysosome for degradation. In contrast, antibodies with low affinity for CD71 allow for receptor recycling and higher brain exposure.

While antibodies or antibody fragments are the most widely used class of therapeutic proteins when high affinity and specificity for a target molecule are desired, non-antibody proteins can be engineered to also bind such targets. These "alternative scaffold" proteins have advantages over traditional antibodies due to their small size, lack of disulphide bonds, high stability, ability to be expressed in prokaryotic hosts, easy purification, and they are easily conjugated to drugs/toxins, penetrate efficiently into tissues and are readily formatted into multispecific binders.

One such alternative scaffold is the immunoglobulin (Ig) fold. This fold is found in the variable regions of antibodies, as well as thousands of non-antibody proteins. It has been shown that one such Ig protein, the tenth fibronectin type III (FN3) repeat from human fibronectin, can tolerate a number of mutations in surface exposed loops while retaining the overall Ig-fold structure. Thus, what is needed is a FN3 domain that can specifically bind to CD71, and methods of using such molecules for cancer therapy.

SUMMARY

In some embodiments, FN3 domains (e.g. polypeptides) that specifically bind CD71 protein are provided. In some embodiments, the FN3 domains are isolated. In some embodiments, the FN3 domains are recombinant. In some embodiments, the FN3 domains are non-naturally occurring.

In some embodiments, FN3 domains are provided that comprise the amino acid sequence of SEQ ID NOs: 33, 34, 35, 36, 37, 38, 39, 40, 41, 42, 43, 44, 45, 46, 47, 48, 49, 50, 51, 52, 53, 54, 55, 56, 57, 58, 59, 60, 61 or 62. In some embodiments, FN3 domains are provided that comprise the amino acid sequence of SEQ ID NOs: 146, 214, 104, 259, 134, 92, 302, 235, 237, 152, 238, 136, 197, 212, 296, 226, 261, 307, 115, 112, 278, 297, 96, 222, 95, 233, 217, 252, 194, 164, 168, 174, 190, 257, 303, 284, 85, or 149. In some embodiments, FN3 domains are provided that comprise the amino acid sequence of SEQ ID NOs: 81-309AM] In some embodiments, the FN3 domains bind to CD71. In some embodiments, the FN3 domain binds to human CD71 at a site on CD71 that does not compete with transferrin binding to CD71. In some embodiments, FN3 domains are provided that comprise the amino acid sequence of SEQ ID NOs: 146, 214, 104, 259, 134, 92, 302, 235, 237, 152, 238, 136, 197, 212, 296, 226, 261, 307, 115, 112, 278, 297, 96, 222, 95, 233, 217, 252, 194, 164, 168, 174, 190, 257, 303, 284, 85, or 149. In some embodiments, the FN3 domains specifically bind to CD71. In some embodiments, the polypeptide is provided that comprises more than one FN3 domains connected by a linker, such as a flexible linker. In some embodiments, the polypeptide comprises 2, 3, or 4 FN3 domains that are connected to one another by one or more linkers between the domains.

In some embodiments, isolated polynucleotides encoding the FN3 domains described herein are provided.

In some embodiments, a vector comprising the polynucleotides described herein are provided.

In some embodiments, a host cell comprising the vectors described herein are provided.

In some embodiments, methods of producing the FN3 domains are provided. In some embodiments, the method comprises culturing a host cell comprising a vector encoding or expressing the FN3 domain. In some embodiments, the method further comprises purifying the FN3 domain. In some embodiments, the FN3 domain specifically binds CD71.

In some embodiments, pharmaceutical compositions comprising a FN3 domain that binds to CD71 and a pharmaceutically acceptable carrier are provided.

In some embodiments, anti-idiotypic antibodies that binds a FN3 domain that binds to CD71 are provided.

In some embodiments, kits comprising one or more of the FN3 domains are provided.

In some embodiments, methods of detecting CD71-expressing cancer cells in a tumor tissue are provided. In some embodiments, the method comprises obtaining a sample of the tumor tissue from a subject and detecting whether CD71 protein is expressed in the tumor tissue by contacting the sample of the tumor tissue with the FN3 domain that binds CD71 protein comprising the amino acid sequence of one of SEQ ID NOs: 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, or 81-309 and detecting the binding between CD71 protein and the FN3 domain.

In some embodiments, methods of isolating CD71 expressing cells are provided. In some embodiments, the method comprises obtaining a sample from a subject; contacting the sample with the FN3 domain that binds CD71 protein comprising the amino acid sequence of one of SEQ ID NOs: 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, or 81-309 and isolating the cells bound to the FN3 domains.

In some embodiments, methods of detecting CD71-expressing cancer cells in a tumor tissue are provided. In some embodiments, the method comprises conjugating the FN3 domain that binds CD71 protein comprising the amino acid sequence of one of SEQ ID NOs: 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, or 81-309 to a detectable label to form a conjugate; administering the conjugate to a subject; and visualizing the CD71 expressing cancer cells to which the conjugate is bound.

In some embodiments, methods of treating cancer in a subject in need thereof are provided. In some embodiments, the method comprises administering a polypeptide that binds to CD71. In some embodiments, that the polypeptide is a FN3 domain that binds to CD71. In some embodiments, the polypeptide comprises a sequence such as SEQ ID Nos: 146, 214, 104, 259, 134, 92, 302, 235, 237, 152, 238, 136, 197, 212, 296, 226, 261, 307, 115, 112, 278, 297, 96, 222, 95, 233, 217, 252, 194, 164, 168, 174, 190, 257, 303, 284, 85, 149, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, or 81-309, or a polypeptide as provided herein that is linked to or conjugated to a therapeutic agent.

In some embodiments, methods of treating a neurological condition and/or a brain tumor are provided. In some embodiments, the methods comprise administering to the subject a polypeptide or the pharmaceutical composition as provided herein. In some embodiments, the brain tumor is selected from the group consisting of nonmalignant, benign, and malignant brain tumors.

In some embodiments, methods of delivering an agent of interest to a CD71 positive cell are provided. In some embodiments, the methods comprise contacting a cell with the agent of interest coupled to a FN3 domain that binds to CD71, such as a polypeptide as provided herein. In some embodiments, the agent of interest is a chemotherapeutic agent, a drug, a growth inhibitory agent, a toxin, a radioactive isotope, an anti-tubulin agent, a polynucleotide, a siRNA molecule, an antisense molecule, a RNA molecule, a DNA molecule, DNA minor groove binders, DNA replication inhibitors, alkylating agents, antibiotics, antifolates, antimetabolites, chemotherapy sensitizers, topoisomerase inhibitors, or a *vinca* alkaloid.

In some embodiments, the polypeptide is a FN3 protein that binds to CD71 at a site that does not compete or inhibit transferrin binding to CD71.

In some embodiments, methods of identifying a FN3 protein that binds to CD71 at a site that does not compete or inhibit transferrin binding to CD71 are provided.

DETAILED DESCRIPTION OF THE DISCLOSURE

As used in this specification and the appended claims, the singular forms "a," "an," and "the" include plural referents unless the content clearly dictates otherwise. Thus, for example, reference to "a cell" includes a combination of two or more cells, and the like.

"Fibronectin type III (FN3) domain" (FN3 domain) refers to a domain occurring frequently in proteins including fibronectins, tenascin, intracellular cytoskeletal proteins, cytokine receptors and prokaryotic enzymes (Bork and Doolittle, Proc Nat Acad Sci USA 89:8990-8994, 1992; Meinke et al., J Bacteriol 175:1910-1918, 1993; Watanabe et al., J Biol Chem 265:15659-15665, 1990). Exemplary FN3 domains are the 15 different FN3 domains present in human tenascin C, the 15 different FN3 domains present in human fibronectin (FN), and non-natural synthetic FN3 domains as described for example in U.S. Pat. No. 8,278,419. Individual FN3 domains are referred to by domain number and protein name, e.g., the $3^{rd}$ FN3 domain of tenascin (TN3), or the $10^{th}$ FN3 domain of fibronectin (FN10).

The term "capture agent" refers to substances that bind to a particular type of cells and enable the isolation of that cell from other cells. Exemplary capture agents are magnetic beads, ferrofluids, encapsulating reagents, molecules that bind the particular cell type and the like.

"Sample" refers to a collection of similar fluids, cells, or tissues isolated from a subject, as well as fluids, cells, or tissues present within a subject. Exemplary samples are tissue biopsies, fine needle aspirations, surgically resected tissue, organ cultures, cell cultures and biological fluids such as blood, serum and serosal fluids, plasma, lymph, urine, saliva, cystic fluid, tear drops, feces, sputum, mucosal secretions of the secretory tissues and organs, vaginal secretions, ascites fluids, fluids of the pleural, pericardial, peritoneal, abdominal and other body cavities, fluids collected by bronchial lavage, synovial fluid, liquid solutions contacted with a subject or biological source, for example, cell and organ culture medium including cell or organ conditioned medium and lavage fluids and the like.

"Substituting" or "substituted" or 'mutating" or "mutated" refers to altering, deleting of inserting one or more amino acids or nucleotides in a polypeptide or polynucleotide sequence to generate a variant of that sequence.

"Variant" refers to a polypeptide or a polynucleotide that differs from a reference polypeptide or a reference polynucleotide by one or more modifications for example, substitutions, insertions or deletions.

"Specifically binds" or "specific binding" refers to the ability of a FN3 domain to bind to its target, such as CD71, with a dissociation constant ($K_D$) of about $1\times10^{-6}$M or less, for example about $1\times10^{-7}$ M or less, about $1\times10^{-8}$M or less, about $1\times10^{-9}$ M or less, about $1\times10^{-10}$ M or less, about $1\times10^{-11}$M or less, about $1\times10^{-12}$M or less, or about $1\times10^{-13}$ M or less. Alternatively, "specific binding" refers to the ability of a FN3 domain to bind to its target (e.g. CD71) at least 5-fold above a negative control in standard ELISA assay. In some embodiments, a negative control is an FN3 domain that does not bind CD71. In some embodiment, an FN3 domain that specifically binds CD71 may have cross-reactivity to other related antigens, for example to the same predetermined antigen from other species (homologs), such as *Macaca Fascicularis* (cynomolgous monkey, cyno) or *Pan troglodytes* (chimpanzee).

"Library" refers to a collection of variants. The library may be composed of polypeptide or polynucleotide variants.

"Stability" refers to the ability of a molecule to maintain a folded state under physiological conditions such that it retains at least one of its normal functional activities, for example, binding to a predetermined antigen such as CD71.

"CD71" refers to human CD71 protein having the amino acid sequence of SEQ ID NOs: 32 or 80. In some embodiments, SEQ ID NO: 32 is full length human CD71 protein. In some embodiments, SEQ ID NO: 80 is the extracellular domain of human CD71.

"Tencon" refers to the synthetic fibronectin type III (FN3) domain having the sequence shown in SEQ ID NO: 1 and described in U.S. Pat. Publ. No. 2010/0216708.

A "cancer cell" or a "tumor cell" refers to a cancerous, pre-cancerous or transformed cell, either in vivo, ex vivo, and in tissue culture, that has spontaneous or induced phenotypic changes that do not necessarily involve the uptake of new genetic material. Although transformation can arise from infection with a transforming virus and incorporation of new genomic nucleic acid, or uptake of exogenous nucleic acid, it can also arise spontaneously or following exposure to a carcinogen, thereby mutating an endogenous gene. Transformation/cancer is exemplified by, e.g., morphological changes, immortalization of cells, aberrant growth control, foci formation, proliferation, malignancy, tumor specific markers levels, invasiveness, tumor growth or suppression in suitable animal hosts such as nude mice, and the like, in vitro, in vivo, and ex vivo (Freshney, Culture of Animal Cells: A Manual of Basic Technique (3rd ed. 1994)).

"Vector" refers to a polynucleotide capable of being duplicated within a biological system or that can be moved between such systems. Vector polynucleotides typically contain elements, such as origins of replication, polyadenylation signal or selection markers that function to facilitate the duplication or maintenance of these polynucleotides in a biological system. Examples of such biological systems may include a cell, virus, animal, plant, and reconstituted biological systems utilizing biological components capable of duplicating a vector. The polynucleotide comprising a vector may be DNA or RNA molecules or a hybrid of these.

"Expression vector" refers to a vector that can be utilized in a biological system or in a reconstituted biological system to direct the translation of a polypeptide encoded by a polynucleotide sequence present in the expression vector.

"Polynucleotide" refers to a synthetic molecule comprising a chain of nucleotides covalently linked by a sugar-phosphate backbone or other equivalent covalent chemistry. cDNA is a typical example of a polynucleotide.

"Polypeptide" or "protein" refers to a molecule that comprises at least two amino acid residues linked by a peptide bond to form a polypeptide. Small polypeptides of less than about 50 amino acids may be referred to as "peptides".

"Valent" refers to the presence of a specified number of binding sites specific for an antigen in a molecule. As such, the terms "monovalent", "bivalent", "tetravalent", and "hexavalent" refer to the presence of one, two, four and six binding sites, respectively, specific for an antigen in a molecule.

"Subject" includes any human or nonhuman animal. "Nonhuman animal" includes all vertebrates, e.g., mammals and non-mammals, such as nonhuman primates, sheep, dogs, cats, horses, cows chickens, amphibians, reptiles, etc. Except when noted, the terms "patient" or "subject" are used interchangeably.

"Isolated" refers to a homogenous population of molecules (such as synthetic polynucleotides or a polypeptide such as FN3 domains) which have been substantially separated and/or purified away from other components of the system the molecules are produced in, such as a recombinant cell, as well as a protein that has been subjected to at least one purification or isolation step. "Isolated FN3 domain" refers to an FN3 domain that is substantially free of other cellular material and/or chemicals and encompasses FN3 domains that are isolated to a higher purity, such as to 80%, 81%, 82%, 83%, 84%, 85%, 86%, 87%, 88%, 89%, 90%, 91%, 92%, 93%, 94%, 95%, 96%, 97%, 98%, 99% or 100% purity.

Compositions of Matter

In some embodiments, proteins comprising a polypeptide comprising an amino acid sequence of SEQ ID NOs: 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, or 81-309 are provided. In some embodiments, proteins comprising a polypeptide comprising an amino acid sequence that is at least 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% identical to a sequence of SEQ ID NOs: 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, or 81-309. In some embodiments, the protein is at least 85%, 86%, 87%, 88%, 89%, 90%, 91%, 92%, 93%, 94%, 95%, 96%, 97%, 98% or 99% identical to a sequence of SEQ ID NOs: 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, or 81-309. In some embodiments, the protein is at least 90%, 91%, 92%, 93%, 94%, 95%, 96%, 97%, 98% or 99% identical to a sequence of SEQ ID NOs: 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, or 81-309. In some embodiments, the protein is at least 95%, 96%, 97%, 98% or 99% identical to a sequence of SEQ ID NOs: 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, or 81-309.

The polypeptides provided herein can be part of a larger polypeptide and can be referred to as a domain. The homology or identity between two domains in different polypeptides is based on the domains that are similar as opposed to the overall polypeptide. For example, if a polypeptide comprises a polypeptide comprising a FN3 domain comprising SEQ ID NO: 81 and said domain is conjugated to a scFV antibody, another protein that has a domain that is similar but not identical to SEQ ID NO: 81 can be at least 90% identical even if the scFV shares no homology. Thus, the % identity can be based on the domain or on the entire length of the polypeptide. Methods of determining % identity are provided for herein or are known to one of skill in the art.

In some embodiments, fibronectin type III (FN3) domains that bind or specifically bind human CD71 protein (SEQ ID Nos: 32 or 80) are provided. As provided herein, the FN3 domains can bind to the CD71 protein. Also provided, even if not explicitly stated is that the domains can also specifically bind to the CD71 protein. Thus, for example, a FN3 domain that binds to CD71 would also encompass a FN3 domain protein that specifically binds to CD71. These molecules can be used, for example, in therapeutic and diagnostic applications and in imaging. In some embodiments, polynucleotides encoding the FN3 domains disclosed herein or complementary nucleic acids thereof, vectors, host cells, and methods of making and using them are provided.

In some embodiments, an isolated FN3 domain that binds or specifically binds CD71 is provided.

In some embodiments, the FN3 domain comprises two FN3 domains connected by a linker. The linker can be a flexible linker. The linker can be a short peptide sequence, such as those described herein. For example, the linker can be a G/S linker and the like.

In some embodiments, the FN3 domain may bind CD71 with a dissociation constant ($K_D$) of less than about $1 \times 10^{-7}$ M, for example less than about $1 \times 10^{-8}$M, less than about $1\times10^{-9}$ M, less than about $1\times10^{-10}$ M, less than about $1\times10^{-11}$ M, less than about $1\times10^{-12}$ M, or less than about $1\times10^{-13}$ M as determined by surface plasmon resonance or the Kinexa method, as practiced by those of skill in the art. The measured affinity of a particular FN3 domain-antigen interaction can vary if measured under different conditions (e.g., osmolarity, pH). Thus, measurements of affinity and other antigen-binding parameters (e.g., $K_D$, $K_{on}$, $K_{off}$) are made with standardized solutions of protein scaffold and antigen, and a standardized buffer, such as the buffers described herein.

In some embodiments, the FN3 domain may bind CD71 at least 5-fold above the signal obtained for a negative control in a standard ELISA assay.

In some embodiments, the FN3 domain that binds or specifically binds CD71 comprises an initiator methionine (Met) linked to the N-terminus of the molecule. In some embodiments, the FN3 domain that binds or specifically binds CD71 comprises a cysteine (Cys) linked to a C-terminus of the FN3 domain. The addition of the N-terminal Met and/or the C-terminal Cys may facilitate expression and/or conjugation of half-life extending molecules.

The FN3 domain can also contain cysteine substitutions, such as those that are described in U.S. Pat. No. 10,196,446, which is hereby incorporated by reference in its entirety. Briefly, in some embodiments, the polypeptides provided herein can comprise at least one cysteine substitution at a position selected from the group consisting of residues 6, 8, 10, 11, 14, 15, 16, 20, 30, 34, 38, 40, 41, 45, 47, 48, 53, 54, 59, 60, 62, 64, 70, 88, 89, 90, 91, and 93 of the FN3 domain based on SEQ ID NO: 6 or SEQ ID NO: 1 of U.S. Pat. No. 10,196,446, and the equivalent positions in related FN3 domains. In some embodiments, the substitution is at residue 6. In some embodiments, the substitution is at residue 8. In some embodiments, the substitution is at residue 10. In some embodiments, the substitution is at residue 11. In some embodiments, the substitution is at residue 14. In some embodiments, the substitution is at residue 15. In some embodiments, the substitution is at residue 16. In some embodiments, the substitution is at residue 20. In some embodiments, the substitution is at residue 30. In some embodiments, the substitution is at residue 34. In some embodiments, the substitution is at residue 38. In some embodiments, the substitution is at residue 40. In some embodiments, the substitution is at residue 41. In some embodiments, the substitution is at residue 45. In some embodiments, the substitution is at residue 47. In some embodiments, the substitution is at residue 48. In some embodiments, the substitution is at residue 53. In some embodiments, the substitution is at residue 54. In some embodiments, the substitution is at residue 59. In some embodiments, the substitution is at residue 60. In some embodiments, the substitution is at residue 62. In some embodiments, the substitution is at residue 64. In some embodiments, the substitution is at residue 70. In some embodiments, the substitution is at residue 88. In some embodiments, the substitution is at residue 89. In some embodiments, the substitution is at residue 90. In some embodiments, the substitution is at residue 91. In some embodiments, the substitution is at residue 93.

A cysteine substitution at a position in the domain or protein comprises a replacement of the existing amino acid residue with a cysteine residue. Other examples of cysteine modifications can be found in, for example, U.S. Patent Application Publication No. 20170362301, which is hereby incorporated by reference in its entirety. The alignment of the sequences can be performed using BlastP using the default parameters at, for example, the NCBI website.

In some embodiments, the FN3 domain that binds CD71 is internalized into a cell. In some embodiments, internalization of the FN3 domain may facilitate delivery of a detectable label or therapeutic into a cell. In some embodiments, internalization of the FN3 domain may facilitate delivery of a cytotoxic agent into a cell. The cytotoxic agent can act as a therapeutic agent. In some embodiments, internalization of the FN3 domain may facilitate the delivery of any detectable label, therapeutic, and/or cytotoxic agent disclosed herein into a cell. In some embodiments, the cell is a tumor cell. In some embodiments, the cell is a liver cell.

In some embodiments, the FN3 domain that binds CD71 is based on Tencon sequence of SEQ ID NO: 1 or Tencon 27 sequence of SEQ ID NO: 4, optionally having substitutions at residues positions 11, 14, 17, 37, 46, 73, or 86 (residue numbering corresponding to SEQ ID NO: 4).

In some embodiments, an isolated FN3 domain that binds CD71 comprises the amino acid sequence of SEQ ID NOs: 33, 34, 35, 36, 37, 38, 39, 40, 41, 42, 43, 44, 45, 46, 47, 48, 49, or 50.

In some embodiments, an isolated FN3 domain that binds CD71 comprises the amino acid sequence of SEQ ID NOs: 51, 52, 53, 54, 55, 56, 57, 58, 59, 60, or 61.

In some embodiments, an isolated FN3 domain that binds CD71 comprises the amino acid sequence of SEQ ID NO: 33.

In some embodiments, an isolated FN3 domain that binds CD71 comprises the amino acid sequence of SEQ ID NO: 34.

In some embodiments, an isolated FN3 domain that binds CD71 comprises the amino acid sequence of SEQ ID NO: 35.

In some embodiments, an isolated FN3 domain that binds CD71 comprises the amino acid sequence of SEQ ID NO: 36.

In some embodiments, an isolated FN3 domain that binds CD71 comprises the amino acid sequence of SEQ ID NO: 37.

In some embodiments, an isolated FN3 domain that binds CD71 comprises the amino acid sequence of SEQ ID NO: 38.

In some embodiments, an isolated FN3 domain that binds CD71 comprises the amino acid sequence of SEQ ID NO: 39.

In some embodiments, an isolated FN3 domain that binds CD71 comprises the amino acid sequence of SEQ ID NO: 40.

In some embodiments, an isolated FN3 domain that binds CD71 comprises the amino acid sequence of SEQ ID NO: 41.

In some embodiments, an isolated FN3 domain that binds CD71 comprises the amino acid sequence of SEQ ID NO: 42.

In some embodiments, an isolated FN3 domain that binds CD71 comprises the amino acid sequence of SEQ ID NO: 43.

In some embodiments, an isolated FN3 domain that binds CD71 comprises the amino acid sequence of SEQ ID NO: 44.

In some embodiments, an isolated FN3 domain that binds CD71 comprises the amino acid sequence of SEQ ID NO: 45.

In some embodiments, an isolated FN3 domain that binds CD71 comprises the amino acid sequence of SEQ ID NO: 46.

In some embodiments, an isolated FN3 domain that binds CD71 comprises the amino acid sequence of SEQ ID NO: 47.
In some embodiments, an isolated FN3 domain that binds CD71 comprises the amino acid sequence of SEQ ID NO: 48.
In some embodiments, an isolated FN3 domain that binds CD71 comprises the amino acid sequence of SEQ ID NO: 49.
In some embodiments, an isolated FN3 domain that binds CD71 comprises the amino acid sequence of SEQ ID NO: 50.
In some embodiments, an isolated FN3 domain that binds CD71 comprises the amino acid sequence of SEQ ID NO: 51.
In some embodiments, an isolated FN3 domain that binds CD71 comprises the amino acid sequence of SEQ ID NO: 52.
In some embodiments, an isolated FN3 domain that binds CD71 comprises the amino acid sequence of SEQ ID NO: 53.
In some embodiments, an isolated FN3 domain that binds CD71 comprises the amino acid sequence of SEQ ID NO: 54.
In some embodiments, an isolated FN3 domain that binds CD71 comprises the amino acid sequence of SEQ ID NO: 55.
In some embodiments, an isolated FN3 domain that binds CD71 comprises the amino acid sequence of SEQ ID NO: 56.
In some embodiments, an isolated FN3 domain that binds CD71 comprises the amino acid sequence of SEQ ID NO: 57.
In some embodiments, an isolated FN3 domain that binds CD71 comprises the amino acid sequence of SEQ ID NO: 58.
In some embodiments, an isolated FN3 domain that binds CD71 comprises the amino acid sequence of SEQ ID NO: 59.
In some embodiments, an isolated FN3 domain that binds CD71 comprises the amino acid sequence of SEQ ID NO: 60.
In some embodiments, an isolated FN3 domain that binds CD71 comprises the amino acid sequence of SEQ ID NO: 61.
In some embodiments, an isolated FN3 domain that binds CD71 comprises the amino acid sequence of SEQ ID NO: 62.
In some embodiments, an isolated FN3 domain that binds CD71 comprises the amino acid sequence of SEQ ID NO: 81. In some embodiments, an isolated FN3 domain that binds CD71 comprises the amino acid sequence of SEQ ID NO: 82. In some embodiments, an isolated FN3 domain that binds CD71 comprises the amino acid sequence of SEQ ID NO: 83. In some embodiments, an isolated FN3 domain that binds CD71 comprises the amino acid sequence of SEQ ID NO: 84. In some embodiments, an isolated FN3 domain that binds CD71 comprises the amino acid sequence of SEQ ID NO: 85. In some embodiments, an isolated FN3 domain that binds CD71 comprises the amino acid sequence of SEQ ID NO: 86. In some embodiments, an isolated FN3 domain that binds CD71 comprises the amino acid sequence of SEQ ID NO: 87. In some embodiments, an isolated FN3 domain that binds CD71 comprises the amino acid sequence of SEQ ID NO: 88. In some embodiments, an isolated FN3 domain that binds CD71 comprises the amino acid sequence of SEQ ID NO: 89. In some embodiments, an isolated FN3 domain that binds CD71 comprises the amino acid sequence of SEQ ID NO: 90. In some embodiments, an isolated FN3 domain that binds CD71 comprises the amino acid sequence of SEQ ID NO: 91. In some embodiments, an isolated FN3 domain that binds CD71 comprises the amino acid sequence of SEQ ID NO: 92. In some embodiments, an isolated FN3 domain that binds CD71 comprises the amino acid sequence of SEQ ID NO: 93. In some embodiments, an isolated FN3 domain that binds CD71 comprises the amino acid sequence of SEQ ID NO: 94. In some embodiments, an isolated FN3 domain that binds CD71 comprises the amino acid sequence of SEQ ID NO: 95. In some embodiments, an isolated FN3 domain that binds CD71 comprises the amino acid sequence of SEQ ID NO: 96. In some embodiments, an isolated FN3 domain that binds CD71 comprises the amino acid sequence of SEQ ID NO: 97. In some embodiments, an isolated FN3 domain that binds CD71 comprises the amino acid sequence of SEQ ID NO: 98. In some embodiments, an isolated FN3 domain that binds CD71 comprises the amino acid sequence of SEQ ID NO: 99. In some embodiments, an isolated FN3 domain that binds CD71 comprises the amino acid sequence of SEQ ID NO: 100. In some embodiments, an isolated FN3 domain that binds CD71 comprises the amino acid sequence of SEQ ID NO: 101. In some embodiments, an isolated FN3 domain that binds CD71 comprises the amino acid sequence of SEQ ID NO: 102. In some embodiments, an isolated FN3 domain that binds CD71 comprises the amino acid sequence of SEQ ID NO: 103. In some embodiments, an isolated FN3 domain that binds CD71 comprises the amino acid sequence of SEQ ID NO: 104. In some embodiments, an isolated FN3 domain that binds CD71 comprises the amino acid sequence of SEQ ID NO: 105. In some embodiments, an isolated FN3 domain that binds CD71 comprises the amino acid sequence of SEQ ID NO: 106. In some embodiments, an isolated FN3 domain that binds CD71 comprises the amino acid sequence of SEQ ID NO: 107. In some embodiments, an isolated FN3 domain that binds CD71 comprises the amino acid sequence of SEQ ID NO: 108. In some embodiments, an isolated FN3 domain that binds CD71 comprises the amino acid sequence of SEQ ID NO: 109. In some embodiments, an isolated FN3 domain that binds CD71 comprises the amino acid sequence of SEQ ID NO: 110. In some embodiments, an isolated FN3 domain that binds CD71 comprises the amino acid sequence of SEQ ID NO: 111. In some embodiments, an isolated FN3 domain that binds CD71 comprises the amino acid sequence of SEQ ID NO: 112. In some embodiments, an isolated FN3 domain that binds CD71 comprises the amino acid sequence of SEQ ID NO: 113. In some embodiments, an isolated FN3 domain that binds CD71 comprises the amino acid sequence of SEQ ID NO: 114. In some embodiments, an isolated FN3 domain that binds CD71 comprises the amino acid sequence of SEQ ID NO: 115. In some embodiments, an isolated FN3 domain that binds CD71 comprises the amino acid sequence of SEQ ID NO: 116. In some embodiments, an isolated FN3 domain that binds CD71 comprises the amino acid sequence of SEQ ID NO: 117. In some embodiments, an isolated FN3 domain that binds CD71 comprises the amino acid sequence of SEQ ID NO: 118. In some embodiments, an isolated FN3 domain that binds CD71 comprises the amino acid sequence of SEQ ID NO: 119. In some embodiments, an isolated FN3 domain that binds CD71 comprises the amino acid sequence of SEQ ID NO: 120. In some embodiments, an isolated FN3 domain that binds CD71 comprises the amino acid sequence of SEQ ID NO: 121. In some embodiments, an isolated FN3 domain that binds CD71 comprises the amino acid sequence of SEQ ID NO: 122. In some embodiments, an isolated FN3 domain that binds CD71 comprises the amino acid sequence of SEQ ID NO: 123. In some embodiments, an isolated FN3 domain that binds CD71 comprises the amino acid sequence of SEQ ID NO: 124. In some embodiments, an isolated FN3 domain that binds CD71 comprises the amino acid sequence of SEQ ID NO: 125. In some embodiments, an isolated FN3 domain that binds CD71 comprises the amino acid sequence of SEQ ID NO: 126. In some embodiments, an isolated FN3 domain that binds CD71 comprises the amino acid sequence of SEQ ID NO: 127. In some embodiments, an isolated FN3 domain that binds CD71 comprises the amino acid sequence of SEQ ID NO: 128. In some embodiments, an isolated FN3 domain that binds CD71 comprises the amino acid sequence of SEQ ID NO: 129. In some embodiments, an isolated FN3 domain that binds CD71 comprises the amino acid sequence of SEQ ID NO: 130. In some embodiments, an isolated FN3 domain that binds CD71 comprises the amino acid sequence of SEQ ID NO: 131. In some embodiments, an isolated FN3 domain that binds CD71 comprises the amino acid sequence of SEQ ID NO: 132. In some embodiments, an isolated FN3 domain that binds CD71 comprises the amino acid sequence of SEQ ID NO: 133. In some embodiments, an isolated FN3 domain that binds CD71 comprises the amino acid sequence of SEQ ID NO: 134. In some embodiments, an isolated FN3 domain that binds CD71 comprises the amino acid sequence of SEQ ID NO: 135. In some embodiments, an isolated FN3 domain that binds CD71 comprises the amino acid sequence of SEQ ID NO: 136. In some embodiments, an isolated FN3 domain that binds CD71 comprises the amino acid sequence of SEQ ID NO: 137. In some embodiments, an isolated FN3 domain that binds CD71 comprises the amino acid sequence of SEQ ID NO: 138. In some embodiments, an isolated FN3 domain that binds CD71 comprises the amino acid sequence of SEQ ID NO: 139. In some embodiments, an isolated FN3 domain that binds CD71 comprises the amino acid sequence of SEQ ID NO: 140. In some embodiments, an isolated FN3 domain that binds CD71 comprises the amino acid sequence of SEQ ID NO: 141. In some embodiments, an isolated FN3 domain that binds CD71 comprises the amino acid sequence of SEQ ID NO: 142. In some embodiments, an isolated FN3 domain that binds CD71 comprises the amino acid sequence of SEQ ID NO: 143. In some embodiments, an isolated FN3 domain that binds CD71 comprises the amino acid sequence of SEQ ID NO: 144. In some embodiments, an isolated FN3 domain that binds CD71 comprises the amino acid sequence of SEQ ID NO: 145. In some embodiments, an isolated FN3 domain that binds CD71 comprises the amino acid sequence of SEQ ID NO: 146. In some embodiments, an isolated FN3 domain that binds CD71 comprises the amino acid sequence of SEQ ID NO: 147. In some embodiments, an isolated FN3 domain that binds CD71 comprises the amino acid sequence of SEQ ID NO: 148. In some embodiments, an isolated FN3 domain that binds CD71 comprises the amino acid sequence of SEQ ID NO: 149. In some embodiments, an isolated FN3 domain that binds CD71 comprises the amino acid sequence of SEQ ID NO: 150. In some embodiments, an isolated FN3 domain that binds CD71 comprises the amino acid sequence of SEQ ID NO: 151. In some embodiments, an isolated FN3 domain that binds CD71 comprises the amino acid sequence of SEQ ID NO: 152. In some embodiments, an isolated FN3 domain that binds CD71 comprises the amino acid sequence of SEQ ID NO: 153. In some embodiments, an isolated FN3 domain that binds CD71 comprises the amino acid sequence of SEQ ID NO: 154. In some embodiments, an isolated FN3 domain that binds CD71 comprises the amino acid sequence of SEQ ID NO: 155. In some embodiments, an isolated FN3 domain that binds CD71 comprises the amino acid sequence of SEQ ID NO: 156. In some embodiments, an isolated FN3 domain that binds CD71 comprises the amino acid sequence of SEQ ID NO: 157. In some embodiments, an isolated FN3 domain that binds CD71 comprises the amino acid sequence of SEQ ID NO: 158. In some embodiments, an isolated FN3 domain that binds CD71 comprises the amino acid sequence of SEQ ID NO: 159. In some embodiments, an isolated FN3 domain that binds CD71 comprises the amino acid sequence of SEQ ID NO: 160. In some embodiments, an isolated FN3 domain that binds CD71 comprises the amino acid sequence of SEQ ID NO: 161. In some embodiments, an isolated FN3 domain that binds CD71 comprises the amino acid sequence of SEQ ID NO: 162. In some embodiments, an isolated FN3 domain that binds CD71 comprises the amino acid sequence of SEQ ID NO: 163. In some embodiments, an isolated FN3 domain that binds CD71 comprises the amino acid sequence of SEQ ID NO: 164. In some embodiments, an isolated FN3 domain that binds CD71 comprises the amino acid sequence of SEQ ID NO: 165. In some embodiments, an isolated FN3 domain that binds CD71 comprises the amino acid sequence of SEQ ID NO: 166. In some embodiments, an isolated FN3 domain that binds CD71 comprises the amino acid sequence of SEQ ID NO: 167. In some embodiments, an isolated FN3 domain that binds CD71 comprises the amino acid sequence of SEQ ID NO: 168. In some embodiments, an isolated FN3 domain that binds CD71 comprises the amino acid sequence of SEQ ID NO: 169. In some embodiments, an isolated FN3 domain that binds CD71 comprises the amino acid sequence of SEQ ID NO: 170. In some embodiments, an isolated FN3 domain that binds CD71 comprises the amino acid sequence of SEQ ID NO: 171. In some embodiments, an isolated FN3 domain that binds CD71 comprises the amino acid sequence of SEQ ID NO: 172. In some embodiments, an isolated FN3 domain that binds CD71 comprises the amino acid sequence of SEQ ID NO: 173. In some embodiments, an isolated FN3 domain that binds CD71 comprises the amino acid sequence of SEQ ID NO: 174. In some embodiments, an isolated FN3 domain that binds CD71 comprises the amino acid sequence of SEQ ID NO: 175. In some embodiments, an isolated FN3 domain that binds CD71 comprises the amino acid sequence of SEQ ID NO: 176. In some embodiments, an isolated FN3 domain that binds CD71 comprises the amino acid sequence of SEQ ID NO: 177. In some embodiments, an isolated FN3 domain that binds CD71 comprises the amino acid sequence of SEQ ID NO: 178. In some embodiments, an isolated FN3 domain that binds CD71 comprises the amino acid sequence of SEQ ID NO: 179. In some embodiments, an isolated FN3 domain that binds CD71 comprises the amino acid sequence of SEQ ID NO: 180. In some embodiments, an isolated FN3 domain that binds CD71 comprises the amino acid sequence of SEQ ID NO: 181. In some embodiments, an isolated FN3 domain that binds CD71 comprises the amino acid sequence of SEQ ID NO: 182. In some embodiments, an isolated FN3 domain that binds CD71 comprises the amino acid sequence of SEQ ID NO: 183. In some embodiments, an isolated FN3 domain that binds CD71 comprises the amino acid sequence of SEQ ID NO: 184. In some embodiments, an isolated FN3 domain that binds CD71 comprises the amino acid sequence of SEQ ID NO: 185. In some embodiments, an isolated FN3 domain that binds CD71 comprises the amino acid sequence of SEQ ID NO: 186. In some embodiments, an isolated FN3 domain that binds CD71 comprises the amino acid sequence of SEQ ID NO: 187. In some embodiments, an isolated FN3 domain that binds CD71 comprises the amino acid sequence of SEQ ID NO: 188. In some embodiments, an isolated FN3 domain that binds CD71 comprises the amino acid sequence of SEQ ID NO: 189. In some embodiments, an isolated FN3 domain that binds CD71 comprises the amino acid sequence of SEQ ID NO: 190. In some embodiments, an isolated FN3 domain that binds CD71 comprises the amino acid sequence of SEQ ID NO: 191. In some embodiments, an isolated FN3 domain that binds CD71 comprises the amino acid sequence of SEQ ID NO: 192. In some embodiments, an isolated FN3 domain that binds CD71 comprises the amino acid sequence of SEQ ID NO: 193. In some embodiments, an isolated FN3 domain that binds CD71 comprises the amino acid sequence of SEQ ID NO: 194. In some embodiments, an isolated FN3 domain that binds CD71 comprises the amino acid sequence of SEQ ID NO: 195. In some embodiments, an isolated FN3 domain that binds CD71 comprises the amino acid sequence of SEQ ID NO: 196. In some embodiments, an isolated FN3 domain that binds CD71 comprises the amino acid sequence of SEQ ID NO: 197. In some embodiments, an isolated FN3 domain that binds CD71 comprises the amino acid sequence of SEQ ID NO: 198. In some embodiments, an isolated FN3 domain that binds CD71 comprises the amino acid sequence of SEQ ID NO: 199. In some embodiments, an isolated FN3 domain that binds CD71 comprises the amino acid sequence of SEQ ID NO: 200. In some embodiments, an isolated FN3 domain that binds CD71 comprises the amino acid sequence of SEQ ID NO: 201. In some embodiments, an isolated FN3 domain that binds CD71 comprises the amino acid sequence of SEQ ID NO: 202. In some embodiments, an isolated FN3 domain that binds CD71 comprises the amino acid sequence of SEQ ID NO: 203. In some embodiments, an isolated FN3 domain that binds CD71 comprises the amino acid sequence of SEQ ID NO: 204. In some embodiments, an isolated FN3 domain that binds CD71 comprises the amino acid sequence of SEQ ID NO: 205. In some embodiments, an isolated FN3 domain that binds CD71 comprises the amino acid sequence of SEQ ID NO: 206. In some embodiments, an isolated FN3 domain that binds CD71 comprises the amino acid sequence of SEQ ID NO: 207. In some embodiments, an isolated FN3 domain that binds CD71 comprises the amino acid sequence of SEQ ID NO: 208. In some embodiments, an isolated FN3 domain that binds CD71 comprises the amino acid sequence of SEQ ID NO: 209. In some embodiments, an isolated FN3 domain that binds CD71 comprises the amino acid sequence of SEQ ID NO: 210. In some embodiments, an isolated FN3 domain that binds CD71 comprises the amino acid sequence of SEQ ID NO: 211. In some embodiments, an isolated FN3 domain that binds CD71 comprises the amino acid sequence of SEQ ID NO: 212. In some embodiments, an isolated FN3 domain that binds CD71 comprises the amino acid sequence of SEQ ID NO: 213. In some embodiments, an isolated FN3 domain that binds CD71 comprises the amino acid sequence of SEQ ID NO: 214. In some embodiments, an isolated FN3 domain that binds CD71 comprises the amino acid sequence of SEQ ID NO: 215. In some embodiments, an isolated FN3 domain that binds CD71 comprises the amino acid sequence of SEQ ID NO: 216. In some embodiments, an isolated FN3 domain that binds CD71 comprises the amino acid sequence of SEQ ID NO: 217. In some embodiments, an isolated FN3 domain that binds CD71 comprises the amino acid sequence of SEQ ID NO: 218. In some embodiments, an isolated FN3 domain that binds CD71 comprises the amino acid sequence of SEQ ID NO: 219. In some embodiments, an isolated FN3 domain that binds CD71 comprises the amino acid sequence of SEQ ID NO: 220. In some embodiments, an isolated FN3 domain that binds CD71 comprises the amino acid sequence of SEQ ID NO: 221. In some embodiments, an isolated FN3 domain that binds CD71 comprises the amino acid sequence of SEQ ID NO: 222. In some embodiments, an isolated FN3 domain that binds CD71 comprises the amino acid sequence of SEQ ID NO: 223. In some embodiments, an isolated FN3 domain that binds CD71 comprises the amino acid sequence of SEQ ID NO: 224. In some embodiments, an isolated FN3 domain that binds CD71 comprises the amino acid sequence of SEQ ID NO: 225. In some embodiments, an isolated FN3 domain that binds CD71 comprises the amino acid sequence of SEQ ID NO: 226. In some embodiments, an isolated FN3 domain that binds CD71 comprises the amino acid sequence of SEQ ID NO: 227. In some embodiments, an isolated FN3 domain that binds CD71 comprises the amino acid sequence of SEQ ID NO: 228. In some embodiments, an isolated FN3 domain that binds CD71 comprises the amino acid sequence of SEQ ID NO: 229. In some embodiments, an isolated FN3 domain that binds CD71 comprises the amino acid sequence of SEQ ID NO: 230. In some embodiments, an isolated FN3 domain that binds CD71 comprises the amino acid sequence of SEQ ID NO: 231. In some embodiments, an isolated FN3 domain that binds CD71 comprises the amino acid sequence of SEQ ID NO: 232. In some embodiments, an isolated FN3 domain that binds CD71 comprises the amino acid sequence of SEQ ID NO: 233. In some embodiments, an isolated FN3 domain that binds CD71 comprises the amino acid sequence of SEQ ID NO: 234. In some embodiments, an isolated FN3 domain that binds CD71 comprises the amino acid sequence of SEQ ID NO: 235. In some embodiments, an isolated FN3 domain that binds CD71 comprises the amino acid sequence of SEQ ID NO: 236. In some embodiments, an isolated FN3 domain that binds CD71 comprises the amino acid sequence of SEQ ID NO: 237. In some embodiments, an isolated FN3 domain that binds CD71 comprises the amino acid sequence of SEQ ID NO: 238. In some embodiments, an isolated FN3 domain that binds CD71 comprises the amino acid sequence of SEQ ID NO: 239. In some embodiments, an isolated FN3 domain that binds CD71 comprises the amino acid sequence of SEQ ID NO: 240. In some embodiments, an isolated FN3 domain that binds CD71 comprises the amino acid sequence of SEQ ID NO: 241. In some embodiments, an isolated FN3 domain that binds CD71 comprises the amino acid sequence of SEQ ID NO: 242. In some embodiments, an isolated FN3 domain that binds CD71 comprises the amino acid sequence of SEQ ID NO: 243. In some embodiments, an isolated FN3 domain that binds CD71 comprises the amino acid sequence of SEQ ID NO: 244. In some embodiments, an isolated FN3 domain that binds CD71 comprises the amino acid sequence of SEQ ID NO: 245. In some embodiments, an isolated FN3 domain that binds CD71 comprises the amino acid sequence of SEQ ID NO: 246. In some embodiments, an isolated FN3 domain that binds CD71 comprises the amino acid sequence of SEQ ID NO: 247. In some embodiments, an isolated FN3 domain that binds CD71 comprises the amino acid sequence of SEQ ID NO: 248. In some embodiments, an isolated FN3 domain that binds CD71 comprises the amino acid sequence of SEQ ID NO: 249. In some embodiments, an isolated FN3 domain that binds CD71 comprises the amino acid sequence of SEQ ID NO: 250. In some embodiments, an isolated FN3 domain that binds CD71 comprises the amino acid sequence of SEQ ID NO: 251. In some embodiments, an isolated FN3 domain that binds CD71 comprises the amino acid sequence of SEQ ID NO: 252. In some embodiments, an isolated FN3 domain that binds CD71 comprises the amino acid sequence of SEQ ID NO: 253. In some embodiments, an isolated FN3 domain that binds CD71 comprises the amino acid sequence of SEQ ID NO: 254. In some embodiments, an isolated FN3 domain that binds CD71 comprises the amino acid sequence of SEQ ID NO: 255. In some embodiments, an isolated FN3 domain that binds CD71 comprises the amino acid sequence of SEQ ID NO: 256. In some embodiments, an isolated FN3 domain that binds CD71 comprises the amino acid sequence of SEQ ID NO: 257. In some embodiments, an isolated FN3 domain that binds CD71 comprises the amino acid sequence of SEQ ID NO: 258. In some embodiments, an isolated FN3 domain that binds CD71 comprises the amino acid sequence of SEQ ID NO: 259. In some embodiments, an isolated FN3 domain that binds CD71 comprises the amino acid sequence of SEQ ID NO: 260. In some embodiments, an isolated FN3 domain that binds CD71 comprises the amino acid sequence of SEQ ID NO: 261. In some embodiments, an isolated FN3 domain that binds CD71 comprises the amino acid sequence of SEQ ID NO: 262. In some embodiments, an isolated FN3 domain that binds CD71 comprises the amino acid sequence of SEQ ID NO: 263. In some embodiments, an isolated FN3 domain that binds CD71 comprises the amino acid sequence of SEQ ID NO: 264. In some embodiments, an isolated FN3 domain that binds CD71 comprises the amino acid sequence of SEQ ID NO: 265. In some embodiments, an isolated FN3 domain that binds CD71 comprises the amino acid sequence of SEQ ID NO: 266. In some embodiments, an isolated FN3 domain that binds CD71 comprises the amino acid sequence of SEQ ID NO: 267. In some embodiments, an isolated FN3 domain that binds CD71 comprises the amino acid sequence of SEQ ID NO: 268. In some embodiments, an isolated FN3 domain that binds CD71 comprises the amino acid sequence of SEQ ID NO: 269. In some embodiments, an isolated FN3 domain that binds CD71 comprises the amino acid sequence of SEQ ID NO: 270. In some embodiments, an isolated FN3 domain that binds CD71 comprises the amino acid sequence of SEQ ID NO: 271. In some embodiments, an isolated FN3 domain that binds CD71 comprises the amino acid sequence of SEQ ID NO: 272. In some embodiments, an isolated FN3 domain that binds CD71 comprises the amino acid sequence of SEQ ID NO: 273. In some embodiments, an isolated FN3 domain that binds CD71 comprises the amino acid sequence of SEQ ID NO: 274. In some embodiments, an isolated FN3 domain that binds CD71 comprises the amino acid sequence of SEQ ID NO: 275. In some embodiments, an isolated FN3 domain that binds CD71 comprises the amino acid sequence of SEQ ID NO: 276. In some embodiments, an isolated FN3 domain that binds CD71 comprises the amino acid sequence of SEQ ID NO: 277. In some embodiments, an isolated FN3 domain that binds CD71 comprises the amino acid sequence of SEQ ID NO: 278. In some embodiments, an isolated FN3 domain that binds CD71 comprises the amino acid sequence of SEQ ID NO: 279. In some embodiments, an isolated FN3 domain that binds CD71 comprises the amino acid sequence of SEQ ID NO: 280. In some embodiments, an isolated FN3 domain that binds CD71 comprises the amino acid sequence of SEQ ID NO: 281. In some embodiments, an isolated FN3 domain that binds CD71 comprises the amino acid sequence of SEQ ID NO: 282. In some embodiments, an isolated FN3 domain that binds CD71 comprises the amino acid sequence of SEQ ID NO: 283. In some embodiments, an isolated FN3 domain that binds CD71 comprises the amino acid sequence of SEQ ID NO: 284. In some embodiments, an isolated FN3 domain that binds CD71 comprises the amino acid sequence of SEQ ID NO: 285. In some embodiments, an isolated FN3 domain that binds CD71 comprises the amino acid sequence of SEQ ID NO: 286. In some embodiments, an isolated FN3 domain that binds CD71 comprises the amino acid sequence of SEQ ID NO: 287. In some embodiments, an isolated FN3 domain that binds CD71 comprises the amino acid sequence of SEQ ID NO: 288. In some embodiments, an isolated FN3 domain that binds CD71 comprises the amino acid sequence of SEQ ID NO: 289. In some embodiments, an isolated FN3 domain that binds CD71 comprises the amino acid sequence of SEQ ID NO: 290. In some embodiments, an isolated FN3 domain that binds CD71 comprises the amino acid sequence of SEQ ID NO: 291. In some embodiments, an isolated FN3 domain that binds CD71 comprises the amino acid sequence of SEQ ID NO: 292. In some embodiments, an isolated FN3 domain that binds CD71 comprises the amino acid sequence of SEQ ID NO: 293. In some embodiments, an isolated FN3 domain that binds CD71 comprises the amino acid sequence of SEQ ID NO: 294. In some embodiments, an isolated FN3 domain that binds CD71 comprises the amino acid sequence of SEQ ID NO: 295. In some embodiments, an isolated FN3 domain that binds CD71 comprises the amino acid sequence of SEQ ID NO: 296. In some embodiments, an isolated FN3 domain that binds CD71 comprises the amino acid sequence of SEQ ID NO: 297. In some embodiments, an isolated FN3 domain that binds CD71 comprises the amino acid sequence of SEQ ID NO: 298. In some embodiments, an isolated FN3 domain that binds CD71 comprises the amino acid sequence of SEQ ID NO: 299. In some embodiments, an isolated FN3 domain that binds CD71 comprises the amino acid sequence of SEQ ID NO: 300. In some embodiments, an isolated FN3 domain that binds CD71 comprises the amino acid sequence of SEQ ID NO: 301. In some embodiments, an isolated FN3 domain that binds CD71 comprises the amino acid sequence of SEQ ID NO: 302. In some embodiments, an isolated FN3 domain that binds CD71 comprises the amino acid sequence of SEQ ID NO: 303. In some embodiments, an isolated FN3 domain that binds CD71 comprises the amino acid sequence of SEQ ID NO: 304. In some embodiments, an isolated FN3 domain that binds CD71 comprises the amino acid sequence of SEQ ID NO: 305. In some embodiments, an isolated FN3 domain that binds CD71 comprises the amino acid sequence of SEQ ID NO: 306. In some embodiments, an isolated FN3 domain that binds CD71 comprises the amino acid sequence of SEQ ID NO: 307. In some embodiments, an isolated FN3 domain that binds CD71 comprises the amino acid sequence of SEQ ID NO: 308. In some embodiments, an isolated FN3 domain that binds CD71 comprises the amino acid sequence of SEQ ID NO: 309.

In some embodiments, the FN3 domain binds to human CD71 at site on CD71 that does not compete with transferrin binding to CD71. In some embodiments, the FN3 domain comprises a sequence of SEQ ID NO: 146, 214, 104, 259, 134, 92, 302, 235, 237, 152, 238, 136, 197, 212, 296, 226, 261, 307, 115, 112, 278, 297, 96, 222, 95, 233, 217, 252, 194, 164, 168, 174, 190, 257, 303, 284, 85, or 149.

In some embodiments, the isolated FN3 domain that binds CD71 comprises an initiator methionine (Met) linked to the N-terminus of the molecule.

In some embodiments, the isolated FN3 domain that binds CD71 comprises an amino acid sequence that is 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% identical to one of the amino acid sequences of SEQ ID NOs: 33-50. In some embodiments, the isolated FN3 domain that binds CD71 comprises an amino acid sequence that is 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% identical to one of the amino acid sequences of SEQ ID NOs: 51-61 or 62. In some embodiments, the isolated FN3 domain that binds CD71 comprises an amino acid sequence that is 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% identical to one of the amino acid sequences of SEQ ID NOs: 81-309. In some embodiments, the isolated FN3 domain that binds CD71 comprises an amino acid sequence that is 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% identical to one of the amino acid sequences of SEQ ID NOs: 146, 214, 104, 259, 134, 92, 302, 235, 237, 152, 238, 136, 197, 212, 296, 226, 261, 307, 115, 112, 278, 297, 96, 222, 95, 233, 217, 252, 194, 164, 168, 174, 190, 257, 303, 284, 85, or 149.

Percent identity can be determined using the default parameters to align two sequences using BlastP available through the NCBI website.

Conjugates of the FN3 Domains that Bind CD71 of the Disclosure

In some embodiments, an isolated FN3 domain that binds CD71 conjugated to a heterologous molecule(s) is provided.

In some embodiments, the FN3 domain is conjugated to an oligonucleotide. For example, the oligonucleotide can be used for inhibiting the expression of a gene or mRNA transcript. The oligonucleotide can be a siRNA, miRNA, antisense oligonucleotide, and the like.

In some embodiments, the peptide is conjugated to a lipid nanoparticle, which can be used, for example, for cell-specific targeting.

In some embodiments, the protein is conjugated to a binding moiety that targets CD71 or another protein for protein degradation. For example, the protein can be conjugated to a PROTACS (binding moieties for an E3 ubiquitin ligase) and thus deliver the protein to the E3 ligase. These can linked through a linker, such as a glycine-serine linker and the like.

The FN3 domain that binds to CD71 can also be conjugated or linked to another FN3 domain that binds to a different target, other than CD71. This would enable the peptide to be multi-specific (e.g. bi-specific, tri-specific, etc.), such that it binds to CD71 and another, for example, protein. In some embodiments, the CD71 FN3 binding domain is linked to another FN3 domain that binds to an antigen expressed by a tumor cell (tumor antigen).

In some embodiments, FN3 domains can be linked together by a linker to form a bivalent FN3 domain. The linker can be a flexible linker. In some embodiments, the linker is a G/S linker. In some embodiments the linker has 1, 2, 3, or 4 G/S repeats. A G/S repeat unit is four glycines followed by a serine.

In some embodiments, the heterologous molecule is a detectable label or a therapeutic agent, such as, but not limited to a cytotoxic agent.

In some embodiments, an FN3 domain that binds CD71 conjugated to a detectable label is provided. Non-limiting examples of detectable labels are provided for herein.

In some embodiments, an FN3 domain that binds CD71 conjugated to a therapeutic agent is provided. Non-limiting examples of therapeutic agents, such as, but not limited to, cytotoxic agents, are provided for herein.

The FN3 domains that bind CD71 conjugated to a detectable label can be used to evaluate expression of CD71 on samples such as tumor tissue in vivo or in vitro.

Detectable labels include compositions that when conjugated to the FN3 domains that bind CD71 renders CD71 detectable, via spectroscopic, photochemical, biochemical, immunochemical, or other chemical methods.

Exemplary detectable labels include, but are not limited to, radioactive isotopes, magnetic beads, metallic beads, colloidal particles, fluorescent dyes, electron-dense reagents, enzymes (for example, as commonly used in an ELISA), biotin, digoxigenin, haptens, luminescent molecules, chemiluminescent molecules, fluorochromes, fluorophores, fluorescent quenching agents, colored molecules, radioactive isotopes, cintillants, avidin, streptavidin, protein A, protein G, antibodies or fragments thereof, polyhistidine, $Ni^{2+}$, Flag tags, myc tags, heavy metals, enzymes, alkaline phosphatase, peroxidase, luciferase, electron donors/acceptors, acridinium esters, and colorimetric substrates.

A detectable label may emit a signal spontaneously, such as when the detectable label is a radioactive isotope. In some embodiments, the detectable label emits a signal as a result of being stimulated by an external stimulus, such as a magnetic or electric, or electromagnetic field.

Exemplary radioactive isotopes may be γ-emitting, Auger-emitting, β-emitting, an alpha-emitting or positron-emitting radioactive isotope. Exemplary radioactive isotopes include $^{3}H$, $^{13}C$, $^{13}C$, $^{15}N$, $^{18}F$, $^{19}F$, $^{55}Co$, $^{57}Co$, $^{60}Co$, $^{61}Cu$, $^{62}Cu$, $^{64}Cu$, $^{67}Cu$, $^{68}Ga$, $^{72}As$, $^{75}Br$, $^{86}Y$, $^{89}Zr$, $^{99}Sr$, $^{94m}Tc$, $^{99m}Tc$, $^{115}In$, $^{123}I$, $^{124}I$, $^{125}I$, $^{131}I$, $^{211}At$, $^{212}Bi$, $^{213}Bi$, $^{223}Ra$, $^{226}Ra$, $^{225}Ac$ and $^{227}Ac$.

Exemplary metal atoms are metals with an atomic number greater than 20, such as calcium atoms, scandium atoms, titanium atoms, vanadium atoms, chromium atoms, manganese atoms, iron atoms, cobalt atoms, nickel atoms, copper atoms, zinc atoms, gallium atoms, germanium atoms, arsenic atoms, selenium atoms, bromine atoms, krypton atoms, rubidium atoms, strontium atoms, yttrium atoms, zirconium atoms, niobium atoms, molybdenum atoms, technetium atoms, ruthenium atoms, rhodium atoms, palladium atoms, silver atoms, cadmium atoms, indium atoms, tin atoms, antimony atoms, tellurium atoms, iodine atoms, xenon atoms, cesium atoms, barium atoms, lanthanum atoms, hafnium atoms, tantalum atoms, tungsten atoms, rhenium atoms, osmium atoms, iridium atoms, platinum atoms, gold atoms, mercury atoms, thallium atoms, lead atoms, bismuth atoms, francium atoms, radium atoms, actinium atoms, cerium atoms, praseodymium atoms, neodymium atoms, promethium atoms, samarium atoms, europium atoms, gadolinium atoms, terbium atoms, dysprosium atoms, holmium atoms, erbium atoms, thulium atoms, ytterbium atoms, lutetium atoms, thorium atoms, protactinium atoms, uranium atoms, neptunium atoms, plutonium atoms, americium atoms, curium atoms, berkelium atoms, californium atoms, einsteinium atoms, fermium atoms, mendelevium atoms, nobelium atoms, or lawrencium atoms.

In some embodiments, the metal atoms may be alkaline earth metals with an atomic number greater than twenty.

In some embodiments, the metal atoms may be lanthanides.

In some embodiments, the metal atoms may be actinides.

In some embodiments, the metal atoms may be transition metals.

In some embodiments, the metal atoms may be poor metals.

In some embodiments, the metal atoms may be gold atoms, bismuth atoms, tantalum atoms, and gadolinium atoms.

In some embodiments, the metal atoms may be metals with an atomic number of 53 (i.e., iodine) to 83 (i.e., bismuth).

In some embodiments, the metal atoms may be atoms suitable for magnetic resonance imaging.

The metal atoms may be metal ions in the form of +1, +2, or +3 oxidation states, such as $Ba^{2+}$, $Bi^{3+}$, $Cs^{+}$, $Ca^{2+}$, $Cr^{2+}$, $Cr^{3+}$, $Cr^{6+}$, $Co^{2+}$, $Co^{3+}$, $Cu^{+}$, $Cu^{2+}$, $Cu^{3+}$, $Ga^{3+}$, $Gd^{3+}$, $Au^{+}$, Au$^{3+}$, Fe$^{2+}$, Fe$^{3+}$, F$^{3+}$, Pb$^{2+}$, Mn$^{2+}$, Mn$^{3+}$, Mn$^{4+}$, Mn$^{7+}$, Hg$^{2+}$, Ni$^{2+}$, Ni$^{3+}$, Ag$^{+}$, Sr$^{2+}$, Sn$^{2+}$, Sn$^{4+}$, and Zn$^{2+}$. The metal atoms may comprise a metal oxide, such as iron oxide, manganese oxide, or gadolinium oxide.

Suitable dyes include any commercially available dyes such as, for example, 5(6)-carboxyfluorescein, IRDye 680RD maleimide or IRDye 800CW, ruthenium polypyridyl dyes, and the like.

Suitable fluorophores are fluorescein isothiocyante (FITC), fluorescein thiosemicarbazide, rhodamine, Texas Red™, CyDyes (e.g., Cy3, Cy5, Cy5.5), Alexa Fluors® (e.g., Alexa488, Alexa555, Alexa594; Alexa647), near infrared (NIR) (700-900 nm) fluorescent dyes, and carbocyanine and aminostyryl dyes.

The FN3 domains that specifically bind CD71 conjugated to a detectable label may be used, for example, as an imaging agent to evaluate tumor distribution, diagnosis for the presence of tumor cells and/or, recurrence of tumor.

In some embodiments, the FN3 domains that specifically bind CD71 are conjugated to a therapeutic agent, such as, but not limited to, a cytotoxic agent.

In some embodiments, the therapeutic agent is a chemotherapeutic agent, a drug, a growth inhibitory agent, a toxin (e.g., an enzymatically active toxin of bacterial, fungal, plant, or animal origin, or fragments thereof), or a radioactive isotope (i.e., a radioconjugate).

The FN3 domains that bind CD71 conjugated to a therapeutic agent disclosed herein may be used in the targeted delivery of the therapeutic agent to CD71 expressing cells (e.g. tumor cells), and intracellular accumulation therein. Although not bound to any particular theory, this type of delivery can be helpful where systemic administration of these unconjugated agents may result in unacceptable levels of toxicity to normal cells.

In some embodiments, the therapeutic agent can elicit their cytotoxic and/or cytostatic effects by mechanisms such as, but not limited to, tubulin binding, DNA binding, topoisomerase inhibition, DNA cross linking, chelation, spliceosome inhibition, NAMPT inhibition, and HDAC inhibition.

In some embodiments, the therapeutic agent is a spliceosome inhibitor, a NAMPT inhibitor, or a HDAC inhibitor. In some embodiments, the agent is an immune system agonist, for example, TLR7,8,9, RIG-I (dsRNA), and STING (CpG) agonists. In some embodiments, the agent is daunomycin, doxorubicin, methotrexate, vindesine, bacterial toxins such as diphtheria toxin, ricin, geldanamycin, maytansinoids or calicheamicin.

In some embodiments, the therapeutic agent is an enzymatically active toxin such as diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, or the tricothecenes.

In some embodiments, the therapeutic agent is a radionuclide, such as $^{212}$Bi, $^{131}$I, $^{131}$In, $^{90}$Y, or $^{186}$Re.

In some embodiments, the therapeutic agent is dolastatin or dolastatin peptidic analogs and derivatives, auristatin or monomethyl auristatin phenylalanine. Exemplary molecules are disclosed in U.S. Pat. Nos. 5,635,483 and 5,780,588. Dolastatins and auristatins have been shown to interfere with microtubule dynamics, GTP hydrolysis, and nuclear and cellular division (Woyke et al (2001) Antimicrob Agents and Chemother. 45(12):3580-3584) and have anticancer and antifungal activity. The dolastatin or auristatin drug moiety may be attached to the FN3 domain through the N (amino) terminus or the C (carboxyl) terminus of the peptidic drug moiety (WO 02/088172), or via any cysteine engineered into the FN3 domain.

In some embodiments, therapeutic agent can be, for example, auristatins, camptothecins, duocarmycins, etoposides, maytansines and maytansinoids, taxanes, benzodiazepines or benzodiazepine containing drugs (e.g., pyrrolo[1,4]-benzodiazepines (PBDs), indolinobenzodiazepines, and oxazolidinobenzodiazepines) or *vinca* alkaloids.

The FN3 domains that specifically bind CD71 may be conjugated to a detectable label using known methods.

In some embodiments, the detectable label is complexed with a chelating agent.

In some embodiments, the detectable label is conjugated to the FN3 domain that binds CD71 via a linker.

The detectable label, therapeutic compound, or the cytotoxic compound may be linked directly, or indirectly, to the FN3 domain that binds CD71 using known methods. Suitable linkers are known in the art and include, for example, prosthetic groups, non-phenolic linkers (derivatives of N-succimidyl-benzoates; dodecaborate), chelating moieties of both macrocyclics and acyclic chelators, such as derivatives of 1,4,7,10-tetraazacyclododecane-1,4,7,10, tetraacetic acid (DOTA), derivatives of diethylenetriaminepentaacetic avid (DTPA), derivatives of S-2-(4-Isothiocyanatobenzyl)-1,4,7-triazacyclononane-1,4,7-triacetic acid (NOTA) and derivatives of 1,4,8,11-tetraazacyclodocedan-1,4,8,11-tetraacetic acid (TETA), N-succinimidyl-3-(2-pyridyldithiol) propionate (SPDP), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis(p-azidobenzoyl)hexanediamine), bis-diazonium derivatives (such as bis(p-diazoniumbenzoyl)ethylenediamine), diisocyanates (such as toluene 2,6-diisocyanate), and bisactive fluorine compounds (such as 1,5-difluoro-2,4-dinitrobenzene) and other chelating moieties. Suitable peptide linkers are well known.

In some embodiment, the FN3 domain that binds CD71 is removed from the blood via renal clearance.

Isolation of CD71 Binding FN3 Domains from a Library Based on Tencon Sequence

Tencon (SEQ ID NO: 1) is a non-naturally occurring fibronectin type III (FN3) domain designed from a consensus sequence of fifteen FN3 domains from human tenascin-C (Jacobs et al., Protein Engineering, Design, and Selection, 25:107-117, 2012; U.S. Pat. Publ. No. 2010/0216708). The crystal structure of Tencon shows six surface-exposed loops that connect seven beta-strands as is characteristic to the FN3 domains, the beta-strands referred to as A, B, C, D, E, F, and G, and the loops referred to as AB, BC, CD, DE, EF, and FG loops (Bork and Doolittle, Proc Natl Acad Sci USA 89:8990-8992, 1992; U.S. Pat. No. 6,673,901). These loops, or selected residues within each loop, may be randomized in order to construct libraries of fibronectin type III (FN3) domains that may be used to select novel molecules that bind CD71. Table 1 shows positions and sequences of each loop and beta-strand in Tencon (SEQ ID NO: 1).

Library designed based on Tencon sequence may thus have randomized FG loop, or randomized BC and FG loops, such as libraries TCL1 or TCL2 as described below. The Tencon BC loop is 7 amino acids long, thus 1, 2, 3, 4, 5, 6 or 7 amino acids may be randomized in the library diversified at the BC loop and designed based on Tencon sequence.

The Tencon FG loop is 7 amino acids long, thus 1, 2, 3, 4, 5, 6 or 7 amino acids may be randomized in the library diversified at the FG loop and designed based on Tencon sequence. Further diversity at loops in the Tencon libraries may be achieved by insertion and/or deletions of residues at loops. For example, the FG and/or BC loops may be extended by 1-22 amino acids, or decreased by 1-3 amino acids. The FG loop in Tencon is 7 amino acids long, whereas the corresponding loop in antibody heavy chains ranges from 4-28 residues. To provide maximum diversity, the FG loop may be diversified in sequence as well as in length to correspond to the antibody CDR3 length range of 4-28 residues. For example, the FG loop can further be diversified in length by extending the loop by additional 1, 2, 3, 4 or 5 amino acids.

Library designed based on Tencon sequence may also have randomized alternative surfaces that form on a side of the FN3 domain and comprise two or more beta strands, and at least one loop. One such alternative surface is formed by amino acids in the C and the F beta-strands and the CD and the FG loops (a C-CD-F-FG surface). A library design based on Tencon alternative C-CD-F-FG surface is described in U.S. Pat. Publ. No. 2013/0226834. Library designed based on Tencon sequence also includes libraries designed based on Tencon variants, such as Tencon variants having substitutions at residues positions 11, 14, 17, 37, 46, 73, or 86 (residue numbering corresponding to SEQ ID NO: 1), and which variants display improve thermal stability. Exemplary Tencon variants are described in US Pat. Publ. No. 2011/0274623, and include Tencon27 (SEQ ID NO: 4) having substitutions E11R, L17A, N46V and E86I when compared to Tencon of SEQ ID NO: 1.

TABLE 1

Tencon topology

| FN3 domain | Tencon (SEQ ID NO: 1) |
|---|---|
| A strand | 1-12 |
| AB loop | 13-16 |
| B strand | 17-21 |
| BC loop | 22-28 |
| C strand | 29-37 |
| CD loop | 38-43 |
| D strand | 44-50 |
| DE loop | 51-54 |
| E strand | 55-59 |
| EF loop | 60-64 |
| F strand | 65-74 |
| FG loop | 75-81 |
| G strand | 82-89 |

Tencon and other FN3 sequence based libraries may be randomized at chosen residue positions using a random or defined set of amino acids. For example, variants in the library having random substitutions may be generated using NNK codons, which encode all 20 naturally occurring amino acids. In other diversification schemes, DVK codons may be used to encode amino acids Ala, Trp, Tyr, Lys, Thr, Asn, Lys, Ser, Arg, Asp, Glu, Gly, and Cys. Alternatively, NNS codons may be used to give rise to all 20 amino acid residues and simultaneously reducing the frequency of stop codons. Libraries of FN3 domains with biased amino acid distribution at positions to be diversified may be synthesized for example using Slonomics® technology (http:_//www_sloning_com). This technology uses a library of pre-made double stranded triplets that act as universal building blocks sufficient for thousands of gene synthesis processes. The triplet library represents all possible sequence combinations necessary to build any desired DNA molecule. The codon designations are according to the well-known IUB code.

The FN3 domains that specifically bind CD71 may be isolated by producing the FN3 library such as the Tencon library using cis display to ligate DNA fragments encoding the scaffold proteins to a DNA fragment encoding RepA to generate a pool of protein-DNA complexes formed after in vitro translation wherein each protein is stably associated with the DNA that encodes it (U.S. Pat. No. 7,842,476; Odegrip et al., Proc Natl Acad Sci USA 101, 2806-2810, 2004), and assaying the library for specific binding to PSMA by any method known in the art and described in the Example Exemplary well known methods which can be used are ELISA, sandwich immunoassays, and competitive and non-competitive assays (see, e.g., Ausubel et al., eds, 1994, Current Protocols in Molecular Biology, Vol. 1, John Wiley & Sons, Inc., New York). The identified FN3 domains that specifically bind CD71 are further characterized for their binding to CD71, modulation of CD71 activity, internalization, stability, and other desired characteristics.

The FN3 domains that specifically bind CD71 may be generated using any FN3 domain as a template to generate a library and screening the library for molecules specifically binding CD71 using methods provided within. Exemplar FN3 domains that may be used are the 3rd FN3 domain of tenascin C (TN3), Fibcon, and the $10^{th}$ FN3 domain of fibronectin (FN10). Accordingly, PCT applications WO 2010/051274, WO 2011/137319, and WO 2013/049275 are incorporated herein in their entirety. Standard cloning and expression techniques are used to clone the libraries into a vector or synthesize double stranded cDNA cassettes of the library, to express, or to translate the libraries in vitro. For example ribosome display (Hanes and Pluckthun, Proc Natl Acad Sci USA, 94, 4937-4942, 1997), mRNA display (Roberts and Szostak, Proc Natl Acad Sci USA, 94, 12297-12302, 1997), or other cell-free systems (U.S. Pat. No. 5,643,768) can be used. The libraries of the FN3 domain variants may be expressed as fusion proteins displayed on the surface for example of any suitable bacteriophage. Methods for displaying fusion polypeptides on the surface of a bacteriophage are well known (U.S. Pat. Publ. No. 2011/0118144; Int. Pat. Publ. No. WO2009/085462; U.S. Pat. Nos. 6,969,108; 6,172,197; 5,223,409; 6,582,915; 6,472, 147).

In some embodiments. the FN3 domain that binds CD71 is based on Tencon sequence of SEQ ID NO: 1 or Tencon27 sequence of SEQ ID NO: 4, the SEQ ID NO: 1 or the SEQ ID NO: 4, optionally having substitutions at residues positions 11, 14, 17, 37, 46, 73, and/or 86.

In some embodiments, the FN3 protein or polypeptide is one that binds to human CD71 at a site on CD71 that does not compete with transferrin binding to CD71. As used herein, a site on CD71 that does not compete with transferrin binding to CD71 refers to an epitope or part of CD71 where the binding of the FN3 protein does not compete or inhibit the binding of transferrin to CD71. The competition, or lack thereof, can be complete or partial. In some embodiments, the binding also does not inhibit the internalization of transferrin into the cell through its interaction with CD71.

In some embodiments, methods for identifying a FN3 protein that binds to CD71 at a site that does not compete or inhibit transferrin binding to CD71 are provided. In some embodiments, the methods comprise contacting CD71 in the presence of transferrin or an agent that binds to the CD71 transferrin binding site with a test FN3 protein; and identifying a test FN3 protein that binds to CD71 in the presence of transferrin or an agent that binds to the CD71 transferrin binding site. In some embodiments, the method comprises isolating the test FN3 protein that binds to CD71 in the presence of transferrin or an agent that binds to the CD71 transferrin binding site. In some embodiments, the methods comprise sequencing the test FN3 protein that binds to CD71 in the presence of transferrin or an agent that binds to the CD71 transferrin binding site. In some embodiments, the methods comprise preparing or obtaining a nucleic acid sequence encoding the test FN3 protein that binds to CD71 in the presence of transferrin or an agent that binds to the CD71 transferrin binding site. In some embodiments, the methods comprise expressing the test FN3 protein that binds to CD71 in the presence of transferrin or an agent that binds to the CD71 transferrin binding site from a nucleic acid sequence encoding the test FN3 protein that binds to CD71 in the presence of transferrin or an agent that binds to the CD71 transferrin binding site. In some embodiments, the test FN3 protein is expressed in a cell. In some embodiments, the methods comprise isolating and/or purifying the expressed test FN3 protein.

In some embodiments a FN3 protein is provided, wherein the FN3 protein is identified according to any method provided herein.

The FN3 domains that specifically bind CD71 may be modified to improve their properties such as improve thermal stability and reversibility of thermal folding and unfolding. Several methods have been applied to increase the apparent thermal stability of proteins and enzymes, including rational design based on comparison to highly similar thermostable sequences, design of stabilizing disulfide bridges, mutations to increase alpha-helix propensity, engineering of salt bridges, alteration of the surface charge of the protein, directed evolution, and composition of consensus sequences (Lehmann and Wyss, Curr. Opin. Biotechnol., 12, 371-375, 2001). High thermal stability may increase the yield of the expressed protein, improve solubility or activity, decrease immunogenicity, and minimize the need of a cold chain in manufacturing. Residues that may be substituted to improve thermal stability of Tencon (SEQ ID NO: 1) are residue positions 11, 14, 17, 37, 46, 73, or 86, and are described in US Pat. Publ. No. 2011/0274623. Substitutions corresponding to these residues may be incorporated to the FN3 domain containing molecules disclosed herein.

Measurement of protein stability and protein lability can be viewed as the same or different aspects of protein integrity. Proteins are sensitive or "labile" to denaturation caused by heat, by ultraviolet or ionizing radiation, changes in the ambient osmolarity and pH if in liquid solution, mechanical shear force imposed by small pore-size filtration, ultraviolet radiation, ionizing radiation, such as by gamma irradiation, chemical or heat dehydration, or any other action or force that may cause protein structure disruption. The stability of the molecule can be determined using standard methods. For example, the stability of a molecule can be determined by measuring the thermal melting ("$T_m$") temperature, the temperature in ° Celsius (° C.) at which half of the molecules become unfolded, using standard methods. Typically, the higher the $T_m$, the more stable the molecule. In addition to heat, the chemical environment also changes the ability of the protein to maintain a particular three dimensional structure.

In some embodiments, the FN3 domain that binds CD71 may exhibit increased stability by at least 5%, 10%, 15%, 20%, 25%, 30%, 35%, 40%, 45%, 50%, 55%, 60%, 65%, 70%, 75%, 80%, 85%, 90%, or 95% or more compared to the same domain prior to engineering measured by the increase in the $T_m$.

Chemical denaturation can likewise be measured by a variety of methods. Chemical denaturants include guanidinium hydrochloride, guanidinium thiocyanate, urea, acetone, organic solvents (DMF, benzene, acetonitrile), salts (ammonium sulfate, lithium bromide, lithium chloride, sodium bromide, calcium chloride, sodium chloride); reducing agents (e.g. dithiothreitol, beta-mercaptoethanol, dinitrothiobenzene, and hydrides, such as sodium borohydride), non-ionic and ionic detergents, acids (e.g. hydrochloric acid (HCl), acetic acid ($CH_3COOH$), halogenated acetic acids), hydrophobic molecules (e.g. phospholipids), and targeted denaturants. Quantitation of the extent of denaturation can rely on loss of a functional property, such as ability to bind a target molecule, or by physiochemical properties, such as tendency to aggregation, exposure of formerly solvent inaccessible residues, or disruption or formation of disulfide bonds.

The FN3 domain that binds CD71 may be generated as monomers, dimers, or multimers, for example, as a means to increase the valency and thus the avidity of target molecule binding, or to generate bi- or multispecific scaffolds simultaneously binding two or more different target molecules. The dimers and multimers may be generated by linking monospecific, bi- or multispecific protein scaffolds, for example, by the inclusion of an amino acid linker, for example a linker containing poly-glycine, glycine and serine, or alanine and proline. Exemplary linker include $(GS)_2$, (SEQ ID NO: 63), $(GGGS)_2$ (SEQ ID NO: 64), $(GGGGS)_5$ (SEQ ID NO: 65), $(AP)_2$ (SEQ ID NO: 66), $(AP)_5$ (SEQ ID NO: 67), $(AP)_{10}$ (SEQ ID NO: 68), $(AP)_{20}$ (SEQ ID NO: 69) and $A(EAAAK)_5AAA$ (SEQ ID NO: 70). The dimers and multimers may be linked to each other in a N- to C-direction. The use of naturally occurring as well as artificial peptide linkers to connect polypeptides into novel linked fusion polypeptides is well known in the literature (Hallewell et al., *J Biol Chem* 264, 5260-5268, 1989; Alfthan et al., *Protein Eng.* 8, 725-731, 1995; Robinson & Sauer, *Biochemistry* 35, 109-116, 1996; U.S. Pat. No. 5,856,456).

Half-Life Extending Moieties

The FN3 domains that specifically bind CD71 may incorporate other subunits for example via covalent interaction. In some embodiments, the FN3 domains that specifically bind CD71 further comprise a half-life extending moiety. Exemplary half-life extending moieties are albumin, albumin variants, albumin-binding proteins and/or domains, transferrin and fragments and analogues thereof, and Fc regions Amino acid sequences of the human Fc regions are well known, and include IgG1, IgG2, IgG3, IgG4, IgM, IgA and IgE Fc regions. In some embodiments, the FN3 domains that specifically bind CD71 may incorporate a second FN3 domain that binds to a molecule that extends the half-life of the entire molecule, such as, but not limited to, any of the half-life extending moieties described herein. In some embodiments, the second FN3 domain binds to albumin, albumin variants, albumin-binding proteins and/or domains, and fragments and analogues thereof.

All or a portion of an antibody constant region may be attached to the FN3 domain that binds CD71 to impart antibody-like properties, especially those properties associated with the Fc region, such as Fc effector functions such as C1q binding, complement dependent cytotoxicity (CDC), Fc receptor binding, antibody-dependent cell-mediated cytotoxicity (ADCC), phagocytosis, down regulation of cell surface receptors (e.g., B cell receptor; BCR), and may be further modified by modifying residues in the Fc responsible for these activities (for review; see Strohl, *Curr Opin Biotechnol.* 20, 685-691, 2009).

Additional moieties may be incorporated into the FN3 domains that specifically bind CD71 such as polyethylene glycol (PEG) molecules, such as PEG5000 or PEG20,000, fatty acids and fatty acid esters of different chain lengths, for example laurate, myristate, stearate, arachidate, behenate, oleate, arachidonate, octanedioic acid, tetradecanedioic acid, octadecanedioic acid, docosanedioic acid, and the like, polylysine, octane, carbohydrates (dextran, cellulose, oligo- or polysaccharides) for desired properties. These moieties may be direct fusions with the protein scaffold coding sequences and may be generated by standard cloning and expression techniques. Alternatively, well known chemical coupling methods may be used to attach the moieties to recombinantly produced molecules disclosed herein.

A pegyl moiety may for example be added to the FN3 domain that binds CD71 by incorporating a cysteine residue to the C-terminus of the molecule, or engineering cysteines into residue positions that face away from the CD71 binding face of the molecule, and attaching a pegyl group to the cysteine using well known methods.

FN3 domains that specifically bind CD71 incorporating additional moieties may be compared for functionality by several well-known assays. For example, altered properties due to incorporation of Fc domains and/or Fc domain variants may be assayed in Fc receptor binding assays using soluble forms of the receptors, such as the FcγRI, FcγRII, FcγRIII or FcRn receptors, or using well known cell-based assays measuring for example ADCC or CDC, or evaluating pharmacokinetic properties of the molecules disclosed herein in in vivo models.

Polynucleotides, Vectors, Host Cells

In some embodiments, nucleic acids encoding the FN3 domains specifically binding CD71 as isolated polynucleotides or as portions of expression vectors or as portions of linear DNA sequences, including linear DNA sequences used for in vitro transcription/translation, vectors compatible with prokaryotic, eukaryotic or filamentous phage expression, secretion and/or display of the compositions or directed mutagens thereof are provided. Certain exemplary polynucleotides are disclosed herein, however, other polynucleotides which, given the degeneracy of the genetic code or codon preferences in a given expression system, encode the FN3 domains disclosed herein are also within the scope of the disclosure.

In some embodiments, an isolated polynucleotide encodes the FN3 domain specifically binding CD71 comprising the amino acid sequence of SEQ ID NOs: 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, or 81-309.

The polynucleotides disclosed herein may be produced by chemical synthesis such as solid phase polynucleotide synthesis on an automated polynucleotide synthesizer and assembled into complete single or double stranded molecules. Alternatively, the polynucleotides disclosed herein may be produced by other techniques such as PCR followed by routine cloning. Techniques for producing or obtaining polynucleotides of a given known sequence are well known in the art.

The polynucleotides disclosed herein may comprise at least one non-coding sequence, such as a promoter or enhancer sequence, intron, polyadenylation signal, a cis sequence facilitating RepA binding, and the like. The polynucleotide sequences may also comprise additional sequences encoding additional amino acids that encode for example a marker or a tag sequence such as a histidine tag or an HA tag to facilitate purification or detection of the protein, a signal sequence, a fusion protein partner such as RepA, Fc or bacteriophage coat protein such as pIX or pIII.

In some embodiments, a vector comprising at least one polynucleotide disclosed herein is provided. Such vectors may be plasmid vectors, viral vectors, vectors for baculovirus expression, transposon based vectors or any other vector suitable for introduction of the polynucleotides disclosed herein into a given organism or genetic background by any means. Such vectors may be expression vectors comprising nucleic acid sequence elements that can control, regulate, cause or permit expression of a polypeptide encoded by such a vector. Such elements may comprise transcriptional enhancer binding sites, RNA polymerase initiation sites, ribosome binding sites, and other sites that facilitate the expression of encoded polypeptides in a given expression system. Such expression systems may be cell-based, or cell-free systems well known in the art.

In some embodiments, a host cell comprising the vector is provided. The FN3 domain that specifically bind CD71 may be optionally produced by a cell line, a mixed cell line, an immortalized cell or clonal population of immortalized cells, as well known in the art. See, e.g., Ausubel, et al., ed., Current Protocols in Molecular Biology, John Wiley & Sons, Inc., NY, NY (1987-2001); Sambrook, et al., Molecular Cloning: A Laboratory Manual, $2^{nd}$ Edition, Cold Spring Harbor, N.Y. (1989); Harlow and Lane, Antibodies, a Laboratory Manual, Cold Spring Harbor, N.Y. (1989); Colligan, et al., eds., Current Protocols in Immunology, John Wiley & Sons, Inc., NY (1994-2001); Colligan et al., Current Protocols in Protein Science, John Wiley & Sons, NY, NY, (1997-2001).

The host cell chosen for expression may be of mammalian origin or may be selected from COS-1, COS-7, HEK293, BHK21, CHO, BSC-1, He G2, SP2/0, HeLa, myeloma, lymphoma, yeast, insect or plant cells, or any derivative, immortalized or transformed cell thereof. Alternatively, the host cell may be selected from a species or organism incapable of glycosylating polypeptides, e.g. a prokaryotic cell or organism, such as BL21, BL21(DE3), BL21-GOLD (DE3), XL1-Blue, JM109, HMS174, HMS174(DE3), and any of the natural or engineered *E. coli* spp, *Klebsiella* spp., or *Pseudomonas* spp strains.

In some embodiments, a method of producing the isolated FN3 domain that binds CD71, comprising culturing the isolated host cell under conditions such that the isolated FN3 domain that binds CD71 is expressed, and purifying the FN3 domain.

The FN3 domains that bind CD71 may be purified from recombinant cell cultures by well-known methods, for example by protein A purification, ammonium sulfate or ethanol precipitation, acid extraction, anion or cation exchange chromatography, phosphocellulose chromatography, hydrophobic interaction chromatography, affinity chromatography, hydroxyapatite chromatography and lectin chromatography, or high performance liquid chromatography (HPLC).

Anti-Idiotypic Antibodies

In some embodiments, an anti-idiotypic antibody binds to the FN3 domain.

In some embodiments, an anti-idiotypic antibody that binds the FN3 domain comprises the amino acid sequences of one of SEQ ID NOs: 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, or 81-309.

Kits

In some embodiments, a kit comprising the FN3 domain that binds CD71 is provided.

The kit may be used for therapeutic uses and as a diagnostic kit.

In some embodiments, the kit comprises the FN3 domain that binds CD71 and reagents for detecting the FN3 domain. In some embodiments, the kit comprises a bivalent FN3 domain. The kit can include one or more other elements including: instructions for use; other reagents, e.g., a label, an agent useful for chelating, or otherwise coupling, a radioprotective composition; devices or other materials for preparing the FN3 domain that binds CD71 for administration for imaging, diagnostic or therapeutic purpose; pharmaceutically acceptable carriers; and devices or other materials for administration to a subject.

In some embodiments, the kit comprises the FN3 domain that binds CD71 comprising the amino acid sequences of one of SEQ ID NOs: 33-50.

In some embodiments, the kit comprises the FN3 domain that binds CD71 comprising the amino acid sequences of one of SEQ ID NOs: 51-61.

In some embodiments, the kit comprises the FN3 domain that binds CD71 comprising the amino acid sequences of one of SEQ ID NOs: 81-309.

In some embodiments, the kit comprises the FN3 domain that binds CD71 comprising the amino acid sequences of one of SEQ ID NOs: 146, 214, 104, 259, 134, 92, 302, 235, 237, 152, 238, 136, 197, 212, 296, 226, 261, 307, 115, 112, 278, 297, 96, 222, 95, 233, 217, 252, 194, 164, 168, 174, 190, 257, 303, 284, 85, or 149.

Uses of CD71 Binding FN3 Domains

The FN3 domains that specifically bind CD71 or conjugates thereof may be used to diagnose, monitor, modulate, treat, alleviate, help prevent the incidence of, or reduce the symptoms of human disease or specific pathologies in cells, tissues, organs, fluid, or, generally, a host.

In some embodiments, the FN3 domains that specifically bind CD71 or conjugates thereof may also be used in imaging CD71 positive tumor tissue in a subject. The methods disclosed herein may be used with an animal patient belonging to any classification. Examples of such animals include mammals such as humans, rodents, dogs, cats and farm animals.

In some embodiments, a method of diagnosing a subject having, or who is likely to develop cancer of a tissue based on the expression of CD71 by cells of the cancer tissue, methods of predicting success of immunotherapy, methods of prognosis, and methods of treatment are provided.

In some embodiments, a method of detecting CD71-expressing cancer cells in a tumor tissue is provided, the method comprising: obtaining a sample of the tumor tissue from a subject; detecting whether CD71 is expressed in the tumor tissue by contacting toe sample of the tumor tissues with the FN3 domain that binds CD71 comprising the amino acid sequence of one of SEQ ID NOs: 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, or 81-309, and detecting the binding between CD71 and the FN3 domain.

In some embodiments, the CD71 cell is a cell involved in a CNS diseases, inflammatory/immune diseases, such as MS & infectious diseases of the brain.

In some embodiments, the tissue can be tissue of any organ or anatomical system, that expresses CD71.

In some embodiments, CD71 expression may be evaluated using known methods, such as immunohistochemistry or ELISA.

In some embodiments, a method of isolating CD71 expressing cells is provided, the method comprising: obtaining a sample from a subject; contacting the sample with the FN3 domain that binds CD71 comprising the amino acid sequence of one of SEQ ID NOs: 33-50, and isolating the cells bound to the FN3 domains.

In some embodiments, a method of isolating CD71 expressing cells is provided, the method comprising: obtaining a sample from a subject; contacting the sample with the FN3 domain that binds CD71 comprising the amino acid sequence of one of SEQ ID NOs: 51-61, and isolating the cells bound to the FN3 domains.

In some embodiments, a method of detecting CD71-expressing cancer cells in a tumor tissue is provided, the method comprising: conjugating the FN3 domain that binds CD71 comprising the amino acid sequence of one of SEQ ID NOs: 33-50 to a detectable label to form a conjugate; administering the conjugate to a subject; and visualizing the CD71 expressing cancer cells to which the conjugate is bound.

In some embodiments, a method of detecting CD71-expressing cancer cells in a tumor tissue is provided, the method comprising: conjugating the FN3 domain that binds CD71 comprising the amino acid sequence of one of SEQ ID NOs: 51-62 or 81-309 to a detectable label to form a conjugate; administering the conjugate to a subject; and visualizing the CD71 expressing cancer cells to which the conjugate is bound.

In some embodiments, a method of treating a subject having cancer is provided, the method comprising administering to the subject a FN3 domain that binds CD71. In some embodiments, the FN3 domain is conjugated to a therapeutic agent (e.g. cytotoxic agent, an oligonucleotide, a FN3 domain that binds to another target, and the like).

In some embodiments, the subject has a solid tumor.

In some embodiments, the solid tumor is a melanoma.

In some embodiments, the solid tumor is a lung cancer. In some embodiments, the solid tumor is a non-small cell lung cancer (NSCLC). In some embodiments, the solid tumor is a squamous non-small cell lung cancer (NSCLC). In some embodiments, the solid tumor is a non-squamous NSCLC. In some embodiments, the solid tumor is a lung adenocarcinoma.

In some embodiments, the solid tumor is a renal cell carcinoma (RCC).

In some embodiments, the solid tumor is a mesothelioma.

In some embodiments, the solid tumor is a nasopharyngeal carcinoma (NPC).

In some embodiments, the solid tumor is a colorectal cancer.

In some embodiments, the solid tumor is a prostate cancer. In some embodiments, the solid tumor is castration-resistant prostate cancer.

In some embodiments, the solid tumor is a stomach cancer.

In some embodiments, the solid tumor is an ovarian cancer.

In some embodiments, the solid tumor is a gastric cancer.

In some embodiments, the solid tumor is a liver cancer.

In some embodiments, the solid tumor is pancreatic cancer.

In some embodiments, the solid tumor is a thyroid cancer.

In some embodiments, the solid tumor is a squamous cell carcinoma of the head and neck.

In some embodiments, the solid tumor is a carcinomas of the esophagus or gastrointestinal tract.

In some embodiments, the solid tumor is a breast cancer.

In some embodiments, the solid tumor is a fallopian tube cancer.

In some embodiments, the solid tumor is a brain cancer.

In some embodiments, the solid tumor is an urethral cancer.

In some embodiments, the solid tumor is a genitourinary cancer.

In some embodiments, the solid tumor is an endometriosis.

In some embodiments, the solid tumor is a cervical cancer.

In some embodiments, the solid tumor is a metastatic lesion of the cancer.

In some embodiments, the subject has a hematological malignancy.

In some embodiments, the hematological malignancy is a lymphoma, a myeloma or a leukemia. In some embodiments, the hematological malignancy is a B cell lymphoma. In some embodiments, the hematological malignancy is Burkitt's lymphoma. In some embodiments, the hematological malignancy is Hodgkin's lymphoma. In some embodiments, the hematological malignancy is a non-Hodgkin's lymphoma.

In some embodiments, the hematological malignancy is a myelodysplastic syndrome.

In some embodiments, the hematological malignancy is an acute myeloid leukemia (AML). In some embodiments, the hematological malignancy is a chronic myeloid leukemia (CML). In some embodiments, the hematological malignancy is a chronic myelomoncytic leukemia (CMML).

In some embodiments, the hematological malignancy is a multiple myeloma (MM).

In some embodiments, the hematological malignancy is a plasmacytoma.

In some embodiments, the compositions or pharmaceutical compositions provided herein may be administered alone or in combination with other therapeutics, that is, simultaneously or sequentially. In some embodiments, the other or additional therapeutics are other anti-tumor agent or therapeutics. Different tumor types and stages of tumors can require the use of various auxiliary compounds useful for treatment of cancer. For example, the compositions provided herein can be used in combination with various chemotherapeutics such as taxol, tyrosine kinase inhibitors, leucovorin, fluorouracil, irinotecan, phosphatase inhibitors, MEK inhibitors, among others. The composition may also be used in combination with drugs which modulate the immune response to the tumor such as anti-PD-1 or anti-CTLA-4, among others. Additional treatments can be agents that modulate the immune system, such antibodies that target PD-1 or PD-L1.

In some embodiments, the FN3 domains that specifically bind CD71 or conjugates thereof that may be used to diagnose, monitor, modulate, treat, alleviate, help prevent the incidence of, or reduce the symptoms of human disease or specific pathologies in cells, tissues, organs, fluid, or, generally, a host, also exhibit the property of being able to cross the blood brain barrier. The blood-brain barrier (BBB) prevents most macromolecules (e.g., DNA, RNA, and polypeptides) and many small molecules from entering the brain. The BBB is principally composed of specialized endothelial cells with highly restrictive tight junctions, consequently, passage of substances, small and large, from the blood into the central nervous system is controlled by the BBB. This structure makes treatment and management of patients with neurological diseases and disorders (e.g., brain cancer) difficult as many therapeutic agents cannot be delivered across the BBB with desirable efficiency. Additional conditions that involve disruptions of the BBB include: stroke, diabetes, seizures, hypertensive encephalopathy, acquired immunodeficiency syndrome, traumatic brain injuries, multiple sclerosis, Parkinson's disease (PD) and Alzheimer disease. This ability is especially useful for treating brain cancers including for example—astrocytoma, medulloblastoma, glioma, ependymoma, germinoma (pinealoma), glioblastoma multiform, oligodendroglioma, schwannoma, retinoblastoma, and congenital tumors; or a cancer of the spinal cord, e.g., neurofibroma, meningioma, glioma, and sarcoma. In certain embodiments, the FN3 domains that specifically bind CD71 comprising the amino acid sequence of one of SEQ ID NOs: 33-50 or conjugates thereof, are useful to deliver a therapeutic or cytotoxic agent, for example, across the blood brain barrier. In certain embodiments, the FN3 domains that specifically bind CD71 comprising the amino acid sequence of one of SEQ ID NOs: 51-61 or conjugates thereof, are useful to deliver a therapeutic or cytotoxic agent, for example, across the blood brain barrier. In some embodiments, the protein comprises a sequence of SEQ ID NOs: 146, 214, 104, 259, 134, 92, 302, 235, 237, 152, 238, 136, 197, 212, 296, 226, 261, 307, 115, 112, 278, 297, 96, 222, 95, 233, 217, 252, 194, 164, 168, 174, 190, 257, 303, 284, 85, 149, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, or 81-309.

In some embodiments, the polypeptide that can facilitates the transport of a therapeutic across the BBB is a protein comprising a sequence of SEQ ID NO: 146, 214, 104, 259, 134, 92, 302, 235, 237, 152, 238, 136, 197, 212, 296, 226, 261, 307, 115, 112, 278, 297, 96, 222, 95, 233, 217, 252, 194, 164, 168, 174, 190, 257, 303, 284, 85, or 149.

"Treat" or "treatment" refers to the therapeutic treatment and prophylactic measures, wherein the object is to prevent or slow down (lessen) an undesired physiological change or disorder, such as the development or spread of cancer. In some embodiments, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

A "therapeutically effective amount" refers to an amount effective, at dosages and for periods of time necessary, to achieve a desired therapeutic result. A therapeutically effective amount of the FN3 domains that specifically bind CD71 may vary according to factors such as the disease state, age, sex, and weight of the individual. Exemplary indicators of an effective FN3 domain that binds CD71 is improved well-being of the patient, decrease or shrinkage of the size of a tumor, arrested or slowed growth of a tumor, and/or absence of metastasis of cancer cells to other locations in the body.

Administration/Pharmaceutical Compositions

In some embodiments, pharmaceutical compositions of the FN3 domains that specifically bind CD71, optionally conjugated to a detectable label, therapeutic, or a cytotoxic agent disclosed herein and a pharmaceutically acceptable carrier, are provided. For therapeutic use, the FN3 domains that specifically bind CD71 may be prepared as pharmaceutical compositions containing an effective amount of the domain or molecule as an active ingredient in a pharmaceutically acceptable carrier. "Carrier" refers to a diluent, adjuvant, excipient, or vehicle with which the active compound is administered. Such vehicles can be liquids, such as water and oils, including those of petroleum, animal, vegetable or synthetic origin, such as peanut oil, soybean oil, mineral oil, sesame oil and the like. For example, 0.4% saline and 0.3% glycine can be used. These solutions are sterile and generally free of particulate matter. They may be sterilized by conventional, well-known sterilization techniques (e.g., filtration). The compositions may contain pharmaceutically acceptable auxiliary substances as required to approximate physiological conditions such as pH adjusting and buffering agents, stabilizing, thickening, lubricating and coloring agents, etc. The concentration of the molecules disclosed herein in such pharmaceutical formulation can vary widely, i.e., from less than about 0.5%, usually at least about 1% to as much as 15 or 20% by weight and will be selected primarily based on required dose, fluid volumes, viscosities, etc., according to the particular mode of administration selected. Suitable vehicles and formulations, inclusive of other human proteins, e.g., human serum albumin, are described, for example, in e.g. Remington: The Science and Practice of Pharmacy, 21$^{st}$ Edition, Troy, D. B. ed., Lipincott Williams and Wilkins, Philadelphia, Pa. 2006, Part 5, Pharmaceutical Manufacturing pp 691-1092, See especially pp. 958-989.

The mode of administration for therapeutic use of the FN3 domains disclosed herein may be any suitable route that delivers the agent to the host, such as parenteral administration, e.g., intradermal, intramuscular, intraperitoneal, intravenous or subcutaneous, pulmonary; transmucosal (oral, intranasal, intravaginal, rectal), using a formulation in a tablet, capsule, solution, powder, gel, particle; and contained in a syringe, an implanted device, osmotic pump, cartridge, micropump; or other means appreciated by the skilled artisan, as well known in the art. Site specific administration may be achieved by for example intra-articular, intrabronchial, intra-abdominal, intracapsular, intracartilaginous, intracavitary, intracelial, intracerebellar, intracerebroventricular, intracolic, intracervical, intragastric, intrahepatic, intracardial, intraosteal, intrapelvic, intraperi-cardial, intraperitoneal, intrapleural, intraprostatic, intrapulmonary, intrarectal, intrarenal, intraretinal, intraspinal, intra-synovial, intrathoracic, intrauterine, intravascular, intravesical, intralesional, vaginal, rectal, buccal, sublingual, intranasal, or transdermal delivery.

Pharmaceutical compositions can be supplied as a kit comprising a container that comprises the pharmaceutical composition as described herein. A pharmaceutical composition can be provided, for example, in the form of an injectable solution for single or multiple doses, or as a sterile powder that will be reconstituted before injection. Alternatively, such a kit can include a dry-powder disperser, liquid aerosol generator, or nebulizer for administration of a pharmaceutical composition. Such a kit can further comprise written information on indications and usage of the pharmaceutical composition.

EXAMPLES

The following examples are illustrative of the embodiments disclosed herein. These examples are provided for the purpose of illustration only and the embodiments should in no way be construed as being limited to these examples, but rather should be construed to encompass any and all variations which become evidence as a result of the teaching provided herein. Those of skill in the art will readily recognize a variety of non-critical parameters that could be changed or modified to yield essentially similar results.

Example 1. Construction of Tencon Libraries with Randomized Loops

Tencon (SEQ ID NO: 1) is an immunoglobulin-like scaffold, fibronectin type III (FN3) domain, designed from a consensus sequence of fifteen FN3 domains from human tenascin-C (Jacobs et al., Protein Engineering, Design, and Selection, 25:107-117, 2012; U.S. Pat. No. 8,278,419). The crystal structure of Tencon shows six surface-exposed loops that connect seven beta-strands. These loops, or selected residues within each loop, can be randomized in order to construct libraries of fibronectin type III (FN3) domains that can be used to select novel molecules that bind to specific targets. Tencon:

```
                                               (SEQ ID NO: 1)
LPAPKNLVVSEVTEDSLRLSWTAPDAAFDSFLIQYQESEKVGEAI

NLTVPGSERSYDLTGLKPGTEYTVSIYGVKGGHRSNPLSAEFTT
```

Various libraries were generated using the Tencon scaffold and various design strategies. In general, libraries TCL1 and TCL2 produced good binders. Generation of TCL1 and TCL2 libraries are described in detail in Int. Pat. Publ. No. WO/2014081944A2.

Construction of TCL1 Library

A library designed to randomize only the FG loop of Tencon (SEQ ID NO: 1), TCL1, was constructed for use with the cis-display system (Jacobs et al., Protein Engineering, Design, and Selection, 25:107-117, 2012). In this system, a single-strand DNA incorporating sequences for a Tac promoter, Tencon library coding sequence, RepA coding sequence, cis-element, and ori element is produced. Upon expression in an in vitro transcription/translation system, a complex is produced of the Tencon-RepA fusion protein bound in cis to the DNA from which it is encoded. Complexes that bind to a target molecule are then isolated and amplified by polymerase chain reaction (PCR), as described below.

Construction of the TCL1 library for use with cis-display was achieved by successive rounds of PCR to produce the final linear, double-stranded DNA molecules in two halves; the 5' fragment contains the promoter and Tencon sequences, while the 3' fragment contains the repA gene and the cis- and ori elements. These two halves are combined by restriction digest in order to produce the entire construct. The TCL1 library was designed to incorporate random amino acids only in the FG loop of Tencon. NNS codons were used in the construction of this library, resulting in the possible incorporation of all 20 amino acids and one stop codon into the FG loop. The TCL1 library contains six separate sub-libraries, each having a different randomized FG loop length, from 7 to 12 residues, in order to further increase diversity.

```
TCL1 library
                                               (SEQ ID NO: 2)
LPAPKNLVVSEVTEDSLRLSWTAPDAAFDSFLIQYQESEKVGEAI

NLTVPGSERSYDLTGLKPGTEYTVSIYGVX₇₋₁₂PLSAEFTT;
``` wherein $X_1$, $X_2$, $X_3$, $X_4$, $X_5$, $X_6$, $X_7$ is any amino acid; and
$X_8$, $X_9$, $X_{10}$, $X_{11}$ and $X_{12}$ are any amino acid or deleted Construction of TCL2 Library TCL2 library was constructed in which both the BC and the FG loops of Tencon were randomized and the distribution of amino acids at each position was strictly controlled. Table 2 shows the amino acid distribution at desired loop positions in the TCL2 library. The designed amino acid distribution had two aims. First, the library was biased toward residues that were predicted to be structurally important for Tencon folding and stability based on analysis of the Tencon crystal structure and/or from homology modeling. For example, position 29 was fixed to be only a subset of hydrophobic amino acids, as this residue was buried in the hydrophobic core of the Tencon fold. A second layer of design included biasing the amino acid distribution toward that of residues preferentially found in the heavy chain HCDR3 of antibodies, to efficiently produce high-affinity binders (Birtalan et al., J Mol Biol 377:1518-28, 2008; Olson et al., Protein Sci 16:476-84, 2007). Towards this goal, the "designed distribution" in Table 2 refers to the distribution as follows: 6% alanine, 6% arginine, 3.9% asparagine, 7.5% aspartic acid, 2.5% glutamic acid, 1.5% glutamine, 15% glycine, 2.3% histidine, 2.5% isoleucine, 5% leucine, 1.5% lysine, 2.5% phenylalanine, 4% proline, 10% serine, 4.5% threonine, 4% tryptophan, 17.3% tyrosine, and 4% valine. This distribution is devoid of methionine, cysteine, and STOP codons.

```
TCL2 library
                                        (SEQ ID NO: 3)
LPAPKNLVVSEVTEDSLRLSWX1X2X3X4X5X6X7X8SFLIQYQES

EKVGEAINLTVPGSERSYDLTGLKPGTEYTVSIYGVX9X10X11X12

X13SX14X15LSAEFTT;
``` wherein $X_1$ is Ala, Arg, Asn, Asp, Glu, Gln, Gly, His, Ile, Leu, Lys, Phe, Pro, Ser, Thr, Trp, Tyr or Val;

$X_2$ is Ala, Arg, Asn, Asp, Glu, Gln, Gly, His, Ile, Leu, Lys, Phe, Pro, Ser, Thr, Trp, Tyr or Val;

$X_3$ Ala, Arg, Asn, Asp, Glu, Gln, Gly, His, Ile, Leu, Lys, Phe, Pro, Ser, Thr, Trp, Tyr or Val;

$X_4$ is Ala, Arg, Asn, Asp, Glu, Gln, Gly, His, Ile, Leu, Lys, Phe, Pro, Ser, Thr, Trp, Tyr or Val;

$X_5$ is Ala, Arg, Asn, Asp, Glu, Gln, Gly, His, Ile, Leu, Lys, Phe, Pro, Ser, Thr, Trp, Tyr or Val;

$X_6$ is Ala, Arg, Asn, Asp, Glu, Gln, Gly, His, Ile, Leu, Lys, Phe, Pro, Ser, Thr, Trp, Tyr or Val;

$X_7$ is Phe, Ile, Leu, Val or Tyr;

$X_8$ is Asp, Glu or Thr;

$X_9$ is Ala, Arg, Asn, Asp, Glu, Gln, Gly, His, Ile, Leu, Lys, Phe, Pro, Ser, Thr, Trp, Tyr or Val;

$X_{10}$ is Ala, Arg, Asn, Asp, Glu, Gln, Gly, His, Ile, Leu, Lys, Phe, Pro, Ser, Thr, Trp, Tyr or Val;

$X_{11}$ is Ala, Arg, Asn, Asp, Glu, Gln, Gly, His, Ile, Leu, Lys, Phe, Pro, Ser, Thr, Trp, Tyr or Val;

$X_{12}$ is Ala, Arg, Asn, Asp, Glu, Gln, Gly, His, Ile, Leu, Lys, Phe, Pro, Ser, Thr, Trp, Tyr or Val;

$X_{13}$ is Ala, Arg, Asn, Asp, Glu, Gln, Gly, His, Ile, Leu, Lys, Phe, Pro, Ser, Thr, Trp, Tyr or Val;

$X_{14}$ is Ala, Arg, Asn, Asp, Glu, Gln, Gly, His, Ile, Leu, Lys, Phe, Pro, Ser, Thr, Trp, Tyr or Val; and $X_{15}$ is Ala, Arg, Asn, Asp, Glu, Gln, Gly, His, Ile, Leu, Lys, Phe, Pro, Ser, Thr, Trp, Tyr or Val.

TABLE 2

Residue distribution in the TCL2 library

| Residue Position* | WT residues | Distribution in the TCL2 library |
|---|---|---|
| 22 | T | designed distribution |
| 23 | A | designed distribution |
| 24 | P | 50% P + designed distribution |
| 25 | D | designed distribution |
| 26 | A | 20% A + 20% G + designed distribution |
| 27 | A | designed distribution |
| 28 | F | 20% F, 20% I, 20% L, 20% V, 20% Y |
| 29 | D | 33% D, 33% E, 33% T |
| 75 | K | designed distribution |
| 76 | G | designed distribution |
| 77 | G | designed distribution |
| 78 | H | designed distribution |
| 79 | R | designed distribution |
| 80 | S | 100% S |
| 81 | N | designed distribution |
| 82 | P | 50% P + designed distribution |

*residue numbering is based on Tencon sequence of SEQ ID NO: 1

Subsequently, these libraries were improved by various ways, including building of the libraries on a stabilized Tencon framework (U.S. Pat. No. 8,569,227) that incorporates substitutions E11R/L17A/N46V/E86I (Tencon27; SEQ ID NO: 4) when compared to the wild type tencon as well as altering of the positions randomized in the BC and FG loops. Tencon27 is described in Int. Pat. Appl. No. WO2013049275. From this, new libraries designed to randomize only the FG loop of Tencon (library TCL9), or a combination of the BC and FG loops (library TCL7) were generated. These libraries were constructed for use with the cis-display system (Odegrip et al., Proc. Natl. Acad. Sci. USA 101: 2806-2810, 2004). The details of this design are shown below:

```
Stabilized Tencon (Tencon27)
                                        (SEQ ID NO: 4)
LPAPKNLVVSRVTEDSARLSWTAPDAAFDSFLIQYQESEKVGEAIVL

TVPGSERSYDLTGLKPGTEYTVSIYGVKGGHRSNPLSAIFTT

TCL7 (randomized FG and BC loops)
                                        (SEQ ID NO: 5)
LPAPKNLVVSRVTEDSARLSWX1X2X3X4X5X6X7X8X9FDSFLIQY

QESEKVGEAIVLTVPGSERSYDLTGLKPGTEYTVSIYGVX10X11X12

X13X14X15X16X17X18X19SNPLSAIFTT;
``` wherein $X_1$, $X_2$, $X_3$, $X_4$, $X_5$, $X_6$, $X_{10}$, $X_{11}$, $X_{12}$, $X_{13}$, $X_{14}$, $X_{15}$ and $X_{16}$ is A, D, E, F, G, H, I, K, L, N, P, Q, R, S, T, V, W or Y; and $X_7$, $X_8$, $X_9$, $X_{17}$, $X_{18}$ and $X_{19}$, is A, D, E, F, G, H, I, K, L, N, P, Q, R, S, T, V, W, Y or deleted.

```
TCL9 (randomized FG loop)
                                        (SEQ ID NO: 6)
LPAPKNLVVSRVTEDSARLSWTAPDAAFDSFLIQYQESEKVGEAIVL

TVPGSERSYDLTGLKPGTEYTVSIYGV X1X2X3X4X5X6X7X8X9

X10X11X12SNPLSAIFTT;
X1, X2, X3, X4, X5, X6 and X7, is A, D, E, F,
G, H, I, K, L, N, P, Q, R, S, T, V, W or Y;
and X8, X9, X10, X11 and X12 is A, D, E, F, G,
H, I, K, L, N, P, Q, R, S, T, V, W, Y
or deleted.
```

For library construction, DNA fragments encoding randomized BC loops (lengths 6-9 positions) or FG loops (lengths 7-12 positions) were synthesized using Slonomics technology (Sloning Biotechnology GmbH) so as to control the amino acid distribution of the library and to eliminate stop codons. Two different sets of DNA molecules randomizing either the BC loop or the FG loops were synthesized independently and later combined using PCR to produce the full library product.

Construction of FG Loop Libraries (TCL9)

A set of synthetic DNA molecules consisting of a 5' Tac promoter followed by the complete gene sequence of Tencon with the exception of randomized codons in the FG loop was produced (SEQ ID NOs: 26-31) For FG loop randomization, all amino acids except cysteine and methionine were encoded at equal percentages. The lengths of the diversified portion are such that they encode for 7, 8, 9, 10, 11, or 12 amino acids in the FG loop. Sub-libraries of each length variation were synthesized individually at a scale of 2 ug and then amplified by PCR using oligos Sloning-FOR (SEQ ID NO: 9) and Sloning-Rev (SEQ ID NO: 10).

The 3' fragment of the library is a constant DNA sequence containing elements for display, including a PspOMI restriction site, the coding region of the repA gene, and the cis- and ori elements. PCR reactions were performed to amplify this fragment using a plasmid (pCR4Blunt) (Invitrogen) as a template with M13 Forward and M13 Reverse primers. The resulting PCR products were digested by PspOMI overnight and gel-purified. To ligate the 5' portion of library DNA to the 3' DNA containing repA gene, 2 pmol (~540 ng to 560 ng) of 5' DNA was ligated to an equal molar (~1.25 µg) of 3' repA DNA in the presence of NotI and PspOMI enzyme and T4 ligase at 37° C. overnight. The ligated library product was amplified by using 12 cycles of PCR with oligos POP2250 (SEQ ID NO: 11) and DigLigRev (SEQ ID NO: 12). For each sub-library, the resulting DNA from 12 PCR reactions were combined and purified by Qiagen spin column. The yield for each sub-library of TCL9 ranged from 32-34 µg.

Construction of FG/BC Loop Libraries (TCL7)

The TCL7 library provides for a library with randomized Tencon BC and FG loops. In this library, BC loops of lengths 6-9 amino acids were mixed combinatorically with randomized FG loops of 7-12 amino acids in length. Synthetic Tencon fragments BC6, BC7, BC8, and BC9 (SEQ ID NOs: 13-16, respectively) were produced to include the Tencon gene encoding for the N-terminal portion of the protein up to and including residue VX such that the BC loop is replaced with either 6, 7, 8, or 9 randomized amino acids, which are represented by the string of "N" in the sequences provided for herein. These fragments were synthesized prior to the discovery of L17A, N46V and E83I mutations (CEN5243) but these mutations were introduced in the molecular biology steps described below. In order to combine this fragment with fragments encoding for randomized FG loops, the following steps were taken.

First, a DNA fragment encoding the Tac promoter and the 5' sequence of Tencon up to the nucleotide encoding for amino acid A17 (130mer-L17A, SEQ ID NO: 17) was produced by PCR using oligos POP2222ext (SEQ ID NO: 18) and LS1114 (SEQ ID NO: 19). This was done to include the L17A mutation in the library (CEN5243). Next, DNA fragments encoding for Tencon residues R18-V75 including randomized BC loops were amplified by PCR using BC6, BC7, BC8, or BC9 as a templates and oligos LS1115 (SEQ ID NO: 20) and LS1117 (SEQ ID NO: 21). This PCR step introduced a BsaI site at the 3' end. These DNA fragments were subsequently joined by overlapping PCR using oligos POP2222ext and LS1117 as primers. The resulting PCR product of 240 bp was pooled and purified by Qiagen PCR purification kit. The purified DNA was digested with BsaI-HF and gel purified.

Fragments encoding the FG loop were amplified by PCR using FG7, FG8, FG9, FG10, FG11, and FG12 as templates with oligonucleotides SDG10 (SEQ ID NO: 22) and SDG24 (SEQ ID NO: 23) to incorporate a BsaI restriction site and N46V and E86I variations (CEN5243).

The digested BC fragments and FG fragments were ligated together in a single step using a 3-way ligation. Four ligation reactions in the 16 possible combinations were set up, with each ligation reaction combining two BC loop lengths with 2 FG loop lengths. Each ligation contained ~300 ng of total BC fragment and 300 ng of the FG fragment. These 4 ligation pools were then amplified by PCR using oligos POP2222 (SEQ ID NO: 24) and SDG28 SEQ ID NO: 25). 7.5 µg of each reaction product were then digested with NotI and cleaned up with a Qiagen PCR purification column. 5.2 µg of this DNA, was ligated to an equal molar amount of RepA DNA fragment (~14 µg) digested with PspOMI and the product amplified by PCR using oligos POP2222.

Example 2: Generation of Tencon Libraries Having Alternative Binding Surfaces

The choice of residues to be randomized in a particular library design governs the overall shape of the interaction surface created. X-ray crystallographic analysis of an FN3 domain containing scaffold protein selected to bind maltose binding protein (MBP) from a library in which the BC, DE, and FG loops were randomized was shown to have a largely curved interface that fits into the active site of MBP (Koide et al., Proc. Natl. Acad. Sci. USA 104: 6632-6637, 2007). In contrast, an ankyrin repeat scaffold protein that was selected to bind to MBP was found to have a much more planar interaction surface and to bind to the outer surface of MBP distant from the active (Binz et al., Nat. Biotechnol. 22: 575-582, 2004). These results suggest that the shape of the binding surface of a scaffold molecule (curved vs. flat) may dictate what target proteins or specific epitopes on those target proteins are able to be bound effectively by the scaffold. Published efforts around engineering protein scaffolds containing FN3 domains for protein binding has relied on engineering adjacent loops for target binding, thus producing curved binding surfaces. This approach may limit the number of targets and epitopes accessible by such scaffolds.

Tencon and other FN3 domains contain two sets of CDR-like loops lying on the opposite faces of the molecule, the first set formed by the BC, DE, and FG loops, and the second set formed by the AB, CD, and EF loops. The two sets of loops are separated by the beta-strands that form the center of the FN3 structure. If the image of the Tencon is rotated by 90 degrees, an alternative surface can be visualized. This slightly concave surface is formed by the CD and FG loops and two antiparallel beta-strands, the C and the F beta-strands, and is herein called the C-CD-F-FG surface. The C-CD-F-FG surface can be used as a template to design libraries of protein scaffold interaction surfaces by randomizing a subset of residues that form the surface. Beta-strands have a repeating structure with the side chain of every other residue exposed to the surface of the protein. Thus, a library can be made by randomizing some or all surface exposed residues in the beta strands. By choosing the appropriate residues in the beta-strands, the inherent stability of the Tencon scaffold should be minimally compromised while providing a unique scaffold surface for interaction with other proteins.

Library TCL14 (SEQ ID NO: 7), was designed into Tencon27 scaffold (SEQ ID NO: 4).

A full description of the methods used to construct this library is described in US. Pat. Publ. No. 2013/0226834.

```
TCL14 library
(SEQ ID NO: 7):
LPAPKNLVVSRVTEDSARLSWTAPDAAFDSFX₁IX₂YX₃EX₄X₅X₆X₇

GEAIVLTVPGSERSYDLTGLKPGTEYX₈VX₉IX₁₀GVKGGX₁₁X₁₂

SX₁₃PLSAIFTT;
``` wherein
$X_1$, $X_2$, $X_3$, $X_4$, $X_5$, $X_6$, $X_7$, $X_8$, $X_9$, $X_{10}$, $X_{11}$, $X_{12}$ and $X_{13}$ are A, D, E, F, G, H, I, K, L, N, P, Q, R, S, T, V, W, Y, C or M.

The two beta strands forming the C-CD-F-FG surface in Tencon27 have a total of 9 surface exposed residues that could be randomized; C-strand: S30, L32, Q34, Q36; F-strand: E66, T68, S70, Y72, and V74, while the CD loop has 6 potential residues: S38, E39, K40, V41, G42, and E43 and the FG loop has 7 potential residues: K75, G76, G77, H78, R79, S80, and N81. Select residues were chosen for inclusion in the TCL14 design due to the larger theoretical size of the library if all 22 residues were randomized.

Thirteen positions in Tencon were chosen for randomizing: L32, Q34 and Q36 in C-strand, S38, E39, K40 and V41 in CD-loop, T68, S70 and Y72 in F-strand, H78, R79, and N81 in FG-loop. In the C and F strands S30 and E66 were not randomized as they lie just beyond the CD and FG loops and do not appear to be as apparently a part of the C-CD-F-FG surface. For the CD loop, G42 and E43 were not randomized as glycine, providing flexibility, can be valuable in loop regions, and E43 lies at the junction of the surface. The FG loop had K75, G76, G77, and S80 excluded. The glycines were excluded for the reasons above while careful inspection of the crystal structures revealed S80 making key contacts with the core to help form the stable FG loop. K75 faces away from the surface of the C-CD-F-FG surface and was a less appealing candidate for randomization. Although the above mentioned residues were not randomized in the original TCL14 design, they could be included in subsequent library designs to provide additional diversity for de novo selection or for example for an affinity maturation library on a select TCL14 target specific hit.

Subsequent to the production of TCL14, 3 additional Tencon libraries of similar design were produced. These two libraries, TCL19, TCL21 and TCL23, are randomized at the same positions as TCL14 (see above) however the distribution of amino acids occurring at these positions is altered (Table 3). TCL19 and TCL21 were designed to include an equal distribution of 18 natural amino acids at every position (5.55% of each), excluding only cysteine and methionine. TCL23 was designed such that each randomized position approximates the amino acid distribution found in the HCDR3 loops of functional antibodies (Birtalan et al., J. Mol. Biol. 377: 1518-1528, 2008) as described in Table 3. As with the TCL21 library, cysteine and methionine were excluded.

A third additional library was built to expand potential target binding surface of the other libraries library. In this library, TCL24, 4 additional Tencon positions were randomized as compared to libraries TCL14, TCL19, TCL21, and TCL23. These positions include N46 and T48 from the D strand and S84 and I86 from the G strand. Positions 46, 48, 84, and 86 were chosen in particular as the side chains of these residues are surface exposed from beta-strands D and G and lie structurally adjacent to the randomized portions of the C and F strand, thus increasing the surface area accessible for binding to target proteins. The amino acid distribution used at each position for TCL24 is identical to that described for TCL19 and TCL21 in Table 3.

```
TCL24 Library
                                    (SEQ ID NO: 8)
LPAPKNLVVSRVTEDSARLSWTAPDAAFDSFX₁IX₂YX₃EX₄X₅X₆X₇

GEAIX₈LX₉VPGSERSYDLTGLKPGTEYX₁₀VX₁₁IX₁₂GVKGGX₁₃

X₁₄SX₁₅PLX₁₆AX₁₇FTT;
``` wherein
$X_1$, $X_2$, $X_3$, $X_4$, $X_5$, $X_6$, $X_{10}$, $X_{11}$, $X_{12}$, $X_{13}$, $X_{14}$, $X_{15}$, $X_{16}$ and $X_{17}$ are A, D, E, F, G, H, I, K, L, N, P, Q, R, S, T, V, Y or W.

TABLE 3

| Amino acid frequency (%) at each randomized position for TCL21, TCL23, and TCL24. | | | | |
|---|---|---|---|---|
| Amino Acid | TCL19 | TCL21 | TCL23 | TCL24 |
| Ala | 5.6 | 5.6 | 6.0 | 5.6 |
| Arg | 5.6 | 5.6 | 6.0 | 5.6 |
| Asn | 5.6 | 5.6 | 3.9 | 5.6 |
| Asp | 5.6 | 5.6 | 7.5 | 5.6 |
| Cys | 0.0 | 0.0 | 0.0 | 0.0 |
| Gln | 5.6 | 5.6 | 1.5 | 5.6 |
| Glu | 5.6 | 5.6 | 2.5 | 5.6 |
| Gly | 5.6 | 5.6 | 15.0 | 5.6 |
| His | 5.6 | 5.6 | 2.3 | 5.6 |
| Ile | 5.6 | 5.6 | 2.5 | 5.6 |
| Leu | 5.6 | 5.6 | 5.0 | 5.6 |
| Lys | 5.6 | 5.6 | 1.5 | 5.6 |
| Met | 0.0 | 0.0 | 0.0 | 0.0 |
| Phe | 5.6 | 5.6 | 2.5 | 5.6 |
| Pro | 5.6 | 5.6 | 4.0 | 5.6 |
| Ser | 5.6 | 5.6 | 10.0 | 5.6 |
| Thr | 5.6 | 5.6 | 4.5 | 5.6 |
| Trp | 5.6 | 5.6 | 4.0 | 5.6 |
| Tyr | 5.6 | 5.6 | 17.3 | 5.6 |
| Val | 5.6 | 5.6 | 4.0 | 5.6 |

Generation of TCL21, TCL23, and TCL24 Libraries

The TCL21 library was generated using Colibra library technology (Isogenica) in order to control amino acid distributions. TCL19, TCL23, and TCL24 gene fragments were generated using Slonomics technology (Morphosys) to control amino acid distributions. PCR was used to amplify each library following initial synthesis followed by ligation to the gene for RepA in order to be used in selections using the CIS-display system (Odegrip et al., Proc. Natl. Acad. Sci. USA 101: 2806-2810, 2004) as described above for the loop libraries.

Example 3: Selection of Fibronectin Type III (FN3) Domains that Bind CD71

Panning and Biochemical Screening

FN3 domains specific for human CD71 were selected via CIS-Display (Odegrip et al 2004) using recombinant biotinylated CD71 extracellular domain (Sino Biologics) with an N-terminal 6His tag. For in vitro transcription and translation (ITT), 3 μg of DNA from FN3 domain libraries TCL18, TCL19, TCL21, TCL23, and TCL24 were used, with unbound library members removed by washing. DNA was eluted from the target protein by heating and amplified by PCR using KOD polymerase for further rounds of panning High affinity binders were isolated by successively lowering the concentration of target CD71 during each round from 400 nM to 100 nM and increasing the washing stringency. Outputs from the fifth round panning were subjected to four additional rounds of off-rate selection. The biotinylated target antigen concentration was reduced from 25 nM in rounds 6 and 7 to 2.5 nM in rounds 8 and 9.

Following panning, genes encoding the selected FN3 domains were amplified by PCR, subcloned into a pET vector modified to include a ligase independent cloning site, and transformed into BL21 (DE3) (Stratagene) cells for soluble expression in *E. coli* using standard molecular biology techniques. A gene sequence encoding a C-terminal poly-histidine tag was added to each FN3 domain to enable purification and detection.

To screen for FN3 domains that specifically bind CD71, streptavidin-coated Maxisorp plates (Nunc catalog 436110) were blocked for 1 hour in Starting Block T20 (Pierce) and then coated with biotinylated CD71 (using same antigen as in panning) or negative controls (an unrelated Fc-fused recombinant protein and human serum albumin) for 1 hour. Plates were rinsed with TBST and diluted lysate was applied to plates for 1 hour. Following additional rinses, wells were treated with HRP-conjugated anti-V5 tag antibody (Abcam, ab1325), for 1 hour and then assayed with POD (Roche, 11582950001). The DNA from FN3 domain lysates with signals at least 10-fold ELISA signal above that of streptavidin controls were sequenced resulting in 23 unique, readable FN3 domain sequences isolated from Round 9 screening (Table 4).

TABLE 4

Summary of Screening Hits

| hCD71 | HSA | huCD71/Fc | SEQ ID |
|---|---|---|---|
| 517840 | 11120 | 46.6 | 33 |
| 310480 | 25920 | 12.0 | 34 |
| 3244640 | 1520 | 2134.6 | 35 |
| 3297120 | 6160 | 535.2 | 36 |
| 1271360 | 2720 | 467.4 | 37 |
| 840480 | 4160 | 202.0 | 38 |
| 506800 | 4160 | 121.8 | 39 |
| 220240 | 2960 | 74.4 | 40 |
| 4267840 | 10080 | 423.4 | 41 |
| 2827520 | 5920 | 477.6 | 42 |
| 1621680 | 8160 | 198.7 | 43 |
| 175760 | 3920 | 44.8 | 44 |
| 1926160 | 2880 | 668.8 | 45 |
| 112560 | 3040 | 37.0 | 46 |
| 264800 | 5200 | 50.9 | 47 |
| 943120 | 2800 | 336.8 | 48 |
| 10915200 | 11520 | 947.5 | 49 |
| 10786240 | 2400 | 4494.3 | 50 |
| 9709680 | 4240 | 2290.0 | 51 |
| 10112800 | 1760 | 5745.9 | 52 |
| 1007840 | 9120 | 110.5 | 53 |
| 6987520 | 6160 | 1134.3 | 54 |
| 11142160 | 7760 | 1435.8 | 55 |
| 11339360 | 7520 | 1507.9 | 56 |
| 1903600 | 16880 | 112.8 | 57 |
| 301680 | 4800 | 62.9 | 58 |
| 1946880 | 3200 | 608.4 | 59 |
| 4479040 | 6480 | 691.21 | 60 |
| 4900320 | 10640 | 460.56 | 61 |

Size Exclusion Chromatography Analysis

Size exclusion chromatography was used to determine the aggregation state of anti-CD71 FN3 domains Aliquots (10 µL) of each purified FN3 domain were injected onto a Superdex 75 5/150 column (GE Healthcare) at a flow rate of 0.3 mL/min in a mobile phase of PBS pH 7.4. Elution from the column was monitored by absorbance at 280 nm. Tencon protein was included in each run as a control. Agilent ChemStation software was used to analyze the elution profiles. Selected SEC parameters for the 18 identified FN3 domains are listed in Table 5.

TABLE 5

Summary of Size Exclusion Chromatography Analysis

| SEQ ID | RT (min) | Height (mAU) | Y/N |
|---|---|---|---|
| 33 | 5.616 | 21578 | Y |
| 34 | 5.729 | 19210 | Y |
| 35 | 5.818 | 36983 | Y |
| 36 | 6.008 | 59654 | Y |
| 37 | 5.486 | 33495 | Y |
| 38 | 5.608 | 32759 | Y |
| 39 | 6.508 | 40533 | Y |
| 40 | 6.043 | 42995 | Y |
| 41 | 6.535 | 12055 | N |
| 42 | 6.243 | 114847 | Y |
| 43 | 6.736 | 64318 | Y |
| 44 | 6.389 | 33849 | Y |
| 45 | 6.196 | 16535 | Y |
| 46 | 5.962 | 56696 | Y |
| 47 | 6.799 | 61095 | Y |
| 48 | 5.405 | 24438 | Y |
| 49 | 6.149 | 118941 | Y |
| 50 | 6.496 | 122793 | Y |
| 51 | 7.729 | 17618 | N |
| 52 | 6.316 | 87040 | Y |
| 53 | 6.118 | 87022 | Y |
| 54 | 5.972 | 34366 | Y |
| 55 | 6.06 | 35099 | Y |
| 56 | 5.496 | 28177 | Y |
| 57 | 6.175 | 13973 | Y |
| 58 | 5.862 | 45603 | Y |
| 59 | 5.589 | 85517 | Y |
| 60 | 5.671 | 8.6 | Y |
| 61 | 5.752 | 8.9 | Y |

High-Throughput Expression and Conjugation

Clones identified were grown in duplicate 5 mL cultures in 24 well deep block plates. Briefly, 5 mL/well of TB media supplemented with 50 µg/mL Kanamycin was seeded with 150 µL of overnight culture and grown for about 3 hours at 37° C. with shaking at 220 rpm (OD600~1). Cultures were induced with IPTG to a final concentration of 1 mM for an additional 4 hours at 37° C., 220 rpm. Bacterial pellets were recovered by centrifugation at 2250×g for 15 minutes. 600 µL/well BugBuster HT (Novagen) supplemented with lysozyme (Sigma) at 0.2 mg/mL was added to each well; pellets were dissociated by pipette and then shaken vigorously on a platform shake for about 30 minutes until pellets were lysed. Plates were spun at 2250×g for 15 minutes to clarify lysates and the 2 600-µL aliquots for each sample were combined. His-tagged FN3 domains were purified on His Trap plates (GE) according to the manufacturer's instructions followed by buffer exchange into TBS using Zeba Spin 7K desalt plates (Thermo Scientific). Protein concentrations were assessed by Nanodrop. For conjugation to GlyGly-VC-MMAF, FN3 domain (30 µM) was mixed with 150 µM GlyGlyVC-MMAF (Concortis) and 1 µM Sortase A in a total volume of 200 µL. Conjugations were allowed to proceed for 1.5 hours at room temperature and purified again using a 96 well His Multitrap HP plate from GE Healthcare according to the manufacturer's instructions. Buffer exchange into PBS was achieved using Zeba desalt plates followed by sterile filtering using Multiscreen HTS GV plates (Durapore) with centrifugation at 3000×g for 2 mins Concentrations were assessed by Nanodrop.

Identification of SK-BR3 Binding FN3 Domains

SK-BR-3 cells are cultured in McCoy's 5a Medium+10% Fetal Bovine Serum. FN3 dilutions are prepared in FACS buffer. 50,000 SK-BR-3 cells are added to each well; media was aspirated after centrifugation and cells are resuspended in 100 μL of FACS buffer containing HiLyte labeled FN3 domains Cells are incubated for 2 hours at 37° C., 5% CO2. Cells are rinsed 3× with FACS buffer and finally resuspended in 100 μL of FACS buffer. Fluorescence is detected by Intellictye. Cell populations are identified by the FSC-SSC dot plot followed by recording of the FL4 MFI. Data are normalized to the average of 8 unstained cells and dose response curves are fit using GraphPad.

Binding of Selected Clones by Dose-Response ELISA

Selected clones are analyzed by ELISA to determine EC50 values for binding. Briefly, Maxisorb plates are coated with streptavidin at 5 μg/ml overnight at 4 C. Plates were then blocked with StartingBlock (ThermoFisher) at room temperature for 1 hour and then washed with TBS-Tween. Biotinylated CD71 (2 μg/ml) was captured onto the streptavidin plates and serially diluted Centyrins were added to appropriate wells for 1 hour at room temperature. After washing, bound Centyrin was detected with anti-V5 tag antibody, which is conjugated to HRP and POD substrate and a luminescence plate reader. Luminescence values are plotted as a function of concentration and fit to a dose response using PRISM to determine EC50 values for binding.

Identification of internalizing FN3 domains via toxin conjugates. The FN3 domains were conjugated to the cytotoxic tubulin inhibitor momomethyl auristatin F (MMAF) via an enzyme-cleavable Val-Cit linker or a non-cleavable PEG4 linker (VC-MMAF) using the methodology described for the NEM conjugation. Cell killing was assessed by measuring viability of the SKBR-3 cells following exposure to the cysteine variant-cytotoxin conjugates. Cells are plated in white-well, opaque bottomed, tissue culture-treated plates (Fisher, PI15042) at 3000/well in 50 μL/well of phenol red RPMI media (Gibco, 11875093) with 10% fetal bovine serum (Gibco). Cells are allowed to attach overnight at 37° C. in a humidified 5% CO2 atmosphere. Cells are treated with 25 uL of fresh media and 25 uL of 4× inhibitor made up in fresh media. Cell viability is determined by an endpoint assay with Cell TiterGlo (Promega) at 72 hours. IC50 values are determined by fitting data to the equation for a sigmoidal dose response with variable slope using GraphPad Prism (GraphPad Software). The results are illustrated in Table 6 and demonstrate that the FN3 domains that bind to CD71 were internalized and cytotoxic.

TABLE 6

IC50 of CD71 FN3- MMAF conjugate molecules in SKBR-3 Cells

| SEQ ID | IC50 (nM) |
|---|---|
| 33 | 3.27 |
| 34 | 0.37 |
| 35 | 2.5 |
| 36 | 7.1 |
| 37 | 0.15 |
| 38 | 3.82 |
| 39 | 0.52 |
| 40 | 3 |
| 41 | 4.7 |
| 42 | 0.19 |
| 43 | 0.069 |
| 44 | 2.5 |
| 45 | 8.3 |
| 46 | 2.69 |
| 47 | 5.9 |
| 48 | 0.42 |
| 49 | 3 |
| 50 | 3.1 |
| 51 | 4.9 |
| 52 | 6.3 |
| 53 | 0.07 |
| 54 | 0.4 |
| 55 | 0.026 |
| 56 | 0.24 |
| 57 | 3.13 |
| 58 | 7.7 |
| 59 | 4 |
| 60 | 0.45 |
| 61 | 1.93 |

Bivalent FN3 Protein

A bivalent FN3 protein is produced using two FN3 domains connected by a 4 repeat G/S linker. The bivalent FN3 protein is conjugated to VC-MMAF as described and assessed for cytotoxicity in SK-BR3 cells. The IC50 value for bivalent molecule is found to be better.

Competition for Transferrin Binding and Internalization

FN3 domain VCMMAF conjugates were screened for competition with human transferrin using the cytotoxicity assay described above. FN3 domains were screened in the absence or presence of 0.6 uM holo-human transferrin (T0665-100MG). The IC50 values for FN3 domain toxin conjugates on SK-BR3 cells screened in the absence or presence of competitor are shown in Table 7.

TABLE 7

IC50 of CD71 FN3 domain - MMAF conjugate molecules on SKBR-3 cells +/− human transferrin

| | IC50 (nM) | |
|---|---|---|
| SEQ ID | huTf competitor | no competitor |
| 33 | ~200 | 4.4 |
| 34 | 195.9 | 1.3 |
| 35 | 41.5 | 0.7 |
| 37 | 142.8 | 0.7 |
| 38 | ~120 | 4 |
| 39 | 31.1 | 1.2 |
| 40 | ~100 | 2.2 |
| 41 | 0.5 | 0.01 |
| 42 | ~70 | 2.4 |
| 43 | ~80 | 0.97 |
| 45 | 0.9 | 0.05 |
| 46 | ~100 | 3 |
| 47 | ~85 | 1.6 |
| 48 | ~70 | 1.3 |
| 53 | ~90 | 3.6 |
| 54 | 5 | 0.13 |
| 55 | 5.5 | 0.15 |
| 56 | 14.7 | 0.35 |
| 57 | 5.3 | 0.38 |

TABLE 7-continued

IC50 of CD71 FN3 domain - MMAF conjugate molecules on SKBR-3 cells +/− human transferrin

| SEQ ID | IC50 (nM) | |
|---|---|---|
| | huTf competitor | no competitor |
| 60 | 14.4 | 0.21 |
| 62 | 0.60 | >0.005 |

```
SEQ ID NO: 1 = Original Tencon Sequence
LPAPKNLVVSEVTEDSLRLSWTAPDAAFDSFLIQYQESEKVGEAIN
LTVPGSERSYDLTGLKPGTEYTVSIYGVKGGHRSNPLSAEFTT SEQ ID NO: 2 = TCL1 library
LPAPKNLVVSEVTEDSLRLSWTAPDAAFDSFLIQYQESEKVGEAINL
TVPGSERSYDLTGLKPGTEYTVSIYGV(X)₇₋₁₂PLSAEFTT;
``` wherein
$X_1, X_2, X_3, X_4, X_5, X_6, X_7$ is any amino acid; and
$X_8, X_9, X_{10}, X_{11}$ and $X_{12}$ are any amino acid or deleted

```
SEQ ID NO: 3 = TCL2 library
LPAPKNLVVSEVTEDSLRLSWX₁X₂X₃X₄X₅X₆X₇X₈SFLIQYQESEK
VGEAINLTVPGSERSYDLTGLKPGTEYTVSIYGVX₉X₁₀X₁₁X₁₂X₁₃
SX₁₄X₁₅LSAEFTT;
``` wherein
$X_1$ is Ala, Arg, Asn, Asp, Glu, Gln, Gly, His, Ile, Leu, Lys, Phe, Pro, Ser, Thr, Trp, Tyr or Val;
$X_2$ is Ala, Arg, Asn, Asp, Glu, Gln, Gly, His, Ile, Leu, Lys, Phe, Pro, Ser, Thr, Trp, Tyr or Val;
$X_3$ Ala, Arg, Asn, Asp, Glu, Gln, Gly, His, Ile, Leu, Lys, Phe, Pro, Ser, Thr, Trp, Tyr or Val;
$X_4$ is Ala, Arg, Asn, Asp, Glu, Gln, Gly, His, Ile, Leu, Lys, Phe, Pro, Ser, Thr, Trp, Tyr or Val;
$X_5$ is Ala, Arg, Asn, Asp, Glu, Gln, Gly, His, Ile, Leu, Lys, Phe, Pro, Ser, Thr, Trp, Tyr or Val;
$X_6$ is Ala, Arg, Asn, Asp, Glu, Gln, Gly, His, Ile, Leu, Lys, Phe, Pro, Ser, Thr, Trp, Tyr or Val;
$X_7$ is Phe, Ile, Leu, Val or Tyr;
$X_8$ is Asp, Glu or Thr;
$X_9$ is Ala, Arg, Asn, Asp, Glu, Gln, Gly, His, Ile, Leu, Lys, Phe, Pro, Ser, Thr, Trp, Tyr or Val;
$X_{10}$ is Ala, Arg, Asn, Asp, Glu, Gln, Gly, His, Ile, Leu, Lys, Phe, Pro, Ser, Thr, Trp, Tyr or Val;
$X_{11}$ is Ala, Arg, Asn, Asp, Glu, Gln, Gly, His, Ile, Leu, Lys, Phe, Pro, Ser, Thr, Trp, Tyr or Val;
$X_{12}$ is Ala, Arg, Asn, Asp, Glu, Gln, Gly, His, Ile, Leu, Lys, Phe, Pro, Ser, Thr, Trp, Tyr or Val;
$X_{13}$ is Ala, Arg, Asn, Asp, Glu, Gln, Gly, His, Ile, Leu, Lys, Phe, Pro, Ser, Thr, Trp, Tyr or Val;
$X_{14}$ is Ala, Arg, Asn, Asp, Glu, Gln, Gly, His, Ile, Leu, Lys, Phe, Pro, Ser, Thr, Trp, Tyr or Val; and
$X_{15}$ is Ala, Arg, Asn, Asp, Glu, Gln, Gly, His, Ile, Leu, Lys, Phe, Pro, Ser, Thr, Trp, Tyr or Val.

```
SEQ ID NO: 4 = Stabilized Tencon
LPAPKNLVVSRVTEDSARLSWTAPDAAFDSFLIQYQESEKVGEAIV
LTVPGSERSYDLTGLKPGTEYTVSIYGVKGGHRSNPLSAIFTT SEQ ID NO: 5 = TCL7 (FG and BC loops)
LPAPKNLVVSRVTEDSARLSWX₁X₂X₃X₄X₅X₆X₇X₈X₉FDSFLIQYQE
SEKVGEAIVLTVPGSERSYDLTGLKPGTEYTVSIYGVX₁₀X₁₁X₁₂X₁₃
X₁₄X₁₅X₁₆X₁₇X₁₈X₁₉SNPLSAIFTT;
``` wherein
$X_1, X_2, X_3, X_4, X_5, X_6, X_{10}, X_{11}, X_{12}, X_{13}, X_{14}, X_{15}$ and $X_{16}$ are A, D, E, F, G, H, I, K, L, N, P, Q, R, S, T, V, W or Y; and
$X_7, X_8, X_9, X_{17}, X_{18}$ and $X_{19}$, are A, D, E, F, G, H, I, K, L, N, P, Q, R, S, T, V, W, Y or deleted

```
SEQ ID NO: 6 = TCL9 (FG loop)
LPAPKNLVVSRVTEDSARLSWTAPDAAFDSFLIQYQESEKVGEAIVL
TVPGSERSYDLTGLKPGTEYTVSIYGVX₁X₂X₃X₄X₅X₆X₇X₈X₉X₁₀X₁₁
X₁₂SNPLSAIFTT;
``` wherein
$X_1, X_2, X_3, X_4, X_5, X_6$ and $X_7$, is A, D, E, F, G, H, I, K, L, N, P, Q, R, S, T, V, W or Y; and
$X_8, X_9, X_{10}, X_{11}$ and $X_{12}$ is A, D, E, F, G, H, I, K, L, N, P, Q, R, S, T, V, W, Y or deleted.

```
TCL14 library                               (SEQ ID NO: 7)
LPAPKNLVVSRVTEDSARLSWTAPDAAFDSFX₁IX₂YX₃EX₄X₅X₆X₇
GEAIVLTVPGSERSYDLTGLKPGTEYX₈VX₉IX₁₀GVKGGX₁₁X₁₂S
X₁₃PLSAIFTT;
``` wherein
$X_1, X_2, X_3, X_4, X_5, X_6, X_7, X_8, X_9, X_{10}, X_{11}, X_{12}$ and $X_{13}$ are A, D, E, F, G, H, I, K, L, N, P, Q, R, S, T, V, W, Y, C or M.

```
TCL24 Library                               (SEQ ID NO: 8)
LPAPKNLVVSRVTEDSARLSWTAPDAAFDSFX₁IX₂YX₃EX₄X₅X₆X₇
GEAIX₈LX₉VPGSERSYDLTGLKPGTEYX₁₀VX₁₁IX₁₂GVKGGX₁₃
X₁₄SX₁₅PLX₁₆AX₁₇FTT;
``` wherein
$X_1, X_2, X_3, X_4, X_5, X_6, X_{10}, X_{11}, X_{12}, X_{13}, X_{14}, X_{15}, X_{16}$ and $X_{17}$ are A, D, E, F, G, H, I, K, L, N, P, Q, R, S, T, V, Y or W.

```
SEQ ID NO: 9 = Sloning-FOR
GT GACACGGCGGTTAGAAC

SEQ ID NO: 10 = Sloning-REV
GCCTTTGGGAAGCTTCTAAG

SEQ ID NO: 11 = POP2250
CGGCGGTTAGAACGCGGCTACAATTAATAC

SEQ ID NO: 12 = DigLigRev
CATGATTACGCCAAGCTCAGAA
SEQ ID NO: 13 = BC9
GTGACACGGCGGTTAGAACGCGGCTACAATTAATACATAACCCCAT
CCCCCTGTTGACAATTAATCATCGGCTCGTATAATGTGTGGAATTG
TGAGCGGATAACAATTTCACACAGGAAACAGGATCTACCATGCTGC
CGGCGCCGAAAAACCTGGTTGTTTCTGAAGTTACCGAAGACTCTCT
```

GCGTCTGTCTTGGNNNNNNNNNNNNNNNNNNNNNNNNNTTYGAC

TCTTTCCTGATCCAGTACCAGGAATCTGAAAAAGTTGGTGAAGCGA

TCAACCTGACCGTTCCGGGTTCTGAACGTTCTTACGACCTGACCGG

TCTGAAACCGGGTACCGAATACACCGTTTCTATCTACGGTGTTCT

TAGAAGCTTCCCAAAGGC (wherein N is any base)
SEQ ID NO: 14 = BC8
GTGACACGGCGGTTAGAACGCGGCTACAATTAATACATAACCCCAT

CCCCCTGTTGACAATTAATCATCGGCTCGTATAATGTGTGGAATTG

TGAGCGGATAACAATTTCACACAGGAAACAGGATCTACCATGCTGC

CGGCGCCGAAAAACCTGGTTGTTTCTGAAGTTACCGAAGACTCTCT

GCGTCTGTCTTGGNNNNNNNNNNNNNNNNNNNNNNNTTYGACTCT

TTCCTGATCCAGTACCAGGAATCTGAAAAAGTTGGTGAAGCGATCA

ACCTGACCGTTCCGGGTTCTGAACGTTCTTACGACCTGACCGGTCT

GAAACCGGGTACCGAATACACCGTTTCTATCTACGGTGTTCTTAG

AAGCTTCCCAAAGGC
(wherein N is any base)

SEQ ID NO: 15 = BC7
GTGACACGGCGGTTAGAACGCGGCTACAATTAATACATAACCCCAT

CCCCCTGTTGACAATTAATCATCGGCTCGTATAATGTGTGGAATTG

TGAGCGGATAACAATTTCACACAGGAAACAGGATCTACCATGCTGC

CGGCGCCGAAAAACCTGGTTGTTTCTGAAGTTACCGAAGACTCTCT

GCGTCTGTCTTGGNNNNNNNNNNNNNNNNNNNNNNNTTYGACTCTTTC

CTGATCCAGTACCAGGAATCTGAAAAAGTTGGTGAAGCGATCAACC

TGACCGTTCCGGGTTCTGAACGTTCTTACGACCTGACCGGTCTGAA

ACCGGGTACCGAATACACCGTTTCTATCTACGGTGTTCTTAGAAGC

TTCCCAAAGGC
(wherein N is any base)

SEQ ID NO: 16 = BC6
GTGACACGGCGGTTAGAACGCGGCTACAATTAATACATAACCCCAT

CCCCCTGTTGACAATTAATCATCGGCTCGTATAATGTGTGGAATTG

TGAGCGGATAACAATTTCACACAGGAAACAGGATCTACCATGCTGC

CGGCGCCGAAAAACCTGGTTGTTTCTGAAGTTACCGAAGACTCTCT

GCGTCTGTCTTGGNNNNNNNNNNNNNNNNNNNNNNNTTYGACTCTTTCCTG

ATCCAGTACCAGGAATCTGAAAAAGTTGGTGAAGCGATCAACCTGA

CCGTTCCGGGTTCTGAACGTTCTTACGACCTGACCGGTCTGAAACC

GGGTACCGAATACACCGTTTCTATCTACGGTGTTCTTAGAAGCTTC

CCAAAGGC
(wherein N is any base)

SEQ ID NO: 17 = 130mer-L17A
CGGCGGTTAGAACGCGGCTACAATTAATACATAACCCCATCCCCCT

GTTGACAATTAATCATCGGCTCGTATAATGTGTGGAATTGTGAGCG

GATAACAATTTCACACAGGAAACAGGATCTACCATGCTG

SEQ ID NO: 18 = POP222ext
CGG CGG TTA GAA CGC GGC TAC AAT TAA TAC

SEQ ID NO: 19 = LS1114
CCA AGA CAG ACG GGC AGA GTC TTC GGT AAC GCG

AGA AAC AAC CAG GTT TTT CGG CGC CGG CAG CAT

GGT AGA TCC TGT TTC

SEQ ID NO: 20 = L51115
CCG AAG ACT CTG CCC GTC TGT CTT GG

SEQ ID NO: 21 = L51117
CAG TGG TCT CAC GGA TTC CTG GTA CTG GAT CAG

GAA AGA GT GAA

SEQ ID NO: 22 = SDG10
CATGCGGTCTCTTCCGAAAAAGTTGGTGAAGCGATCGTCCTGACCG

TTCCGGGT

SEQ ID NO: 23 = SDG24
GGTGGTGAAGATCGCAGACAGCGGGTTAG

SEQ ID NO: 24 = POP2222
CGGCGGTTAGAACGCGGCTAC

SEQ ID NO: 25 = SDG28
AAGATCAGTTGCGGCCGCTAGACTAGAACCGCTGCCACCGCCGGTG

GTGAAGATCGCAGAC

SEQ ID NO: 26 = FG12
GTGACACGGCGGTTAGAACGCGGCTACAATTAATACATAACCCCAT

CCCCCTGTTGACAATTAATCATCGGCTCGTATAATGTGTGGAATTG

TGAGCGGATAACAATTTCACACAGGAAACAGGATCTACCATGCTGC

CGGCGCCGAAAAACCTGGTTGTTTCTCGCGTTACCGAAGACTCTGC

GCGTCTGTCTTGGACCGCGCCGGACGCGGCGTTCGACTCTTTCCTG

ATCCAGTACCAGGAATCTGAAAAAGTTGGTGAAGCGATCGTGCTGA

CCGTTCCGGGTTCTGAACGTTCTTACGACCTGACCGGTCTGAAACC

GGGTACCGAATACACCGTTTCTATCTACGGTGTTNNNNNNNNNNNN

NNNNNNNNNNNNNNNNNNNNNNNNNTCTAACCCGCTGTCTGCGATCT

TCACCACCGGCGGTCACCATCACCATCACCATGGCAGCGGTTCTAG

TCTAGCGGCCGCAACTGATCTTGGC
(wherein N is any base)

SEQ ID NO: 27 = FG11
GTGACACGGCGGTTAGAACGCGGCTACAATTAATACATAACCCCAT

CCCCCTGTTGACAATTAATCATCGGCTCGTATAATGTGTGGAATTG

TGAGCGGATAACAATTTCACACAGGAAACAGGATCTACCATGCTGC

CGGCGCCGAAAAACCTGGTTGTTTCTCGCGTTACCGAAGACTCTGC

GCGTCTGTCTTGGACCGCGCCGGACGCGGCGTTCGACTCTTTCCTG

ATCCAGTACCAGGAATCTGAAAAAGTTGGTGAAGCGATCGTGCTGA

CCGTTCCGGGTTCTGAACGTTCTTACGACCTGACCGGTCTGAAACC

GGGTACCGAATACACCGTTTCTATCTACGGTGTTNNNNNNNNNNN

NNNNNNNNNNNNNNNNNNNNNTCTAACCCGCTGTCTGCGATCTTCA

SEQ ID NO: 28 = FG10
GTGACACGGCGGTTAGAACGCGGCTACAATTAATACATAACCCCAT

CCCCCTGTTGACAATTAATCATCGGCTCGTATAATGTGTGGAATTG

TGAGCGGATAACAATTTCACACAGGAAACAGGATCTACCATGCTGC

CGGCGCCGAAAAACCTGGTTGTTTCTCGCGTTACCGAAGACTCTGC

GCGTCTGTCTTGGACCGCGCCGGACGCGGCGTTCGACTCTTTCCTG

ATCCAGTACCAGGAATCTGAAAAAGTTGGTGAAGCGATCGTGCTGA

CCGTTCCGGGTTCTGAACGTTCTTACGACCTGACCGGTCTGAAACC

GGGTACCGAATACACCGTTTCTATCTACGGTGTTNNNNNNNNNNNN

NNNNNNNNNNNNNNNNNTCTAACCCGCTGTCTGCGATCTTCACCA

CCGGCGGTCACCATCACCATCACCATGGCAGCGGTTCTAGTCTAGC

GGCCGCAACTGATCTTGGC
(wherein N is any base)

SEQ ID NO: 29 = FG9
GTGACACGGCGGTTAGAACGCGGCTACAATTAATACATAACCCCAT

CCCCCTGTTGACAATTAATCATCGGCTCGTATAATGTGTGGAATTG

TGAGCGGATAACAATTTCACACAGGAAACAGGATCTACCATGCTGC

CGGCGCCGAAAAACCTGGTTGTTTCTCGCGTTACCGAAGACTCTGC

GCGTCTGTCTTGGACCGCGCCGGACGCGGCGTTCGACTCTTTCCTG

ATCCAGTACCAGGAATCTGAAAAAGTTGGTGAAGCGATCGTGCTGA

CCGTTCCGGGTTCTGAACGTTCTTACGACCTGACCGGTCTGAAACC

GGGTACCGAATACACCGTTTCTATCTACGGTGTTNNNNNNNNNNNN

NNNNNNNNNNNNNNNTCTAACCCGCTGTCTGCGATCTTCACCACCG

GCGGTCACCATCACCATCACCATGGCAGCGGTTCTAGTCTAGCGGC

CGCAACTGATCTTGGC
(wherein N is any base)

SEQ ID NO: 30 = FG8
GTGACACGGCGGTTAGAACGCGGCTACAATTAATACATAACCCCAT

CCCCCTGTTGACAATTAATCATCGGCTCGTATAATGTGTGGAATTG

TGAGCGGATAACAATTTCACACAGGAAACAGGATCTACCATGCTGC

CGGCGCCGAAAAACCTGGTTGTTTCTCGCGTTACCGAAGACTCTGC

GCGTCTGTCTTGGACCGCGCCGGACGCGGCGTTCGACTCTTTCCTG

ATCCAGTACCAGGAATCTGAAAAAGTTGGTGAAGCGATCGTGCTGA

CCGTTCCGGGTTCTGAACGTTCTTACGACCTGACCGGTCTGAAACC

GGGTACCGAATACACCGTTTCTATCTACGGTGTTNNNNNNNNNNNN

NNNNNNNNNNNNNNNTCTAACCCGCTGTCTGCGATCTTCACCACCGGCG

GTCACCATCACCATCACCATGGCAGCGGTTCTAGTCTAGCGGCCGC

AACTGATCTTGGC
(wherein N is any base)

SEQ ID NO: 31 = FG7
GTGACACGGCGGTTAGAACGCGGCTACAATTAATACATAACCCCAT

CCCCCTGTTGACAATTAATCATCGGCTCGTATAATGTGTGGAATTG

TGAGCGGATAACAATTTCACACAGGAAACAGGATCTACCATGCTGC

CGGCGCCGAAAAACCTGGTTGTTTCTCGCGTTACCGAAGACTCTGC

GCGTCTGTCTTGGACCGCGCCGGACGCGGCGTTCGACTCTTTCCTG

ATCCAGTACCAGGAATCTGAAAAAGTTGGTGAAGCGATCGTGCTGA

CCGTTCCGGGTTCTGAACGTTCTTACGACCTGACCGGTCTGAAACC

GGGTACCGAATACACCGTTTCTATCTACGGTGTTNNNNNNNNNNNN

NNNNNNNNNNNTCTAACCCGCTGTCTGCGATCTTCACCACCGGCGGTC

ACCATCACCATCACCATGGCAGCGGTTCTAGTCTAGCGGCCGCAACT

GATCTTGGC
(wherein N is any base)

SEQ ID NO: 32 = human mature CD71
MTKEYQDLQHLDNEESDHHQLRKGPPPPQPLLQRLCSGPRLLLLSL

GLSLLLLVVVCVIGSQNSQLQEELRGLRETFSNFTASTEAQVKGLS

TQGGNVGRKMKSLESQLEKQQKDLSEDHSSLLLHVKQFVSDLRSLS

CQMAALQGNGSERTCCPVNWVEHERSCYWFSRSGKAWADADNYCRL

EDAHLVVVTSWEEQKFVQHHIGPVNTWMGLHDQNGPWKWVDGTDYE

TGFKNWRPEQPDDWYGHGLGGGEDCAHFTDDGRWNDDVCQRPYRWV

CETELDKASQEPPLL

SEQ ID NO: 80 = human mature CD71
extracellular domain
QNSQLQEELRGLRETFSNFTASTEAQVKGLSTQGGNVGRKMKSLES

QLEKQQKDLSEDHSSLLLHVKQFVSDLRSLSCQMAALQGNGSERTC

CPVNWVEHERSCYWFSRSGKAWADADNYCRLEDAHLVVVTSWEEQK

FVQHHIGPVNTWMGLHDQNGPWKWVDGTDYETGFKNWRPEQPDDWY

GHGLGGGEDCAHFTDDGRWNDDVCQRPYRWVCETELDKASQEPPLL

| SEQ ID | Amino Acid sequence of FN3 domains that bind to CD71 |
|---|---|
| 33 | MLPAPKNLVVSRVTEDSARLSWTAPDAAFDSFTIQYEELTTVGEA<br>IYLRVPGSERSYDLTGLKPGTEYVVWIEGVKGGLRSNPLGAAFTT |
| 34 | MLPAPKNLVVSRVTEDSARLSWTAPDAAFDSFAITYIEWWDVGEA<br>IGLKVPGSERSYDLTGLKPGTEYRVHIQGVKGGNNSYPLDALFTT |
| 35 | MLPAPKNLVVSRVTEDSARLSWTAPDAAFDSFEIAYFEAIWNGEA<br>IYLTVPGSERSYDLTGLKPGTEYQVEIRGVKGGPTSRPLFAWFTT |
| 36 | MLPAPKNLVVSRVTEDSARLSWTAPDAAFDSFTITYIEWWENGEA<br>IALSVPGSERSYDLTGLKPGTEYQVGIAGVKGGYKSYPLWALFTT |
| 37 | MLPAPKNLVVSRVTEDSARLSWTAPDAAFDSHIIYTEEEKEGEA<br>IYLRVPGSERSYDLTGLKPGTEYLVEIEGVKGGKRSVPLNASFTT |
| 38 | MLPAPKNLVVSRVTEDSARLSWTAPDAAFDSFHIAYEESHTTGEA<br>IFLRVPGSERSYDLTGLKPGTEYSVSIEGVKGGHYSPPLTAKFTT |
| 39 | MLPAPKNLVVSRVTEDSARLSWTAPDAAFDSFDIDYREWWTLGEA<br>IVLTVPGSERSYDLTGLKPGTEYYVNIQGVKGGLRSYPLSAIFTT |
| 40 | MLPAPKNLVVSRVTEDSARLSWTAPDAAFDSFVIEYWEYVGHGEA<br>IVLTVPGSERSYDLTGLKPGTEYSVGIYGVKGGSLSRPLSAIFTT |

-continued

| SEQ ID | Amino Acid sequence of FN3 domains that bind to CD71 |
|---|---|
| 41 | MLPAPKNLVISRVTEDSARLSWTAPDAAFDSFFIYYIESYPAGEA IVLTVPGSERSYDLTGLKPGTEYWVGIDGVKGGRWSTPLSAIFTT |
| 42 | MLPAPKNLVVSRVTEDSARLSWTAPDAAFDSFTIEYYESFYGGEA IVLTVPGSERSYDLTGLKPGTEYYVSIYGVKGGWLSRPLSAIFTT |
| 43 | MLPAPKNLVVSRVTEDSARLSWTAPDAAFDSFYIEYYESYPGGEA IVLTVPGSERSYDLTGLKPGTEYDVYIYGVKGGYWSRPLSAIFTT |
| 44 | MLPAPKNLVVSRVTEDSARLSWTAPDAAFDSFYIEYYESLPDGEA IVLTVPGSERSYDLTGLKPGTEYAVYIYGVKGGYYSRPLSAIFTT |
| 45 | MLPAPKNLVVSRVTEDSARLSWTAPDAAFDSFAIYYLESYPEGEA IVLTVPGSERSYDLTGLKPGTEYWVGIDGVKGGTWSSPLSAIFTT |
| 46 | MLPAPKNLVVSRVTEDSARLSWTAPDAAFDSFTIEYFEFTGTGEA IVLTVPGSERSYDLTGLKPGTEYYVSIYGVKGGLLSAPLSAIFTT |
| 47 | MLPAPKNLVVSRVTEDSARLSWTAPDAAFDSFTIWYAEALGDGEA IVLTVPGSERSYDLTGLKPGTEYFVDIYGVKGGFWSLPLSAIFTT |
| 48 | MLPAPKNLVVSRVTEDSARLSWTAPDAAFDSFVIEYFEQFNLGEA IVLTVPGSERSYDLTGLKPGTEYWVGIYGVKGGWLSHPLSAIFTT |
| 49 | MLPAPKNLVVSRVTEDSARLSWTAPDAAFDSFGISYLEWWEDGEA IVLTVPGSERSYDLTGLKPGTEYWVSIAGVKGGKRSYPLSAIFTT |
| 50 | MLPAPKNLVVSRVTEDSARLSWTAPDAAFDSFVIEYREGAWYGEA IVLTVPGSERSYDLTGLKPGTEYFVDITGVKGGWWSDPLSAIFTT |
| 51 | MLPAPKNLVVSRVTEDSARLSWTAPDAAFDSFFIKYIEWWADGEA IVLTVPGSERSYDLTGLKPGTEYLVEIYGVKGGKWSWPLSAIFTT |
| 52 | MLPAPKNLVVSRVTEDSARLSWTAPDAAFDSFKISYQEWWEDGEA IVLTVPGSERSYDLTGLKPGTEYWVNISGVKGGVQSYPLSAIFTT |
| 53 | MLPAPKNLVVSRVTEDSARLSWTAPDAAFDSFFISYIEWWDLGEA IVLTVPGSERSYDLTGLKPGTEYHVEIFGVKGGTQSYPLSAIFTT |
| 54 | MLPAPKNLVVSRVTEDSARLSWTAPDAAFDSFQILYQENAFEGEA IVLTVPGSERSYDLTGLKPGTEYWVYIYGVKGGYPSVPLSAIFTT |
| 55 | MLPAPKNLVVSRVTEDSARLSWTAPDAAFDSFIIEYWEFVGYEAG IVLTVPGSERSYDLTGLKPGTEYWVAIYGVKGGDLSKPLSAIFTT |
| 56 | MLPAPKNLVVSRVTEDSARLSWTAPDAAFDSFVIEYFEALEGGEA IVLTVPGSERSYDLTGLKPGTEYFVGIYGVKGGPLSKPLSAIFTT |
| 57 | MLPAPKNLVVSRVTEDSARLSWTAPDAAFDSFSIKYLEWWQDGEA IVLTVPGSERSYDLTGLKPGTEYYVHIAGVKGGYRSYPLSAIFTT |
| 58 | MLPAPKNLVVSRVTEDSARLSWTAPDAAFDSFTIWYAEADGWGEA IVLTVPGSERSYDLTGLKPGTEYFVDIYGVKGGYLSVPLSAIFTT |
| 59 | MLPAPKNLVVSRVTEDSARLSWTAPDAAFDSFTIWYAEWEDEGEA IVLTVPGSERSYDLTGLKPGTEYRVEIYGVKGGYPSKPLSAIFTT |
| 60 | MLPAPKNLVVSRVTEDSARLSWTAPDAAFDSFTIWYAEAIGHGEA IVLTVPGSERSYDLTGLKPGTEYWVDIWGVKGGQQSKPLSAIFTT |
| 61 | MLPAPKNLVVSRVTEDSARLSWRVESRTFDSFLIQYQESEKVGEA IVLTVPGSERSYDLTGLKPGTEYTVSIYGVVWDTRDNPISNPLSA IFTT |
| 62 | MLPAPKNLVVSRVTEDSARLSWTAPDAAFDSFPILYLELNHHGEE IVLTVPGSERSYDLTGLKPGTEYWVYIFGVKGGMYSAPLSAIFTT GG |

Example 4: Selection of Fibronectin Type III (FN3) Domains that Bind CD71

Panning and Biochemical Screening Methods for Identifying FN3 domains that bind to CD71 that do not inhibit transferrin binding to CD71. To screen for FN3 domains that specifically bind CD71 and do not inhibit transferring binding to CD71, streptavidin-coated Maxisorp plates (Nunc catalog 436110) are blocked for 1 hour in Starting Block T20 (Pierce) and then are coated with biotinylated CD71 (using same antigen as in panning) or negative controls (an unrelated Fc-fused recombinant protein and human serum albumin) for 1 hour in the presence of transferring or with FN3 protein that binds to the CD71 transferrin binding site. The concentration of transferrin is up to 35 μM. Without being bound to any particular theory, the inclusion of the transferrin or the FN3 protein that binds to the CD71 transferrin binding site pushes the selection of the FN3 domains to those that do not compete or inhibit with transferrin binding to CD71. Plates are rinsed with TBST and diluted lysate is applied to plates for 1 hour. Following additional rinses, wells are treated with HRP-conjugated anti-V5 tag antibody (Abcam, ab1325), for 1 hour and then are assayed with POD (Roche, 11582950001). The DNA from FN3 domain lysates with signals at least 10-fold ELISA signal above that of streptavidin controls are sequenced resulting in FN3 domain sequences isolated from the screening.

Example 5: Selection of Fibronectin Type III (FN3) Domains that Bind CD71 and are not Competitive with Transferrin To identify CD71 binding FN3 domains that were either not competitive or minimally competitive with transferrin a biased CIS-display strategy was designed. In short, using the output recovered after 5 rounds of panning on the ECD of human CD71 (Example 3). Additional rounds of off-rate selection were performed as described in Example 3 with the addition of either 1) a wash step with human holo transferrin to elute Centyrins that bound at the same site as transferrin before the final elution step or 2) elution of FN3 domain binders with monoclonal antibody OKT9. FN3 domains recovered from the transferrin wash strategy and the OKT9 elution strategy were PCR amplified and cloned into pET vector as previously described (Example 3). 228 FN3 domains that specifically bound huCD71 were confirmed by ELISA for binding to huCD71 ECD (Table 8). A subset of the unique binders was analyzed by SEC (Table 9), conjugated to MMAF and assessed for internalization via cell viability assay in SKBR-3 cells +/−holo human transferrin (Table 10). The polypeptides were found to be internalized by the receptor. The data and sequences of the hits are identified in the following tables.

TABLE 8

Summary of Screening Hits

| hCD71 | HSA | hCD71:HSA | SEQ ID NO: |
|---|---|---|---|
| 536550 | 28550 | 19 | 81 |
| 3525900 | 18900 | 187 | 82 |
| 1926800 | 1300 | 1482 | 83 |
| 1728500 | 3850 | 449 | 84 |
| 2912250 | 2500 | 1165 | 85 |
| 3387400 | 2250 | 1506 | 86 |
| 2833200 | 1100 | 2576 | 87 |
| 708250 | 6000 | 118 | 88 |
| 3444800 | 2000 | 1722 | 89 |
| 1093700 | 2550 | 429 | 90 |
| 1440400 | 1800 | 800 | 91 |
| 3845200 | 1300 | 2958 | 92 |
| 2162550 | 1650 | 1311 | 93 |
| 439050 | 9900 | 44 | 94 |
| 4206300 | 1900 | 2214 | 95 |

TABLE 8-continued

Summary of Screening Hits

| hCD71 | HSA | hCD71:HSA | SEQ ID NO: |
|---|---|---|---|
| 2714300 | 1500 | 1810 | 96 |
| 2405750 | 2200 | 1094 | 97 |
| 1159200 | 15500 | 75 | 98 |
| 853050 | 8150 | 105 | 99 |
| 2954050 | 2350 | 1257 | 100 |
| 1965650 | 9100 | 216 | 101 |
| 3476400 | 13450 | 258 | 102 |
| 4828150 | 1200 | 4023 | 103 |
| 3575700 | 1700 | 2103 | 104 |
| 1758350 | 1400 | 1256 | 105 |
| 593650 | 1200 | 495 | 106 |
| 419800 | 4050 | 104 | 107 |
| 3189250 | 1300 | 2453 | 108 |
| 4831750 | 1250 | 3865 | 109 |
| 1680700 | 18850 | 89 | 110 |
| 2399600 | 7450 | 322 | 111 |
| 3652100 | 7100 | 514 | 112 |
| 2138900 | 22550 | 95 | 113 |
| 3274950 | 4200 | 780 | 114 |
| 2917250 | 3450 | 846 | 115 |
| 536350 | 1500 | 358 | 116 |
| 1498750 | 23500 | 64 | 117 |
| 2244850 | 18850 | 119 | 118 |
| 3156200 | 1850 | 1706 | 119 |
| 3636800 | 1850 | 1966 | 120 |
| 2372350 | 28600 | 83 | 121 |
| 2305100 | 29550 | 78 | 122 |
| 707200 | 3100 | 228 | 123 |
| 605100 | 3450 | 175 | 124 |
| 2329300 | 1050 | 2218 | 125 |
| 4494550 | 1750 | 2568 | 126 |
| 3556050 | 93300 | 38 | 127 |
| 663600 | 3250 | 204 | 128 |
| 2311100 | 1500 | 1541 | 129 |
| 1446000 | 6050 | 239 | 130 |
| 2183100 | 2400 | 910 | 131 |
| 2747200 | 2350 | 1169 | 132 |
| 4277350 | 5000 | 855 | 133 |
| 3080150 | 1950 | 1580 | 134 |
| 2056200 | 1500 | 1371 | 135 |
| 4026050 | 5700 | 706 | 136 |
| 484350 | 2050 | 236 | 137 |
| 4178200 | 3500 | 1194 | 138 |
| 3034550 | 2100 | 1445 | 139 |
| 4175400 | 1600 | 2610 | 140 |
| 2041000 | 3150 | 648 | 141 |
| 3413400 | 3400 | 1004 | 142 |
| 3940800 | 9250 | 426 | 143 |
| 2711900 | 2750 | 986 | 144 |
| 1615500 | 48450 | 33 | 145 |
| 3074850 | 3800 | 809 | 146 |
| 2363750 | 71250 | 33 | 147 |
| 3976550 | 2000 | 1988 | 148 |
| 2768350 | 3350 | 826 | 149 |
| 2617600 | 3500 | 748 | 150 |
| 1770200 | 54950 | 32 | 151 |
| 2831150 | 5300 | 534 | 152 |
| 956700 | 13100 | 73 | 153 |
| 2779300 | 4150 | 670 | 154 |
| 1837850 | 25950 | 71 | 155 |
| 1028500 | 5000 | 206 | 156 |
| 2657950 | 2450 | 1085 | 157 |
| 2055750 | 1350 | 1523 | 158 |
| 2581000 | 1950 | 1324 | 159 |
| 2759200 | 3300 | 836 | 160 |
| 1214400 | 5050 | 240 | 161 |
| 3876250 | 1850 | 2095 | 162 |
| 3047800 | 4400 | 693 | 163 |
| 2605000 | 1100 | 2368 | 164 |
| 2642300 | 65200 | 41 | 165 |
| 2421600 | 5050 | 480 | 166 |
| 2618650 | 3600 | 727 | 167 |
| 2896650 | 1950 | 1485 | 168 |
| 2853900 | 2700 | 1057 | 169 |
| 981650 | 16800 | 58 | 170 |
| 3720500 | 1900 | 1958 | 171 |
| 4309800 | 3700 | 1165 | 172 |
| 979050 | 20850 | 47 | 173 |
| 2422100 | 2200 | 1101 | 174 |
| 3550650 | 1600 | 2219 | 175 |
| 1336350 | 10350 | 129 | 176 |
| 2608650 | 2450 | 1065 | 177 |
| 1447950 | 2250 | 644 | 178 |
| 2684550 | 74700 | 36 | 179 |
| 1678750 | 33500 | 50 | 180 |
| 2945100 | 6000 | 491 | 181 |
| 3116750 | 2950 | 1057 | 182 |
| 1724000 | 10700 | 161 | 183 |
| 470400 | 2000 | 235 | 184 |
| 1809500 | 9950 | 182 | 185 |
| 2024550 | 1850 | 1094 | 186 |
| 3061100 | 7250 | 422 | 187 |
| 2669350 | 3350 | 797 | 188 |
| 1962850 | 67500 | 29 | 189 |
| 3214200 | 4900 | 656 | 190 |
| 1465100 | 33950 | 43 | 191 |
| 2666650 | 4100 | 650 | 192 |
| 3872950 | 2500 | 1549 | 193 |
| 562350 | 17800 | 32 | 194 |
| 2532200 | 90200 | 28 | 195 |
| 1719750 | 34550 | 50 | 196 |
| 4566550 | 18900 | 242 | 197 |
| 3441600 | 3050 | 1128 | 198 |
| 1461350 | 14450 | 101 | 199 |
| 3626550 | 2100 | 1727 | 200 |
| 1197600 | 11350 | 106 | 201 |
| 4503050 | 2800 | 1608 | 202 |
| 3382850 | 3300 | 1025 | 203 |
| 2766650 | 24550 | 113 | 204 |
| 434050 | 3350 | 130 | 205 |
| 833350 | 2650 | 314 | 206 |
| 1596550 | 25600 | 62 | 207 |
| 2289200 | 46700 | 49 | 208 |
| 790150 | 13750 | 57 | 209 |
| 1156900 | 2250 | 514 | 210 |
| 1001850 | 3000 | 334 | 211 |
| 2490750 | 2250 | 1107 | 212 |
| 2105500 | 9800 | 215 | 213 |
| 2143100 | 2200 | 974 | 214 |
| 2125250 | 1750 | 1214 | 215 |
| 2192150 | 21800 | 101 | 216 |
| 3902700 | 11750 | 332 | 217 |
| 2388200 | 33800 | 71 | 218 |
| 3307550 | 2600 | 1272 | 219 |
| 4247800 | 9400 | 452 | 220 |
| 1959700 | 3650 | 537 | 221 |
| 1741200 | 3950 | 441 | 222 |
| 1666800 | 51950 | 32 | 223 |
| 2017650 | 16500 | 122 | 224 |
| 2962400 | 14100 | 210 | 225 |
| 4332150 | 2850 | 1520 | 226 |
| 3853700 | 2300 | 1676 | 227 |
| 2542750 | 2400 | 1059 | 228 |
| 570000 | 3700 | 154 | 229 |
| 1998400 | 1900 | 1052 | 230 |
| 2268400 | 26500 | 86 | 231 |
| 1699150 | 2700 | 629 | 232 |
| 3412150 | 2600 | 1312 | 233 |
| 680200 | 7200 | 94 | 234 |
| 3923600 | 1350 | 2906 | 235 |
| 3444750 | 1500 | 2297 | 236 |
| 4148900 | 1850 | 2243 | 237 |
| 2883800 | 4250 | 679 | 238 |
| 418900 | 5050 | 83 | 239 |
| 3033700 | 2050 | 1480 | 240 |
| 2696100 | 2200 | 1226 | 241 |
| 871750 | 4900 | 178 | 242 |
| 2402150 | 10150 | 237 | 243 |
| 545300 | 1650 | 330 | 244 |
| 2617750 | 2900 | 903 | 245 |

TABLE 8-continued

Summary of Screening Hits

| hCD71 | HSA | hCD71:HSA | SEQ ID NO: |
|---|---|---|---|
| 1573350 | 1400 | 1124 | 246 |
| 916150 | 53050 | 17 | 247 |
| 831650 | 15100 | 55 | 248 |
| 1047250 | 7100 | 148 | 249 |
| 1094500 | 18750 | 58 | 250 |
| 2738000 | 9650 | 284 | 251 |
| 2979550 | 2500 | 1192 | 252 |
| 2801100 | 2450 | 1143 | 253 |
| 3243550 | 90000 | 36 | 254 |
| 1835800 | 4550 | 403 | 255 |
| 1978900 | 2200 | 900 | 256 |
| 2374200 | 3950 | 601 | 257 |
| 1041700 | 10600 | 98 | 258 |
| 2443600 | 2100 | 1164 | 259 |
| 1301700 | 14450 | 90 | 260 |
| 4233400 | 5550 | 763 | 261 |
| 4380350 | 2350 | 1864 | 262 |
| 1878900 | 20400 | 92 | 263 |
| 2977200 | 2550 | 1168 | 264 |
| 3606650 | 3950 | 913 | 265 |
| 894150 | 2650 | 337 | 266 |
| 1969550 | 11900 | 166 | 267 |
| 1597000 | 2550 | 626 | 268 |
| 690150 | 4150 | 166 | 269 |
| 1809350 | 2400 | 754 | 270 |
| 2114700 | 3050 | 693 | 271 |
| 1784450 | 8950 | 199 | 272 |
| 4651050 | 9150 | 508 | 273 |
| 522300 | 11900 | 44 | 274 |
| 2245050 | 3800 | 591 | 275 |
| 720100 | 12350 | 58 | 276 |
| 3110300 | 5200 | 598 | 277 |
| 3689600 | 6500 | 568 | 278 |
| 4089350 | 3150 | 1298 | 279 |
| 445950 | 21550 | 21 | 280 |
| 1073150 | 22400 | 48 | 281 |
| 3851150 | 18650 | 206 | 282 |
| 2952800 | 6250 | 472 | 283 |
| 2901100 | 5250 | 553 | 284 |
| 2435900 | 2200 | 1107 | 285 |
| 1270750 | 10750 | 118 | 286 |
| 3882900 | 5500 | 706 | 287 |
| 658700 | 40800 | 16 | 288 |
| 2268450 | 2150 | 1055 | 289 |
| 2810350 | 11850 | 237 | 290 |
| 3829050 | 2150 | 1781 | 291 |
| 2620700 | 8850 | 296 | 292 |
| 3588450 | 6900 | 520 | 293 |
| 1436450 | 8250 | 174 | 294 |
| 3384850 | 3800 | 891 | 295 |
| 2701450 | 3200 | 844 | 296 |
| 2594250 | 52550 | 49 | 297 |
| 2514000 | 34050 | 74 | 298 |
| 4270100 | 2200 | 1941 | 299 |
| 2311150 | 4050 | 571 | 300 |
| 659800 | 12050 | 55 | 301 |
| 2672850 | 21200 | 126 | 302 |
| 3513150 | 2650 | 1326 | 303 |
| 3343900 | 2700 | 1238 | 304 |
| 1207900 | 25000 | 48 | 305 |
| 4068850 | 2250 | 1808 | 306 |
| 2185950 | 4350 | 503 | 307 |
| 608900 | 12300 | 50 | 308 |
| 3142450 | 2850 | 1103 | 309 |

TABLE 9

Summary of Size Exclusion Chromatography Analysis

| SEQ ID NO: | RT (min) | Height (mAU) |
|---|---|---|
| 81 | 5.117 | 14621 |
| 82 | 5.11 | 24062 |
| 83 | 5.114 | 91333 |
| 84 | 5.032 | 65838 |
| 85 | 5.075 | 78484 |
| 86 | 5.149 | 210493 |
| 87 | 5.1 | 77812 |
| 88 | 5.14 | 194249 |
| 89 | 5.006 | 61555 |
| 90 | 5.071 | 177756 |
| 91 | 5.092 | 127220 |
| 92 | 5.217 | 179747 |
| 93 | 5.043 | 35064 |
| 94 | 6.706 | 2222 |
| 95 | 5.112 | 75615 |
| 96 | 5.066 | 71880 |
| 97 | 5.144 | 101200 |
| 98 | 4.561 | 29769 |
| 99 | 3.764 | 3242 |
| 100 | 5.158 | 163566 |
| 101 | 5.049 | 70310 |
| 102 | 5.06 | 48409 |
| 103 | 5.047 | 85919 |
| 104 | 5.04 | 67751 |
| 105 | 5.076 | 79635 |
| 106 | 5.092 | 100250 |
| 107 | 3.755 | 3878 |
| 108 | 5.131 | 109212 |
| 109 | 5.048 | 72864 |
| 110 | 5.037 | 25838 |
| 111 | 5.046 | 82613 |
| 112 | 5.037 | 69662 |
| 113 | 5.06 | 1660 |
| 114 | 5.058 | 93289 |
| 115 | 5.008 | 59386 |
| 116 | 6.701 | 78 |
| 117 | 5.001 | 16853 |
| 119 | 5.026 | 49470 |
| 120 | 5.247 | 131571 |
| 121 | 4.494 | 4134 |
| 122 | 4.576 | 20348 |
| 123 | 4.572 | 16021 |
| 124 | 5.018 | 69849 |
| 125 | 5.007 | 69810 |
| 126 | 5.075 | 64475 |
| 127 | 5.07 | 12214 |
| 128 | 5.107 | 58225 |
| 129 | 5.005 | 122592 |
| 130 | 5.051 | 116931 |
| 131 | 5.073 | 95190 |
| 132 | 5.038 | 106856 |
| 133 | 5.082 | 20172 |
| 134 | 5.118 | 97944 |
| 135 | 5.032 | 97600 |
| 136 | 5.157 | 66595 |
| 137 | 5.032 | 156482 |
| 138 | 5.181 | 124800 |
| 139 | 4.978 | 96486 |
| 140 | 5.024 | 78145 |
| 141 | 5.095 | 115919 |
| 142 | 5.067 | 52467 |
| 143 | 5.042 | 50518 |
| 144 | 5.062 | 82962 |
| 145 | 4.542 | 18503 |
| 146 | 5.031 | 88958 |
| 147 | 4.509 | 8929 |
| 148 | 5.098 | 91401 |
| 149 | 5.055 | 79364 |
| 150 | 4.976 | 57089 |
| 151 | 4.469 | 10958 |
| 152 | 5.017 | 67201 |
| 153 | 5.108 | 89015 |
| 154 | 5.083 | 73990 |
| 155 | 4.57 | 3820 |
| 156 | 5.053 | 125648 |

TABLE 9-continued

Summary of Size Exclusion Chromatography Analysis

| SEQ ID NO: | RT (min) | Height (mAU) |
|---|---|---|
| 157 | 5.131 | 96835 |
| 158 | 4.964 | 86205 |
| 159 | 4.994 | 66919 |
| 160 | 5.11 | 94133 |
| 161 | 5.018 | 103592 |
| 162 | 5.157 | 96072 |
| 163 | 5.049 | 121129 |
| 164 | 5.115 | 79403 |
| 165 | 4.547 | 6562 |
| 166 | 5.023 | 125865 |
| 167 | 4.975 | 63859 |
| 168 | 5.043 | 86853 |
| 169 | 5.017 | 95640 |
| 170 | 5.04 | 54100 |
| 171 | 5.18 | 180492 |
| 172 | 5.229 | 70453 |
| 173 | 3.662 | 17075 |
| 174 | 4.999 | 268853 |
| 175 | 5.044 | 272743 |
| 178 | 5.063 | 40232 |
| 179 | 5.11 | 233798 |
| 180 | 5.028 | 268714 |
| 181 | 5.049 | 175217 |
| 182 | 5.024 | 347191 |
| 183 | 5.161 | 269305 |
| 184 | 4.967 | 236502 |
| 185 | 5.018 | 190752 |
| 186 | 5.081 | 342318 |
| 187 | 5.038 | 127542 |
| 188 | 5.043 | 140513 |
| 189 | 5.058 | 218023 |
| 190 | 4.535 | 55627 |
| 191 | 5.026 | 199881 |
| 192 | 4.708 | 31553 |
| 193 | 5.086 | 1933389 |
| 194 | 5.046 | 253626 |
| 195 | 4.969 | 143010 |
| 196 | 4.996 | 80332 |
| 197 | 5.009 | 141197 |
| 198 | 5.1 | 139202 |
| 199 | 5.126 | 123977 |
| 200 | 5.449 | 1886 |
| 201 | 5.047 | 226703 |
| 203 | 4.955 | 172346 |
| 204 | 4.987 | 159535 |
| 205 | 5.09 | 237874 |
| 206 | 5.01 | 182142 |
| 207 | 5.144 | 190642 |
| 208 | 5.034 | 190328 |
| 209 | 5.104 | 221965 |
| 210 | 5053 | 5060 |
| 211 | 5.009 | 287859 |
| 212 | 4.969 | 187947 |
| 213 | 5.026 | 219651 |
| 214 | 4.999 | 181968 |
| 215 | 5.034 | 111935 |
| 216 | 5.158 | 401933 |
| 217 | 5.197 | 275205 |
| 218 | 4.447 | 74121 |
| 219 | 4.97 | 215336 |
| 220 | 5.051 | 260942 |
| 221 | 4.957 | 123233 |
| 222 | 5.03 | 1674429 |
| 223 | 5.012 | 145280 |
| 224 | 5.534 | 2310 |
| 225 | 5.017 | 54242 |
| 226 | 5.001 | 142955 |
| 227 | 5.024 | 212808 |
| 228 | 5.039 | 1149, 33 |
| 229 | 5.064 | 177947 |
| 230 | 4.983 | 202000 |
| 231 | 5.013 | 182975 |
| 232 | 5.121 | 223657 |
| 233 | 5.092 | 172952 |
| 234 | 3.951 | 84866 |
| 235 | 5.058 | 142138 |
| 236 | 5.063 | 367688 |
| 237 | 5.004 | 165516 |
| 238 | 5.069 | 218298 |
| 239 | 5.086 | 361567 |
| 240 | 5.127 | 252675 |
| 241 | 5.071 | 233781 |
| 242 | 5.008 | 268637 |
| 243 | 5.092 | 168008 |
| 244 | 5.119 | 79488 |
| 245 | 5.06 | 215547 |
| 246 | 5.008 | 53653 |
| 247 | 5.075 | 250310 |
| 248 | 5.094 | 194793 |
| 249 | 3.616 | 37488 |
| 250 | 5.036 | 301239 |
| 251 | 5.101 | 297658 |
| 252 | 4.965 | 53405 |
| 253 | 4.65 | 4466 |
| 254 | 3.66 | 16463 |
| 255 | 5.032 | 253885 |
| 256 | 4.976 | 244457 |
| 257 | 5.072 | 289009 |
| 258 | 5.106 | 273939 |
| 259 | 5.041 | 166066 |
| 260 | 5.004 | 160654 |
| 261 | 4.972 | 164451 |
| 262 | 5.148 | 513577 |
| 263 | 5.089 | 208950 |
| 264 | 5.099 | 206909 |
| 265 | 5.051 | 68567 |
| 266 | 4.996 | 72025 |
| 267 | 5.085 | 106826 |
| 268 | 4.865 | 7221 |
| 269 | 5.138 | 63713 |
| 270 | 5.186 | 149808 |
| 271 | 5.019 | 85191 |
| 272 | 5.277 | 118699 |
| 273 | 5.069 | 104693 |
| 274 | 5.022 | 17776 |
| 275 | 5.055 | 138448 |
| 276 | 4.95 | 16306 |
| 277 | 5.079 | 139094 |
| 278 | 5 | 82052 |
| 279 | 5.088 | 3310 |
| 280 | 5.22 | 127670 |
| 281 | 5.039 | 157800 |
| 282 | 5.003 | 109468 |
| 283 | 5.074 | 123519 |
| 284 | 5.039 | 12331 |
| 285 | 5.223 | 148145 |
| 286 | 5.136 | 148676 |
| 287 | 3.665 | 7404 |
| 288 | 5.575 | 1112 |
| 289 | 3.696 | 9460 |
| 290 | 5.029 | 93755 |
| 291 | 5.095 | 169623 |
| 292 | 3.689 | 14445 |
| 293 | 4.634 | 36542 |
| 294 | 5.004 | 77308 |
| 295 | 4.998 | 17822 |
| 296 | 5.003 | 74551 |
| 297 | 5.085 | 68904 |
| 298 | 5.192 | 129131 |
| 299 | 4.54 | 30337 |
| 300 | 5.025 | 142111 |
| 301 | 5.028 | 84156 |
| 302 | 4.992 | 78611 |
| 303 | 4.527 | 25755 |
| 304 | 5.065 | 122824 |
| 305 | 3.668 | 7392 |
| 306 | 5.065 | 145979 |
| 307 | 5.097 | 135403 |

TABLE 9-continued

Summary of Size Exclusion Chromatography Analysis

| SEQ ID NO: | RT (min) | Height (mAU) |
|---|---|---|
| 308 | 5.059 | 18037 |
| 309 | 5.198 | 111922 |

TABLE 10

IC50 of CD71 FN3 domain - MMAF conjugate molecules 5 on SKBR-3 cells +/- human transferrin

| | IC50 (nM) | |
|---|---|---|
| SEQ ID NO: | huTf competitor | no competitor |
| 146 | 7.131 | 3.457 |
| 214 | 28.15 | 29.23 |
| 104 | 301.3 | 5.9 |
| 259 | 27.46 | N.D. |
| 134 | 164.9 | 8.543 |
| 92 | 5.489 | 1.061 |
| 302 | 164.3 | 27.81 |
| 235 | 1.755 | 10.58 |
| 237 | 28.12 | 3.762 |
| 152 | 19.56 | 5.239 |
| 238 | N.D. | 7.232 |
| 136 | 2.32 | 0.5026 |
| 197 | N.D. | 0.4675 |
| 212 | N.D. | 6.691 |
| 296 | 29.31 | 18.61 |
| 226 | N.D. | 8.32 |
| 261 | 1.235 | 31.2 |
| 307 | 47.89 | 30.75 |
| 115 | 24.22 | 10.43 |
| 112 | 27.33 | 4.549 |
| 278 | 13.24 | 3.702 |
| 297 | N.D. | N.D. |
| 96 | 79.5 | 27 |
| 222 | N.D. | 28.23 |
| 95 | 28.27 | 12.68 |
| 233 | 54.61 | 17.7 |
| 217 | 15.78 | 2.458 |
| 252 | 24.55 | 7.736 |
| 194 | N.D. | 5.091 |
| 164 | 18.7 | 55.8 |
| 168 | 32 | 7.2 |
| 174 | ND | 158 |
| 190 | 36 | 12 |
| 257 | 22 | 6.5 |
| 303 | 33 | 39 |
| 284 | 98 | 32 |
| 85 | ND | 89 |
| 149 | 9.7 | 5.5 |

| SEQ ID NO: | Amino Acid sequence of FN3 domains that bind to CD71 |
|---|---|
| 81 | MLPAPKNLVVSRVTEDSARLSWTAPDAAFDSFVIEYREGAWYGEA IVLTVPGSERSYDLTGLKPGTEYAVYIPGVKGGPRSPPLSAIFTT |
| 82 | MLPAPKNLVVSRVTEDSARLSWTAPDAAFDSFAIAYVEWWKLGEA IVLTVPGSERSYDLTGLKPGTEYVVPIPGVKGGHSSPPLSAIFTT |
| 83 | MLPAPKNLVVSRVTEDSARLSWTAPDAAFDSFYIYYYESSGTGEA IVLTVPGSERSYDLTGLKPGTEYFVDIGGVKGGSYSLPLSAIFTT |
| 84 | MLPAPKNLVVSRVTEDSARLSWTAPDAAFDSFPIYYWEVFPAGEA IELDVPGSERSYDLTGLKPGTEYFVRIEGVKGGASSYPLRAEFTT |
| 85 | MLPAPKNLVVSRVTEDSARLSWTAPDAAFDSFFIWYWEKSVDGEA IVLTVPGSERSYDLTGLKPGTEYNVGIQGVKGGTPSDPLSAIFTT |
| 86 | MLPAPKNLVVSRVTEDSARLSWTAPDAAFDSFIIWYAEWVNDGEA IVLTVPGSERSYDLTGLKPGTEYRVEITGVKGGTWSRPLSAIFTT |
| 87 | MLPAPKNLVVSRVTEDSARLSWTAPDAAFDSFAIEYYEPVPAGEA IYLDVPGSERSYDLTGLKPGTEYDVTIYGVKGGYYSHPLFASFTT |
| 88 | MLPAPKNLVVSRVTEDSARLSWTAPDAAFDSFWIEYFEWTVGGEA IVLTVPGSERSYDLTGLKPGTEYYVSIYGVKGGWLSPPLSAIFTT |
| 89 | MLPAPKNLVVSRVTEDSARLSWTAPDAAFDSFHISYEETPVVGEA IYLRVPGSERSYDLTGLKPGTEYTVAIHGVKGGRESTPLIAPFTT |
| 90 | MLPAPKNLVVSRVTEDSARLSWTAPDAAFDSFTIHYWEFDPPGEA IVLTVPGSERSYDLTGLKPGTEYTVYIEGVKGGWWSKPLSAIFTT |
| 91 | MLPAPKNLVVSRVTEDSARLSWTAPDAAFDSFVIEYWERTQPGEA IVLTVPGSERSYDLTGLKPGTEYDVWISGVKGGKWSEPLSAIFTT |
| 92 | MLPAPKNLVVSRVTEDSARLSWTAPDAAFDSFLIRYWEWYVLGEA IVLTVPGSERSYDLTGLKPGTEYYVEISGVKGGWQSWPLSAIFTT |
| 93 | MLPAPKNLVVSRVTEDSARLSWTAPDAAFDSFYIGYLEPGDNGEA IVLTVPGSERSYDLTGLKPGTEYNVSIGGVKGGLGSYPLSAIFTT |
| 94 | MLPAPKNLVVSRITEDSARLSWTAPDAAFDSFGIYYYEWWSTGEA IVLTVPGSERSYDLTGPKPGTEYYVKISGVKGGYRSYPLSAIFTT |
| 95 | MLPAPKNLVVSRVTEDSARLSWTAPDAAFDSFRISYYEWYDLGEA IVLTVPGSERSYDLTGLKPGTEYWVDIAGVKGGYYSYPLSAIFIT |
| 96 | MLPAPKNLVVSRVTEDSARLSWTAPDAAFDSFFIGYLEPQPPGEA IVLTVPGSERSYDLTGLKPGTEYNVTIQGVKGGFPSMPLSAIFTT |
| 97 | MLPAPKNLVVSRVTEDSARLSWTAPDAAFDSFFISYFEGWASGEA IHLYVPGSERSYDLTGLKPGTEYSVHIQGVKGGQPSTPLSAIFTT |
| 98 | MLPAPKNLVVSRITEDSARLSWTAPDAAFDSFDIPYGEFDTIGEA IVLTVPGSERSYDLTGLKPGTEYDVYIEGVKGGHLSWPLSAIFTT |
| 99 | MLPAPKNLVVSRVTEDSARLSWTAPDAAFDSFGIQYNEFVFRGEA IVLTVPGSERSYDLTGLKPGTEYFVPISGVKGGDDSRPLSAIFTT |
| 100 | MLPAPKNLVVSRVTEDSARLSWTAPDAAFDSFWIEYWEVVGFGEA IVLTVPGSERSYDLTGLKPGTEYWVGIYGVKGGNPSVPLSAIFTT |
| 101 | MLPAPKNLVVSRVTEDSARLSWTAPDAAFDSFAIDYDEPINSGEA IVLTVPGSERSYDLTGPKPGTEYEVEIYGVKGGYLSRPLSAIFTT |
| 102 | MLPAPKNLVVSRVTEDSARLSWTAPDAAFDSFSIDYDEPQPVGEA IVLTVPGSERSYDLTGLKPGTEYRVDIWGVKGGPTSGPLRATFTT |
| 103 | MLLAPKNLVVSRVTEDSARLSWTAPDAAFDSFAIEYFEYTGEGEA IVLTVPGSERSYDLTGLKPGTEYYVGIYGVKGGYLSRPLSAIFTT |
| 104 | MLPAPKNLVVSHVTEDSARLSWTAPDAAFDSFDIEYYELVGSGEA IVLTVPGSERSYDLTGLKPGTEYYVAIYGVKGGYLSRPLSAIFTT |
| 105 | MLPAPKNLVVSRVTEDSARLSWTAPDAAFDSFGIAYYERSGAGEA IVLTVPGSERSYDLTGLKPGTEYMVYINGVKGGFVSSPLSAIFTT |
| 106 | MLPAPKNLVVSRVTEDSARLSWTAPDAAFDSFTIAYEEHGLVGEA IYLRVPGSERSYDLTGLKPGTEYHVGIMGVKGGVFSSPLSAIFTT |
| 107 | MLPAPKNLVVSRVTEDSARLSWTAPDAAFDSFFIQYTESHWVGEA IVLTVPGSERSYDLTGLKPGTEYAVPIEGVKGGDSSTPLSAIFTT |
| 108 | MLPAPKNLVVSRVTEDSARLSWTAPDAAFDSFTIIYGEVNPYGEA IVLTVPGSERSYDLTGLKPGTEYDVFIEGVKGGHLSWPLSAIFTT |
| 109 | MLPAPKNLVVSRVTEDSARLSWTAPDAAFDSFHIAYEELVTEGEA IYLRVPGSERSYDLTGLKPGTEYLVDIEGVKGGHLSSPLSAIFTT |
| 110 | MLPAPKNLVVSRVTEDSARLSWTAPDAAFDSFFIHYHEWWEAGEA IVLTVPGSERSYDLTGLKPGTEYLVDIPGVKGGDLSVPLSAIFTT |

-continued

| SEQ ID NO: | Amino Acid sequence of FN3 domains that bind to CD71 |
|---|---|
| 111 | MLPAPKNLVVSRVTEDSARLSWTAPDAAFDSFWIYYYESVGTGEA IVLTVPGSERSYDLTGLKPGTEYFVDISGVKVGTYSLPLSAIFTT |
| 112 | MLPAPKNLVVSRVTEDSARLSWTAPDAAFDSFFIAYFEFANPGEA IVLTVPGSERSYDLTGLKPGTEYKVVIQGVKGGTPSEPLSAISTT |
| 113 | MLPAPKNLVVSRVTEDSARLSWTAPDAAFDSFDIHYKEHSWWGEA IVLTVPGSERSYDLTGLKPGTEYIVPIPGVKGGGISRPLSAIFTT |
| 114 | MLPAPKNLVVSRVTEDSARLSWTAPDAAFDSFAIEYWEAVGSGEA IVLTVPGSERSYDLTGLKPGTEYHVYIYGVKGGYLSLPLSAIFTT |
| 115 | MLPAPKNLVVSRVTEDSARLSWTAPDAAFDSFFIGYLEPQPPGEA IVLTVPGSERSYDLTGLKPGTEYNVTIQGVKGGFPSMPLSAIFTT T |
| 116 | MLPAPKNLVVSRVTEDSARLSWTAPDAAFDSFSIAYSEVRYDGEA IVLTVPGSERSYDLTGLKPGTEYVVPIGGVKGGGSSSPLSAIFTT |
| 117 | MLPAPKNLVVSRVTEDSARLSWTAPDAAFDSFTIPYGEAFNPGEA IVLTVPGSERSYDLTGLKPGTEYDVFIEGVKGGTLSWPLSAIFTT |
| 118 | MLPAPKNLVVSRVTEDSARLSWTAPDAAFDSFRILYGEVDPWGEA IVLTVPGSERSYDLTGLKPGTEYDVWIEGVKGGKLSWPLSAIFTT |
| 119 | MLPAPKNLVVSRVTEDSARLSWTAPDAAFDSFHIEYEETPQKGEA IFLRVPGSERSYDLTGLKPGTEYVVNIRGVKGGDLSSPLGALFTT |
| 120 | MLPAPKNLVVSRVTEDSARLSWTAPDAAFDSFRIEYIEWWVGGEA IVLTVPGSERSYDLTGLKPGTEYWVDIKGVKGGKRSYPLSAIFTT |
| 121 | MLPAPKNLVVSRVTEDSARLSWTAPDAAFDSFSIDYPEFPVRGEA IVLTVPGSERSYDLTGPKPGTEYNVTIQGVKGGFPSMPLSAIFTT |
| 122 | MLPAPKNLVVSRVTEDSARLSWTAPDAAFDSFQIPYWEQSLGGEA IVLTVPGSERSYDLTGLKPGTEYEVWIEGVKGGDLSFPLSAISTT |
| 123 | MLPAPKNLVVSRVTEDSARLSWTAPDAAFDSFVIPYEEYLYTGEA IVLTVPGSERSYDLTGLKPGTEYDVWIEGVKGGLTSWPLSAIFTT |
| 124 | MLPAPKNLVVSRVTEDSARLSWTAPDAAFDSFSIDYPEFPVRGEA IVLTVPGSERSYDLTGLKPGTEYAVTIWGVKGGFTSQPLSAIFTT |
| 125 | MLPAPKNLVVSRVTEDSARLSWTAPDAAFDSFVIEYFEFVGEGEA IVLTVPGSERSYDLTGLKPGTEYDVGIYGVKGGSLSSPLSAIFTT |
| 126 | MLPAPKNLVVSRVTEDSARLSWTAPDAAFDSFSIDYLELGESGEA IVLTVPGSERSYDLTGLKPGTEYWVYIFGVKGGYPSAPLSAIFTT |
| 127 | MLPAPKNLVVSRVTEDSARLSWTAPDAAFDSFPIPYGESPPSGEA IVLTVPGSERSYDLTGLKPGTEYVVIIRGVKGGGRSGPLSAISTT |
| 128 | MLPAPKNLVVSRVTEDSARLSWTAPDAAFDSFIINYIEIVQYGEA IVLTVPGSERSYDLTGLKPGTEYPESIWGVKGGGASSPLSAIFTT |
| 129 | MLPAPKNLVVSRVTEDSARLSWTAPDAAFDSFDIEYYEAVGAGEA IVLTVPGSERSYDLTGLKPGTEYTVGIYGVKGGWLSKPLSVIFTT |
| 130 | MLPAPKNLVVSRVTEDSARLSWTAPDAAFDSFHIPYVEAEVPGEA IQLHVPGSERSYDLTGLKPGTEYYVEIWGVKGGFYSPPLIAEFTT |
| 131 | MLPAPKNLVVSRVTEDSARLSWTAPDAAFDSFSIDYYEGKGYGEA IVLTVPGSERSYDLTGLKPGTEYQVLISGVKGGKYSLPLSAIFTT |
| 132 | MLPAPKNLVVSRVTEDSARLSWTAPDAAFDSFTIVYAEVTYDGEA IVLTVPGSERSYDLTGLKPGTEYDVFIEGVKGGELSWPLSAIFTT |
| 133 | MLPAPKNLVVSRVTEDSARLSWTAPDAAFDSFPIVYGEAWVTGEA IVLTVPGSERSYDLTGLKPGTEYDVWIEGVKGGELSWPLSAIFTT |
| 134 | MLPAPKNLVVSRVTEDSARLSWTAPDAAFDSFWIDYYERKYVGEA IVLTVPGSERSYDLTGLKPGTEYEVTIYGVKGGWYSDPLSAIFTT |
| 135 | MLPAPKNLVVSRVTEDSARLSWTAPDAAFDSFPISYYEMSGLGEA IVLTVPGSERSYDLTGLKPGTEYMVYIFGVKGGLNSLPLSAIFTT |
| 136 | MLPAPKNLVVSRVTEDSARLSWTAPDAAFDSFFIYYIESYPAGEA IVLTVPGSERSYDLTGLKPGTEYWMGIDGVKGGRWSTPLSAIFTT |
| 137 | MLPAPKNLVVSRVTEDSARLSWTAPDAAFDSFEIEYDEPSVAGEA IVLTVPGSERSYDLTGLKPGTEYRVFIWGVKGGNQSWPLSAIFTT |
| 138 | MLPAPKNLVVSRVTEDSARLSWTAPDAAFDSFFIKYIEWWADGEA IVLTVPGSERSYDLTGLKPGTEYLVEIYGVKGGRQSYPLSAIFTT |
| 139 | MLPAPKNLVVSRVTEDSARLSWTAPDAAFDSFDISYWESGKYGEA IVLTVPGSESSYDLTGLKPGTEYLVDIFGVKGGYPSEPLSAIFTT |
| 140 | MLPAPKNLVVSRVTEDSARLSWTAPDAAFDSFWISYEESDTEGEA IYLRVPGSERSYDLTGLKPGTEYNVTIQGVKGGFPSMPLSAIFTT |
| 141 | MLPAPKNLVVSRVTEDSARLSWTAPDAAFDSFVIEYFEQFNLGEA IVLTVPGSERSYDLTGLKPGTEYLVGIYGVKGGWLSHPLSAIFTT |
| 142 | MLPAPKNLVVSRVTKDSARLSWTAPDAAFDSFHIAYEEATTYGEA IFLRVPGSERSYDLTGLKPGTEYEVKIHGVKGGADSKPLVAPFTT |
| 143 | MLPAPKNLVVSRVTEDSARLSWTAPDAAFDSFHIAYEEADSEGEA IYLRVPGSERSYDLTGLKPGTEYSVNIQGVKGGIVSFPLHAEFTT |
| 144 | MLPAPKNLVVSRVTEDSARLSWTAPDAAFDSFIIPYAEVRPDGEA IVLTVPGSERSYDLTGLKPGTEYSVLIHGVKGGKLSLPLSAIFTT |
| 145 | MLPAPKNLVVSRVTEDSARLSWTAPDAAFDSFFIPYAEPSPTGEA IVLTVPGSERSYDLTGLKPGTEYDVWIEGVKGGTLSWPLSAIFTT |
| 146 | MLPAPKNLVVSRVTEDSARLSWTAPDAAFDSFYIAYAEPRPDGEA IVLTVPGSERSYDLTGLKPGTEYSVLIHGVKGGLLSSPLSAIFTT |
| 147 | MLPAPKNLVVSRVTEDSARLSWTAPDAAFDSFFIGYLEPQPPGEA IVLTVPGSERSYDLTGLKPGTEYSVLIHGVKGGRNSDPLSAISTT |
| 148 | MLPAPKNLVVSRVTEDSARLSWTAPDAAFDSFHIEYEEQYSTGEA IYLRVPGSERSYDLTGLKPGTEYHVDIEGVKGGRRSFPLNAFFTT |
| 149 | MLPAPKNLVVSRVTEDSARLSWTAPDAAFDSFIIPYAEVRPDGEA IVLTVPGSERSYDLTGLKPGTEYSVLIHGVKGGKLSEPLSAIFTT |
| 150 | MLPAPKNLVVSRVTEDSARLSWTAPDAAFDSFPIAYAEPSPTGEA IVLTVPGSERSYDLTGLKPGTEYSVLIHGVKGGHLSDPLSAIFTT |
| 151 | MLPAPKNLVVSRVTEDSARLSWTAPDAAFDSFFIPYAEPSPTGEA IVLTVPGSERSYDLTGLKPGTEYGVVILGVKGGYGSDPLSAIFTT |
| 152 | MLPAPKNLVVSRVTEDSARLSWTAPDAAFDSFFIGYLEPQPPGEA IVLTVPGSERSYDLTGLKPGTEYNVTIQGVKGGFPSSPLSAIFTT |
| 153 | MLPAPKNLVVSRVTEDSARLSWTAPDAALDSFRIAYTEYFVGGEA IVLTVPGSERSYDLTGLKPGTEYGVGIYGVKGGAGSSPLSAIFTT |
| 154 | MLPAPKNLVVSRVTEDSARLSWTAPDAAFDSFFIPYAEPRPDGEA IVLTVPGSERSYDLTGLKPGTEYSVLIHGVKGGLLSSPLSAIFTT |
| 155 | MLPAPKNLVVSRVTEDSARLSWTAPDAAFDSFPITYRERSQYGEA IVLTVPGSERSYDLTGLKPGTEYVVPIEGVKGGRGSKPLSAIFTT |
| 156 | MLPAPKNLVVSRVTEDSARLSWTAPDAAFDSFAIEYFENLGIGEA IVLTVPGSERSYDLTGLKPGTEYVVNIYGVKGGWLSSPLSAIFTT |
| 157 | MLPAPKNLVVSRVTEDSARLSWTAPDAAFDSFAIEYYEYVGNGEA IVLTVPGSERSYDLTGLKPGTEYQVGIYGVKGGYYSRPLSAIFTT |
| 158 | MLPAPKNLVVSRVTEDSARLSWTAPDAAFDSFIIDYLELDDYGEA IVLTVPGSERSYDLTGLKPGTEYPVYIYGVKGGLPSTPLSAIFIT |
| 159 | MLPAPKNLVVSRVTEDSARLSWTAPDAAFDSFLIPYAETSPSGEA IVLTVPGSERSYDLTGLKPGTEYSVLIHGVKGGRNSDPLSAIFTT |

| SEQ ID NO: | Amino Acid sequence of FN3 domains that bind to CD71 |
|---|---|
| 160 | MLPAPKNLVVSRVTEDSARLSWTAPDAAFDSFNIAYGEWRQHGEAIVLTVPGSERSYDLTGLKPGTEYDVFIDGVKGGNLSWPLSAIFTT |
| 161 | MLPAPKNLVVSRVTEDSARLSWTAPDAAFDSFTIRYWEELPTGEAIVLTVPGSERSYDLTGLKPGTEYTVEIFGVKGGYLSRPLSAISTT |
| 162 | MLPAPKNLVVSRVTEDSARLSWTAPDAAFDSFHIAYEEATTYGEAIFLRVPGSERSYDLTGLKPGTEYDVWIEGVKGGTISGPLSAIFTT |
| 163 | MLPAPKNLVVSRVTEDSARLSWTAPDAAFDSFPIAYAEPRPDGEAIVLTVPGSERSYDLTGLKPGTEYFVDIFGVKGGILSRPLSAIFTT |
| 164 | MLPAPKNLVVSRVTEDSARLSWTAPDAAFDSFLIPYAETSPSGEAIVLTVPGSERSYDLTGLKPGTEYSVLIHGVKGGHLSDPLSAIFTT |
| 165 | MLPARKNLVVSRVTEDSARLSWTAPDAAFDSFFIPYAEPSPTGEAIVLTVPGSERSYDLTGLKPGTEYSVLIHGVKGGHLSDPLSAISTT |
| 166 | MLPAPKNLVVSRVTEDSARLSWTAPDAAFDSFTILYNEIQNVGEAIVLTVPGSERSYDLTGLKPGTEYDVWIEGVKGGELSWPLSAIFTT |
| 167 | MLPAPKNLVVSRVTEDSARLSWTAPDAAFDSFFIGYLEPQPPGEAIVLTVPGSERSYDLTGLKPGTEYNVTIQGVKGGTPSEPLSAIFTT |
| 168 | MLPAPKNLVVSRVTEDSARLSWTTPDAAFDSFFIGYLEPYPPGEAIVLTVPGSERSYDLTGLKPGTEYVVSIQGVKGGKPSDPLSAIFTT |
| 169 | MLPAPKNLVVSRVTEDSARLSWTAPDAAFDSFFIGYLEPQPPGEAIVLTVPGSERSYDLTGLKPGTEYNVTIQGVKGGFPSVPLSAIFTT |
| 170 | MLPAPKNLVVSRVTEDSARLSWTAPDAAFDSFFIGYPEYPATGEAIVLTVPGSERSYDLTGLKPGTEYFVDINGVKGGSLSYPLSAIFTT |
| 171 | MLPAPKNLVVSRVTEDSARLSWTAPDAAFDSFAIRYLEWWDVGEAIVLTVPGSERSYDLTGLKPGTEYLVEIKGVKGGKFSYPLSAIFTT |
| 172 | MLPAPKNLVVSRVTEDSARLSWTAPDAAFDSFPIEYDEWWALGEAITLIVPASERSYDLTGLKPGTEYVVKIHGVKGGQRSYPLIAFFTT |
| 173 | MLPAPKNLVVSRVTEDSARLSWTAPDAAFDSFTIHYRELYVQAIVLTVPGSERSYDLTGLKPGTEYLVMIPGVKGGPTSVPLSAIFTT |
| 174 | MLPAPKNLVVSRVTEDSARLSWTAPDAAFDSFFIGYLEPQPPGEAIVLTVPGSERSYDLTGLKPGTEYKVVIQGVKGGTPSEPLSAIFTT |
| 175 | MLPAPKNLVVSRVTEDSARLSWTAPDAAFDSFFIGYLEPQPPGEAIVLTVPGSERSYDLTGLKPGTEYSVVIQGVKGGFPSDPLSAIFTT |
| 176 | MLPAPKNLVVSRVTEDSARLSWTAPDAAFDSFPIAYAEPRPDGEAIVLTVPGSERSYDLTGLKPGTEYSVGIHGVKGGHDSSPLSAIFTT |
| 177 | MLPAPKNLVVSRVTEDSARLSWTAPDAAFDSFFIGYLEPQPPGEAIVLTVPGSERSYDLTGLKPGTEYNVTIQGVKGGRASGPLSAIFTT |
| 178 | MLPAPKNLVVSRVTEDSARLSWTAPDAAFDSFDIAYAEPIPRGEAIVLTVPGSERSYDLTGLKPGTEYSVLIHGVKGGRRSVPLSAIFTT |
| 179 | MLPAPKNLVVSRVTEDSARLSWTAPDAAFDSFYIAYAEPRPDGEAIVLTVPGSERSYDLTGLKPGTEYPVPIPGVKGGPGSSPLSAIFTT |
| 180 | MLPAPKNLVVSRVTEDSARLSWTAPDAAFDSFEISYYEMRGYGEAIVLTVPGSERSYDLTGLKPGTEYSVLIHGVEGGDYSSPLSAISTT |
| 181 | MLPAPKNLVVSHVTEDSARLSWTAPDAAFDSFPIAYAEPRPDGEAIVLTVPGSERSYDLTGLKPGTEYSVLIHGVKGGLLSSPLSAIFTT |
| 182 | MLPAPKNLVVSRVTEDSARLSWTAPDAAFDSFFIGYLEPYPPGEAIVLTVPGSERSYDLTGLKPGTEYVVSIQGVKGGTPSQPLSAIFTT |
| 183 | MLPAPKNLVVSRVTEDSARLSWTAPDAAFDSFLIPYAETSPSGEAIVLTVPGSERSYDLTGLKPGTEYSVLIHGVKGGRPSNPLVAAFTT |
| 184 | MLPAPKNLVVSRITEDSARLSWTAPDAAFDSFGIGYYEHKRFGEAIQLSVPGSERSYDLTGLKPGTEYEVDIEGVKGGVLSWPLFAEFTT |
| 185 | MLPAPKNLVVSRVTEDSARLSWTAPDAAFDSFEIDYDELAIYGEAIVLTVPGSERSYDLTGLKPGTEYGVMIIGVKGGLPSDPLSAIFTT |
| 186 | MLPAPKNLVVSRVTEDSARLSWTAPDAAFDSFFIGYLESAEAIVLTVPGSERSYDLTGLKPGTEYLVTIQGVKGGIASDPLSAIFTT |
| 187 | MLPAPKNLVVSRVTEDSARLSWTAPDAAFDSFVIEYFEFVGYGEAIVLTVPGSERSYDLTGLKPGTEYSVGIYGVKGGKLSPPLSAIFTT |
| 188 | MLPAPKNLVVSRVTEDSARLSWTAPDAAFDSFLIPYAETSPSGEAIVLTVPGSERSYDLTGLKPGTEYSVLIHGVKGGKLSLPLSAIFTT |
| 189 | MLPAPKNLVVSRVTEDSARLSWTAPDAAFDSFHEWVYFGEAIVLTVPGSERSYDLTGLKPGTEYFVDIWGVKGGTVSKPLSAIFTT |
| 190 | MLPAPKNLVVSRVTEDSARLSWTAPDAAFDSFFIGYPEYPATGEAITLFVPGSERSYDLTGLKPGTEYNVVIQGVKGGRPSNPLVVAFTT |
| 191 | MLPAPENLVVSRVTEDSARLSWTAPDAAFDSFEITYEENWRRGEAIVLTVPGSERSYDLTGPKPGTEYIVIIQGVKGGAESWPLSAIFTT |
| 192 | MLPAPKNLVVSRVTEDSARLSWTALDAAFDSFFIGYLEPQPPGEAIVLTVPGSERSYDLTGLKPGTEYNVTIQGVKGGFPSMPLSAIFTT |
| 193 | MLPAPKNLVVSRVTEDSARLSWTAPDAAFDSFTIWYAEAVGNGEAIVLTVPGSERSYDLTGLKPGTEYWVDIWGVKGGEFSSPLSAIFTT |
| 194 | MLPAPKNLVVSRVTEDSARLSWTAPDAAFDSFEIDYDELAIYGEAIVLTVPGSERSYDLTGLKPGTEYRVFIYGVKGGWTSWPLSTIFTT |
| 195

| SEQ ID NO: | Amino Acid sequence of FN3 domains that bind to CD71 |
|---|---|
| 210 | MLPAPKNLVVSRVTEDSARLSWTAPDAAFDSFSIVYGERFVNGEA IVLTVPGSERSYDLTGLKPGTEYHVYIDGVKGGDLSWPLSAIFTT |
| 211 | MLPAPKNLVVSRVTEDSARLSWTAPDAAFDSFWINYYEAQPDEA IVLTVPGSERSYDLTGLKPGTEYDVEIAGVKGGTASLPLSAIFTT |
| 212 | MLPAPKNLVVSRVTEDSARLSWTAPDAAFDSFIIEYWEQIGVGEA IVLTVPGSERSYDLTGLKPGTEYWVGIYGVKGGLLSSPLSAIFTT |
| 213 | MLPAPKNLVVSRVTEDSARLSWTAPDAAFDSFWIYYWEIERAGEA IRLDVPGSERSYDLTGLKPGTEYRVDIWGVKGGPTSGPLRATFTT |
| 214 | MLPAPKNLVVSRVTEDSARLSWTAPDAAFDSFAIPYGERQELGEA IVLTVPGSERSYDLTGLKPGTEYFVVIQGVKGGQPSYPLSAIFTT |
| 215 | MLPAPKNLVVSRVTEDSARLSWTAPDAAFDSFLIPYAETSPTGEA IVLTVPGSERSYDLTGLKPGTEYSVLIHGVKGGYPSSPLSAIFTT |
| 216 | MLPAPKNLVVSRVTEDSARLSWTAPDAAFDSFPIAYAEPTPSGEA IVLTVPGSERSYDLTGLKPGTEYSVLIHGVKGGGLSLPLSAIFTT |
| 217 | MLPAPKNLVVSRVTEDSARLSWTAPDAAFDSFIIEYWEWYFAGEA IVLTVPGSERSYDLTGLKPGTEYTVWITGVKGGTWSEPLSAIFTT |
| 218 | MLPAPKNLVVSRVTEDSARLSWTAPDAAFDSFTILYYEMVGEGEA IVLTVPGSERSYDLTGPKPGTEYWVDIYGVKGGGWSRPLSAIFTT |
| 219 | MLPAPKNLVVSRVTEDSARLSWTAPDAAFDSFHIDYLELTYAGEA IVLTVPGSERSYDLTGLKPGTEYYVTIYGVKGGYPSSPLSAIFTT |
| 220 | MLPAPKNLVVSRVTEDSARLSWTAPDAAFDSFHIIYEEDGTEGEA IYLRVPGSERSYDLTGLKPGTEYEVDIEGVKGGVLSWPLFAEFTT |
| 221

| SEQ ID NO: | Amino Acid sequence of FN3 domains that bind to CD71 |
|---|---|
| 259 | MLPAPKNLVVSRVTEDSARLSWTAPDAAFDSFTIEYFEFVDAGEA IVLTVPGSERSYDLTGLKPGTEYWVEIWGVKGGSWSKPLSAIFTT |
| 260 | MLPAPKNLVVSRVTEDSARLSWTAPDAAFDSFNISYYEYFVHGEA IVLTVPGSERSYDLTGLKPGTEYYVIDGVKGGDPSEPLSAIFTT |
| 261 | MLPAPKNLVVSRVTEDSARLSWTAPDAAFDSFTIVYGEWGVPGEA IVLTVPGSERSYDLTGLKPGTEYDVWIEGVKGGDLSWPLSAIVTT |
| 262 | MLPAPKNLVVSRVTEDSARLSWTAPDAAFDSFAIEYFEYTGEGEA IVLTVPGSERSYDLTGLKPGTEYYVGIYGVKGGYLSRPLSAIFTT |
| 263 | MLPAPKNLVVSRVTEDSARLSWTAPDAAFDSFFIGYLEPQPPGEA IVLTVPGSERSYDLTGLKPGTEYNVTIQGVKGGFPSMPLSAISTT |
| 264 | MLPAPKNLVVSRVTEDSARLSWTAPDAAFDSFRIKYQEWWVEGEA IVLTVPGSERSYDLTGLKPGTEYVVQIAGVKGGLSSYPLSAIFIT |
| 265 | MLPAPKNLVVSRVTEDSARLSWTAPDAAFDSFWIYYIETSHQGEA IVLTVPGSERSYDLTGLKPGTEYFVLIKGVKGGYDSVPLSAIFTT |
| 266 | MLPAPKNLVVSRVTEDSARLSWTAPDAAFDSFMIRYQEGTRWGEA IVLTVPGSERSYDLTGLKPGTEYIVMIAGVKGGQISLPLSAIFTT |
| 267 | MLPAPKNLVVSRVTEDSARLSWTAPDAAFDSFPIVYSEIHVIGEA IVLTVPGSERSYDLTGLKPGTEYDVWIEGVKGGHLSEPLSAIFTT |
| 268 | MLPAPKNLVVSRVTEDSARLSWTAPDAAFDSFTIVYGEAGAFGEA IVLTVPGSERSYDLTGLKPGTEYDVLIEGVKGGNLSWPLSAIFTT |
| 269 | MLPAPKNLVVSRVTEDSARLSWTAPDAAFDSFHINYAEVYTKGEA ILLTVPGSERSYDLTGLKPGTEYEVYIPGVKGGPFSRPLNAQFTT |
| 270 | MLPAPKNLVVSRVTEDSARLSWTAPDAAFDSFLIRYQEWQRWGEA IVLTVPGSERSYDLTGLKPGTEYTVHIAGVKGGMLSLPLSAIFTT |
| 271 | MLPAPKNLVVSRVTEDSARLSWTAPDAAFDSFYIPYAETRDDGEA IVLTVPGSERSYDLTGLKPGTEYSVLIHGVKGGDLSSPLSAIFTT |
| 272 | MLPAPKNLVVSRVTEDSARLSWTAPDAAFDSFGIPYAESTPTGEA IVLTVPGSERSYDLTGLKPGTEYSVLIHGVKGGHLSDPLSAIFTT |
| 273 | MLPAPKNLVVSRVTEDSARLSWTAPDAAFDSFTIFKDGEAIVLTV PGSERSYDLTGLKPGTEYYVYIYGVKGGYPSKPLSAIFTT |
| 274 | MLPAPKNLVVSRVTEDSVRLSWTAPDAAFDSFAISYEEWWVHGEA IVLTVPGSERSYDLTGLKPGTEYSVVIPGVKGGLYSWTLSAISTT |
| 275 | MLPAPKNLVVSRVTEDSARLSWTAPDAAFDSFLIAYAEVTLHGEA IVLTVPGSERSYDLTGLKPGTEYSVLIHGVKGGRNSDPLSAIFTT |
| 276 | MLPAPKNLVVSRVTEDSARLSWTAPDAAFDSFRIDYLELTSLGEA IVLTVPGSERSYDLTGLKPGTEYPVPILGVKGGLSSWPLSAIFTT |
| 277 | MLPAPKNLVVSRVTEDSARLSWTAPDAAFDSFWINYYEGIGEGEA IVLTVPGSERSYDLTGLKPGTEYYVDISGVKGGSYSLPLSAIFTT |
| 278 | MLPAPKNLVVSRVTEDSARLSWTAPDAAFDSFPIAYAEPRPDGEA IVLTVPGSERSYDLTGLKPGTEYSVLIHGVKGGHLSDPLSAIFTT |
| 279 | MLPAPKNLVVSRVTEDSARLSWTAPDAAFDSFSIEYYESVGLGEA IVLTVPGSERSYDLTGLKPGTEYDVSIYGVKGGYLSRPLSAIFIT |
| 280 | MLPAPKNLVVRXVTEDSARLSWTAPDAAFDSFEIEYDEPYRGGEA IVLTVPGSERSYDLTSLKPGTEYPVSIGGVKGGITSDPLSAIFTT |
| 281 | MLPAPKNLVVSRVTEDSARLSWTAPDAAFDSFYIDYDEIHDWGEA IVLTVPGSERSYDLTGLKPGTEYAVQIGGVKGGSFSWILSAIFTT |
| 282 | MLPAPKNLVVSRVTEDSARLSWTAPDAAFDSFAIVYHEPRPDGEA IVLTVPGSERSYDLTGLKPGTEYEVVILGVKGGVHSYPLSAIFTT |
| 283 | MLPAPKNLVVSRVTEDSARLSWTAPDAAFDSFPIAYAEPRPDGEA IVLTVPGSERSYDLTGLKPGTEYSVLIHGVKGGLLSSPLSAIFTT |
| 284 | MLPAPKNLVVSRVTEDSARLSWTAPDAAFDSFFIGYLEPQPPGEA IVLTVPGSERSYDLTGLKPGTEYNVTIQGVKGGFPSMPLSAIFTT |
| 285 | MLPAPKNLVVSRVTEDSARLSWTAPDAAFDSFLIPYAETSPSGEA IVLTVPGSERSYDLTGLKPGTEYSVLIHGVKGGDYSSPLSAIFIT |
| 286 | MLPAPKNLVVSRVTEDSARLSWTAPDAAFDSFNIYYPEFPVRGEA IVLTVPGSERSYDLTGLKPGTEYVVSIWGVKGGTQSWPLSAIFTT |
| 287 | MLPAPKNLVVSRVTEDSARLSWTAPDAAFDSFTIEYHESGPVGEA IVLTVPGSERSYDLTGLKPGTEYMVWIFGVKGGFVSRPLSAIFTT |
| 288 | MLPAPKNLVVSRVTEDSARLSWTAPDAAFDSFLIPYAETSPSGEA IVLTVPGSERSYDLTGLKPGTEYSVLIHGVKGGDYSSPLSAISTT |
| 289 | MLPAPKNLVVSRVTEDSARLSWTAPDAAFDSFAIPYYEDTNDGEA IVLTVPGSERSYDLTGLKPGTEYWVSIQGVKGGTVSGPLSAIFTT |
| 290 | MLPAPKNLVVSRVTEDSARLSWTAPDAAFDSFFYLEQAWGGEAIV LTVPGSERSYDLTGLKPGTEYWVEITGVKGGYASSPLSAIFTT |
| 291 | MLPAPKNLVVSRVTEDSARLSWTAPDAAFDSFHIEYEEPETEGEA IYLHVPGSERSYDLTGLKPGTEYKVLIRGVKGGSYSIPLQAPFTT |
| 292 | MLPAPKNLVVSRVTEDSARLSWTAPDAAFDSFDIAYWELTPSGEA IELLVPGSERSYDLTGLKPGTEYRVDIIGVKGGFISEPLGATFTT |
| 293 | MLPAPKNLVVSRVTEDSARLSWTAPDAAFDSFTIEYWEFTGSGEA IVLTVPGSERSYDLTGLKPGTEYDVSIYGVKGGWLSYPLSAIFTT |
| 294 | MLPAPKNLVVSRVTEDSARLSWTAPDAAFDSFSIIYSEWNVTGEA IVLTVPGSERSYDLTGLKPGTEYDVWIEGVKGGGMSKPLSAISTT |
| 295 | MLPAPKNLVVSRVTEDSARLSWTAPDAAFDSFFIGYLEPIPSGEA IVLTVPGSERSYDLTGLKPGTEYPVVIQGVKGGHPSQPLSAIFIT |
| 296 | MLPAPKNLVVSRVTEDSARLSWTAPDAAFDSFFIGYLEPQPPGEA IILTVPGSERSYDLTGLKPGTEYNVTIQGVKGGFPSMPLSAIFTT |
| 297 | MLPAPKNLVVSRVTEDSARLSWTAPDAAFDSFLIPYAETSPSGEA ITLFVPGSERSYDLTGLKPGTEYNVVIQGVKGGRPSNPLVAASTT |
| 298 | MLPAPKNLVVSRVTEDSARLSWTAPDAAFDSFPIAYAEPRPDGEA IVLTVPGSERSYDLTGLKPGTEYSVLIHGVKGGLLSSPLSAISTT |
| 299 | MLPAPKNLVVSRVTEDSARLSWTAPDAAFDSFLIEYWESVGYGEA IVLTVPGSERSYDLTGLKPGTEYWVGIYGVKGGYYSRPLSAIFTT |
| 300 | MLPAPKNLVVSRVTEDSARLSWTAPDAAFDSFFIGYLEPQPPGEA IVLTVPGSERSYDLTGLKPGTEYNVTIHGVKGGTPSMPLSAIFTT |
| 301 | MLPAPKNLVVSRVTEDSARLSWTAPDAAFDSFEIEYDEPYRGGEA IVLTVPGSERSYDLTSLKPGTEYPVSIGGVKGGITSDPLSAIFTT |
| 302 | MLPAPKNLVVSRVTEDSARLSWTAPDAAFDSFDIYYPEYYDRGEA IVLTVPGSERSYDLTGLKPGTEYTVYIDGVKGGGGSGPLSAIFTT |
| 303 | MLPAPKNLVVSRVTEDSARLSWTAPDAAFDSFFIAYFEFANPGEA IVLTVPGSERSYDLTGLKPGTEYKVVIQGVKGGTPSEPLSAIFTT |
| 304 | MLPAPKNLVVSRVTEDSARLSWTAPDAAFDSFIITYWEHVGDGEA IVLTVPGSERSYDLTGLKPGTEYFVEIYGVKGGYLSKPLSAIFTT |
| 305 | MLPAPKNLVVSRVTEDSARLSWTAPDAAFDSFEIDYDEPFVYGEA IVLTVPGSERSYDLTGLKPGTEYRVFIFGVKGGNGSWPLSAIFTT |
| 306 | MLPAPKNLVVSRVTEDSARLSWTAPDAAFDSFYIEYFETQGYGEA IVLTVPGSERSYDLTGLKPGTEYYVAIYGVKGGYLSRPLSAIFTT |
| 307 | MLPAPKNLVVSRVTEDSARLSWTAPDAAFDSFPITYSEPAHYGEA IVLTVPGSERSYDLTGLKPGTEYHVGIMGVKGGVFSSPLSAIFTT |
| 308 | MLPAPKNLVVSEVTEDSARLSWQGVARAFDSFLITYREQIFAGEV IVLTVPGSERSYDLTGLKPGTEYPVWIQGVKGGSPSAPLSAISTT |

-continued

| SEQ ID NO: | Amino Acid sequence of FN3 domains that bind to CD71 |
|---|---|
| 309 | MLPAPKNLVVSRVTEDSARLSWTAPDAAFDSFIIDYLELDQEGEA IVLTVPGSERSYDLTGLKPGTEYAVYIFGVKGGYPSTPLSAIFTT |

Example 6

Knockdown of mRNA in muscle cells using CD71 FN3 domain-oligonucleotide conjugates. muCD71 binding FN3 domains are conjugated to siRNA oligonucleotides or antisense oligonucleotides (ASOs) using maleimide chemistry via a cysteine that is uniquely engineered into the FN3 domain. The cysteine substitutions can be one such as those provided for herein and also as provided for in U.S. Patent Application Publication No. 20150104808, which is hereby incorporated by reference in its entirety. siRNAs or ASOs are modified with standard chemical modifications and confirmed to enable knockdown of the targeted mRNA in vitro. FN3 domain-oligonucleotide conjugates are dosed intravenously in mice at doses up to 10 mg/kg oligonucleotide payload. At various time points following dosing, mice are sacrificed; skeletal muscle, heart muscle and various other tissues will be recovered and stored in RNAlater™ (Sigma Aldrich) until needed. Target gene knockdown is assessed using standard qPCR $\Delta\Delta C_T$ methods and primers specific for the target gene and a control gene. The target gene is found to be knock downed in the muscles and such knockdown is enhanced by conjugating the siRNA or ASO to the CD71 FN3 binding domain.

Example 7. General Methods

Standard methods in molecular biology are described Sambrook, Fritsch and Maniatis (1982 & 1989 $2^{nd}$ Edition, 2001 $3^{rd}$ Edition) *Molecular Cloning, A Laboratory Manual*, Cold Spring Harbor Laboratory Press, Cold Spring Harbor, N.Y.; Sambrook and Russell (2001) *Molecular Cloning, $3^{rd}$* ed., Cold Spring Harbor Laboratory Press, Cold Spring Harbor, N.Y.; Wu (1993) *Recombinant DNA*, Vol. 217, Academic Press, San Diego, Calif.). Standard methods also appear in Ausbel, et al. (2001) *Current Protocols in Molecular Biology*, Vols. 1-4, John Wiley and Sons, Inc. New York, N.Y., which describes cloning in bacterial cells and DNA mutagenesis (Vol. 1), cloning in mammalian cells and yeast (Vol. 2), glycoconjugates and protein expression (Vol. 3), and bioinformatics (Vol. 4).

Methods for protein purification including immunoprecipitation, chromatography, electrophoresis, centrifugation, and crystallization are described (Coligan, et al. (2000) *Current Protocols in Protein Science, Vol.* 1, John Wiley and Sons, Inc., New York). Chemical analysis, chemical modification, post-translational modification, production of fusion proteins, glycosylation of proteins are described (see, e.g., Coligan, et al. (2000) *Current Protocols in Protein Science, Vol.* 2, John Wiley and Sons, Inc., New York; Ausubel, et al. (2001) *Current Protocols in Molecular Biology, Vol.* 3, John Wiley and Sons, Inc., NY, NY, pp. 16.0.5-16.22.17; Sigma-Aldrich, Co. (2001) *Products for Life Science Research*, St. Louis, Mo.; pp. 45-89; Amersham Pharmacia Biotech (2001) *BioDirectory*, Piscataway, N.J., pp. 384-391). Production, purification, and fragmentation of polyclonal and monoclonal antibodies are described (Coligan, et al. (2001) *Current Protocols in Immunology, Vol.* 1, John Wiley and Sons, Inc., New York; Harlow and Lane (1999) *Using Antibodies*, Cold Spring Harbor Laboratory Press, Cold Spring Harbor, N.Y.; Harlow and Lane, supra). Standard techniques for characterizing ligand/receptor interactions are available (see, e.g., Coligan, et al. (2001) *Current Protocols in Immunology, Vol.* 4, John Wiley, Inc., New York).

All references cited herein are incorporated by reference to the same extent as if each individual publication, database entry (e.g. Genbank sequences or GeneID entries), patent application, or patent, was specifically and individually indicated to be incorporated by reference. This statement of incorporation by reference is intended by Applicants, pursuant to 37 C.F.R. § 1.57(b)(1), to relate to each and every individual publication, database entry (e.g. Genbank sequences or GeneID entries), patent application, or patent, each of which is clearly identified in compliance with 37 C.F.R. § 1.57(b)(2), even if such citation is not immediately adjacent to a dedicated statement of incorporation by reference. The inclusion of dedicated statements of incorporation by reference, if any, within the specification does not in any way weaken this general statement of incorporation by reference. Citation of the references herein is not intended as an admission that the reference is pertinent prior art, nor does it constitute any admission as to the contents or date of these publications or documents.

The present embodiments are not to be limited in scope by the specific embodiments described herein. Indeed, various modifications of the embodiments in addition to those described herein will become apparent to those skilled in the art from the foregoing description. Such modifications are intended to fall within the scope of the appended claims.

The foregoing written specification is considered to be sufficient to enable one skilled in the art to practice the embodiments. Various modifications of the embodiments in addition to those shown and described herein will become apparent to those skilled in the art from the foregoing description and fall within the scope of the appended claims.

What is claimed:

1. A polypeptide comprising the amino acid sequence that is at least 90% identical to the amino acid sequence selected from the group consisting of SEQ ID NOs: 33-39, 41-62, 81-136, 138-186, 188-261, and 263-309, or at least 91% identical to the amino acid sequence selected from the group consisting of SEQ ID NOs: 40, 137, 187, and 262, or any combination thereof.

2. The polypeptide of claim 1, wherein the polypeptide comprises two amino acid sequences selected from the group consisting of SEQ ID NOs: 33-62 and 81-309.

3. The polypeptide of claim 1, wherein the polypeptide comprises the amino acid sequence selected from the group consisting of SEQ ID NOs: 33-62 and or 81-309.

4. The polypeptide of claim 1, wherein the polypeptide is conjugated to a detectable label, an oligonucleotide, a therapeutic agent, or any combination thereof.

5. The polypeptide of claim 4, wherein the detectable label is a radioactive isotope, magnetic beads, metallic beads, colloidal particles, a fluorescent dye, an electron-dense reagent, an enzyme, biotin, digoxigenin, or hapten.

6. The polypeptide of claim 4, wherein the therapeutic agent is auristatin, monomethyl auristatin phenylalanine, dolostatin, a chemotherapeutic agent, a drug, a growth inhibitory agent, a toxin, or a radioactive isotope.

7. The polypeptide of claim 4, wherein the therapeutic agent is a chemotherapeutic agent, a drug, an antibody, a growth inhibitory agent, a toxin, a radioactive isotope, an anti-tubulin agent, a polynucleotide, a double stranded short interfering ribonucleic acid (siRNA) molecule or a sense or an antisense strand thereof, a double stranded antisense molecule or a strand thereof, a RNA molecule, a deoxyribonucleic acid (DNA) molecule, DNA minor groove binders, DNA replication inhibitors, alkylating agents, antibiotics, antifolates, antimetabolites, chemotherapy sensitizers, topoisomerase inhibitors, or a *vinca* alkaloid.

8. The polypeptide of claim 1, wherein the polypeptide comprises the amino acid sequence that is at least 90% identical to SEQ ID NO: 140.

9. The polypeptide of claim 8, wherein the polypeptide is conjugated to a detectable label, an oligonucleotide, a therapeutic agent, or any combination thereof.

10. The polypeptide of claim 1, wherein the polypeptide comprises the amino acid sequence that is at least 95% identical to SEQ ID NO: 140.

11. The polypeptide of claim 1, wherein the polypeptide comprises the amino acid sequence that is at least 90% identical to SEQ ID NO: 146.

12. The polypeptide of claim 11, wherein the polypeptide is conjugated to a detectable label, an oligonucleotide, a therapeutic agent, or any combination thereof.

13. The polypeptide of claim 1, wherein the polypeptide comprises the amino acid sequence that is at least 95% identical to SEQ ID NO: 146.

14. The polypeptide of claim 1, wherein the polypeptide comprises the amino acid sequence that is at least 90% identical to SEQ ID NO: 179.

15. The polypeptide of claim 14, wherein the polypeptide is conjugated to a detectable label, an oligonucleotide, a therapeutic agent, or any combination thereof.

16. The polypeptide of claim 1, wherein the polypeptide comprises the amino acid sequence that is at least 95% identical to SEQ ID NO: 179.

17. The polypeptide of claim 1, wherein the polypeptide comprises the amino acid sequence that is at least 90% identical to SEQ ID NO: 182.

18. The polypeptide of claim 17, wherein the polypeptide is conjugated to a detectable label, an oligonucleotide, a therapeutic agent, or any combination thereof.

19. The polypeptide of claim 1, wherein the polypeptide comprises the amino acid sequence that is at least 95% identical to SEQ ID NO: 182.

20. A pharmaceutical composition comprising the polypeptide of claim 1 and a pharmaceutically acceptable carrier.

21. A pharmaceutical composition comprising the polypeptide of claim 8 and a pharmaceutically acceptable carrier.

22. A pharmaceutical composition comprising the polypeptide of claim 10 and a pharmaceutically acceptable carrier.

23. A pharmaceutical composition comprising the polypeptide of claim 11 and a pharmaceutically acceptable carrier.

24. A pharmaceutical composition comprising the polypeptide of claim 13 and a pharmaceutically acceptable carrier.

25. A pharmaceutical composition comprising the polypeptide of claim 14 and a pharmaceutically acceptable carrier.

26. A pharmaceutical composition comprising the polypeptide of claim 16 and a pharmaceutically acceptable carrier.

27. A pharmaceutical composition comprising the polypeptide of claim 17 and a pharmaceutically acceptable carrier.

28. A pharmaceutical composition comprising the polypeptide of claim 19 and a pharmaceutically acceptable carrier.

29. A method of delivering an agent of interest to a cluster of differentiation 71 (CD71) positive cell, wherein the method comprises contacting the cell with a conjugate comprising the agent of interest coupled to a polypeptide comprising the amino acid sequence selected from the group consisting of SEQ ID NOs: 33-62 and 81-309.

30. The method of claim 29, wherein the cell is a muscle cell a brain cell, or a cell inside of the blood brain barrier.

31. A method of delivering an agent of interest to a CD71 positive cell, wherein the method comprises contacting the cell with a pharmaceutical composition comprising:
   a conjugate comprising the agent of interest coupled to the polypeptide of claim 8; and
   a pharmaceutically acceptable carrier.

32. A method of delivering an agent of interest to a CD71 positive cell, wherein the method comprises contacting the cell with a pharmaceutical composition comprising:
   a conjugate comprising the agent of interest coupled to the polypeptide of claim 11; and
   a pharmaceutically acceptable carrier.

33. A method of delivering an agent of interest to a CD71 positive cell, wherein the method comprises contacting the cell with a pharmaceutical composition comprising:
   a conjugate comprising the agent of interest coupled to the polypeptide of claim 14; and
   a pharmaceutically acceptable carrier.

34. A method of delivering an agent of interest to a CD71 positive cell, wherein the method comprises contacting the cell with a pharmaceutical composition comprising:
   a conjugate comprising the agent of interest coupled to the polypeptide of claim 17; and
   a pharmaceutically acceptable carrier.

* * * * *

SEQUENCE LISTING

<160> NUMBER OF SEQ ID NOS: 309

<210> SEQ ID NO 1
<211> LENGTH: 89
<212> TYPE: PRT
<213> ORGANISM: Homo sapiens

<400> SEQUENCE: 1

Leu Pro Ala Pro Lys Asn Leu Val Val Ser Glu Val Thr Glu Asp Ser
1               5                   10                  15

Leu Arg Leu Ser Trp Thr Ala Pro Asp Ala Ala Phe Asp Ser Phe Leu
            20                  25                  30

Ile Gln Tyr Gln Glu Ser Glu Lys Val Gly Glu Ala Ile Asn Leu Thr
            35                  40                  45

Val Pro Gly Ser Glu Arg Ser Tyr Asp Leu Thr Gly Leu Lys Pro Gly
 50                  55                  60

Thr Glu Tyr Thr Val Ser Ile Tyr Gly Val Lys Gly Gly His Arg Ser
 65                  70                  75                  80

Asn Pro Leu Ser Ala Glu Phe Thr Thr
                 85

<210> SEQ ID NO 2
<211> LENGTH: 94
<212> TYPE: PRT
<213> ORGANISM: Artificial Sequence
<220> FEATURE:
<223> OTHER INFORMATION: synthetic sequence
<220> FEATURE:
<221> NAME/KEY: MISC_FEATURE
<222> LOCATION: (75)..(81)
<223> OTHER INFORMATION: X is any amino acid
<220> FEATURE:
<221> NAME/KEY: MISC_FEATURE
<222> LOCATION: (82)..(86)
<223> OTHER INFORMATION: X is any amino acid or deleted

<400> SEQUENCE: 2

Leu Pro Ala Pro Lys Asn Leu Val Val Ser Glu Val Thr Glu Asp Ser
 1               5                  10                  15

Leu Arg Leu Ser Trp Thr Ala Pro Asp Ala Ala Phe Asp Ser Phe Leu
            20                  25                  30

Ile Gln Tyr Gln Glu Ser Glu Lys Val Gly Glu Ala Ile Asn Leu Thr
            35                  40                  45

Val Pro Gly Ser Glu Arg Ser Tyr Asp Leu Thr Gly Leu Lys Pro Gly
 50                  55                  60

Thr Glu Tyr Thr Val Ser Ile Tyr Gly Val Xaa Xaa Xaa Xaa Xaa Xaa
 65                  70                  75                  80

Xaa Xaa Xaa Xaa Xaa Xaa Pro Leu Ser Ala Glu Phe Thr Thr
            85                  90

<210> SEQ ID NO 3
<211> LENGTH: 89
<212> TYPE: PRT
<213> ORGANISM: Artificial Sequence
<220> FEATURE:
<223> OTHER INFORMATION: synthetic sequence
<220> FEATURE:
<221> NAME/KEY: MISC_FEATURE
<222> LOCATION: (22)..(27)
<223> OTHER INFORMATION: each X is Ala, Arg, Asn, Asp, Glu, Gln, Gly,
      His, Ile, Leu, Lys, Phe, Pro, Ser, Thr, Trp, Tyr or Val
<220> FEATURE:
<221> NAME/KEY: MISC_FEATURE
<222> LOCATION: (28)..(28)
<223> OTHER INFORMATION: X is Phe, Ile, Leu, Val or Tyr
<220> FEATURE:
<221> NAME/KEY: MISC_FEATURE
<222> LOCATION: (29)..(29)
<223> OTHER INFORMATION: X is Asp, Glu or Thr
<220> FEATURE:
<221> NAME/KEY: MISC_FEATURE
<222> LOCATION: (75)..(79)
<223> OTHER INFORMATION: each X is Ala, Arg, Asn, Asp, Glu, Gln, Gly,
      His, Ile, Leu, Lys, Phe, Pro, Ser, Thr, Trp, Tyr or Val
<220> FEATURE:
<221> NAME/KEY: MISC_FEATURE

```
<222> LOCATION: (81)..(82)
<223> OTHER INFORMATION: each X is Ala, Arg, Asn, Asp, Glu, Gln, Gly,
      His, Ile, Leu, Lys, Phe, Pro, Ser, Thr, Trp, Tyr or Val

<400> SEQUENCE: 3

Leu Pro Ala Pro Lys Asn Leu Val Val Ser Glu Val Thr Glu Asp Ser
1               5                   10                  15

Leu Arg Leu Ser Trp Xaa Xaa Xaa Xaa Xaa Xaa Xaa Ser Phe Leu
            20                  25                  30

Ile Gln Tyr Gln Glu Ser Glu Lys Val Gly Glu Ala Ile Asn Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val Xaa Xaa Xaa Xaa Xaa Ser
65                  70                  75                  80

Xaa Xaa Leu Ser Ala Glu Phe Thr Thr
                85

<210> SEQ ID NO 4
<211> LENGTH: 89
<212> TYPE: PRT
<213> ORGANISM: Artificial Sequence
<220> FEATURE:
<223> OTHER INFORMATION: synthetic sequence

<400> SEQUENCE: 4

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Leu
            20                  25                  30

Ile Gln Tyr Gln Glu Ser Glu Lys Val Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val Lys Gly Gly His Arg Ser
65                  70                  75                  80

Asn Pro Leu Ser Ala Ile Phe Thr Thr
                85

<210> SEQ ID NO 5
<211> LENGTH: 97
<212> TYPE: PRT
<213> ORGANISM: Artificial Sequence
<220> FEATURE:
<223> OTHER INFORMATION: synthetic sequence
<220> FEATURE:
<221> NAME/KEY: MISC_FEATURE
<222> LOCATION: (22)..(27)
<223> OTHER INFORMATION: each X is A, D, E, F, G, H, I, K, L, N, P, Q,
      R, S, T, V, W or Y
<220> FEATURE:
<221> NAME/KEY: MISC_FEATURE
<222> LOCATION: (28)..(30)
<223> OTHER INFORMATION: each X is A, D, E, F, G, H, I, K, L, N, P, Q,
      R, S, T, V, W, Y or deleted
<220> FEATURE:
<221> NAME/KEY: MISC_FEATURE
<222> LOCATION: (78)..(84)
<223> OTHER INFORMATION: each X is A, D, E, F, G, H, I, K, L, N, P, Q,
      R, S, T, V, W or Y
<220> FEATURE:
<221> NAME/KEY: MISC_FEATURE
<222> LOCATION: (85)..(87)
<223> OTHER INFORMATION: each X is A, D, E, F, G, H, I, K, L, N, P, Q,
      R, S, T, V, W, Y or deleted
```

<400> SEQUENCE: 5

Leu Pro Ala Pro Lys Asn Leu Val Val Ser Arg Val Thr Glu Asp Ser
1               5                   10                  15

Ala Arg Leu Ser Trp Xaa Xaa Xaa Xaa Xaa Xaa Xaa Xaa Phe Asp
            20                  25                  30

Ser Phe Leu Ile Gln Tyr Gln Glu Ser Glu Lys Val Gly Glu Ala Ile
        35                  40                  45

Val Leu Thr Val Pro Gly Ser Glu Arg Ser Tyr Asp Leu Thr Gly Leu
50                  55                  60

Lys Pro Gly Thr Glu Tyr Thr Val Ser Ile Tyr Gly Val Xaa Xaa Xaa
65                  70                  75                  80

Xaa Xaa Xaa Xaa Xaa Xaa Xaa Ser Asn Pro Leu Ser Ala Ile Phe Thr
                85                  90                  95

Thr

<210> SEQ ID NO 6
<211> LENGTH: 96
<212> TYPE: PRT
<213> ORGANISM: Artificial Sequence
<220> FEATURE:
<223> OTHER INFORMATION: synthetic sequence
<220> FEATURE:
<221> NAME/KEY: MISC_FEATURE
<222> LOCATION: (75)..(81)
<223> OTHER INFORMATION: each X is A, D, E, F, G, H, I, K, L, N, P, Q,
      R, S, T, V, W or Y
<220> FEATURE:
<221> NAME/KEY: MISC_FEATURE
<222> LOCATION: (82)..(86)
<223> OTHER INFORMATION: each X is A, D, E, F, G, H, I, K, L, N, P, Q,
      R, S, T, V, W, Y or deleted

<400> SEQUENCE: 6

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Leu
            20                  25                  30

Ile Gln Tyr Gln Glu Ser Glu Lys Val Gly Glu Ala Ile Val Leu Thr
        35                  40                  45

Val Pro Gly Ser Glu Arg Ser Tyr Asp Leu Thr Gly Leu Lys Pro Gly
50                  55                  60

Thr Glu Tyr Thr Val Ser Ile Tyr Gly Val Xaa Xaa Xaa Xaa Xaa
65                  70                  75                  80

Xaa Xaa Xaa Xaa Xaa Xaa Ser Asn Pro Leu Ser Ala Ile Phe Thr Thr
                85                  90                  95

<210> SEQ ID NO 7
<211> LENGTH: 89
<212> TYPE: PRT
<213> ORGANISM: Artificial Sequence
<220> FEATURE:
<223> OTHER INFORMATION: synthetic sequence
<220> FEATURE:
<221> NAME/KEY: MISC_FEATURE
<222> LOCATION: (32)..(32)
<223> OTHER INFORMATION: X is A, D, E, F, G, H, I, K, L, N, P, Q, R, S,
      T, V, W,Y, C or M
<220> FEATURE:
<221> NAME/KEY: MISC_FEATURE
<222> LOCATION: (34)..(34)
<223> OTHER INFORMATION: X is A, D, E, F, G, H, I, K, L, N, P, Q, R, S,
      T, V, W,Y, C or M
<220> FEATURE:

```
<221> NAME/KEY: MISC_FEATURE
<222> LOCATION: (36)..(36)
<223> OTHER INFORMATION: X is A, D, E, F, G, H, I, K, L, N, P, Q, R, S,
      T, V, W,Y, C or M
<220> FEATURE:
<221> NAME/KEY: MISC_FEATURE
<222> LOCATION: (38)..(41)
<223> OTHER INFORMATION: X is A, D, E, F, G, H, I, K, L, N, P, Q, R, S,
      T, V, W,Y, C or M
<220> FEATURE:
<221> NAME/KEY: MISC_FEATURE
<222> LOCATION: (68)..(68)
<223> OTHER INFORMATION: X is A, D, E, F, G, H, I, K, L, N, P, Q, R, S,
      T, V, W,Y, C or M
<220> FEATURE:
<221> NAME/KEY: MISC_FEATURE
<222> LOCATION: (70)..(70)
<223> OTHER INFORMATION: X is A, D, E, F, G, H, I, K, L, N, P, Q, R, S,
      T, V, W,Y, C or M
<220> FEATURE:
<221> NAME/KEY: MISC_FEATURE
<222> LOCATION: (72)..(72)
<223> OTHER INFORMATION: X is A, D, E, F, G, H, I, K, L, N, P, Q, R, S,
      T, V, W,Y, C or M
<220> FEATURE:
<221> NAME/KEY: MISC_FEATURE
<222> LOCATION: (78)..(79)
<223> OTHER INFORMATION: X is A, D, E, F, G, H, I, K, L, N, P, Q, R, S,
      T, V, W,Y, C or M
<220> FEATURE:
<221> NAME/KEY: MISC_FEATURE
<222> LOCATION: (81)..(81)
<223> OTHER INFORMATION: X is A, D, E, F, G, H, I, K, L, N, P, Q, R, S,
      T, V, W,Y, C or M

<400> SEQUENCE: 7

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Xaa
            20                  25                  30

Ile Xaa Tyr Xaa Glu Xaa Xaa Xaa Xaa Gly Glu Ala Ile Val Leu Thr
        35                  40                  45

Val Pro Gly Ser Glu Arg Ser Tyr Asp Leu Thr Gly Leu Lys Pro Gly
    50                  55                  60

Thr Glu Tyr Xaa Val Xaa Ile Xaa Gly Val Lys Gly Gly Xaa Xaa Ser
65                  70                  75                  80

Xaa Pro Leu Ser Ala Ile Phe Thr Thr
                85

<210> SEQ ID NO 8
<211> LENGTH: 89
<212> TYPE: PRT
<213> ORGANISM: Artificial Sequence
<220> FEATURE:
<223> OTHER INFORMATION: synthetic sequence
<220> FEATURE:
<221> NAME/KEY: MISC_FEATURE
<222> LOCATION: (32)..(32)
<223> OTHER INFORMATION: X is A, D, E, F, G, H, I, K, L, N, P, Q, R, S,
      T, V, Y or W
<220> FEATURE:
<221> NAME/KEY: MISC_FEATURE
<222> LOCATION: (34)..(34)
<223> OTHER INFORMATION: X is A, D, E, F, G, H, I, K, L, N, P, Q, R, S,
      T, V, Y or W
<220> FEATURE:
<221> NAME/KEY: MISC_FEATURE
<222> LOCATION: (36)..(36)
<223> OTHER INFORMATION: X is A, D, E, F, G, H, I, K, L, N, P, Q, R, S,
      T, V, Y or W
<220> FEATURE:
<221> NAME/KEY: MISC_FEATURE
```

```
<222> LOCATION: (38)..(41)
<223> OTHER INFORMATION: X is A, D, E, F, G, H, I, K, L, N, P, Q, R, S,
      T, V, Y or W
<220> FEATURE:
<221> NAME/KEY: MISC_FEATURE
<222> LOCATION: (46)..(46)
<223> OTHER INFORMATION: X is A, D, E, F, G, H, I, K, L, N, P, Q, R, S,
      T, V, Y or W
<220> FEATURE:
<221> NAME/KEY: MISC_FEATURE
<222> LOCATION: (48)..(48)
<223> OTHER INFORMATION: X is A, D, E, F, G, H, I, K, L, N, P, Q, R, S,
      T, V, Y or W
<220> FEATURE:
<221> NAME/KEY: MISC_FEATURE
<222> LOCATION: (68)..(68)
<223> OTHER INFORMATION: X is A, D, E, F, G, H, I, K, L, N, P, Q, R, S,
      T, V, Y or W
<220> FEATURE:
<221> NAME/KEY: MISC_FEATURE
<222> LOCATION: (70)..(70)
<223> OTHER INFORMATION: X is A, D, E, F, G, H, I, K, L, N, P, Q, R, S,
      T, V, Y or W
<220> FEATURE:
<221> NAME/KEY: MISC_FEATURE
<222> LOCATION: (72)..(72)
<223> OTHER INFORMATION: X is A, D, E, F, G, H, I, K, L, N, P, Q, R, S,
      T, V, Y or W
<220> FEATURE:
<221> NAME/KEY: MISC_FEATURE
<222> LOCATION: (78)..(79)
<223> OTHER INFORMATION: X is A, D, E, F, G, H, I, K, L, N, P, Q, R, S,
      T, V, Y or W
<220> FEATURE:
<221> NAME/KEY: MISC_FEATURE
<222> LOCATION: (81)..(81)
<223> OTHER INFORMATION: X is A, D, E, F, G, H, I, K, L, N, P, Q, R, S,
      T, V, Y or W
<220> FEATURE:
<221> NAME/KEY: MISC_FEATURE
<222> LOCATION: (84)..(84)
<223> OTHER INFORMATION: X is A, D, E, F, G, H, I, K, L, N, P, Q, R, S,
      T, V, Y or W
<220> FEATURE:
<221> NAME/KEY: MISC_FEATURE
<222> LOCATION: (86)..(86)
<223> OTHER INFORMATION: X is A, D, E, F, G, H, I, K, L, N, P, Q, R, S,
      T, V, Y or W

<400> SEQUENCE: 8

Leu Pro Ala Pro Lys Asn Leu Val Val Ser Arg Val Thr Glu Asp Ser
1               5                   10                  15

Ala Arg Leu Ser Trp Thr Ala Pro Asp Ala Ala Phe Asp Ser Phe Xaa
                20                  25                  30

Ile Xaa Tyr Xaa Glu Xaa Xaa Xaa Gly Glu Ala Ile Xaa Leu Xaa
            35                  40                  45

Val Pro Gly Ser Glu Arg Ser Tyr Asp Leu Thr Gly Leu Lys Pro Gly
    50                  55                  60

Thr Glu Tyr Xaa Val Xaa Ile Xaa Gly Val Lys Gly Gly Xaa Xaa Ser
65                  70                  75                  80

Xaa Pro Leu Xaa Ala Xaa Phe Thr Thr
                85

<210> SEQ ID NO 9
<211> LENGTH: 19
<212> TYPE: DNA
<213> ORGANISM: Artificial Sequence
<220> FEATURE:
<223> OTHER INFORMATION: synthetic sequence

<400> SEQUENCE: 9
```

```
gtgacacggc ggttagaac                                                    19
```

<210> SEQ ID NO 10
<211> LENGTH: 20
<212> TYPE: DNA
<213> ORGANISM: Artificial Sequence
<220> FEATURE:
<223> OTHER INFORMATION: synthetic sequence

<400> SEQUENCE: 10

```
gcctttggga agcttctaag                                                   20
```

<210> SEQ ID NO 11
<211> LENGTH: 30
<212> TYPE: DNA
<213> ORGANISM: Artificial Sequence
<220> FEATURE:
<223> OTHER INFORMATION: synthetic sequence

<400> SEQUENCE: 11

```
cggcggttag aacgcggcta caattaatac                                        30
```

<210> SEQ ID NO 12
<211> LENGTH: 22
<212> TYPE: DNA
<213> ORGANISM: Artificial Sequence
<220> FEATURE:
<223> OTHER INFORMATION: synthetic sequence

<400> SEQUENCE: 12

```
catgattacg ccaagctcag aa                                                22
```

<210> SEQ ID NO 13
<211> LENGTH: 385
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (198)..(224)
<223> OTHER INFORMATION: n is any base

<400> SEQUENCE: 13

```
gtgacacggc ggttagaacg cggctacaat taatacataa ccccatcccc ctgttgacaa       60
ttaatcatcg gctcgtataa tgtgtggaat tgtgagcgga taacaatttc acacaggaaa      120
caggatctac catgctgccg gcgccgaaaa acctggttgt ttctgaagtt accgaagact      180
ctctgcgtct gtcttggnnn nnnnnnnnn nnnnnnnnn nnnnttygac tctttcctga       240
tccagtacca ggaatctgaa aaagttggtg aagcgatcaa cctgaccgtt ccgggttctg      300
aacgttctta cgacctgacc ggtctgaaac cgggtaccga atacaccgtt tctatctacg      360
gtgttcttag aagcttccca aaggc                                            385
```

<210> SEQ ID NO 14
<211> LENGTH: 382
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (198)..(221)
<223> OTHER INFORMATION: n is any base

<400> SEQUENCE: 14

```
gtgacacggc ggttagaacg cggctacaat taatacataa ccccatcccc ctgttgacaa    60
ttaatcatcg gctcgtataa tgtgtggaat tgtgagcgga taacaatttc acacaggaaa   120
caggatctac catgctgccg gcgccgaaaa acctggttgt ttctgaagtt accgaagact   180
ctctgcgtct gtcttggnnn nnnnnnnnnn nnnnnnnnnn nttygactct ttcctgatcc   240
agtaccagga atctgaaaaa gttggtgaag cgatcaacct gaccgttccg ggttctgaac   300
gttcttacga cctgaccggt ctgaaaccgg gtaccgaata caccgtttct atctacggtg   360
ttcttagaag cttcccaaag gc                                            382
```

```
<210> SEQ ID NO 15
<211> LENGTH: 379
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (198)..(218)
<223> OTHER INFORMATION: n is any base

<400> SEQUENCE: 15
gtgacacggc ggttagaacg cggctacaat taatacataa ccccatcccc ctgttgacaa    60
ttaatcatcg gctcgtataa tgtgtggaat tgtgagcgga taacaatttc acacaggaaa   120
caggatctac catgctgccg gcgccgaaaa acctggttgt ttctgaagtt accgaagact   180
ctctgcgtct gtcttggnnn nnnnnnnnnn nnnnnnnntt ygactctttc ctgatccagt   240
accaggaatc tgaaaaagtt ggtgaagcga tcaacctgac cgttccgggt tctgaacgtt   300
cttacgacct gaccggtctg aaaccgggta ccgaatacac cgtttctatc tacggtgttc   360
ttagaagctt cccaaaggc                                                379
```

```
<210> SEQ ID NO 16
<211> LENGTH: 376
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (198)..(215)
<223> OTHER INFORMATION: n is any base

<400> SEQUENCE: 16
gtgacacggc ggttagaacg cggctacaat taatacataa ccccatcccc ctgttgacaa    60
ttaatcatcg gctcgtataa tgtgtggaat tgtgagcgga taacaatttc acacaggaaa   120
caggatctac catgctgccg gcgccgaaaa acctggttgt ttctgaagtt accgaagact   180
ctctgcgtct gtcttggnnn nnnnnnnnnn nnnnnttyga ctctttcctg atccagtacc   240
aggaatctga aaaagttggt gaagcgatca acctgaccgt tccgggttct gaacgttctt   300
acgacctgac cggtctgaaa ccgggtaccg aatacaccgt ttctatctac ggtgttctta   360
gaagcttccc aaaggc                                                   376
```

```
<210> SEQ ID NO 17
<211> LENGTH: 131
<212> TYPE: DNA
<213> ORGANISM: Artificial Sequence
<220> FEATURE:
<223> OTHER INFORMATION: synthetic sequence
```

-continued

<400> SEQUENCE: 17
cggcggttag aacgcggcta caattaatac ataaccccat cccctgttg acaattaatc    60 atcggctcgt ataatgtgtg gaattgtgag cggataacaa tttcacacag gaaacaggat   120
ctaccatgct g                                                       131

<210> SEQ ID NO 18
<211> LENGTH: 30
<212> TYPE: DNA
<213> ORGANISM: Artificial Sequence
<220> FEATURE:
<223> OTHER INFORMATION: synthetic sequence

<400> SEQUENCE: 18
cggcggttag aacgcggcta caattaatac                                    30

<210> SEQ ID NO 19
<211> LENGTH: 81
<212> TYPE: DNA
<213> ORGANISM: Artificial Sequence
<220> FEATURE:
<223> OTHER INFORMATION: synthetic sequence

<400> SEQUENCE: 19
ccaagacaga cgggcagagt cttcggtaac gcgagaaaca accaggtttt tcggcgccgg    60
cagcatggta gatcctgttt c                                             81

<210> SEQ ID NO 20
<211> LENGTH: 26
<212> TYPE: DNA
<213> ORGANISM: Artificial Sequence
<220> FEATURE:
<223> OTHER INFORMATION: synthetic sequence

<400> SEQUENCE: 20
ccgaagactc tgcccgtctg tcttgg                                        26

<210> SEQ ID NO 21
<211> LENGTH: 45
<212> TYPE: DNA
<213> ORGANISM: Artificial Sequence
<220> FEATURE:
<223> OTHER INFORMATION: synthetic sequence

<400> SEQUENCE: 21
cagtggtctc acggattcct ggtactggat caggaaagag tcgaa                   45

<210> SEQ ID NO 22
<211> LENGTH: 54
<212> TYPE: DNA
<213> ORGANISM: Artificial Sequence
<220> FEATURE:
<223> OTHER INFORMATION: synthetic sequence

<400> SEQUENCE: 22
catgcggtct cttccgaaaa agttggtgaa gcgatcgtcc tgaccgttcc gggt         54

<210> SEQ ID NO 23
<211> LENGTH: 29
<212> TYPE: DNA
<213> ORGANISM: Artificial Sequence
<220> FEATURE:
<223> OTHER INFORMATION: synthetic sequence

<400> SEQUENCE: 23

```
ggtggtgaag atcgcagaca gcgggttag                                    29

<210> SEQ ID NO 24
<211> LENGTH: 21
<212> TYPE: DNA
<213> ORGANISM: Artificial Sequence
<220> FEATURE:
<223> OTHER INFORMATION: synthetic sequence

<400> SEQUENCE: 24
cggcggttag aacgcggcta c                                            21

<210> SEQ ID NO 25
<211> LENGTH: 61
<212> TYPE: DNA
<213> ORGANISM: Artificial Sequence
<220> FEATURE:
<223> OTHER INFORMATION: synthetic sequence

<400> SEQUENCE: 25
aagatcagtt gcggccgcta gactagaacc gctgccaccg ccggtggtga agatcgcaga   60
c                                                                  61

<210> SEQ ID NO 26
<211> LENGTH: 485
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (357)..(392)
<223> OTHER INFORMATION: n is any base

<400> SEQUENCE: 26
gtgacacggc ggttagaacg cggctacaat taatacataa ccccatcccc ctgttgacaa   60
ttaatcatcg gctcgtataa tgtgtggaat tgtgagcgga taacaatttc acacaggaaa  120
caggatctac catgctgccg gcgccgaaaa acctggttgt ttctcgcgtt accgaagact  180
ctgcgcgtct gtcttggacc gcgccggacg cggcgttcga ctctttcctg atccagtacc  240
aggaatctga aaaagttggt gaagcgatcg tgctgaccgt tccgggttct gaacgttctt  300
acgacctgac cggtctgaaa ccgggtaccg aatacaccgt ttctatctac ggtgttnnnn  360
nnnnnnnnnn nnnnnnnnnn nnnnnnnnnn nntctaaccc gctgtctgcg atcttcacca  420
ccggcggtca ccatcaccat caccatggca gcggttctag tctagcggcc gcaactgatc  480
ttggc                                                             485

<210> SEQ ID NO 27
<211> LENGTH: 482
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (357)..(389)
<223> OTHER INFORMATION: n is any base

<400> SEQUENCE: 27
gtgacacggc ggttagaacg cggctacaat taatacataa ccccatcccc ctgttgacaa   60
ttaatcatcg gctcgtataa tgtgtggaat tgtgagcgga taacaatttc acacaggaaa  120
```

```
caggatctac catgctgccg gcgccgaaaa acctggttgt ttctcgcgtt accgaagact      180
ctgcgcgtct gtcttggacc gcgccggacg cggcgttcga ctctttcctg atccagtacc      240
aggaatctga aaaagttggt gaagcgatcg tgctgaccgt tccgggttct gaacgttctt      300
acgacctgac cggtctgaaa ccgggtaccg aatacaccgt ttctatctac ggtgttnnnn      360
nnnnnnnnnn nnnnnnnnnn nnnnnnnnnt ctaacccgct gtctgcgatc ttcaccaccg      420
gcggtcacca tcaccatcac catggcagcg gttctagtct agcggccgca actgatcttg      480
gc                                                                     482
```

<210> SEQ ID NO 28
<211> LENGTH: 479
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (357)..(386)
<223> OTHER INFORMATION: n is any base

<400> SEQUENCE: 28

```
gtgacacggc ggttagaacg cggctacaat taatacataa ccccatcccc ctgttgacaa       60
ttaatcatcg gctcgtataa tgtgtggaat tgtgagcgga taacaatttc acacaggaaa      120
caggatctac catgctgccg gcgccgaaaa acctggttgt ttctcgcgtt accgaagact      180
ctgcgcgtct gtcttggacc gcgccggacg cggcgttcga ctctttcctg atccagtacc      240
aggaatctga aaaagttggt gaagcgatcg tgctgaccgt tccgggttct gaacgttctt      300
acgacctgac cggtctgaaa ccgggtaccg aatacaccgt ttctatctac ggtgttnnnn      360
nnnnnnnnnn nnnnnnnnnn nnnnntcta acccgctgtc tgcgatcttc accaccggcg      420
gtcaccatca ccatcaccat ggcagcggtt ctagtctagc ggccgcaact gatcttggc      479
```

<210> SEQ ID NO 29
<211> LENGTH: 476
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (357)..(383)
<223> OTHER INFORMATION: n is any base

<400> SEQUENCE: 29

```
gtgacacggc ggttagaacg cggctacaat taatacataa ccccatcccc ctgttgacaa       60
ttaatcatcg gctcgtataa tgtgtggaat tgtgagcgga taacaatttc acacaggaaa      120
caggatctac catgctgccg gcgccgaaaa acctggttgt ttctcgcgtt accgaagact      180
ctgcgcgtct gtcttggacc gcgccggacg cggcgttcga ctctttcctg atccagtacc      240
aggaatctga aaaagttggt gaagcgatcg tgctgaccgt tccgggttct gaacgttctt      300
acgacctgac cggtctgaaa ccgggtaccg aatacaccgt ttctatctac ggtgttnnnn      360
nnnnnnnnnn nnnnnnnnnn nnntctaacc cgctgtctgc gatcttcacc accggcggtc      420
accatcacca tcaccatggc agcggttcta gtctagcggc cgcaactgat cttggc         476
```

<210> SEQ ID NO 30
<211> LENGTH: 473
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (357)..(380)
<223> OTHER INFORMATION: n is any base

<400> SEQUENCE: 30

```
gtgacacggc ggttagaacg cggctacaat taatacataa ccccatcccc ctgttgacaa      60
ttaatcatcg gctcgtataa tgtgtggaat tgtgagcgga taacaatttc acacaggaaa     120
caggatctac catgctgccg gcgccgaaaa acctggttgt ttctcgcgtt accgaagact     180
ctgcgcgtct gtcttggacc gcgccggacg cggcgttcga ctctttcctg atccagtacc     240
aggaatctga aaaagttggt gaagcgatcg tgctgaccgt tccgggttct gaacgttctt     300
acgacctgac cggtctgaaa ccgggtaccg aatacaccgt ttctatctac ggtgttnnnn     360
nnnnnnnnnn nnnnnnnnnn tctaacccgc tgtctgcgat cttcaccacc ggcggtcacc     420
atcaccatca ccatggcagc ggttctagtc tagcggccgc aactgatctt ggc            473
```

<210> SEQ ID NO 31
<211> LENGTH: 470
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (357)..(377)
<223> OTHER INFORMATION: n is any base

<400> SEQUENCE: 31

```
gtgacacggc ggttagaacg cggctacaat taatacataa ccccatcccc ctgttgacaa      60
ttaatcatcg gctcgtataa tgtgtggaat tgtgagcgga taacaatttc acacaggaaa     120
caggatctac catgctgccg gcgccgaaaa acctggttgt ttctcgcgtt accgaagact     180
ctgcgcgtct gtcttggacc gcgccggacg cggcgttcga ctctttcctg atccagtacc     240
aggaatctga aaaagttggt gaagcgatcg tgctgaccgt tccgggttct gaacgttctt     300
acgacctgac cggtctgaaa ccgggtaccg aatacaccgt ttctatctac ggtgttnnnn     360
nnnnnnnnnn nnnnnnntct aacccgctgt ctgcgatctt caccaccggc ggtcaccatc     420
accatcacca tggcagcggt tctagtctag cggccgcaac tgatcttggc                470
```

<210> SEQ ID NO 32
<211> LENGTH: 291
<212> TYPE: PRT
<213> ORGANISM: Homo sapiens

<400> SEQUENCE: 32

Met Thr Lys Glu Tyr Gln Asp Leu Gln His Leu Asp Asn Glu Glu Ser
1               5                   10                  15

Asp His His Gln Leu Arg Lys Gly Pro Pro Pro Gln Pro Leu Leu
            20                  25                  30

Gln Arg Leu Cys Ser Gly Pro Arg Leu Leu Leu Ser Leu Gly Leu
        35                  40                  45

Ser Leu Leu Leu Leu Val Val Cys Val Ile Gly Ser Gln Asn Ser
    50                  55                  60

Gln Leu Gln Glu Glu Leu Arg Gly Leu Arg Glu Thr Phe Ser Asn Phe
65                  70                  75                  80

Thr Ala Ser Thr Glu Ala Gln Val Lys Gly Leu Ser Thr Gln Gly Gly

```
                85                  90                  95
Asn Val Gly Arg Lys Met Lys Ser Leu Glu Ser Gln Leu Glu Lys Gln
            100                 105                 110

Gln Lys Asp Leu Ser Glu Asp His Ser Ser Leu Leu Leu His Val Lys
        115                 120                 125

Gln Phe Val Ser Asp Leu Arg Ser Leu Ser Cys Gln Met Ala Ala Leu
    130                 135                 140

Gln Gly Asn Gly Ser Glu Arg Thr Cys Cys Pro Val Asn Trp Val Glu
145                 150                 155                 160

His Glu Arg Ser Cys Tyr Trp Phe Ser Arg Ser Gly Lys Ala Trp Ala
                165                 170                 175

Asp Ala Asp Asn Tyr Cys Arg Leu Glu Asp Ala His Leu Val Val Val
            180                 185                 190

Thr Ser Trp Glu Glu Lys Phe Val Gln His Ile Gly Pro Val
        195                 200                 205

Asn Thr Trp Met Gly Leu His Asp Gln Asn Gly Pro Trp Lys Trp Val
    210                 215                 220

Asp Gly Thr Asp Tyr Glu Thr Gly Phe Lys Asn Trp Arg Pro Glu Gln
225                 230                 235                 240

Pro Asp Asp Trp Tyr Gly His Gly Leu Gly Gly Glu Asp Cys Ala
                245                 250                 255

His Phe Thr Asp Asp Gly Arg Trp Asn Asp Asp Val Cys Gln Arg Pro
            260                 265                 270

Tyr Arg Trp Val Cys Gly Thr Glu Leu Asp Lys Ala Ser Gln Glu Pro
        275                 280                 285

Pro Leu Leu
    290

<210> SEQ ID NO 33
<211> LENGTH: 90
<212> TYPE: PRT
<213> ORGANISM: Artificial Sequence
<220> FEATURE:
<223> OTHER INFORMATION: synthetic sequence

<400> SEQUENCE: 33

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Thr Ile Gln Tyr Glu Glu Leu Thr Thr Val Gly Glu Ala Ile Tyr Leu
        35                  40                  45

Arg Val Pro Gly Ser Glu Arg Ser Tyr Asp Leu Thr Gly Leu Lys Pro
    50                  55                  60

Gly Thr Glu Tyr Val Val Trp Ile Glu Gly Val Lys Gly Gly Leu Arg
65                  70                  75                  80

Ser Asn Pro Leu Gly Ala Ala Phe Thr Thr
                85                  90

<210> SEQ ID NO 34
<211> LENGTH: 90
<212> TYPE: PRT
<213> ORGANISM: Artificial Sequence
<220> FEATURE:
<223> OTHER INFORMATION: synthetic sequence

<400> SEQUENCE: 34
```

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Ala Ile Thr Tyr Ile Glu Trp Trp Asp Val Gly Glu Ala Ile Gly Leu
            35                  40                  45

Lys Val Pro Gly Ser Glu Arg Ser Tyr Asp Leu Thr Gly Leu Lys Pro
        50                  55                  60

Gly Thr Glu Tyr Arg Val His Ile Gln Gly Val Lys Gly Gly Asn Asn
65                  70                  75                  80

Ser Tyr Pro Leu Asp Ala Leu Phe Thr Thr
            85                  90

<210> SEQ ID NO 35
<211> LENGTH: 90
<212> TYPE: PRT
<213> ORGANISM: Artificial Sequence
<220> FEATURE:
<223> OTHER INFORMATION: synthetic sequence

<400> SEQUENCE: 35

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Glu Ile Ala Tyr Phe Glu Ala Ile Trp Asn Gly Glu Ala Ile Tyr Leu
            35                  40                  45

Thr Val Pro Gly Ser Glu Arg Ser Tyr Asp Leu Thr Gly Leu Lys Pro
        50                  55                  60

Gly Thr Glu Tyr Gln Val Glu Ile Arg Gly Val Lys Gly Gly Pro Thr
65                  70                  75                  80

Ser Arg Pro Leu Phe Ala Trp Phe Thr Thr
            85                  90

<210> SEQ ID NO 36
<211> LENGTH: 90
<212> TYPE: PRT
<213> ORGANISM: Artificial Sequence
<220> FEATURE:
<223> OTHER INFORMATION: synthetic sequence

<400> SEQUENCE: 36

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Thr Ile Thr Tyr Ile Glu Trp Trp Glu Asn Gly Glu Ala Ile Ala Leu
            35                  40                  45

Ser Val Pro Gly Ser Glu Arg Ser Tyr Asp Leu Thr Gly Leu Lys Pro
        50                  55                  60

Gly Thr Glu Tyr Gln Val Gly Ile Ala Gly Val Lys Gly Gly Tyr Lys
65                  70                  75                  80

Ser Tyr Pro Leu Trp Ala Leu Phe Thr Thr
            85                  90

<210> SEQ ID NO 37
<211> LENGTH: 90
<212> TYPE: PRT
<213> ORGANISM: Artificial Sequence
<220> FEATURE:
<223> OTHER INFORMATION: synthetic sequence

<400> SEQUENCE: 37

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

His Ile Ile Tyr Thr Glu Glu Lys Glu Gly Glu Ala Ile Tyr Leu
        35                  40                  45

Arg Val Pro Gly Ser Glu Arg Ser Tyr Asp Leu Thr Gly Leu Lys Pro
        50                  55                  60

Gly Thr Glu Tyr Leu Val Glu Ile Glu Gly Val Lys Gly Gly Lys Arg
65                  70                  75                  80

Ser Val Pro Leu Asn Ala Ser Phe Thr Thr
                85                  90

<210> SEQ ID NO 38
<211> LENGTH: 90
<212> TYPE: PRT
<213> ORGANISM: Artificial Sequence
<220> FEATURE:
<223> OTHER INFORMATION: synthetic sequence

<400> SEQUENCE: 38

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

His Ile Ala Tyr Glu Glu Ser His Thr Thr Gly Glu Ala Ile Phe Leu
        35                  40                  45

Arg Val Pro Gly Ser Glu Arg Ser Tyr Asp Leu Thr Gly Leu Lys Pro
        50                  55                  60

Gly Thr Glu Tyr Ser Val Ser Ile Glu Gly Val Lys Gly Gly His Tyr
65                  70                  75                  80

Ser Pro Pro Leu Thr Ala Lys Phe Thr Thr
                85                  90

<210> SEQ ID NO 39
<211> LENGTH: 90
<212> TYPE: PRT
<213> ORGANISM: Artificial Sequence
<220> FEATURE:
<223> OTHER INFORMATION: synthetic sequence

<400> SEQUENCE: 39

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Asp Ile Asp Tyr Arg Glu Trp Trp Thr Leu Gly Glu Ala Ile Val Leu
        35                  40                  45

Thr Val Pro Gly Ser Glu Arg Ser Tyr Asp Leu Thr Gly Leu Lys Pro
        50                  55                  60

Gly Thr Glu Tyr Tyr Val Asn Ile Gln Gly Val Lys Gly Gly Leu Arg
65                  70                  75                  80

Ser Tyr Pro Leu Ser Ala Ile Phe Thr Thr
                85                  90

```
<210> SEQ ID NO 40
<211> LENGTH: 90
<212> TYPE: PRT
<213> ORGANISM: Artificial Sequence
<220> FEATURE:
<223> OTHER INFORMATION: synthetic sequence

<400> SEQUENCE: 40

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

Val Ile Glu Tyr Trp Glu Tyr Val Gly His Gly Glu Ala Ile Val Leu
            35                  40                  45

Thr Val Pro Gly Ser Glu Arg Ser Tyr Asp Leu Thr Gly Leu Lys Pro
        50                  55                  60

Gly Thr Glu Tyr Ser Val Gly Ile Tyr Gly Val Lys Gly Gly Ser Leu
65                  70                  75                  80

Ser Arg Pro Leu Ser Ala Ile Phe Thr Thr
                85                  90

<210> SEQ ID NO 41
<211> LENGTH: 90
<212> TYPE: PRT
<213> ORGANISM: Artificial Sequence
<220> FEATURE:
<223> OTHER INFORMATION: synthetic sequence

<400> SEQUENCE: 41

Met Leu Pro Ala Pro Lys Asn Leu Val Ile Ser Arg Val Thr Glu Asp
1               5                   10                  15

Ser Ala Arg Leu Ser Trp Thr Ala Pro Asp Ala Ala Phe Asp Ser Phe
                20                  25                  30

Phe Ile Tyr Tyr Ile Glu Ser Tyr Pro Ala Gly Glu Ala Ile Val Leu
            35                  40                  45

Thr Val Pro Gly Ser Glu Arg Ser Tyr Asp Leu Thr Gly Leu Lys Pro
        50                  55                  60

Gly Thr Glu Tyr Trp Val Gly Ile Asp Gly Val Lys Gly Gly Arg Trp
65                  70                  75                  80

Ser Thr Pro Leu Ser Ala Ile Phe Thr Thr
                85                  90

<210> SEQ ID NO 42
<211> LENGTH: 90
<212> TYPE: PRT
<213> ORGANISM: Artificial Sequence
<220> FEATURE:
<223> OTHER INFORMATION: synthetic sequence

<400> SEQUENCE: 42

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

Thr Ile Glu Tyr Tyr Glu Ser Phe Tyr Gly Gly Glu Ala Ile Val Leu
            35                  40                  45

Thr Val Pro Gly Ser Glu Arg Ser Tyr Asp Leu Thr Gly Leu Lys Pro
        50                  55                  60

Gly Thr Glu Tyr Tyr Val Ser Ile Tyr Gly Val Lys Gly Gly Trp Leu
```

```
                 65                  70                  75                  80
Ser Arg Pro Leu Ser Ala Ile Phe Thr Thr
                 85                  90

<210> SEQ ID NO 43
<211> LENGTH: 90
<212> TYPE: PRT
<213> ORGANISM: Artificial Sequence
<220> FEATURE:
<223> OTHER INFORMATION: synthetic sequence

<400> SEQUENCE: 43

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

Tyr Ile Glu Tyr Tyr Glu Ser Tyr Pro Gly Gly Glu Ala Ile Val Leu
            35                  40                  45

Thr Val Pro Gly Ser Glu Arg Ser Tyr Asp Leu Thr Gly Leu Lys Pro
        50                  55                  60

Gly Thr Glu Tyr Asp Val Tyr Ile Tyr Gly Val Lys Gly Gly Tyr Trp
65                  70                  75                  80

Ser Arg Pro Leu Ser Ala Ile Phe Thr Thr
                85                  90

<210> SEQ ID NO 44
<211> LENGTH: 90
<212> TYPE: PRT
<213> ORGANISM: Artificial Sequence
<220> FEATURE:
<223> OTHER INFORMATION: synthetic sequence

<400> SEQUENCE: 44

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

Tyr Ile Glu Tyr Tyr Glu Ser Leu Pro Asp Gly Glu Ala Ile Val Leu
            35                  40                  45

Thr Val Pro Gly Ser Glu Arg Ser Tyr Asp Leu Thr Gly Leu Lys Pro
        50                  55                  60

Gly Thr Glu Tyr Ala Val Tyr Ile Tyr Gly Val Lys Gly Gly Tyr Tyr
65                  70                  75                  80

Ser Arg Pro Leu Ser Ala Ile Phe Thr Thr
                85                  90

<210> SEQ ID NO 45
<211> LENGTH: 90
<212> TYPE: PRT
<213> ORGANISM: Artificial Sequence
<220> FEATURE:
<223> OTHER INFORMATION: synthetic sequence

<400> SEQUENCE: 45

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

Ala Ile Tyr Tyr Leu Glu Ser Tyr Pro Glu Gly Glu Ala Ile Val Leu
            35                  40                  45
```

```
Thr Val Pro Gly Ser Glu Arg Ser Tyr Asp Leu Thr Gly Leu Lys Pro
        50                  55                  60

Gly Thr Glu Tyr Trp Val Gly Ile Asp Gly Val Lys Gly Gly Thr Trp
 65                  70                  75                  80

Ser Ser Pro Leu Ser Ala Ile Phe Thr Thr
                85                  90

<210> SEQ ID NO 46
<211> LENGTH: 90
<212> TYPE: PRT
<213> ORGANISM: Artificial Sequence
<220> FEATURE:
<223> OTHER INFORMATION: synthetic sequence

<400> SEQUENCE: 46

Met Leu Pro Ala Pro Lys Asn Leu Val Val Ser Arg Val Thr Glu Asp
 1               5                  10                  15

Ser Ala Arg Leu Ser Trp Thr Ala Pro Asp Ala Ala Phe Asp Ser Phe
                20                  25                  30

Thr Ile Glu Tyr Phe Glu Phe Thr Gly Thr Gly Glu Ala Ile Val Leu
            35                  40                  45

Thr Val Pro Gly Ser Glu Arg Ser Tyr Asp Leu Thr Gly Leu Lys Pro
        50                  55                  60

Gly Thr Glu Tyr Tyr Val Ser Ile Tyr Gly Val Lys Gly Gly Leu Leu
 65                  70                  75                  80

Ser Ala Pro Leu Ser Ala Ile Phe Thr Thr
                85                  90

<210> SEQ ID NO 47
<211> LENGTH: 90
<212> TYPE: PRT
<213> ORGANISM: Artificial Sequence
<220> FEATURE:
<223> OTHER INFORMATION: synthetic sequence

<400> SEQUENCE: 47

Met Leu Pro Ala Pro Lys Asn Leu Val Val Ser Arg Val Thr Glu Asp
 1               5                  10                  15

Ser Ala Arg Leu Ser Trp Thr Ala Pro Asp Ala Ala Phe Asp Ser Phe
                20                  25                  30

Thr Ile Trp Tyr Ala Glu Ala Leu Gly Asp Gly Glu Ala Ile Val Leu
            35                  40                  45

Thr Val Pro Gly Ser Glu Arg Ser Tyr Asp Leu Thr Gly Leu Lys Pro
        50                  55                  60

Gly Thr Glu Tyr Phe Val Asp Ile Tyr Gly Val Lys Gly Gly Phe Trp
 65                  70                  75                  80

Ser Leu Pro Leu Ser Ala Ile Phe Thr Thr
                85                  90

<210> SEQ ID NO 48
<211> LENGTH: 90
<212> TYPE: PRT
<213> ORGANISM: Artificial Sequence
<220> FEATURE:
<223> OTHER INFORMATION: synthetic sequence

<400> SEQUENCE: 48

Met Leu Pro Ala Pro Lys Asn Leu Val Val Ser Arg Val Thr Glu Asp
 1               5                  10                  15
```

```
Ser Ala Arg Leu Ser Trp Thr Ala Pro Asp Ala Ala Phe Asp Ser Phe
            20                  25                  30

Val Ile Glu Tyr Phe Glu Gln Phe Asn Leu Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Trp Val Gly Ile Tyr Gly Val Lys Gly Gly Trp Leu
65                  70                  75                  80

Ser His Pro Leu Ser Ala Ile Phe Thr Thr
                85                  90
```

<210> SEQ ID NO 49
<211> LENGTH: 90
<212> TYPE: PRT
<213> ORGANISM: Artificial Sequence
<220> FEATURE:
<223> OTHER INFORMATION: synthetic sequence

<400> SEQUENCE: 49

```
Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Gly Ile Ser Tyr Leu Glu Trp Trp Glu Asp Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Trp Val Ser Ile Ala Gly Val Lys Gly Gly Lys Arg
65                  70                  75                  80

Ser Tyr Pro Leu Ser Ala Ile Phe Thr Thr
                85                  90
```

<210> SEQ ID NO 50
<211> LENGTH: 90
<212> TYPE: PRT
<213> ORGANISM: Artificial Sequence
<220> FEATURE:
<223> OTHER INFORMATION: synthetic sequence

<400> SEQUENCE: 50

```
Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Val Ile Glu Tyr Arg Glu Gly Ala Trp Tyr Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Phe Val Asp Ile Thr Gly Val Lys Gly Gly Trp Trp
65                  70                  75                  80

Ser Asp Pro Leu Ser Ala Ile Phe Thr Thr
                85                  90
```

<210> SEQ ID NO 51
<211> LENGTH: 90
<212> TYPE: PRT
<213> ORGANISM: Artificial Sequence
<220> FEATURE:
<223> OTHER INFORMATION: synthetic sequence

<400> SEQUENCE: 51

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Phe Ile Lys Tyr Ile Glu Trp Trp Ala Asp Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Leu Val Glu Ile Tyr Gly Val Lys Gly Gly Lys Trp
65                  70                  75                  80

Ser Trp Pro Leu Ser Ala Ile Phe Thr Thr
                85                  90

<210> SEQ ID NO 52
<211> LENGTH: 90
<212> TYPE: PRT
<213> ORGANISM: Artificial Sequence
<220> FEATURE:
<223> OTHER INFORMATION: synthetic sequence

<400> SEQUENCE: 52

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Lys Ile Ser Tyr Gln Glu Trp Trp Glu Asp Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Trp Val Asn Ile Ser Gly Val Lys Gly Gly Val Gln
65                  70                  75                  80

Ser Tyr Pro Leu Ser Ala Ile Phe Thr Thr
                85                  90

<210> SEQ ID NO 53
<211> LENGTH: 90
<212> TYPE: PRT
<213> ORGANISM: Artificial Sequence
<220> FEATURE:
<223> OTHER INFORMATION: synthetic sequence

<400> SEQUENCE: 53

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Phe Ile Ser Tyr Ile Glu Trp Trp Asp Leu Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr His Val Glu Ile Phe Gly Val Lys Gly Gly Thr Gln
65                  70                  75                  80

Ser Tyr Pro Leu Ser Ala Ile Phe Thr Thr
                85                  90

<210> SEQ ID NO 54
<211> LENGTH: 90

```
<212> TYPE: PRT
<213> ORGANISM: Artificial Sequence
<220> FEATURE:
<223> OTHER INFORMATION: synthetic sequence

<400> SEQUENCE: 54

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Gln Ile Leu Tyr Gln Glu Asn Ala Phe Glu Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Trp Val Tyr Ile Tyr Gly Val Lys Gly Gly Tyr Pro
65                  70                  75                  80

Ser Val Pro Leu Ser Ala Ile Phe Thr Thr
                85                  90

<210> SEQ ID NO 55
<211> LENGTH: 90
<212> TYPE: PRT
<213> ORGANISM: Artificial Sequence
<220> FEATURE:
<223> OTHER INFORMATION: synthetic sequence

<400> SEQUENCE: 55

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Ile Ile Glu Tyr Trp Glu Phe Val Gly Tyr Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Trp Val Ala Ile Tyr Gly Val Lys Gly Gly Asp Leu
65                  70                  75                  80

Ser Lys Pro Leu Ser Ala Ile Phe Thr Thr
                85                  90

<210> SEQ ID NO 56
<211> LENGTH: 90
<212> TYPE: PRT
<213> ORGANISM: Artificial Sequence
<220> FEATURE:
<223> OTHER INFORMATION: synthetic sequence

<400> SEQUENCE: 56

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Val Ile Glu Tyr Phe Glu Ala Leu Glu Gly Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Phe Val Gly Ile Tyr Gly Val Lys Gly Gly Pro Leu
65                  70                  75                  80

Ser Lys Pro Leu Ser Ala Ile Phe Thr Thr
```

-continued

```
                    85                  90

<210> SEQ ID NO 57
<211> LENGTH: 90
<212> TYPE: PRT
<213> ORGANISM: Artificial Sequence
<220> FEATURE:
<223> OTHER INFORMATION: synthetic sequence

<400> SEQUENCE: 57

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Ser Ile Lys Tyr Leu Glu Trp Trp Gln Asp Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Tyr Val His Ile Ala Gly Val Lys Gly Gly Tyr Arg
65                  70                  75                  80

Ser Tyr Pro Leu Ser Ala Ile Phe Thr Thr
                85                  90

<210> SEQ ID NO 58
<211> LENGTH: 90
<212> TYPE: PRT
<213> ORGANISM: Artificial Sequence
<220> FEATURE:
<223> OTHER INFORMATION: synthetic sequence

<400> SEQUENCE: 58

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Thr Ile Trp Tyr Ala Glu Ala Asp Gly Trp Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Phe Val Asp Ile Tyr Gly Val Lys Gly Gly Tyr Leu
65                  70                  75                  80

Ser Val Pro Leu Ser Ala Ile Phe Thr Thr
                85                  90

<210> SEQ ID NO 59
<211> LENGTH: 90
<212> TYPE: PRT
<213> ORGANISM: Artificial Sequence
<220> FEATURE:
<223> OTHER INFORMATION: synthetic sequence

<400> SEQUENCE: 59

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Thr Ile Trp Tyr Ala Glu Trp Glu Asp Glu Gly Glu Ala Ile Val Leu
        35                  40                  45

Thr Val Pro Gly Ser Glu Arg Ser Tyr Asp Leu Thr Gly Leu Lys Pro
    50                  55                  60
```

```
Gly Thr Glu Tyr Arg Val Glu Ile Tyr Gly Val Lys Gly Tyr Pro
65                  70                  75                  80

Ser Lys Pro Leu Ser Ala Ile Phe Thr Thr
                85                  90

<210> SEQ ID NO 60
<211> LENGTH: 90
<212> TYPE: PRT
<213> ORGANISM: Artificial Sequence
<220> FEATURE:
<223> OTHER INFORMATION: synthetic sequence

<400> SEQUENCE: 60

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

Thr Ile Trp Tyr Ala Glu Ala Ile Gly His Gly Glu Ala Ile Val Leu
            35                  40                  45

Thr Val Pro Gly Ser Glu Arg Ser Tyr Asp Leu Thr Gly Leu Lys Pro
        50                  55                  60

Gly Thr Glu Tyr Trp Val Asp Ile Trp Gly Val Lys Gly Gly Gln Gln
65                  70                  75                  80

Ser Lys Pro Leu Ser Ala Ile Phe Thr Thr
                85                  90

<210> SEQ ID NO 61
<211> LENGTH: 94
<212> TYPE: PRT
<213> ORGANISM: Artificial Sequence
<220> FEATURE:
<223> OTHER INFORMATION: synthetic sequence

<400> SEQUENCE: 61

Met Leu Pro Ala Pro Lys Asn Leu Val Val Ser Arg Val Thr Glu Asp
1               5                   10                  15

Ser Ala Arg Leu Ser Trp Arg Val Glu Ser Arg Thr Phe Asp Ser Phe
                20                  25                  30

Leu Ile Gln Tyr Gln Glu Ser Glu Lys Val Gly Glu Ala Ile Val Leu
            35                  40                  45

Thr Val Pro Gly Ser Glu Arg Ser Tyr Asp Leu Thr Gly Leu Lys Pro
        50                  55                  60

Gly Thr Glu Tyr Thr Val Ser Ile Tyr Gly Val Val Trp Asp Thr Arg
65                  70                  75                  80

Asp Asn Pro Ile Ser Asn Pro Leu Ser Ala Ile Phe Thr Thr
                85                  90

<210> SEQ ID NO 62
<211> LENGTH: 92
<212> TYPE: PRT
<213> ORGANISM: Artificial Sequence
<220> FEATURE:
<223> OTHER INFORMATION: synthetic sequence

<400> SEQUENCE: 62

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30
```

```
Pro Ile Leu Tyr Leu Glu Leu Asn His His Gly Glu Glu Ile Val Leu
            35                  40                  45
Thr Val Pro Gly Ser Glu Arg Ser Tyr Asp Leu Thr Gly Leu Lys Pro
     50                  55                  60
Gly Thr Glu Tyr Trp Val Tyr Ile Phe Gly Val Lys Gly Gly Met Tyr
 65                  70                  75                  80
Ser Ala Pro Leu Ser Ala Ile Phe Thr Thr Gly Gly
                 85                  90

<210> SEQ ID NO 63
<211> LENGTH: 4
<212> TYPE: PRT
<213> ORGANISM: Artificial Sequence
<220> FEATURE:
<223> OTHER INFORMATION: synthetic sequence

<400> SEQUENCE: 63

Gly Ser Gly Ser
1

<210> SEQ ID NO 64
<211> LENGTH: 8
<212> TYPE: PRT
<213> ORGANISM: Artificial Sequence
<220> FEATURE:
<223> OTHER INFORMATION: synthetic sequence

<400> SEQUENCE: 64

Gly Gly Gly Ser Gly Gly Gly Ser
1               5

<210> SEQ ID NO 65
<211> LENGTH: 25
<212> TYPE: PRT
<213> ORGANISM: Artificial Sequence
<220> FEATURE:
<223> OTHER INFORMATION: synthetic sequence

<400> SEQUENCE: 65

Gly Gly Gly Gly Ser Gly Gly Gly Ser Gly Gly Gly Ser Gly
1               5                   10                  15

Gly Gly Ser Gly Gly Gly Gly Ser
            20                  25

<210> SEQ ID NO 66
<211> LENGTH: 4
<212> TYPE: PRT
<213> ORGANISM: Artificial Sequence
<220> FEATURE:
<223> OTHER INFORMATION: synthetic sequence

<400> SEQUENCE: 66

Ala Pro Ala Pro
1

<210> SEQ ID NO 67
<211> LENGTH: 10
<212> TYPE: PRT
<213> ORGANISM: Artificial Sequence
<220> FEATURE:
<223> OTHER INFORMATION: synthetic sequence

<400> SEQUENCE: 67

Ala Pro Ala Pro Ala Pro Ala Pro Ala Pro
1               5                   10
```

<210> SEQ ID NO 68
<211> LENGTH: 20
<212> TYPE: PRT
<213> ORGANISM: Artificial Sequence
<220> FEATURE:
<223> OTHER INFORMATION: synthetic sequence

<400> SEQUENCE: 68

Ala Pro Ala Pro Ala Pro Ala Pro Ala Pro Ala Pro Ala Pro Ala Pro
1               5                   10                  15

Ala Pro Ala Pro
            20

<210> SEQ ID NO 69
<211> LENGTH: 40
<212> TYPE: PRT
<213> ORGANISM: Artificial Sequence
<220> FEATURE:
<223> OTHER INFORMATION: synthetic sequence

<400> SEQUENCE: 69

Ala Pro Ala Pro Ala Pro Ala Pro Ala Pro Ala Pro Ala Pro Ala Pro
1               5                   10                  15

Ala Pro Ala Pro Ala Pro Ala Pro Ala Pro Ala Pro Ala Pro Ala Pro
            20                  25                  30

Ala Pro Ala Pro Ala Pro Ala Pro
        35                  40

<210> SEQ ID NO 70
<211> LENGTH: 29
<212> TYPE: PRT
<213> ORGANISM: Artificial Sequence
<220> FEATURE:
<223> OTHER INFORMATION: synthetic sequence

<400> SEQUENCE: 70

Ala Glu Ala Ala Ala Lys Glu Ala Ala Ala Lys Glu Ala Ala Ala Lys
1               5                   10                  15

Glu Ala Ala Ala Lys Glu Ala Ala Ala Lys Ala Ala Ala
            20                  25

<210> SEQ ID NO 71

<400> SEQUENCE: 71

000

<210> SEQ ID NO 72

<400> SEQUENCE: 72

000

<210> SEQ ID NO 73

<400> SEQUENCE: 73

000

<210> SEQ ID NO 74

<400> SEQUENCE: 74

000

<210> SEQ ID NO 75

<400> SEQUENCE: 75

000

<210> SEQ ID NO 76

<400> SEQUENCE: 76

000

<210> SEQ ID NO 77

<400> SEQUENCE: 77

000

<210> SEQ ID NO 78

<400> SEQUENCE: 78

000

<210> SEQ ID NO 79

<400> SEQUENCE: 79

000

<210> SEQ ID NO 80
<211> LENGTH: 230
<212> TYPE: PRT
<213> ORGANISM: Homo sapiens

<400> SEQUENCE: 80

```
Gln Asn Ser Gln Leu Gln Glu Glu Leu Arg Gly Leu Arg Glu Thr Phe
1               5                   10                  15

Ser Asn Phe Thr Ala Ser Thr Glu Ala Gln Val Lys Gly Leu Ser Thr
            20                  25                  30

Gln Gly Gly Asn Val Gly Arg Lys Met Lys Ser Leu Glu Ser Gln Leu
        35                  40                  45

Glu Lys Gln Gln Lys Asp Leu Ser Glu Asp His Ser Ser Leu Leu Leu
    50                  55                  60

His Val Lys Gln Phe Val Ser Asp Leu Arg Ser Leu Ser Cys Gln Met
65                  70                  75                  80

Ala Ala Leu Gln Gly Asn Gly Ser Glu Arg Thr Cys Cys Pro Val Asn
                85                  90                  95

Trp Val Glu His Glu Arg Ser Cys Tyr Trp Phe Ser Arg Ser Gly Lys
            100                 105                 110

Ala Trp Ala Asp Ala Asp Asn Tyr Cys Arg Leu Glu Asp Ala His Leu
        115                 120                 125

Val Val Val Thr Ser Trp Glu Glu Gln Lys Phe Val Gln His His Ile
    130                 135                 140

Gly Pro Val Asn Thr Trp Met Gly Leu His Asp Gln Asn Gly Pro Trp
145                 150                 155                 160

Lys Trp Val Asp Gly Thr Asp Tyr Glu Thr Gly Phe Lys Asn Trp Arg
                165                 170                 175

Pro Glu Gln Pro Asp Asp Trp Tyr Gly His Gly Leu Gly Gly Gly Glu
            180                 185                 190
```

```
Asp Cys Ala His Phe Thr Asp Asp Gly Arg Trp Asn Asp Asp Val Cys
            195                 200                 205

Gln Arg Pro Tyr Arg Trp Val Cys Glu Thr Glu Leu Asp Lys Ala Ser
            210                 215                 220

Gln Glu Pro Pro Leu Leu
225                 230
```

<210> SEQ ID NO 81
<211> LENGTH: 90
<212> TYPE: PRT
<213> ORGANISM: Artificial Sequence
<220> FEATURE:
<223> OTHER INFORMATION: synthetic sequence

<400> SEQUENCE: 81

```
Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

Val Ile Glu Tyr Arg Glu Gly Ala Trp Tyr Gly Glu Ala Ile Val Leu
            35                  40                  45

Thr Val Pro Gly Ser Glu Arg Ser Tyr Asp Leu Thr Gly Leu Lys Pro
        50                  55                  60

Gly Thr Glu Tyr Ala Val Tyr Ile Pro Gly Val Lys Gly Gly Pro Arg
65                  70                  75                  80

Ser Phe Pro Leu Ser Ala Ile Phe Thr Thr
                85                  90
```

<210> SEQ ID NO 82
<211> LENGTH: 90
<212> TYPE: PRT
<213> ORGANISM: Artificial Sequence
<220> FEATURE:
<223> OTHER INFORMATION: synthetic sequence

<400> SEQUENCE: 82

```
Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

Ala Ile Ala Tyr Val Glu Trp Trp Lys Leu Gly Glu Ala Ile Val Leu
            35                  40                  45

Thr Val Pro Gly Ser Glu Arg Ser Tyr Asp Leu Thr Gly Leu Lys Pro
        50                  55                  60

Gly Thr Glu Tyr Val Val Pro Ile Pro Gly Val Lys Gly Gly Gly His
65                  70                  75                  80

Ser Ser Pro Leu Ser Ala Ile Phe Thr Thr
                85                  90
```

<210> SEQ ID NO 83
<211> LENGTH: 90
<212> TYPE: PRT
<213> ORGANISM: Artificial Sequence
<220> FEATURE:
<223> OTHER INFORMATION: synthetic sequence

<400> SEQUENCE: 83

```
Met Leu Pro Ala Pro Lys Asn Leu Val Val Ser Arg Val Thr Glu Asp
1               5                   10                  15
```

```
Ser Ala Arg Leu Ser Trp Thr Ala Pro Asp Ala Ala Phe Asp Ser Phe
            20                  25                  30

Tyr Ile Tyr Tyr Tyr Glu Ser Ser Gly Thr Gly Glu Ala Ile Val Leu
            35                  40                  45

Thr Val Pro Gly Ser Glu Arg Ser Tyr Asp Leu Thr Gly Leu Lys Pro
50                  55                  60

Gly Thr Glu Tyr Phe Val Asp Ile Gly Gly Val Lys Gly Gly Ser Tyr
65                  70                  75                  80

Ser Leu Pro Leu Ser Ala Ile Phe Thr Thr
            85                  90
```

<210> SEQ ID NO 84
<211> LENGTH: 90
<212> TYPE: PRT
<213> ORGANISM: Artificial Sequence
<220> FEATURE:
<223> OTHER INFORMATION: synthetic sequence

<400> SEQUENCE: 84

```
Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Pro Ile Tyr Tyr Trp Glu Val Phe Pro Ala Gly Glu Ala Ile Glu Leu
            35                  40                  45

Asp Val Pro Gly Ser Glu Arg Ser Tyr Asp Leu Thr Gly Leu Lys Pro
50                  55                  60

Gly Thr Glu Tyr Phe Val Arg Ile Glu Gly Val Lys Gly Gly Ala Ser
65                  70                  75                  80

Ser Tyr Pro Leu Arg Ala Glu Phe Thr Thr
            85                  90
```

<210> SEQ ID NO 85
<211> LENGTH: 90
<212> TYPE: PRT
<213> ORGANISM: Artificial Sequence
<220> FEATURE:
<223> OTHER INFORMATION: synthetic sequence

<400> SEQUENCE: 85

```
Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Phe Ile Trp Tyr Trp Glu Lys Ser Val Asp Gly Glu Ala Ile Val Leu
            35                  40                  45

Thr Val Pro Gly Ser Glu Arg Ser Tyr Asp Leu Thr Gly Leu Lys Pro
50                  55                  60

Gly Thr Glu Tyr Asn Val Gly Ile Gln Gly Val Lys Gly Gly Thr Pro
65                  70                  75                  80

Ser Asp Pro Leu Ser Ala Ile Phe Thr Thr
            85                  90
```

<210> SEQ ID NO 86
<211> LENGTH: 90
<212> TYPE: PRT
<213> ORGANISM: Artificial Sequence
<220> FEATURE:
<223> OTHER INFORMATION: synthetic sequence

<400> SEQUENCE: 86

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Ile Ile Trp Tyr Ala Glu Trp Val Asn Asp Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Arg Val Glu Ile Thr Gly Val Lys Gly Gly Thr Trp
65                  70                  75                  80

Ser Arg Pro Leu Ser Ala Ile Phe Thr Thr
                85                  90

<210> SEQ ID NO 87
<211> LENGTH: 90
<212> TYPE: PRT
<213> ORGANISM: Artificial Sequence
<220> FEATURE:
<223> OTHER INFORMATION: synthetic sequence

<400> SEQUENCE: 87

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Ala Ile Glu Tyr Tyr Glu Pro Val Pro Ala Gly Glu Ala Ile Tyr Leu
        35                  40                  45

Asp Val Pro Gly Ser Glu Arg Ser Tyr Asp Leu Thr Gly Leu Lys Pro
    50                  55                  60

Gly Thr Glu Tyr Asp Val Thr Ile Tyr Gly Val Lys Gly Gly Tyr Tyr
65                  70                  75                  80

Ser His Pro Leu Phe Ala Ser Phe Thr Thr
                85                  90

<210> SEQ ID NO 88
<211> LENGTH: 90
<212> TYPE: PRT
<213> ORGANISM: Artificial Sequence
<220> FEATURE:
<223> OTHER INFORMATION: synthetic sequence

<400> SEQUENCE: 88

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Trp Ile Glu Tyr Phe Glu Trp Thr Val Gly Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Tyr Val Ser Ile Tyr Gly Val Lys Gly Gly Trp Leu
65                  70                  75                  80

Ser Pro Pro Leu Ser Ala Ile Phe Thr Thr
                85                  90

<210> SEQ ID NO 89
<211> LENGTH: 90

```
<212> TYPE: PRT
<213> ORGANISM: Artificial Sequence
<220> FEATURE:
<223> OTHER INFORMATION: synthetic sequence

<400> SEQUENCE: 89

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

His Ile Ser Tyr Glu Glu Thr Pro Val Val Gly Glu Ala Ile Tyr Leu
        35                  40                  45

Arg Val Pro Gly Ser Glu Arg Ser Tyr Asp Leu Thr Gly Leu Lys Pro
    50                  55                  60

Gly Thr Glu Tyr Thr Val Ala Ile His Gly Val Lys Gly Gly Arg Glu
65                  70                  75                  80

Ser Thr Pro Leu Ile Ala Pro Phe Thr Thr
                85                  90

<210> SEQ ID NO 90
<211> LENGTH: 90
<212> TYPE: PRT
<213> ORGANISM: Artificial Sequence
<220> FEATURE:
<223> OTHER INFORMATION: synthetic sequence

<400> SEQUENCE: 90

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Thr Ile His Tyr Trp Glu Phe Asp Pro Pro Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Thr Val Tyr Ile Glu Gly Val Lys Gly Gly Trp Trp
65                  70                  75                  80

Ser Lys Pro Leu Ser Ala Ile Phe Thr Thr
                85                  90

<210> SEQ ID NO 91
<211> LENGTH: 90
<212> TYPE: PRT
<213> ORGANISM: Artificial Sequence
<220> FEATURE:
<223> OTHER INFORMATION: synthetic sequence

<400> SEQUENCE: 91

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Val Ile Glu Tyr Trp Glu Arg Thr Gln Pro Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Asp Val Trp Ile Ser Gly Val Lys Gly Gly Lys Trp
65                  70                  75                  80

Ser Glu Pro Leu Ser Ala Ile Phe Thr Thr
```

<210> SEQ ID NO 92
<211> LENGTH: 90
<212> TYPE: PRT
<213> ORGANISM: Artificial Sequence
<220> FEATURE:
<223> OTHER INFORMATION: synthetic sequence

<400> SEQUENCE: 92

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

Leu Ile Arg Tyr Trp Glu Trp Tyr Val Leu Gly Glu Ala Ile Val Leu
            35                  40                  45

Thr Val Pro Gly Ser Glu Arg Ser Tyr Asp Leu Thr Gly Leu Lys Pro
        50                  55                  60

Gly Thr Glu Tyr Tyr Val Glu Ile Ser Gly Val Lys Gly Gly Trp Gln
65                  70                  75                  80

Ser Trp Pro Leu Ser Ala Ile Phe Thr Thr
                85                  90

<210> SEQ ID NO 93
<211> LENGTH: 90
<212> TYPE: PRT
<213> ORGANISM: Artificial Sequence
<220> FEATURE:
<223> OTHER INFORMATION: synthetic sequence

<400> SEQUENCE: 93

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

Tyr Ile Gly Tyr Leu Glu Pro Gly Asp Asn Gly Glu Ala Ile Val Leu
            35                  40                  45

Thr Val Pro Gly Ser Glu Arg Ser Tyr Asp Leu Thr Gly Leu Lys Pro
        50                  55                  60

Gly Thr Glu Tyr Asn Val Ser Ile Gly Gly Val Lys Gly Gly Leu Gly
65                  70                  75                  80

Ser Tyr Pro Leu Ser Ala Ile Phe Thr Thr
                85                  90

<210> SEQ ID NO 94
<211> LENGTH: 90
<212> TYPE: PRT
<213> ORGANISM: Artificial Sequence
<220> FEATURE:
<223> OTHER INFORMATION: synthetic sequence

<400> SEQUENCE: 94

Met Leu Pro Ala Pro Lys Asn Leu Val Val Ser Arg Ile Thr Glu Asp
1               5                   10                  15

Ser Ala Arg Leu Ser Trp Thr Ala Pro Asp Ala Ala Phe Asp Ser Phe
                20                  25                  30

Gly Ile Tyr Tyr Tyr Glu Trp Trp Ser Thr Gly Glu Ala Ile Val Leu
            35                  40                  45

Thr Val Pro Gly Ser Glu Arg Ser Tyr Asp Leu Thr Gly Pro Lys Pro
        50                  55                  60

Gly Thr Glu Tyr Tyr Val Lys Ile Ser Gly Val Lys Gly Gly Tyr Arg
65                  70                  75                  80

Ser Tyr Pro Leu Ser Ala Ile Phe Thr Thr
                85                  90

<210> SEQ ID NO 95
<211> LENGTH: 90
<212> TYPE: PRT
<213> ORGANISM: Artificial Sequence
<220> FEATURE:
<223> OTHER INFORMATION: synthetic sequence

<400> SEQUENCE: 95

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

Arg Ile Ser Tyr Tyr Glu Trp Tyr Asp Leu Gly Glu Ala Ile Val Leu
            35                  40                  45

Thr Val Pro Gly Ser Glu Arg Ser Tyr Asp Leu Thr Gly Leu Lys Pro
        50                  55                  60

Gly Thr Glu Tyr Trp Val Asp Ile Ala Gly Val Lys Gly Gly Tyr Tyr
65                  70                  75                  80

Ser Tyr Pro Leu Ser Ala Ile Phe Thr Thr
                85                  90

<210> SEQ ID NO 96
<211> LENGTH: 90
<212> TYPE: PRT
<213> ORGANISM: Artificial Sequence
<220> FEATURE:
<223> OTHER INFORMATION: synthetic sequence

<400> SEQUENCE: 96

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

Phe Ile Gly Tyr Leu Glu Pro Gln Pro Gly Glu Ala Ile Val Leu
            35                  40                  45

Thr Val Pro Gly Ser Glu Arg Ser Tyr Asp Leu Thr Gly Leu Lys Pro
        50                  55                  60

Gly Thr Glu Tyr Asn Val Thr Ile Gln Gly Val Lys Gly Gly Phe Pro
65                  70                  75                  80

Ser Met Pro Leu Ser Ala Ile Phe Thr Thr
                85                  90

<210> SEQ ID NO 97
<211> LENGTH: 90
<212> TYPE: PRT
<213> ORGANISM: Artificial Sequence
<220> FEATURE:
<223> OTHER INFORMATION: synthetic sequence

<400> SEQUENCE: 97

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

```
Phe Ile Ser Tyr Phe Glu Gly Trp Ala Ser Gly Glu Ala Ile His Leu
            35                  40                  45

Tyr Val Pro Gly Ser Glu Arg Ser Tyr Asp Leu Thr Gly Leu Lys Pro
    50                  55                  60

Gly Thr Glu Tyr Ser Val His Ile Gln Gly Val Lys Gly Gly Gln Pro
65                  70                  75                  80

Ser Thr Pro Leu Ser Ala Ile Phe Thr Thr
                85                  90

<210> SEQ ID NO 98
<211> LENGTH: 90
<212> TYPE: PRT
<213> ORGANISM: Artificial Sequence
<220> FEATURE:
<223> OTHER INFORMATION: synthetic sequence

<400> SEQUENCE: 98

Met Leu Pro Ala Pro Lys Asn Leu Val Val Ser Arg Ile Thr Glu Asp
1               5                   10                  15

Ser Ala Arg Leu Ser Trp Thr Ala Pro Asp Ala Ala Phe Asp Ser Phe
            20                  25                  30

Asp Ile Pro Tyr Gly Glu Phe Asp Thr Ile Gly Glu Ala Ile Val Leu
            35                  40                  45

Thr Val Pro Gly Ser Glu Arg Ser Tyr Asp Leu Thr Gly Leu Lys Pro
    50                  55                  60

Gly Thr Glu Tyr Asp Val Tyr Ile Glu Gly Val Lys Gly Gly His Leu
65                  70                  75                  80

Ser Trp Pro Leu Ser Ala Ile Phe Thr Thr
                85                  90

<210> SEQ ID NO 99
<211> LENGTH: 90
<212> TYPE: PRT
<213> ORGANISM: Artificial Sequence
<220> FEATURE:
<223> OTHER INFORMATION: synthetic sequence

<400> SEQUENCE: 99

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Gly Ile Gln Tyr Asn Glu Phe Val Phe Arg Gly Glu Ala Ile Val Leu
            35                  40                  45

Thr Val Pro Gly Ser Glu Arg Ser Tyr Asp Leu Thr Gly Leu Lys Pro
    50                  55                  60

Gly Thr Glu Tyr Phe Val Pro Ile Ser Gly Val Lys Gly Gly Asp Asp
65                  70                  75                  80

Ser Arg Pro Leu Ser Ala Ile Phe Thr Thr
                85                  90

<210> SEQ ID NO 100
<211> LENGTH: 90
<212> TYPE: PRT
<213> ORGANISM: Artificial Sequence
<220> FEATURE:
<223> OTHER INFORMATION: synthetic sequence

<400> SEQUENCE: 100

Met Leu Pro Ala Pro Lys Asn Leu Val Val Ser Arg Val Thr Glu Asp
```

```
1               5                   10                  15
Ser Ala Arg Leu Ser Trp Thr Ala Pro Asp Ala Ala Phe Asp Ser Phe
                20                  25                  30

Trp Ile Glu Tyr Trp Glu Val Val Gly Phe Gly Glu Ala Ile Val Leu
                35                  40                  45

Thr Val Pro Gly Ser Glu Arg Ser Tyr Asp Leu Thr Gly Leu Lys Pro
                50                  55                  60

Gly Thr Glu Tyr Trp Val Gly Ile Tyr Gly Val Lys Gly Gly Asn Pro
65                  70                  75                  80

Ser Val Pro Leu Ser Ala Ile Phe Thr Thr
                85                  90

<210> SEQ ID NO 101
<211> LENGTH: 90
<212> TYPE: PRT
<213> ORGANISM: Artificial Sequence
<220> FEATURE:
<223> OTHER INFORMATION: synthetic sequence

<400> SEQUENCE: 101

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

Ala Ile Asp Tyr Asp Glu Pro Ile Asn Ser Gly Glu Ala Ile Val Leu
                35                  40                  45

Thr Val Pro Gly Ser Glu Arg Ser Tyr Asp Leu Thr Gly Pro Lys Pro
                50                  55                  60

Gly Thr Glu Tyr Glu Val Glu Ile Tyr Gly Val Lys Gly Gly Tyr Leu
65                  70                  75                  80

Ser Arg Pro Leu Ser Ala Ile Phe Thr Thr
                85                  90

<210> SEQ ID NO 102
<211> LENGTH: 90
<212> TYPE: PRT
<213> ORGANISM: Artificial Sequence
<220> FEATURE:
<223> OTHER INFORMATION: synthetic sequence

<400> SEQUENCE: 102

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

Ser Ile Asp Tyr Asp Glu Pro Gln Pro Val Gly Glu Ala Ile Val Leu
                35                  40                  45

Thr Val Pro Gly Ser Glu Arg Ser Tyr Asp Leu Thr Gly Leu Lys Pro
                50                  55                  60

Gly Thr Glu Tyr Arg Val Asp Ile Trp Gly Val Lys Gly Gly Pro Thr
65                  70                  75                  80

Ser Gly Pro Leu Arg Ala Thr Phe Thr Thr
                85                  90

<210> SEQ ID NO 103
<211> LENGTH: 90
<212> TYPE: PRT
<213> ORGANISM: Artificial Sequence
<220> FEATURE:
```

<223> OTHER INFORMATION: synthetic sequence

<400> SEQUENCE: 103

Met Leu Leu Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Ala Ile Glu Tyr Phe Glu Tyr Thr Gly Glu Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Tyr Val Gly Ile Tyr Gly Val Lys Gly Gly Tyr Leu
65                  70                  75                  80

Ser Arg Pro Leu Ser Ala Ile Phe Thr Thr
                85                  90

<210> SEQ ID NO 104
<211> LENGTH: 90
<212> TYPE: PRT
<213> ORGANISM: Artificial Sequence
<220> FEATURE:
<223> OTHER INFORMATION: synthetic sequence

<400> SEQUENCE: 104

Met Leu Pro Ala Pro Lys Asn Leu Val Val Ser His Val Thr Glu Asp
1               5                   10                  15

Ser Ala Arg Leu Ser Trp Thr Ala Pro Asp Ala Ala Phe Asp Ser Phe
            20                  25                  30

Asp Ile Glu Tyr Tyr Glu Leu Val Gly Ser Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Tyr Val Ala Ile Tyr Gly Val Lys Gly Gly Tyr Leu
65                  70                  75                  80

Ser Arg Pro Leu Ser Ala Ile Phe Thr Thr
                85                  90

<210> SEQ ID NO 105
<211> LENGTH: 90
<212> TYPE: PRT
<213> ORGANISM: Artificial Sequence
<220> FEATURE:
<223> OTHER INFORMATION: synthetic sequence

<400> SEQUENCE: 105

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Gly Ile Ala Tyr Tyr Glu Arg Ser Gly Ala Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Met Val Tyr Ile Asn Gly Val Lys Gly Gly Phe Val
65                  70                  75                  80

Ser Ser Pro Leu Ser Ala Ile Phe Thr Thr
                85                  90

```
<210> SEQ ID NO 106
<211> LENGTH: 90
<212> TYPE: PRT
<213> ORGANISM: Artificial Sequence
<220> FEATURE:
<223> OTHER INFORMATION: synthetic sequence

<400> SEQUENCE: 106

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Thr Ile Ala Tyr Glu Glu His Gly Leu Val Gly Glu Ala Ile Tyr Leu
        35                  40                  45

Arg Val Pro Gly Ser Glu Arg Ser Tyr Asp Leu Thr Gly Leu Lys Pro
    50                  55                  60

Gly Thr Glu Tyr His Val Gly Ile Met Gly Val Lys Gly Gly Val Phe
65                  70                  75                  80

Ser Ser Pro Leu Ser Ala Ile Phe Thr Thr
                85                  90

<210> SEQ ID NO 107
<211> LENGTH: 90
<212> TYPE: PRT
<213> ORGANISM: Artificial Sequence
<220> FEATURE:
<223> OTHER INFORMATION: synthetic sequence

<400> SEQUENCE: 107

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Phe Ile Gln Tyr Thr Glu Ser His Trp Val Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Ala Val Pro Ile Glu Gly Val Lys Gly Gly Asp Ser
65                  70                  75                  80

Ser Thr Pro Leu Ser Ala Ile Phe Thr Thr
                85                  90

<210> SEQ ID NO 108
<211> LENGTH: 90
<212> TYPE: PRT
<213> ORGANISM: Artificial Sequence
<220> FEATURE:
<223> OTHER INFORMATION: synthetic sequence

<400> SEQUENCE: 108

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Thr Ile Ile Tyr Gly Glu Val Asn Pro Tyr Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Asp Val Phe Ile Glu Gly Val Lys Gly Gly His Leu
65                  70                  75                  80
```

Ser Trp Pro Leu Ser Ala Ile Phe Thr Thr
            85                  90

<210> SEQ ID NO 109
<211> LENGTH: 90
<212> TYPE: PRT
<213> ORGANISM: Artificial Sequence
<220> FEATURE:
<223> OTHER INFORMATION: synthetic sequence

<400> SEQUENCE: 109

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

His Ile Ala Tyr Glu Glu Leu Val Thr Glu Gly Glu Ala Ile Tyr Leu
        35                  40                  45

Arg Val Pro Gly Ser Glu Arg Ser Tyr Asp Leu Thr Gly Leu Lys Pro
    50                  55                  60

Gly Thr Glu Tyr Leu Val Asp Ile Glu Gly Val Lys Gly Gly His Leu
65                  70                  75                  80

Ser Ser Pro Leu Ser Ala Ile Phe Thr Thr
            85                  90

<210> SEQ ID NO 110
<211> LENGTH: 90
<212> TYPE: PRT
<213> ORGANISM: Artificial Sequence
<220> FEATURE:
<223> OTHER INFORMATION: synthetic sequence

<400> SEQUENCE: 110

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Phe Ile His Tyr His Glu Trp Trp Glu Ala Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Leu Val Asp Ile Pro Gly Val Lys Gly Gly Asp Leu
65                  70                  75                  80

Ser Val Pro Leu Ser Ala Ile Phe Thr Thr
            85                  90

<210> SEQ ID NO 111
<211> LENGTH: 90
<212> TYPE: PRT
<213> ORGANISM: Artificial Sequence
<220> FEATURE:
<223> OTHER INFORMATION: synthetic sequence

<400> SEQUENCE: 111

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Trp Ile Tyr Tyr Tyr Glu Ser Val Gly Thr Gly Glu Ala Ile Val Leu
        35                  40                  45

Thr Val Pro Gly Ser Glu Arg Ser Tyr Asp Leu Thr Gly Leu Lys Pro
            50                  55                  60

Gly Thr Glu Tyr Phe Val Asp Ile Ser Gly Val Lys Val Gly Thr Tyr
 65                  70                  75                  80

Ser Leu Pro Leu Ser Ala Ile Phe Thr Thr
                 85                  90

<210> SEQ ID NO 112
<211> LENGTH: 90
<212> TYPE: PRT
<213> ORGANISM: Artificial Sequence
<220> FEATURE:
<223> OTHER INFORMATION: synthetic sequence

<400> SEQUENCE: 112

Met Leu Pro Ala Pro Lys Asn Leu Val Val Ser Arg Val Thr Glu Asp
  1               5                  10                  15

Ser Ala Arg Leu Ser Trp Thr Ala Pro Asp Ala Ala Phe Asp Ser Phe
                 20                  25                  30

Phe Ile Ala Tyr Phe Glu Phe Ala Asn Pro Gly Glu Ala Ile Val Leu
                 35                  40                  45

Thr Val Pro Gly Ser Glu Arg Ser Tyr Asp Leu Thr Gly Leu Lys Pro
            50                  55                  60

Gly Thr Glu Tyr Lys Val Val Ile Gln Gly Val Lys Gly Gly Thr Pro
 65                  70                  75                  80

Ser Glu Pro Leu Ser Ala Ile Ser Thr Thr
                 85                  90

<210> SEQ ID NO 113
<211> LENGTH: 90
<212> TYPE: PRT
<213> ORGANISM: Artificial Sequence
<220> FEATURE:
<223> OTHER INFORMATION: synthetic sequence

<400> SEQUENCE: 113

Met Leu Pro Ala Pro Lys Asn Leu Val Val Ser Arg Val Thr Glu Asp
  1               5                  10                  15

Ser Ala Arg Leu Ser Trp Thr Ala Pro Asp Ala Ala Phe Asp Ser Phe
                 20                  25                  30

Asp Ile His Tyr Lys Glu His Ser Trp Trp Gly Glu Ala Ile Val Leu
                 35                  40                  45

Thr Val Pro Gly Ser Glu Arg Ser Tyr Asp Leu Thr Gly Leu Lys Pro
            50                  55                  60

Gly Thr Glu Tyr Ile Val Pro Ile Pro Gly Val Lys Gly Gly Gly Ile
 65                  70                  75                  80

Ser Arg Pro Leu Ser Ala Ile Phe Thr Thr
                 85                  90

<210> SEQ ID NO 114
<211> LENGTH: 90
<212> TYPE: PRT
<213> ORGANISM: Artificial Sequence
<220> FEATURE:
<223> OTHER INFORMATION: synthetic sequence

<400> SEQUENCE: 114

Met Leu Pro Ala Pro Lys Asn Leu Val Val Ser Arg Val Thr Glu Asp
  1               5                  10                  15

Ser Ala Arg Leu Ser Trp Thr Ala Pro Asp Ala Ala Phe Asp Ser Phe

```
                    20                  25                  30

Ala Ile Glu Tyr Trp Glu Ala Val Gly Ser Gly Glu Ala Ile Val Leu
            35                  40                  45

Thr Val Pro Gly Ser Glu Arg Ser Tyr Asp Leu Thr Gly Leu Lys Pro
        50                  55                  60

Gly Thr Glu Tyr His Val Tyr Ile Tyr Gly Val Lys Gly Gly Tyr Leu
65                  70                  75                  80

Ser Leu Pro Leu Ser Ala Ile Phe Thr Thr
                85                  90

<210> SEQ ID NO 115
<211> LENGTH: 91
<212> TYPE: PRT
<213> ORGANISM: Artificial Sequence
<220> FEATURE:
<223> OTHER INFORMATION: synthetic sequence

<400> SEQUENCE: 115

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Phe Ile Gly Tyr Leu Glu Pro Gln Pro Pro Gly Glu Ala Ile Val Leu
            35                  40                  45

Thr Val Pro Gly Ser Glu Arg Ser Tyr Asp Leu Thr Gly Leu Lys Pro
        50                  55                  60

Gly Thr Glu Tyr Asn Val Thr Ile Gln Gly Val Lys Gly Gly Phe Pro
65                  70                  75                  80

Ser Met Pro Leu Ser Ala Ile Phe Thr Thr Thr
                85                  90

<210> SEQ ID NO 116
<211> LENGTH: 90
<212> TYPE: PRT
<213> ORGANISM: Artificial Sequence
<220> FEATURE:
<223> OTHER INFORMATION: synthetic sequence

<400> SEQUENCE: 116

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Ser Ile Ala Tyr Ser Glu Val Arg Tyr Asp Gly Glu Ala Ile Val Leu
            35                  40                  45

Thr Val Pro Gly Ser Glu Arg Ser Tyr Asp Leu Thr Gly Leu Lys Pro
        50                  55                  60

Gly Thr Glu Tyr Val Val Pro Ile Gly Gly Val Lys Gly Gly Gly Ser
65                  70                  75                  80

Ser Ser Pro Leu Ser Ala Ile Phe Thr Thr
                85                  90

<210> SEQ ID NO 117
<211> LENGTH: 90
<212> TYPE: PRT
<213> ORGANISM: Artificial Sequence
<220> FEATURE:
<223> OTHER INFORMATION: synthetic sequence

<400> SEQUENCE: 117
```

```
Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Thr Ile Pro Tyr Gly Glu Ala Phe Asn Pro Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Asp Val Phe Ile Glu Gly Val Lys Gly Gly Thr Leu
65                  70                  75                  80

Ser Trp Pro Leu Ser Ala Ile Phe Thr Thr
                85                  90

<210> SEQ ID NO 118
<211> LENGTH: 90
<212> TYPE: PRT
<213> ORGANISM: Artificial Sequence
<220> FEATURE:
<223> OTHER INFORMATION: synthetic sequence

<400> SEQUENCE: 118

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Arg Ile Leu Tyr Gly Glu Val Asp Pro Trp Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Asp Val Trp Ile Glu Gly Val Lys Gly Gly Lys Leu
65                  70                  75                  80

Ser Trp Pro Leu Ser Ala Ile Phe Thr Thr
                85                  90

<210> SEQ ID NO 119
<211> LENGTH: 90
<212> TYPE: PRT
<213> ORGANISM: Artificial Sequence
<220> FEATURE:
<223> OTHER INFORMATION: synthetic sequence

<400> SEQUENCE: 119

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

His Ile Glu Tyr Glu Glu Thr Pro Gln Lys Gly Glu Ala Ile Phe Leu
        35                  40                  45

Arg Val Pro Gly Ser Glu Arg Ser Tyr Asp Leu Thr Gly Leu Lys Pro
    50                  55                  60

Gly Thr Glu Tyr Val Val Asn Ile Arg Gly Val Lys Gly Gly Asp Leu
65                  70                  75                  80

Ser Ser Pro Leu Gly Ala Leu Phe Thr Thr
                85                  90

<210> SEQ ID NO 120
<211> LENGTH: 90
<212> TYPE: PRT
```

```
<213> ORGANISM: Artificial Sequence
<220> FEATURE:
<223> OTHER INFORMATION: synthetic sequence

<400> SEQUENCE: 120

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Arg Ile Glu Tyr Ile Glu Trp Trp Val Gly Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Trp Val Asp Ile Lys Gly Val Lys Gly Gly Lys Arg
65                  70                  75                  80

Ser Tyr Pro Leu Ser Ala Ile Phe Thr Thr
                85                  90

<210> SEQ ID NO 121
<211> LENGTH: 90
<212> TYPE: PRT
<213> ORGANISM: Artificial Sequence
<220> FEATURE:
<223> OTHER INFORMATION: synthetic sequence

<400> SEQUENCE: 121

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Ser Ile Asp Tyr Pro Glu Phe Pro Val Arg Gly Glu Ala Ile Val Leu
        35                  40                  45

Thr Val Pro Gly Ser Glu Arg Ser Tyr Asp Leu Thr Gly Pro Lys Pro
    50                  55                  60

Gly Thr Glu Tyr Asn Val Thr Ile Gln Gly Val Lys Gly Gly Phe Pro
65                  70                  75                  80

Ser Met Pro Leu Ser Ala Ile Phe Thr Thr
                85                  90

<210> SEQ ID NO 122
<211> LENGTH: 90
<212> TYPE: PRT
<213> ORGANISM: Artificial Sequence
<220> FEATURE:
<223> OTHER INFORMATION: synthetic sequence

<400> SEQUENCE: 122

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Gln Ile Pro Tyr Trp Glu Gln Ser Leu Gly Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Glu Val Trp Ile Glu Gly Val Lys Gly Gly Asp Leu
65                  70                  75                  80

Ser Phe Pro Leu Ser Ala Ile Ser Thr Thr
                85                  90
```

```
<210> SEQ ID NO 123
<211> LENGTH: 90
<212> TYPE: PRT
<213> ORGANISM: Artificial Sequence
<220> FEATURE:
<223> OTHER INFORMATION: synthetic sequence

<400> SEQUENCE: 123

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Val Ile Pro Tyr Glu Glu Tyr Leu Tyr Thr Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Asp Val Trp Ile Glu Gly Val Lys Gly Gly Leu Thr
65                  70                  75                  80

Ser Trp Pro Leu Ser Ala Ile Phe Thr Thr
                85                  90

<210> SEQ ID NO 124
<211> LENGTH: 90
<212> TYPE: PRT
<213> ORGANISM: Artificial Sequence
<220> FEATURE:
<223> OTHER INFORMATION: synthetic sequence

<400> SEQUENCE: 124

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Ser Ile Asp Tyr Pro Glu Phe Pro Val Arg Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Ala Val Thr Ile Trp Gly Val Lys Gly Gly Phe Thr
65                  70                  75                  80

Ser Gln Pro Leu Ser Ala Ile Phe Thr Thr
                85                  90

<210> SEQ ID NO 125
<211> LENGTH: 90
<212> TYPE: PRT
<213> ORGANISM: Artificial Sequence
<220> FEATURE:
<223> OTHER INFORMATION: synthetic sequence

<400> SEQUENCE: 125

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Val Ile Glu Tyr Phe Glu Phe Val Gly Glu Gly Glu Ala Ile Val Leu
        35                  40                  45

Thr Val Pro Gly Ser Glu Arg Ser Tyr Asp Leu Thr Gly Leu Lys Pro
    50                  55                  60
```

```
Gly Thr Glu Tyr Asp Val Gly Ile Tyr Gly Val Lys Gly Gly Ser Leu
 65                  70                  75                  80

Ser Ser Pro Leu Ser Ala Ile Phe Thr Thr
                 85                  90

<210> SEQ ID NO 126
<211> LENGTH: 90
<212> TYPE: PRT
<213> ORGANISM: Artificial Sequence
<220> FEATURE:
<223> OTHER INFORMATION: synthetic sequence

<400> SEQUENCE: 126

Met Leu Pro Ala Pro Lys Asn Leu Val Val Ser Arg Val Thr Glu Asp
  1               5                  10                  15

Ser Ala Arg Leu Ser Trp Thr Ala Pro Asp Ala Ala Phe Asp Ser Phe
                 20                  25                  30

Ser Ile Asp Tyr Leu Glu Leu Gly Glu Ser Gly Glu Ala Ile Val Leu
                 35                  40                  45

Thr Val Pro Gly Ser Glu Arg Ser Tyr Asp Leu Thr Gly Leu Lys Pro
     50                  55                  60

Gly Thr Glu Tyr Trp Val Tyr Ile Phe Gly Val Lys Gly Gly Tyr Pro
 65                  70                  75                  80

Ser Ala Pro Leu Ser Ala Ile Phe Thr Thr
                 85                  90

<210> SEQ ID NO 127
<211> LENGTH: 90
<212> TYPE: PRT
<213> ORGANISM: Artificial Sequence
<220> FEATURE:
<223> OTHER INFORMATION: synthetic sequence

<400> SEQUENCE: 127

Met Leu Pro Ala Pro Lys Asn Leu Val Val Ser Arg Val Thr Glu Asp
  1               5                  10                  15

Ser Ala Arg Leu Ser Trp Thr Ala Pro Asp Ala Ala Phe Asp Ser Phe
                 20                  25                  30

Pro Ile Pro Tyr Gly Glu Ser Pro Ser Gly Glu Ala Ile Val Leu
                 35                  40                  45

Thr Val Pro Gly Ser Glu Arg Ser Tyr Asp Leu Thr Gly Leu Lys Pro
     50                  55                  60

Gly Thr Glu Tyr Val Val Ile Ile Arg Gly Val Lys Gly Gly Gly Arg
 65                  70                  75                  80

Ser Gly Pro Leu Ser Ala Ile Ser Thr Thr
                 85                  90

<210> SEQ ID NO 128
<211> LENGTH: 90
<212> TYPE: PRT
<213> ORGANISM: Artificial Sequence
<220> FEATURE:
<223> OTHER INFORMATION: synthetic sequence

<400> SEQUENCE: 128

Met Leu Pro Ala Pro Lys Asn Leu Val Val Ser Arg Val Thr Glu Asp
  1               5                  10                  15

Ser Ala Arg Leu Ser Trp Thr Ala Pro Asp Ala Ala Phe Asp Ser Phe
                 20                  25                  30

Ile Ile Asn Tyr Ile Glu Ile Val Gln Tyr Gly Glu Ala Ile Val Leu
```

```
                35                  40                  45
Thr Val Pro Gly Ser Glu Arg Ser Tyr Asp Leu Thr Gly Leu Lys Pro
            50                  55                  60
Gly Thr Glu Tyr Pro Glu Ser Ile Trp Gly Val Lys Gly Gly Gly Ala
65                  70                  75                  80
Ser Ser Pro Leu Ser Ala Ile Phe Thr Thr
                85                  90
```

<210> SEQ ID NO 129
<211> LENGTH: 90
<212> TYPE: PRT
<213> ORGANISM: Artificial Sequence
<220> FEATURE:
<223> OTHER INFORMATION: synthetic sequence

<400> SEQUENCE: 129

```
Met Leu Pro Ala Pro Lys Asn Leu Val Val Ser Arg Val Thr Glu Asp
1               5                   10                  15
Ser Ala Arg Leu Ser Trp Thr Ala Pro Asp Ala Ala Phe Asp Ser Phe
            20                  25                  30
Asp Ile Glu Tyr Tyr Glu Ala Val Gly Ala Gly Glu Ala Ile Val Leu
            35                  40                  45
Thr Val Pro Gly Ser Glu Arg Ser Tyr Asp Leu Thr Gly Leu Lys Pro
            50                  55                  60
Gly Thr Glu Tyr Thr Val Gly Ile Tyr Gly Val Lys Gly Gly Trp Leu
65                  70                  75                  80
Ser Lys Pro Leu Ser Val Ile Phe Thr Thr
                85                  90
```

<210> SEQ ID NO 130
<211> LENGTH: 90
<212> TYPE: PRT
<213> ORGANISM: Artificial Sequence
<220> FEATURE:
<223> OTHER INFORMATION: synthetic sequence

<400> SEQUENCE: 130

```
Met Leu Pro Ala Pro Lys Asn Leu Val Val Ser Arg Val Thr Glu Asp
1               5                   10                  15
Ser Ala Arg Leu Ser Trp Thr Ala Pro Asp Ala Ala Phe Asp Ser Phe
            20                  25                  30
His Ile Pro Tyr Val Glu Ala Glu Val Pro Gly Glu Ala Ile Gln Leu
            35                  40                  45
His Val Pro Gly Ser Glu Arg Ser Tyr Asp Leu Thr Gly Leu Lys Pro
            50                  55                  60
Gly Thr Glu Tyr Val Glu Ile Trp Gly Val Lys Gly Gly Phe Tyr
65                  70                  75                  80
Ser Pro Pro Leu Ile Ala Glu Phe Thr Thr
                85                  90
```

<210> SEQ ID NO 131
<211> LENGTH: 90
<212> TYPE: PRT
<213> ORGANISM: Artificial Sequence
<220> FEATURE:
<223> OTHER INFORMATION: synthetic sequence

<400> SEQUENCE: 131

```
Met Leu Pro Ala Pro Lys Asn Leu Val Val Ser Arg Val Thr Glu Asp
1               5                   10                  15
```

```
Ser Ala Arg Leu Ser Trp Thr Ala Pro Asp Ala Ala Phe Asp Ser Phe
            20                  25                  30

Ser Ile Asp Tyr Tyr Glu Gly Lys Gly Tyr Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Gln Val Leu Ile Ser Gly Val Lys Gly Gly Lys Tyr
65                  70                  75                  80

Ser Leu Pro Leu Ser Ala Ile Phe Thr Thr
                85                  90

<210> SEQ ID NO 132
<211> LENGTH: 90
<212> TYPE: PRT
<213> ORGANISM: Artificial Sequence
<220> FEATURE:
<223> OTHER INFORMATION: synthetic sequence

<400> SEQUENCE: 132

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Thr Ile Val Tyr Ala Glu Val Thr Tyr Asp Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Asp Val Phe Ile Glu Gly Val Lys Gly Gly Glu Leu
65                  70                  75                  80

Ser Trp Pro Leu Ser Ala Ile Phe Thr Thr
                85                  90

<210> SEQ ID NO 133
<211> LENGTH: 90
<212> TYPE: PRT
<213> ORGANISM: Artificial Sequence
<220> FEATURE:
<223> OTHER INFORMATION: synthetic sequence

<400> SEQUENCE: 133

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Pro Ile Val Tyr Gly Glu Ala Trp Val Thr Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Asp Val Trp Ile Glu Gly Val Lys Gly Gly Glu Leu
65                  70                  75                  80

Ser Trp Pro Leu Ser Ala Ile Phe Thr Thr
                85                  90

<210> SEQ ID NO 134
<211> LENGTH: 90
<212> TYPE: PRT
<213> ORGANISM: Artificial Sequence
<220> FEATURE:
<223> OTHER INFORMATION: synthetic sequence
```

<400> SEQUENCE: 134

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

Trp Ile Asp Tyr Tyr Glu Arg Lys Tyr Val Gly Glu Ala Ile Val Leu
            35                  40                  45

Thr Val Pro Gly Ser Glu Arg Ser Tyr Asp Leu Thr Gly Leu Lys Pro
        50                  55                  60

Gly Thr Glu Tyr Glu Val Thr Ile Tyr Gly Val Lys Gly Gly Trp Tyr
65                  70                  75                  80

Ser Asp Pro Leu Ser Ala Ile Phe Thr Thr
                85                  90

<210> SEQ ID NO 135
<211> LENGTH: 90
<212> TYPE: PRT
<213> ORGANISM: Artificial Sequence
<220> FEATURE:
<223> OTHER INFORMATION: synthetic sequence

<400> SEQUENCE: 135

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

Pro Ile Ser Tyr Tyr Glu Met Ser Gly Leu Gly Glu Ala Ile Val Leu
            35                  40                  45

Thr Val Pro Gly Ser Glu Arg Ser Tyr Asp Leu Thr Gly Leu Lys Pro
        50                  55                  60

Gly Thr Glu Tyr Met Val Tyr Ile Phe Gly Val Lys Gly Gly Leu Asn
65                  70                  75                  80

Ser Leu Pro Leu Ser Ala Ile Phe Thr Thr
                85                  90

<210> SEQ ID NO 136
<211> LENGTH: 90
<212> TYPE: PRT
<213> ORGANISM: Artificial Sequence
<220> FEATURE:
<223> OTHER INFORMATION: synthetic sequence

<400> SEQUENCE: 136

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

Phe Ile Tyr Tyr Ile Glu Ser Tyr Pro Ala Gly Glu Ala Ile Val Leu
            35                  40                  45

Thr Val Pro Gly Ser Glu Arg Ser Tyr Asp Leu Thr Gly Leu Lys Pro
        50                  55                  60

Gly Thr Glu Tyr Trp Met Gly Ile Asp Gly Val Lys Gly Gly Arg Trp
65                  70                  75                  80

Ser Thr Pro Leu Ser Ala Ile Phe Thr Thr
                85                  90

<210> SEQ ID NO 137

```
<211> LENGTH: 90
<212> TYPE: PRT
<213> ORGANISM: Artificial Sequence
<220> FEATURE:
<223> OTHER INFORMATION: synthetic sequence

<400> SEQUENCE: 137

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Glu Ile Glu Tyr Asp Glu Pro Ser Val Ala Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Arg Val Phe Ile Trp Gly Val Lys Gly Gly Asn Gln
65                  70                  75                  80

Ser Trp Pro Leu Ser Ala Ile Phe Thr Thr
                85                  90

<210> SEQ ID NO 138
<211> LENGTH: 90
<212> TYPE: PRT
<213> ORGANISM: Artificial Sequence
<220> FEATURE:
<223> OTHER INFORMATION: synthetic sequence

<400> SEQUENCE: 138

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Phe Ile Lys Tyr Ile Glu Trp Trp Ala Asp Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Leu Val Glu Ile Tyr Gly Val Lys Gly Gly Arg Gln
65                  70                  75                  80

Ser Tyr Pro Leu Ser Ala Ile Phe Thr Thr
                85                  90

<210> SEQ ID NO 139
<211> LENGTH: 90
<212> TYPE: PRT
<213> ORGANISM: Artificial Sequence
<220> FEATURE:
<223> OTHER INFORMATION: synthetic sequence

<400> SEQUENCE: 139

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Asp Ile Ser Tyr Trp Glu Ser Gly Lys Tyr Gly Glu Ala Ile Val Leu
        35                  40                  45

Thr Val Pro Gly Ser Glu Ser Ser Tyr Asp Leu Thr Gly Leu Lys Pro
    50                  55                  60

Gly Thr Glu Tyr Leu Val Asp Ile Phe Gly Val Lys Gly Gly Tyr Pro
65                  70                  75                  80
```

```
Ser Glu Pro Leu Ser Ala Ile Phe Thr Thr
                85                  90

<210> SEQ ID NO 140
<211> LENGTH: 90
<212> TYPE: PRT
<213> ORGANISM: Artificial Sequence
<220> FEATURE:
<223> OTHER INFORMATION: synthetic sequence

<400> SEQUENCE: 140

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Trp Ile Ser Tyr Glu Glu Ser Asp Thr Glu Gly Glu Ala Ile Tyr Leu
        35                  40                  45

Arg Val Pro Gly Ser Glu Arg Ser Tyr Asp Leu Thr Gly Leu Lys Pro
    50                  55                  60

Gly Thr Glu Tyr Asn Val Thr Ile Gln Gly Val Lys Gly Gly Phe Pro
65                  70                  75                  80

Ser Met Pro Leu Ser Ala Ile Phe Thr Thr
                85                  90

<210> SEQ ID NO 141
<211> LENGTH: 90
<212> TYPE: PRT
<213> ORGANISM: Artificial Sequence
<220> FEATURE:
<223> OTHER INFORMATION: synthetic sequence

<400> SEQUENCE: 141

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Val Ile Glu Tyr Phe Glu Gln Phe Asn Leu Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Leu Val Gly Ile Tyr Gly Val Lys Gly Gly Trp Leu
65                  70                  75                  80

Ser His Pro Leu Ser Ala Ile Phe Thr Thr
                85                  90

<210> SEQ ID NO 142
<211> LENGTH: 90
<212> TYPE: PRT
<213> ORGANISM: Artificial Sequence
<220> FEATURE:
<223> OTHER INFORMATION: synthetic sequence

<400> SEQUENCE: 142

Met Leu Pro Ala Pro Lys Asn Leu Val Val Ser Arg Val Thr Lys Asp
1               5                   10                  15

Ser Ala Arg Leu Ser Trp Thr Ala Pro Asp Ala Ala Phe Asp Ser Phe
            20                  25                  30

His Ile Ala Tyr Glu Glu Ala Thr Thr Tyr Gly Glu Ala Ile Phe Leu
        35                  40                  45

Arg Val Pro Gly Ser Glu Arg Ser Tyr Asp Leu Thr Gly Leu Lys Pro
```

```
                50                  55                  60
Gly Thr Glu Tyr Glu Val Lys Ile His Gly Val Lys Gly Gly Ala Asp
 65                  70                  75                  80

Ser Lys Pro Leu Val Ala Pro Phe Thr Thr
                 85                  90

<210> SEQ ID NO 143
<211> LENGTH: 90
<212> TYPE: PRT
<213> ORGANISM: Artificial Sequence
<220> FEATURE:
<223> OTHER INFORMATION: synthetic sequence

<400> SEQUENCE: 143

Met Leu Pro Ala Pro Lys Asn Leu Val Val Ser Arg Val Thr Glu Asp
  1               5                  10                  15

Ser Ala Arg Leu Ser Trp Thr Ala Pro Asp Ala Ala Phe Asp Ser Phe
                 20                  25                  30

His Ile Ala Tyr Glu Glu Ala Asp Ser Glu Gly Glu Ala Ile Tyr Leu
                 35                  40                  45

Arg Val Pro Gly Ser Glu Arg Ser Tyr Asp Leu Thr Gly Leu Lys Pro
 50                  55                  60

Gly Thr Glu Tyr Ser Val Asn Ile Gln Gly Val Lys Gly Gly Ile Val
 65                  70                  75                  80

Ser Phe Pro Leu His Ala Glu Phe Thr Thr
                 85                  90

<210> SEQ ID NO 144
<211> LENGTH: 90
<212> TYPE: PRT
<213> ORGANISM: Artificial Sequence
<220> FEATURE:
<223> OTHER INFORMATION: synthetic sequence

<400> SEQUENCE: 144

Met Leu Pro Ala Pro Lys Asn Leu Val Val Ser Arg Val Thr Glu Asp
  1               5                  10                  15

Ser Ala Arg Leu Ser Trp Thr Ala Pro Asp Ala Ala Phe Asp Ser Phe
                 20                  25                  30

Ile Ile Pro Tyr Ala Glu Val Arg Pro Asp Gly Glu Ala Ile Val Leu
                 35                  40                  45

Thr Val Pro Gly Ser Glu Arg Ser Tyr Asp Leu Thr Gly Leu Lys Pro
 50                  55                  60

Gly Thr Glu Tyr Ser Val Leu Ile His Gly Val Lys Gly Gly Lys Leu
 65                  70                  75                  80

Ser Leu Pro Leu Ser Ala Ile Phe Thr Thr
                 85                  90

<210> SEQ ID NO 145
<211> LENGTH: 90
<212> TYPE: PRT
<213> ORGANISM: Artificial Sequence
<220> FEATURE:
<223> OTHER INFORMATION: synthetic sequence

<400> SEQUENCE: 145

Met Leu Pro Ala Pro Lys Asn Leu Val Val Ser Arg Val Thr Glu Asp
  1               5                  10                  15

Ser Ala Arg Leu Ser Trp Thr Ala Pro Asp Ala Ala Phe Asp Ser Phe
                 20                  25                  30
```

```
Phe Ile Pro Tyr Ala Glu Pro Ser Pro Thr Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Asp Val Trp Ile Glu Gly Val Lys Gly Gly Thr Leu
65                  70                  75                  80

Ser Trp Pro Leu Ser Ala Ile Phe Thr Thr
                85                  90

<210> SEQ ID NO 146
<211> LENGTH: 90
<212> TYPE: PRT
<213> ORGANISM: Artificial Sequence
<220> FEATURE:
<223> OTHER INFORMATION: synthetic sequence

<400> SEQUENCE: 146

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Tyr Ile Ala Tyr Ala Glu Pro Arg Pro Asp Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Ser Val Leu Ile His Gly Val Lys Gly Gly Leu Leu
65                  70                  75                  80

Ser Ser Pro Leu Ser Ala Ile Phe Thr Thr
                85                  90

<210> SEQ ID NO 147
<211> LENGTH: 90
<212> TYPE: PRT
<213> ORGANISM: Artificial Sequence
<220> FEATURE:
<223> OTHER INFORMATION: synthetic sequence

<400> SEQUENCE: 147

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Phe Ile Gly Tyr Leu Glu Pro Gln Pro Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Ser Val Leu Ile His Gly Val Lys Gly Gly Arg Asn
65                  70                  75                  80

Ser Asp Pro Leu Ser Ala Ile Ser Thr Thr
                85                  90

<210> SEQ ID NO 148
<211> LENGTH: 90
<212> TYPE: PRT
<213> ORGANISM: Artificial Sequence
<220> FEATURE:
<223> OTHER INFORMATION: synthetic sequence

<400> SEQUENCE: 148
```

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

His Ile Glu Tyr Glu Glu Gln Tyr Ser Thr Gly Glu Ala Ile Tyr Leu
            35                  40                  45

Arg Val Pro Gly Ser Glu Arg Ser Tyr Asp Leu Thr Gly Leu Lys Pro
        50                  55                  60

Gly Thr Glu Tyr His Val Asp Ile Glu Gly Val Lys Gly Gly Arg Arg
65                  70                  75                  80

Ser Phe Pro Leu Asn Ala Phe Phe Thr Thr
                85                  90

<210> SEQ ID NO 149
<211> LENGTH: 90
<212> TYPE: PRT
<213> ORGANISM: Artificial Sequence
<220> FEATURE:
<223> OTHER INFORMATION: synthetic sequence

<400> SEQUENCE: 149

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

Ile Ile Pro Tyr Ala Glu Val Arg Pro Asp Gly Glu Ala Ile Val Leu
            35                  40                  45

Thr Val Pro Gly Ser Glu Arg Ser Tyr Asp Leu Thr Gly Leu Lys Pro
        50                  55                  60

Gly Thr Glu Tyr Ser Val Leu Ile His Gly Val Lys Gly Gly Lys Leu
65                  70                  75                  80

Ser Glu Pro Leu Ser Ala Ile Phe Thr Thr
                85                  90

<210> SEQ ID NO 150
<211> LENGTH: 90
<212> TYPE: PRT
<213> ORGANISM: Artificial Sequence
<220> FEATURE:
<223> OTHER INFORMATION: synthetic sequence

<400> SEQUENCE: 150

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

Pro Ile Ala Tyr Ala Glu Pro Ser Pro Thr Gly Glu Ala Ile Val Leu
            35                  40                  45

Thr Val Pro Gly Ser Glu Arg Ser Tyr Asp Leu Thr Gly Leu Lys Pro
        50                  55                  60

Gly Thr Glu Tyr Ser Val Leu Ile His Gly Val Lys Gly Gly His Leu
65                  70                  75                  80

Ser Asp Pro Leu Ser Ala Ile Phe Thr Thr
                85                  90

<210> SEQ ID NO 151
<211> LENGTH: 90
<212> TYPE: PRT
<213> ORGANISM: Artificial Sequence
<220> FEATURE:
<223> OTHER INFORMATION: synthetic sequence

<400> SEQUENCE: 151

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Phe Ile Pro Tyr Ala Glu Pro Ser Pro Thr Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Gly Val Val Ile Leu Gly Val Lys Gly Gly Tyr Gly
65                  70                  75                  80

Ser Asp Pro Leu Ser Ala Ile Phe Thr Thr
                85                  90

<210> SEQ ID NO 152
<211> LENGTH: 90
<212> TYPE: PRT
<213> ORGANISM: Artificial Sequence
<220> FEATURE:
<223> OTHER INFORMATION: synthetic sequence

<400> SEQUENCE: 152

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Phe Ile Gly Tyr Leu Glu Pro Gln Pro Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Asn Val Thr Ile Gln Gly Val Lys Gly Gly Phe Pro
65                  70                  75                  80

Ser Ser Pro Leu Ser Ala Ile Phe Thr Thr
                85                  90

<210> SEQ ID NO 153
<211> LENGTH: 90
<212> TYPE: PRT
<213> ORGANISM: Artificial Sequence
<220> FEATURE:
<223> OTHER INFORMATION: synthetic sequence

<400> SEQUENCE: 153

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Leu Asp Ser Phe
            20                  25                  30

Arg Ile Ala Tyr Thr Glu Tyr Phe Val Gly Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Gly Val Gly Ile Tyr Gly Val Lys Gly Gly Ala Gly
65                  70                  75                  80

Ser Ser Pro Leu Ser Ala Ile Phe Thr Thr
                85                  90

```
<210> SEQ ID NO 154
<211> LENGTH: 90
<212> TYPE: PRT
<213> ORGANISM: Artificial Sequence
<220> FEATURE:
<223> OTHER INFORMATION: synthetic sequence

<400> SEQUENCE: 154

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

Phe Ile Pro Tyr Ala Glu Pro Arg Pro Asp Gly Glu Ala Ile Val Leu
            35                  40                  45

Thr Val Pro Gly Ser Glu Arg Ser Tyr Asp Leu Thr Gly Leu Lys Pro
        50                  55                  60

Gly Thr Glu Tyr Ser Val Leu Ile His Gly Val Lys Gly Gly Leu Leu
65                  70                  75                  80

Ser Ser Pro Leu Ser Ala Ile Phe Thr Thr
                85                  90

<210> SEQ ID NO 155
<211> LENGTH: 90
<212> TYPE: PRT
<213> ORGANISM: Artificial Sequence
<220> FEATURE:
<223> OTHER INFORMATION: synthetic sequence

<400> SEQUENCE: 155

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

Pro Ile Thr Tyr Arg Glu Arg Ser Gln Tyr Gly Glu Ala Ile Val Leu
            35                  40                  45

Thr Val Pro Gly Ser Glu Arg Ser Tyr Asp Leu Thr Gly Leu Lys Pro
        50                  55                  60

Gly Thr Glu Tyr Val Val Pro Ile Glu Gly Val Lys Gly Gly Arg Gly
65                  70                  75                  80

Ser Lys Pro Leu Ser Ala Ile Phe Thr Thr
                85                  90

<210> SEQ ID NO 156
<211> LENGTH: 90
<212> TYPE: PRT
<213> ORGANISM: Artificial Sequence
<220> FEATURE:
<223> OTHER INFORMATION: synthetic sequence

<400> SEQUENCE: 156

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

Ala Ile Glu Tyr Phe Glu Asn Leu Gly Ile Gly Glu Ala Ile Val Leu
            35                  40                  45

Thr Val Pro Gly Ser Glu Arg Ser Tyr Asp Leu Thr Gly Leu Lys Pro
        50                  55                  60

Gly Thr Glu Tyr Val Val Asn Ile Tyr Gly Val Lys Gly Gly Trp Leu
```

```
                65                  70                  75                  80
Ser Ser Pro Leu Ser Ala Ile Phe Thr Thr
                85                  90

<210> SEQ ID NO 157
<211> LENGTH: 90
<212> TYPE: PRT
<213> ORGANISM: Artificial Sequence
<220> FEATURE:
<223> OTHER INFORMATION: synthetic sequence

<400> SEQUENCE: 157

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

Ala Ile Glu Tyr Tyr Glu Tyr Val Gly Asn Gly Glu Ala Ile Val Leu
            35                  40                  45

Thr Val Pro Gly Ser Glu Arg Ser Tyr Asp Leu Thr Gly Leu Lys Pro
        50                  55                  60

Gly Thr Glu Tyr Gln Val Gly Ile Tyr Gly Val Lys Gly Gly Tyr Tyr
65                  70                  75                  80

Ser Arg Pro Leu Ser Ala Ile Phe Thr Thr
                85                  90

<210> SEQ ID NO 158
<211> LENGTH: 90
<212> TYPE: PRT
<213> ORGANISM: Artificial Sequence
<220> FEATURE:
<223> OTHER INFORMATION: synthetic sequence

<400> SEQUENCE: 158

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

Ile Ile Asp Tyr Leu Glu Leu Asp Asp Tyr Gly Glu Ala Ile Val Leu
            35                  40                  45

Thr Val Pro Gly Ser Glu Arg Ser Tyr Asp Leu Thr Gly Leu Lys Pro
        50                  55                  60

Gly Thr Glu Tyr Pro Val Tyr Ile Tyr Gly Val Lys Gly Gly Leu Pro
65                  70                  75                  80

Ser Thr Pro Leu Ser Ala Ile Phe Thr Thr
                85                  90

<210> SEQ ID NO 159
<211> LENGTH: 90
<212> TYPE: PRT
<213> ORGANISM: Artificial Sequence
<220> FEATURE:
<223> OTHER INFORMATION: synthetic sequence

<400> SEQUENCE: 159

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

Leu Ile Pro Tyr Ala Glu Thr Ser Pro Ser Gly Glu Ala Ile Val Leu
            35                  40                  45
```

Thr Val Pro Gly Ser Glu Arg Ser Tyr Asp Leu Thr Gly Leu Lys Pro
            50                  55                  60

Gly Thr Glu Tyr Ser Val Leu Ile His Gly Val Lys Gly Gly Arg Asn
 65                  70                  75                  80

Ser Asp Pro Leu Ser Ala Ile Phe Thr Thr
                 85                  90

<210> SEQ ID NO 160
<211> LENGTH: 90
<212> TYPE: PRT
<213> ORGANISM: Artificial Sequence
<220> FEATURE:
<223> OTHER INFORMATION: synthetic sequence

<400> SEQUENCE: 160

Met Leu Pro Ala Pro Lys Asn Leu Val Val Ser Arg Val Thr Glu Asp
 1               5                  10                  15

Ser Ala Arg Leu Ser Trp Thr Ala Pro Asp Ala Ala Phe Asp Ser Phe
                20                  25                  30

Asn Ile Ala Tyr Gly Glu Trp Arg Gln His Gly Glu Ala Ile Val Leu
             35                  40                  45

Thr Val Pro Gly Ser Glu Arg Ser Tyr Asp Leu Thr Gly Leu Lys Pro
         50                  55                  60

Gly Thr Glu Tyr Asp Val Phe Ile Asp Gly Val Lys Gly Gly Asn Leu
 65                  70                  75                  80

Ser Trp Pro Leu Ser Ala Ile Phe Thr Thr
                 85                  90

<210> SEQ ID NO 161
<211> LENGTH: 90
<212> TYPE: PRT
<213> ORGANISM: Artificial Sequence
<220> FEATURE:
<223> OTHER INFORMATION: synthetic sequence

<400> SEQUENCE: 161

Met Leu Pro Ala Pro Lys Asn Leu Val Val Ser Arg Val Thr Glu Asp
 1               5                  10                  15

Ser Ala Arg Leu Ser Trp Thr Ala Pro Asp Ala Ala Phe Asp Ser Phe
                20                  25                  30

Thr Ile Arg Tyr Trp Glu Glu Leu Pro Thr Gly Glu Ala Ile Val Leu
             35                  40                  45

Thr Val Pro Gly Ser Glu Arg Ser Tyr Asp Leu Thr Gly Leu Lys Pro
         50                  55                  60

Gly Thr Glu Tyr Thr Val Glu Ile Phe Gly Val Lys Gly Gly Tyr Leu
 65                  70                  75                  80

Ser Arg Pro Leu Ser Ala Ile Ser Thr Thr
                 85                  90

<210> SEQ ID NO 162
<211> LENGTH: 90
<212> TYPE: PRT
<213> ORGANISM: Artificial Sequence
<220> FEATURE:
<223> OTHER INFORMATION: synthetic sequence

<400> SEQUENCE: 162

Met Leu Pro Ala Pro Lys Asn Leu Val Val Ser Arg Val Thr Glu Asp
 1               5                  10                  15

Ser Ala Arg Leu Ser Trp Thr Ala Pro Asp Ala Ala Phe Asp Ser Phe
            20                  25                  30

His Ile Ala Tyr Glu Glu Ala Thr Thr Tyr Gly Glu Ala Ile Phe Leu
        35                  40                  45

Arg Val Pro Gly Ser Glu Arg Ser Tyr Asp Leu Thr Gly Leu Lys Pro
    50                  55                  60

Gly Thr Glu Tyr Asp Val Trp Ile Glu Gly Val Lys Gly Gly Thr Ile
65                  70                  75                  80

Ser Gly Pro Leu Ser Ala Ile Phe Thr Thr
                85                  90

<210> SEQ ID NO 163
<211> LENGTH: 90
<212> TYPE: PRT
<213> ORGANISM: Artificial Sequence
<220> FEATURE:
<223> OTHER INFORMATION: synthetic sequence

<400> SEQUENCE: 163

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Pro Ile Ala Tyr Ala Glu Pro Arg Pro Asp Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Phe Val Asp Ile Phe Gly Val Lys Gly Gly Thr Leu
65                  70                  75                  80

Ser Arg Pro Leu Ser Ala Ile Phe Thr Thr
                85                  90

<210> SEQ ID NO 164
<211> LENGTH: 90
<212> TYPE: PRT
<213> ORGANISM: Artificial Sequence
<220> FEATURE:
<223> OTHER INFORMATION: synthetic sequence

<400> SEQUENCE: 164

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Leu Ile Pro Tyr Ala Glu Thr Ser Pro Ser Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Ser Val Leu Ile His Gly Val Lys Gly Gly His Leu
65                  70                  75                  80

Ser Asp Pro Leu Ser Ala Ile Phe Thr Thr
                85                  90

<210> SEQ ID NO 165
<211> LENGTH: 90
<212> TYPE: PRT
<213> ORGANISM: Artificial Sequence
<220> FEATURE:
<223> OTHER INFORMATION: synthetic sequence

```
<400> SEQUENCE: 165

Met Leu Pro Ala Arg Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Phe Ile Pro Tyr Ala Glu Pro Ser Pro Thr Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Ser Val Leu Ile His Gly Val Lys Gly Gly His Leu
65                  70                  75                  80

Ser Asp Pro Leu Ser Ala Ile Ser Thr Thr
                85                  90

<210> SEQ ID NO 166
<211> LENGTH: 90
<212> TYPE: PRT
<213> ORGANISM: Artificial Sequence
<220> FEATURE:
<223> OTHER INFORMATION: synthetic sequence

<400> SEQUENCE: 166

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Thr Ile Leu Tyr Asn Glu Ile Gln Asn Val Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Asp Val Trp Ile Glu Gly Val Lys Gly Gly Glu Leu
65                  70                  75                  80

Ser Trp Pro Leu Ser Ala Ile Phe Thr Thr
                85                  90

<210> SEQ ID NO 167
<211> LENGTH: 90
<212> TYPE: PRT
<213> ORGANISM: Artificial Sequence
<220> FEATURE:
<223> OTHER INFORMATION: synthetic sequence

<400> SEQUENCE: 167

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Phe Ile Gly Tyr Leu Glu Pro Gln Pro Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Asn Val Thr Ile Gln Gly Val Lys Gly Gly Thr Pro
65                  70                  75                  80

Ser Glu Pro Leu Ser Ala Ile Phe Thr Thr
                85                  90

<210> SEQ ID NO 168
<211> LENGTH: 90
```

<210> SEQ ID NO 169
<211> LENGTH: 90
<212> TYPE: PRT
<213> ORGANISM: Artificial Sequence
<220> FEATURE:
<223> OTHER INFORMATION: synthetic sequence

<400> SEQUENCE: 168

Met Leu Pro Ala Pro Lys Asn Leu Val Val Ser Arg Val Thr Glu Asp
1               5                   10                  15

Ser Ala Arg Leu Ser Trp Thr Thr Pro Asp Ala Ala Phe Asp Ser Phe
            20                  25                  30

Phe Ile Gly Tyr Leu Glu Pro Tyr Pro Pro Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Val Val Ser Ile Gln Gly Val Lys Gly Gly Lys Pro
65                  70                  75                  80

Ser Asp Pro Leu Ser Ala Ile Phe Thr Thr
            85                  90

<210> SEQ ID NO 169
<211> LENGTH: 90
<212> TYPE: PRT
<213> ORGANISM: Artificial Sequence
<220> FEATURE:
<223> OTHER INFORMATION: synthetic sequence

<400> SEQUENCE: 169

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Phe Ile Gly Tyr Leu Glu Pro Gln Pro Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Asn Val Thr Ile Gln Gly Val Lys Gly Gly Phe Pro
65                  70                  75                  80

Ser Val Pro Leu Ser Ala Ile Phe Thr Thr
            85                  90

<210> SEQ ID NO 170
<211> LENGTH: 90
<212> TYPE: PRT
<213> ORGANISM: Artificial Sequence
<220> FEATURE:
<223> OTHER INFORMATION: synthetic sequence

<400> SEQUENCE: 170

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Phe Ile Gly Tyr Pro Glu Tyr Pro Ala Thr Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Phe Val Asp Ile Asn Gly Val Lys Gly Gly Ser Leu
65                  70                  75                  80

Ser Tyr Pro Leu Ser Ala Ile Phe Thr Thr

```
                     85                  90

<210> SEQ ID NO 171
<211> LENGTH: 90
<212> TYPE: PRT
<213> ORGANISM: Artificial Sequence
<220> FEATURE:
<223> OTHER INFORMATION: synthetic sequence

<400> SEQUENCE: 171

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Ala Ile Arg Tyr Leu Glu Trp Trp Asp Val Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Leu Val Glu Ile Lys Gly Val Lys Gly Gly Lys Phe
65                  70                  75                  80

Ser Tyr Pro Leu Ser Ala Ile Phe Thr Thr
                85                  90

<210> SEQ ID NO 172
<211> LENGTH: 90
<212> TYPE: PRT
<213> ORGANISM: Artificial Sequence
<220> FEATURE:
<223> OTHER INFORMATION: synthetic sequence

<400> SEQUENCE: 172

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Pro Ile Glu Tyr Asp Glu Trp Trp Ala Leu Gly Glu Ala Ile Thr Leu
        35                  40                  45

Ile Val Pro Ala Ser Glu Arg Ser Tyr Asp Leu Thr Gly Leu Lys Pro
    50                  55                  60

Gly Thr Glu Tyr Val Val Lys Ile His Gly Val Lys Gly Gly Gln Arg
65                  70                  75                  80

Ser Tyr Pro Leu Ile Ala Phe Phe Thr Thr
                85                  90

<210> SEQ ID NO 173
<211> LENGTH: 88
<212> TYPE: PRT
<213> ORGANISM: Artificial Sequence
<220> FEATURE:
<223> OTHER INFORMATION: synthetic sequence

<400> SEQUENCE: 173

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Thr Ile His Tyr Arg Glu Leu Tyr Val Gln Ala Ile Val Leu Thr Val
        35                  40                  45

Pro Gly Ser Glu Arg Ser Tyr Asp Leu Thr Gly Leu Lys Pro Gly Thr
    50                  55                  60
```

```
Glu Tyr Leu Val Met Ile Pro Gly Val Lys Gly Pro Thr Ser Val
65                  70                  75                  80

Pro Leu Ser Ala Ile Phe Thr Thr
                85
```

<210> SEQ ID NO 174
<211> LENGTH: 90
<212> TYPE: PRT
<213> ORGANISM: Artificial Sequence
<220> FEATURE:
<223> OTHER INFORMATION: synthetic sequence

<400> SEQUENCE: 174

```
Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

Phe Ile Gly Tyr Leu Glu Pro Gln Pro Pro Gly Glu Ala Ile Val Leu
            35                  40                  45

Thr Val Pro Gly Ser Glu Arg Ser Tyr Asp Leu Thr Gly Leu Lys Pro
        50                  55                  60

Gly Thr Glu Tyr Lys Val Val Ile Gln Gly Val Lys Gly Gly Thr Pro
65                  70                  75                  80

Ser Glu Pro Leu Ser Ala Ile Phe Thr Thr
                85                  90
```

<210> SEQ ID NO 175
<211> LENGTH: 90
<212> TYPE: PRT
<213> ORGANISM: Artificial Sequence
<220> FEATURE:
<223> OTHER INFORMATION: synthetic sequence

<400> SEQUENCE: 175

```
Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

Phe Ile Gly Tyr Leu Glu Pro Gln Pro Pro Gly Glu Ala Ile Val Leu
            35                  40                  45

Thr Val Pro Gly Ser Glu Arg Ser Tyr Asp Leu Thr Gly Leu Lys Pro
        50                  55                  60

Gly Thr Glu Tyr Ser Val Val Ile Gln Gly Val Lys Gly Gly Phe Pro
65                  70                  75                  80

Ser Asp Pro Leu Ser Ala Ile Phe Thr Thr
                85                  90
```

<210> SEQ ID NO 176
<211> LENGTH: 90
<212> TYPE: PRT
<213> ORGANISM: Artificial Sequence
<220> FEATURE:
<223> OTHER INFORMATION: synthetic sequence

<400> SEQUENCE: 176

```
Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30
```

```
Pro Ile Ala Tyr Ala Glu Pro Arg Pro Asp Gly Glu Ala Ile Val Leu
            35                  40                  45

Thr Val Pro Gly Ser Glu Arg Ser Tyr Asp Leu Thr Gly Leu Lys Pro
 50                      55                  60

Gly Thr Glu Tyr Ser Val Gly Ile His Gly Val Lys Gly Gly His Asp
 65                  70                  75                  80

Ser Ser Pro Leu Ser Ala Ile Phe Thr Thr
                 85                  90

<210> SEQ ID NO 177
<211> LENGTH: 90
<212> TYPE: PRT
<213> ORGANISM: Artificial Sequence
<220> FEATURE:
<223> OTHER INFORMATION: synthetic sequence

<400> SEQUENCE: 177

Met Leu Pro Ala Pro Lys Asn Leu Val Val Ser Arg Val Thr Glu Asp
 1               5                  10                  15

Ser Ala Arg Leu Ser Trp Thr Ala Pro Asp Ala Ala Phe Asp Ser Phe
                 20                  25                  30

Phe Ile Gly Tyr Leu Glu Pro Gln Pro Gly Glu Ala Ile Val Leu
            35                  40                  45

Thr Val Pro Gly Ser Glu Arg Ser Tyr Asp Leu Thr Gly Leu Lys Pro
 50                      55                  60

Gly Thr Glu Tyr Asn Val Thr Ile Gln Gly Val Lys Gly Gly Arg Ala
 65                  70                  75                  80

Ser Gly Pro Leu Ser Ala Ile Phe Thr Thr
                 85                  90

<210> SEQ ID NO 178
<211> LENGTH: 90
<212> TYPE: PRT
<213> ORGANISM: Artificial Sequence
<220> FEATURE:
<223> OTHER INFORMATION: synthetic sequence

<400> SEQUENCE: 178

Met Leu Pro Ala Pro Lys Asn Leu Val Val Ser Arg Val Thr Glu Asp
 1               5                  10                  15

Ser Ala Arg Leu Ser Trp Thr Ala Pro Asp Ala Ala Phe Asp Ser Phe
                 20                  25                  30

Asp Ile Ala Tyr Ala Glu Pro Ile Pro Arg Gly Glu Ala Ile Val Leu
            35                  40                  45

Thr Val Pro Gly Ser Glu Arg Ser Tyr Asp Leu Thr Gly Leu Lys Pro
 50                      55                  60

Gly Thr Glu Tyr Ser Val Leu Ile His Gly Val Lys Gly Gly Arg Arg
 65                  70                  75                  80

Ser Val Pro Leu Ser Ala Ile Phe Thr Thr
                 85                  90

<210> SEQ ID NO 179
<211> LENGTH: 90
<212> TYPE: PRT
<213> ORGANISM: Artificial Sequence
<220> FEATURE:
<223> OTHER INFORMATION: synthetic sequence

<400> SEQUENCE: 179

Met Leu Pro Ala Pro Lys Asn Leu Val Val Ser Arg Val Thr Glu Asp
```

```
1               5                   10                  15
Ser Ala Arg Leu Ser Trp Thr Ala Pro Asp Ala Ala Phe Asp Ser Phe
            20                  25                  30

Tyr Ile Ala Tyr Ala Glu Pro Arg Pro Asp Gly Glu Ala Ile Val Leu
            35                  40                  45

Thr Val Pro Gly Ser Glu Arg Ser Tyr Asp Leu Thr Gly Leu Lys Pro
            50                  55                  60

Gly Thr Glu Tyr Pro Val Pro Ile Pro Gly Val Lys Gly Gly Pro Gly
65                      70                  75                  80

Ser Ser Pro Leu Ser Ala Ile Phe Thr Thr
                85                  90

<210> SEQ ID NO 180
<211> LENGTH: 90
<212> TYPE: PRT
<213> ORGANISM: Artificial Sequence
<220> FEATURE:
<223> OTHER INFORMATION: synthetic sequence

<400> SEQUENCE: 180

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Glu Ile Ser Tyr Tyr Glu Met Arg Gly Tyr Gly Glu Ala Ile Val Leu
            35                  40                  45

Thr Val Pro Gly Ser Glu Arg Ser Tyr Asp Leu Thr Gly Leu Lys Pro
            50                  55                  60

Gly Thr Glu Tyr Ser Val Leu Ile His Gly Val Glu Gly Gly Asp Tyr
65                      70                  75                  80

Ser Ser Pro Leu Ser Ala Ile Ser Thr Thr
                85                  90

<210> SEQ ID NO 181
<211> LENGTH: 90
<212> TYPE: PRT
<213> ORGANISM: Artificial Sequence
<220> FEATURE:
<223> OTHER INFORMATION: synthetic sequence

<400> SEQUENCE: 181

Met Leu Pro Ala Pro Lys Asn Leu Val Val Ser His Val Thr Glu Asp
1               5                   10                  15

Ser Ala Arg Leu Ser Trp Thr Ala Pro Asp Ala Ala Phe Asp Ser Phe
            20                  25                  30

Pro Ile Ala Tyr Ala Glu Pro Arg Pro Asp Gly Glu Ala Ile Val Leu
            35                  40                  45

Thr Val Pro Gly Ser Glu Arg Ser Tyr Asp Leu Thr Gly Leu Lys Pro
            50                  55                  60

Gly Thr Glu Tyr Ser Val Leu Ile His Gly Val Lys Gly Gly Leu Leu
65                      70                  75                  80

Ser Ser Pro Leu Ser Ala Ile Phe Thr Thr
                85                  90

<210> SEQ ID NO 182
<211> LENGTH: 90
<212> TYPE: PRT
<213> ORGANISM: Artificial Sequence
<220> FEATURE:
```

<223> OTHER INFORMATION: synthetic sequence

<400> SEQUENCE: 182

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Phe Ile Gly Tyr Leu Glu Pro Tyr Pro Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Val Val Ser Ile Gln Gly Val Lys Gly Gly Thr Pro
65                  70                  75                  80

Ser Gln Pro Leu Ser Ala Ile Phe Thr Thr
            85                  90

<210> SEQ ID NO 183
<211> LENGTH: 90
<212> TYPE: PRT
<213> ORGANISM: Artificial Sequence
<220> FEATURE:
<223> OTHER INFORMATION: synthetic sequence

<400> SEQUENCE: 183

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Leu Ile Pro Tyr Ala Glu Thr Ser Pro Ser Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Ser Val Leu Ile His Gly Val Lys Gly Gly Arg Pro
65                  70                  75                  80

Ser Asn Pro Leu Val Ala Ala Phe Thr Thr
            85                  90

<210> SEQ ID NO 184
<211> LENGTH: 90
<212> TYPE: PRT
<213> ORGANISM: Artificial Sequence
<220> FEATURE:
<223> OTHER INFORMATION: synthetic sequence

<400> SEQUENCE: 184

Met Leu Pro Ala Pro Lys Asn Leu Val Val Ser Arg Ile Thr Glu Asp
1               5                   10                  15

Ser Ala Arg Leu Ser Trp Thr Ala Pro Asp Ala Ala Phe Asp Ser Phe
            20                  25                  30

Gly Ile Gly Tyr Tyr Glu His Lys Arg Phe Gly Glu Ala Ile Gln Leu
        35                  40                  45

Ser Val Pro Gly Ser Glu Arg Ser Tyr Asp Leu Thr Gly Leu Lys Pro
    50                  55                  60

Gly Thr Glu Tyr Glu Val Asp Ile Glu Gly Val Lys Gly Gly Val Leu
65                  70                  75                  80

Ser Trp Pro Leu Phe Ala Glu Phe Thr Thr
            85                  90

<210> SEQ ID NO 185
<211> LENGTH: 90
<212> TYPE: PRT
<213> ORGANISM: Artificial Sequence
<220> FEATURE:
<223> OTHER INFORMATION: synthetic sequence

<400> SEQUENCE: 185

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Glu Ile Asp Tyr Asp Glu Leu Ala Ile Tyr Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Gly Val Met Ile Ile Gly Val Lys Gly Gly Leu Pro
65                  70                  75                  80

Ser Asp Pro Leu Ser Ala Ile Phe Thr Thr
                85                  90

<210> SEQ ID NO 186
<211> LENGTH: 87
<212> TYPE: PRT
<213> ORGANISM: Artificial Sequence
<220> FEATURE:
<223> OTHER INFORMATION: synthetic sequence

<400> SEQUENCE: 186

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Phe Ile Gly Tyr Leu Glu Ser Ala Glu Ala Ile Val Leu Thr Val Pro
        35                  40                  45

Gly Ser Glu Arg Ser Tyr Asp Leu Thr Gly Leu Lys Pro Gly Thr Glu
    50                  55                  60

Tyr Leu Val Thr Ile Gln Gly Val Lys Gly Gly Ile Ala Ser Asp Pro
65                  70                  75                  80

Leu Ser Ala Ile Phe Thr Thr
                85

<210> SEQ ID NO 187
<211> LENGTH: 90
<212> TYPE: PRT
<213> ORGANISM: Artificial Sequence
<220> FEATURE:
<223> OTHER INFORMATION: synthetic sequence

<400> SEQUENCE: 187

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Val Ile Glu Tyr Phe Glu Phe Val Gly Tyr Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Ser Val Gly Ile Tyr Gly Val Lys Gly Gly Lys Leu
65                  70                  75                  80

Ser Pro Pro Leu Ser Ala Ile Phe Thr Thr
                85                  90

<210> SEQ ID NO 188
<211> LENGTH: 90
<212> TYPE: PRT
<213> ORGANISM: Artificial Sequence
<220> FEATURE:
<223> OTHER INFORMATION: synthetic sequence

<400> SEQUENCE: 188

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

Leu Ile Pro Tyr Ala Glu Thr Ser Pro Ser Gly Glu Ala Ile Val Leu
            35                  40                  45

Thr Val Pro Gly Ser Glu Arg Ser Tyr Asp Leu Thr Gly Leu Lys Pro
        50                  55                  60

Gly Thr Glu Tyr Ser Val Leu Ile His Gly Val Lys Gly Gly Lys Leu
65                  70                  75                  80

Ser Leu Pro Leu Ser Ala Ile Phe Thr Thr
                85                  90

<210> SEQ ID NO 189
<211> LENGTH: 86
<212> TYPE: PRT
<213> ORGANISM: Artificial Sequence
<220> FEATURE:
<223> OTHER INFORMATION: synthetic sequence

<400> SEQUENCE: 189

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

His Glu Trp Val Tyr Phe Gly Glu Ala Ile Val Leu Thr Val Pro Gly
            35                  40                  45

Ser Glu Arg Ser Tyr Asp Leu Thr Gly Leu Lys Pro Gly Thr Glu Tyr
        50                  55                  60

Phe Val Asp Ile Trp Gly Val Lys Gly Gly Thr Val Ser Lys Pro Leu
65                  70                  75                  80

Ser Ala Ile Phe Thr Thr
                85

<210> SEQ ID NO 190
<211> LENGTH: 90
<212> TYPE: PRT
<213> ORGANISM: Artificial Sequence
<220> FEATURE:
<223> OTHER INFORMATION: synthetic sequence

<400> SEQUENCE: 190

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

Phe Ile Gly Tyr Pro Glu Tyr Pro Ala Thr Gly Glu Ala Ile Thr Leu
            35                  40                  45

```
Phe Val Pro Gly Ser Glu Arg Ser Tyr Asp Leu Thr Gly Leu Lys Pro
 50                  55                  60

Gly Thr Glu Tyr Asn Val Val Ile Gln Gly Val Lys Gly Gly Arg Pro
 65                  70                  75                  80

Ser Asn Pro Leu Val Val Ala Phe Thr Thr
                 85                  90
```

<210> SEQ ID NO 191
<211> LENGTH: 90
<212> TYPE: PRT
<213> ORGANISM: Artificial Sequence
<220> FEATURE:
<223> OTHER INFORMATION: synthetic sequence

<400> SEQUENCE: 191

```
Met Leu Pro Ala Pro Glu Asn Leu Val Val Ser Arg Val Thr Glu Asp
 1               5                  10                  15

Ser Ala Arg Leu Ser Trp Thr Ala Pro Asp Ala Ala Phe Asp Ser Phe
                 20                  25                  30

Glu Ile Thr Tyr Glu Glu Asn Trp Arg Arg Gly Glu Ala Ile Val Leu
                 35                  40                  45

Thr Val Pro Gly Ser Glu Arg Ser Tyr Asp Leu Thr Gly Pro Lys Pro
 50                  55                  60

Gly Thr Glu Tyr Ile Val Ile Gln Gly Val Lys Gly Gly Ala Glu
 65                  70                  75                  80

Ser Trp Pro Leu Ser Ala Ile Phe Thr Thr
                 85                  90
```

<210> SEQ ID NO 192
<211> LENGTH: 90
<212> TYPE: PRT
<213> ORGANISM: Artificial Sequence
<220> FEATURE:
<223> OTHER INFORMATION: synthetic sequence

<400> SEQUENCE: 192

```
Met Leu Pro Ala Pro Lys Asn Leu Val Val Ser Arg Val Thr Glu Asp
 1               5                  10                  15

Ser Ala Arg Leu Ser Trp Thr Ala Leu Asp Ala Ala Phe Asp Ser Phe
                 20                  25                  30

Phe Ile Gly Tyr Leu Glu Pro Gln Pro Pro Gly Glu Ala Ile Val Leu
                 35                  40                  45

Thr Val Pro Gly Ser Glu Arg Ser Tyr Asp Leu Thr Gly Leu Lys Pro
 50                  55                  60

Gly Thr Glu Tyr Asn Val Thr Ile Gln Gly Val Lys Gly Gly Phe Pro
 65                  70                  75                  80

Ser Met Pro Leu Ser Ala Ile Phe Thr Thr
                 85                  90
```

<210> SEQ ID NO 193
<211> LENGTH: 90
<212> TYPE: PRT
<213> ORGANISM: Artificial Sequence
<220> FEATURE:
<223> OTHER INFORMATION: synthetic sequence

<400> SEQUENCE: 193

```
Met Leu Pro Ala Pro Lys Asn Leu Val Val Ser Arg Val Thr Glu Asp
 1               5                  10                  15

Ser Ala Arg Leu Ser Trp Thr Ala Pro Asp Ala Ala Phe Asp Ser Phe
```

```
                    20                  25                  30

Thr Ile Trp Tyr Ala Glu Ala Val Gly Asn Gly Glu Ala Ile Val Leu
            35                  40                  45

Thr Val Pro Gly Ser Glu Arg Ser Tyr Asp Leu Thr Gly Leu Lys Pro
        50                  55                  60

Gly Thr Glu Tyr Trp Val Asp Ile Trp Gly Val Lys Gly Gly Glu Phe
65                  70                  75                  80

Ser Ser Pro Leu Ser Ala Ile Phe Thr Thr
                85                  90

<210> SEQ ID NO 194
<211> LENGTH: 90
<212> TYPE: PRT
<213> ORGANISM: Artificial Sequence
<220> FEATURE:
<223> OTHER INFORMATION: synthetic sequence

<400> SEQUENCE: 194

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Glu Ile Asp Tyr Asp Glu Leu Ala Ile Tyr Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Arg Val Phe Ile Tyr Gly Val Lys Gly Gly Trp Thr
65                  70                  75                  80

Ser Trp Pro Leu Ser Thr Ile Phe Thr Thr
                85                  90

<210> SEQ ID NO 195
<211> LENGTH: 90
<212> TYPE: PRT
<213> ORGANISM: Artificial Sequence
<220> FEATURE:
<223> OTHER INFORMATION: synthetic sequence

<400> SEQUENCE: 195

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Pro Ile Glu Tyr Asp Glu Ile Pro Phe Trp Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Arg Val Trp Ile His Gly Val Lys Gly Gly Asn Ser
65                  70                  75                  80

Ser Trp Pro Leu Ser Ala Ile Phe Thr Thr
                85                  90

<210> SEQ ID NO 196
<211> LENGTH: 90
<212> TYPE: PRT
<213> ORGANISM: Artificial Sequence
<220> FEATURE:
<223> OTHER INFORMATION: synthetic sequence

<400> SEQUENCE: 196
```

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Asn Ile His Tyr Val Glu Trp Trp Val Leu Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Pro Val Tyr Ile Tyr Gly Val Lys Gly Gly Pro Lys
65                  70                  75                  80

Ser Ile Pro Leu Ser Ala Ile Phe Thr Thr
                85                  90

<210> SEQ ID NO 197
<211> LENGTH: 90
<212> TYPE: PRT
<213> ORGANISM: Artificial Sequence
<220> FEATURE:
<223> OTHER INFORMATION: synthetic sequence

<400> SEQUENCE: 197

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Lys Ile Asp Tyr Leu Glu Ile Asn Asp Asn Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Pro Val Tyr Ile Trp Gly Val Lys Gly Gly Tyr Pro
65                  70                  75                  80

Ser Ser Pro Leu Ser Ala Ile Phe Thr Thr
                85                  90

<210> SEQ ID NO 198
<211> LENGTH: 90
<212> TYPE: PRT
<213> ORGANISM: Artificial Sequence
<220> FEATURE:
<223> OTHER INFORMATION: synthetic sequence

<400> SEQUENCE: 198

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Leu Ile Ala Tyr Asn Glu Asp Arg Lys Phe Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Asp Val Trp Ile Glu Gly Val Lys Gly Gly Ser Leu
65                  70                  75                  80

Ser Phe Pro Leu Ser Ala Ile Phe Thr Thr
                85                  90

<210> SEQ ID NO 199
<211> LENGTH: 90
<212> TYPE: PRT

<213> ORGANISM: Artificial Sequence
<220> FEATURE:
<223> OTHER INFORMATION: synthetic sequence

<400> SEQUENCE: 199

```
Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Gly Ile Arg Tyr Phe Glu Trp Trp Asp Leu Gly Glu Ala Ile Val Leu
        35                  40                  45

Thr Val Pro Gly Ser Glu Arg Ser Tyr Asp Pro Thr Gly Leu Lys Pro
    50                  55                  60

Gly Thr Glu Tyr Asn Val Thr Ile Gln Gly Val Lys Gly Gly Phe Pro
65                  70                  75                  80

Ser Met Pro Leu Ser Ala Ile Phe Thr Thr
                85                  90
```

<210> SEQ ID NO 200
<211> LENGTH: 90
<212> TYPE: PRT
<213> ORGANISM: Artificial Sequence
<220> FEATURE:
<223> OTHER INFORMATION: synthetic sequence

<400> SEQUENCE: 200

```
Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Tyr Ile Glu Tyr Tyr Glu Trp Met His Thr Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Ser Val Tyr Ile Tyr Gly Val Lys Gly Gly Tyr Pro
65                  70                  75                  80

Ser Ser Pro Leu Ser Ala Ile Phe Thr Thr
                85                  90
```

<210> SEQ ID NO 201
<211> LENGTH: 90
<212> TYPE: PRT
<213> ORGANISM: Artificial Sequence
<220> FEATURE:
<223> OTHER INFORMATION: synthetic sequence

<400> SEQUENCE: 201

```
Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Asn Ile Asp Tyr Trp Glu Thr Trp Val Ile Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Glu Val Ile Ile Pro Gly Val Lys Gly Gly Thr Ile
65                  70                  75                  80

Ser Pro Pro Leu Ser Ala Ile Phe Thr Thr
                85                  90
```

<210> SEQ ID NO 202
<211> LENGTH: 90
<212> TYPE: PRT
<213> ORGANISM: Artificial Sequence
<220> FEATURE:
<223> OTHER INFORMATION: synthetic sequence

<400> SEQUENCE: 202

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Tyr Ile Asp Tyr Leu Glu Leu Thr Tyr Ser Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Tyr Val Tyr Ile Tyr Gly Val Lys Gly Gly Tyr Pro
65                  70                  75                  80

Ser Ser Pro Leu Ser Ala Ile Phe Thr Thr
                85                  90

<210> SEQ ID NO 203
<211> LENGTH: 90
<212> TYPE: PRT
<213> ORGANISM: Artificial Sequence
<220> FEATURE:
<223> OTHER INFORMATION: synthetic sequence

<400> SEQUENCE: 203

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Leu Asp Ser Phe
            20                  25                  30

Arg Ile Glu Tyr Tyr Glu Ser Tyr Gly His Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Asp Val Gly Ile Tyr Gly Val Lys Gly Gly Tyr Tyr
65                  70                  75                  80

Ser Arg Pro Leu Ser Ala Ile Phe Thr Thr
                85                  90

<210> SEQ ID NO 204
<211> LENGTH: 90
<212> TYPE: PRT
<213> ORGANISM: Artificial Sequence
<220> FEATURE:
<223> OTHER INFORMATION: synthetic sequence

<400> SEQUENCE: 204

Met Leu Pro Ala Pro Lys Asn Leu Val Val Ser Arg Val Thr Glu Asp
1               5                   10                  15

Ser Ala Arg Leu Pro Trp Thr Ala Pro Asp Ala Ala Phe Asp Ser Phe
            20                  25                  30

Trp Ile Ser Tyr Tyr Glu Ser Val Gly Tyr Gly Glu Ala Ile Val Leu
        35                  40                  45

Thr Val Pro Gly Ser Glu Arg Ser Tyr Asp Leu Thr Gly Leu Lys Pro
    50                  55                  60

```
Gly Thr Glu Tyr Tyr Val Asp Ile Ser Gly Val Lys Gly Gly Val Tyr
 65                  70                  75                  80

Ser Leu Pro Leu Ser Ala Ile Phe Thr Thr
                 85                  90

<210> SEQ ID NO 205
<211> LENGTH: 90
<212> TYPE: PRT
<213> ORGANISM: Artificial Sequence
<220> FEATURE:
<223> OTHER INFORMATION: synthetic sequence

<400> SEQUENCE: 205

Met Leu Pro Ala Pro Lys Asn Leu Val Val Ser Arg Val Thr Glu Asp
  1               5                  10                  15

Ser Ala Arg Leu Ser Trp Thr Ala Pro Asp Ala Ala Phe Asp Ser Phe
                 20                  25                  30

Asp Ile Asp Tyr Asp Glu Pro Ala Trp Asn Gly Glu Ala Ile Val Leu
             35                  40                  45

Thr Val Pro Gly Ser Glu Arg Ser Tyr Asp Leu Thr Gly Leu Lys Pro
         50                  55                  60

Gly Thr Glu Tyr Arg Val Phe Ile Tyr Val Lys Gly Gly Asn Thr
 65                  70                  75                  80

Ser Trp Pro Leu Ser Ala Ile Phe Thr Thr
                 85                  90

<210> SEQ ID NO 206
<211> LENGTH: 90
<212> TYPE: PRT
<213> ORGANISM: Artificial Sequence
<220> FEATURE:
<223> OTHER INFORMATION: synthetic sequence

<400> SEQUENCE: 206

Met Leu Pro Ala Pro Lys Asn Leu Val Val Ser Arg Val Thr Glu Asp
  1               5                  10                  15

Ser Ala Arg Leu Ser Trp Thr Ala Pro Asp Ala Ala Phe Asp Ser Phe
                 20                  25                  30

Asp Ile Glu Tyr Asp Glu Leu Trp Lys Asn Gly Glu Ala Ile Val Leu
             35                  40                  45

Thr Val Pro Gly Ser Glu Arg Ser Tyr Asp Leu Thr Gly Leu Lys Pro
         50                  55                  60

Gly Thr Glu Tyr Arg Val Phe Ile Tyr Val Lys Gly Gly Tyr Gly
 65                  70                  75                  80

Ser Phe Pro Leu Ser Ala Ile Phe Thr Thr
                 85                  90

<210> SEQ ID NO 207
<211> LENGTH: 90
<212> TYPE: PRT
<213> ORGANISM: Artificial Sequence
<220> FEATURE:
<223> OTHER INFORMATION: synthetic sequence

<400> SEQUENCE: 207

Met Leu Pro Ala Pro Lys Asn Leu Val Val Ser Arg Val Thr Glu Asp
  1               5                  10                  15

Ser Ala Arg Leu Ser Trp Thr Ala Pro Asp Ala Ala Phe Asp Ser Phe
                 20                  25                  30

Phe Ile Gly Tyr Leu Glu Pro Gln Pro Pro Gly Glu Ala Ile Val Leu
```

35                  40                  45

Thr Val Pro Gly Ser Glu Arg Ser Tyr Asp Leu Thr Gly Leu Lys Pro
    50                  55                  60

Gly Thr Glu Tyr Asn Val Thr Ile Gln Gly Val Lys Gly Gly Thr Pro
65                  70                  75                  80

Ser Glu Pro Leu Ser Ala Ile Ser Thr Thr
                85                  90

<210> SEQ ID NO 208
<211> LENGTH: 90
<212> TYPE: PRT
<213> ORGANISM: Artificial Sequence
<220> FEATURE:
<223> OTHER INFORMATION: synthetic sequence

<400> SEQUENCE: 208

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

Gly Ile Val Tyr Arg Glu Pro Tyr Val Gly Gly Glu Ala Ile Val Leu
            35                  40                  45

Thr Val Pro Gly Ser Glu Arg Ser Tyr Asp Leu Thr Gly Leu Lys Pro
    50                  55                  60

Gly Thr Glu Tyr Gly Val Pro Ile Pro Gly Val Lys Gly Gly Tyr Asp
65                  70                  75                  80

Ser Gly Pro Leu Ser Ala Ile Phe Thr Thr
                85                  90

<210> SEQ ID NO 209
<211> LENGTH: 90
<212> TYPE: PRT
<213> ORGANISM: Artificial Sequence
<220> FEATURE:
<223> OTHER INFORMATION: synthetic sequence

<400> SEQUENCE: 209

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

Thr Ile Pro Tyr Ile Glu Tyr Val Trp Trp Gly Glu Ala Ile Val Leu
            35                  40                  45

Thr Val Gln Gly Ser Glu Arg Ser Tyr Asp Leu Thr Gly Leu Lys Pro
    50                  55                  60

Gly Thr Glu Tyr Pro Val Thr Ile Gly Gly Val Lys Gly Gly Ser Arg
65                  70                  75                  80

Ser His Pro Leu His Ala His Phe Thr Thr
                85                  90

<210> SEQ ID NO 210
<211> LENGTH: 90
<212> TYPE: PRT
<213> ORGANISM: Artificial Sequence
<220> FEATURE:
<223> OTHER INFORMATION: synthetic sequence

<400> SEQUENCE: 210

Met Leu Pro Ala Pro Lys Asn Leu Val Val Ser Arg Val Thr Glu Asp
1               5                   10                  15

```
Ser Ala Arg Leu Ser Trp Thr Ala Pro Asp Ala Ala Phe Asp Ser Phe
            20                  25                  30

Ser Ile Val Tyr Gly Glu Arg Phe Val Asn Gly Glu Ala Ile Val Leu
            35                  40                  45

Thr Val Pro Gly Ser Glu Arg Ser Tyr Asp Leu Thr Gly Leu Lys Pro
50                      55                  60

Gly Thr Glu Tyr His Val Tyr Ile Asp Gly Val Lys Gly Gly Asp Leu
65                      70                  75                  80

Ser Trp Pro Leu Ser Ala Ile Phe Thr Thr
                85                  90

<210> SEQ ID NO 211
<211> LENGTH: 90
<212> TYPE: PRT
<213> ORGANISM: Artificial Sequence
<220> FEATURE:
<223> OTHER INFORMATION: synthetic sequence

<400> SEQUENCE: 211

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Trp Ile Asn Tyr Tyr Glu Ala Gln Pro Asp Gly Glu Ala Ile Val Leu
            35                  40                  45

Thr Val Pro Gly Ser Glu Arg Ser Tyr Asp Leu Thr Gly Leu Lys Pro
50                      55                  60

Gly Thr Glu Tyr Asp Val Glu Ile Ala Gly Val Lys Gly Gly Thr Ala
65                      70                  75                  80

Ser Leu Pro Leu Ser Ala Ile Phe Thr Thr
                85                  90

<210> SEQ ID NO 212
<211> LENGTH: 90
<212> TYPE: PRT
<213> ORGANISM: Artificial Sequence
<220> FEATURE:
<223> OTHER INFORMATION: synthetic sequence

<400> SEQUENCE: 212

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Ile Ile Glu Tyr Trp Glu Gln Ile Gly Val Gly Glu Ala Ile Val Leu
            35                  40                  45

Thr Val Pro Gly Ser Glu Arg Ser Tyr Asp Leu Thr Gly Leu Lys Pro
50                      55                  60

Gly Thr Glu Tyr Trp Val Gly Ile Tyr Gly Val Lys Gly Gly Leu Leu
65                      70                  75                  80

Ser Ser Pro Leu Ser Ala Ile Phe Thr Thr
                85                  90

<210> SEQ ID NO 213
<211> LENGTH: 90
<212> TYPE: PRT
<213> ORGANISM: Artificial Sequence
<220> FEATURE:
<223> OTHER INFORMATION: synthetic sequence
```

<400> SEQUENCE: 213

Met Leu Pro Ala Pro Lys Asn Leu Val Val Ser Arg Val Thr Glu Asp
1               5                  10                  15

Ser Ala Arg Leu Ser Trp Thr Ala Pro Asp Ala Ala Phe Asp Ser Phe
            20                  25                  30

Trp Ile Tyr Tyr Trp Glu Ile Glu Arg Ala Gly Glu Ala Ile Arg Leu
        35                  40                  45

Asp Val Pro Gly Ser Glu Arg Ser Tyr Asp Leu Thr Gly Leu Lys Pro
    50                  55                  60

Gly Thr Glu Tyr Arg Val Asp Ile Trp Gly Val Lys Gly Gly Pro Thr
65                  70                  75                  80

Ser Gly Pro Leu Arg Ala Thr Phe Thr Thr
                85                  90

<210> SEQ ID NO 214
<211> LENGTH: 90
<212> TYPE: PRT
<213> ORGANISM: Artificial Sequence
<220> FEATURE:
<223> OTHER INFORMATION: synthetic sequence

<400> SEQUENCE: 214

Met Leu Pro Ala Pro Lys Asn Leu Val Val Ser Arg Val Thr Glu Asp
1               5                  10                  15

Ser Ala Arg Leu Ser Trp Thr Ala Pro Asp Ala Ala Phe Asp Ser Phe
            20                  25                  30

Ala Ile Pro Tyr Gly Glu Arg Gln Glu Leu Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Phe Val Val Ile Gln Gly Val Lys Gly Gly Gln Pro
65                  70                  75                  80

Ser Tyr Pro Leu Ser Ala Ile Phe Thr Thr
                85                  90

<210> SEQ ID NO 215
<211> LENGTH: 90
<212> TYPE: PRT
<213> ORGANISM: Artificial Sequence
<220> FEATURE:
<223> OTHER INFORMATION: synthetic sequence

<400> SEQUENCE: 215

Met Leu Pro Ala Pro Lys Asn Leu Val Val Ser Arg Val Thr Glu Asp
1               5                  10                  15

Ser Ala Arg Leu Ser Trp Thr Ala Pro Asp Ala Ala Phe Asp Ser Phe
            20                  25                  30

Leu Ile Pro Tyr Ala Glu Thr Ser Pro Thr Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Ser Val Leu Ile His Gly Val Lys Gly Gly Tyr Pro
65                  70                  75                  80

Ser Ser Pro Leu Ser Ala Ile Phe Thr Thr
                85                  90

<210> SEQ ID NO 216

```
<211> LENGTH: 90
<212> TYPE: PRT
<213> ORGANISM: Artificial Sequence
<220> FEATURE:
<223> OTHER INFORMATION: synthetic sequence

<400> SEQUENCE: 216

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

Pro Ile Ala Tyr Ala Glu Pro Thr Pro Ser Gly Glu Ala Ile Val Leu
            35                  40                  45

Thr Val Pro Gly Ser Glu Arg Ser Tyr Asp Leu Thr Gly Leu Lys Pro
        50                  55                  60

Gly Thr Glu Tyr Ser Val Leu Ile His Gly Val Lys Gly Gly Gly Leu
65                  70                  75                  80

Ser Leu Pro Leu Ser Ala Ile Phe Thr Thr
                85                  90

<210> SEQ ID NO 217
<211> LENGTH: 90
<212> TYPE: PRT
<213> ORGANISM: Artificial Sequence
<220> FEATURE:
<223> OTHER INFORMATION: synthetic sequence

<400> SEQUENCE: 217

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

Ile Ile Glu Tyr Trp Glu Trp Tyr Phe Ala Gly Glu Ala Ile Val Leu
            35                  40                  45

Thr Val Pro Gly Ser Glu Arg Ser Tyr Asp Leu Thr Gly Leu Lys Pro
        50                  55                  60

Gly Thr Glu Tyr Thr Val Trp Ile Thr Gly Val Lys Gly Gly Thr Trp
65                  70                  75                  80

Ser Glu Pro Leu Ser Ala Ile Phe Thr Thr
                85                  90

<210> SEQ ID NO 218
<211> LENGTH: 90
<212> TYPE: PRT
<213> ORGANISM: Artificial Sequence
<220> FEATURE:
<223> OTHER INFORMATION: synthetic sequence

<400> SEQUENCE: 218

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

Thr Ile Leu Tyr Tyr Glu Met Val Gly Glu Gly Glu Ala Ile Val Leu
            35                  40                  45

Thr Val Pro Gly Ser Glu Arg Ser Tyr Asp Leu Thr Gly Pro Lys Pro
        50                  55                  60

Gly Thr Glu Tyr Trp Val Asp Ile Tyr Gly Val Lys Gly Gly Gly Trp
65                  70                  75                  80
```

Ser Arg Pro Leu Ser Ala Ile Phe Thr Thr
                85                  90

<210> SEQ ID NO 219
<211> LENGTH: 90
<212> TYPE: PRT
<213> ORGANISM: Artificial Sequence
<220> FEATURE:
<223> OTHER INFORMATION: synthetic sequence

<400> SEQUENCE: 219

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

His Ile Asp Tyr Leu Glu Leu Thr Tyr Ala Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Tyr Val Thr Ile Tyr Gly Val Lys Gly Gly Tyr Pro
65                  70                  75                  80

Ser Ser Pro Leu Ser Ala Ile Phe Thr Thr
                85                  90

<210> SEQ ID NO 220
<211> LENGTH: 90
<212> TYPE: PRT
<213> ORGANISM: Artificial Sequence
<220> FEATURE:
<223> OTHER INFORMATION: synthetic sequence

<400> SEQUENCE: 220

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

His Ile Ile Tyr Glu Glu Asp Gly Thr Glu Gly Glu Ala Ile Tyr Leu
        35                  40                  45

Arg Val Pro Gly Ser Glu Arg Ser Tyr Asp Leu Thr Gly Leu Lys Pro
    50                  55                  60

Gly Thr Glu Tyr Glu Val Asp Ile Glu Gly Val Lys Gly Gly Val Leu
65                  70                  75                  80

Ser Trp Pro Leu Phe Ala Glu Phe Thr Thr
                85                  90

<210> SEQ ID NO 221
<211> LENGTH: 90
<212> TYPE: PRT
<213> ORGANISM: Artificial Sequence
<220> FEATURE:
<223> OTHER INFORMATION: synthetic sequence

<400> SEQUENCE: 221

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

His Ile Ser Tyr Gln Glu Val Val Ala Glu Gly Glu Ala Ile Tyr Leu
        35                  40                  45

Arg Val Pro Gly Ser Glu Arg Ser Tyr Asp Leu Thr Gly Leu Lys Pro

```
                    50                  55                  60
Gly Thr Glu Tyr Tyr Val Leu Ile His Gly Val Lys Gly Gly Tyr Glu
 65                  70                  75                  80

Ser Lys Pro Leu Asp Ala Ser Phe Thr Thr
                 85                  90
```

<210> SEQ ID NO 222
<211> LENGTH: 90
<212> TYPE: PRT
<213> ORGANISM: Artificial Sequence
<220> FEATURE:
<223> OTHER INFORMATION: synthetic sequence

<400> SEQUENCE: 222

```
Met Leu Pro Ala Pro Lys Asn Leu Val Val Ser Arg Val Thr Glu Asp
 1               5                  10                  15

Ser Ala Arg Leu Ser Trp Thr Ala Pro Asp Ala Ala Phe Asp Ser Phe
                20                  25                  30

Tyr Ile Glu Tyr Phe Glu Trp Thr Gly Ser Gly Glu Ala Ile Val Leu
            35                  40                  45

Thr Val Pro Gly Ser Glu Arg Ser Tyr Asp Leu Thr Gly Leu Lys Pro
        50                  55                  60

Gly Thr Glu Tyr Asn Val Ala Ile Tyr Gly Val Lys Gly Gly Ala Val
 65                  70                  75                  80

Ser Tyr Pro Leu Ser Ala Ile Phe Thr Thr
                 85                  90
```

<210> SEQ ID NO 223
<211> LENGTH: 90
<212> TYPE: PRT
<213> ORGANISM: Artificial Sequence
<220> FEATURE:
<223> OTHER INFORMATION: synthetic sequence

<400> SEQUENCE: 223

```
Met Leu Pro Ala Pro Lys Asn Leu Val Val Ser Arg Val Thr Glu Asp
 1               5                  10                  15

Ser Ala Arg Leu Ser Trp Thr Ala Pro Asp Ala Ala Phe Asp Ser Phe
                20                  25                  30

Thr Ile Trp Tyr Ala Glu Ala Leu Gly Asp Gly Glu Ala Ile Val Leu
            35                  40                  45

Thr Val Pro Gly Ser Glu Arg Ser Tyr Asp Leu Thr Gly Leu Lys Pro
        50                  55                  60

Gly Thr Glu Tyr Phe Val Asp Ile Pro Gly Val Lys Gly Gly Thr Arg
 65                  70                  75                  80

Ser Ser Pro Leu Ser Ala Ile Ser Thr Thr
                 85                  90
```

<210> SEQ ID NO 224
<211> LENGTH: 88
<212> TYPE: PRT
<213> ORGANISM: Artificial Sequence
<220> FEATURE:
<223> OTHER INFORMATION: synthetic sequence

<400> SEQUENCE: 224

```
Met Leu Leu Ala Pro Lys Asn Leu Val Val Ser Arg Val Thr Glu Asp
 1               5                  10                  15

Ser Ala Arg Leu Ser Trp Thr Ala Pro Asp Ala Ala Phe Asp Ser Phe
                20                  25                  30
```

Arg Tyr Leu Glu Gln Gly Leu Tyr Gly Glu Ala Ile Val Leu Thr Val
                35                  40                  45

Pro Gly Ser Glu Arg Ser Tyr Asp Leu Thr Gly Leu Lys Pro Gly Thr
 50                  55                  60

Glu Tyr Trp Val Glu Ile Ile Gly Val Lys Gly Gly Tyr Ser Thr
 65                  70                  75                  80

Pro Leu Ser Ala Ile Phe Thr Thr
                85

<210> SEQ ID NO 225
<211> LENGTH: 90
<212> TYPE: PRT
<213> ORGANISM: Artificial Sequence
<220> FEATURE:
<223> OTHER INFORMATION: synthetic sequence

<400> SEQUENCE: 225

Met Leu Pro Ala Pro Lys Asn Leu Val Val Ser Arg Val Thr Glu Asp
 1               5                  10                  15

Ser Ala Arg Leu Ser Trp Thr Ala Pro Asp Ala Ala Phe Asp Ser Phe
                20                  25                  30

Lys Ile Glu Tyr Phe Glu Tyr Val Gly Tyr Gly Ala Ile Val Leu
                35                  40                  45

Thr Val Pro Gly Ser Glu Arg Ser Tyr Asp Leu Thr Gly Leu Lys Pro
 50                  55                  60

Gly Thr Glu Tyr Tyr Val Ala Ile Tyr Gly Val Lys Gly Gly Trp Tyr
 65                  70                  75                  80

Ser Arg Pro Leu Ser Ala Ile Phe Thr Thr
                85                  90

<210> SEQ ID NO 226
<211> LENGTH: 90
<212> TYPE: PRT
<213> ORGANISM: Artificial Sequence
<220> FEATURE:
<223> OTHER INFORMATION: synthetic sequence

<400> SEQUENCE: 226

Met Leu Pro Ala Pro Lys Asn Leu Val Val Ser Arg Val Thr Glu Asp
 1               5                  10                  15

Ser Ala Arg Leu Ser Trp Thr Ala Pro Asp Ala Ala Phe Asp Ser Phe
                20                  25                  30

His Ile Ile Tyr Glu Glu Val Leu Thr Glu Gly Glu Ala Ile Tyr Leu
                35                  40                  45

Arg Val Pro Gly Ser Glu Arg Ser Tyr Asp Leu Thr Gly Leu Lys Pro
 50                  55                  60

Gly Thr Glu Tyr Gly Val Thr Ile Lys Gly Val Lys Gly Gly Ala Tyr
 65                  70                  75                  80

Ser Ile Pro Leu Ile Ala Thr Phe Thr Thr
                85                  90

<210> SEQ ID NO 227
<211> LENGTH: 90
<212> TYPE: PRT
<213> ORGANISM: Artificial Sequence
<220> FEATURE:
<223> OTHER INFORMATION: synthetic sequence

<400> SEQUENCE: 227

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

Arg Ile Arg Tyr Leu Glu Trp Trp Asn Ile Gly Glu Ala Ile Val Leu
            35                  40                  45

Thr Val Pro Gly Ser Glu Arg Ser Tyr Asp Leu Thr Gly Leu Lys Pro
        50                  55                  60

Gly Thr Glu Tyr His Val Asp Ile Trp Gly Val Lys Gly Gly Tyr Ser
65                  70                  75                  80

Ser Tyr Pro Leu Ser Ala Ile Phe Thr Thr
                85                  90

<210> SEQ ID NO 228
<211> LENGTH: 90
<212> TYPE: PRT
<213> ORGANISM: Artificial Sequence
<220> FEATURE:
<223> OTHER INFORMATION: synthetic sequence

<400> SEQUENCE: 228

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

Glu Ile Tyr Tyr Val Glu Trp Ser Glu Ala Gly Glu Ala Ile Val Leu
            35                  40                  45

Thr Val Pro Gly Ser Glu Arg Ser Tyr Asp Leu Thr Gly Leu Lys Pro
        50                  55                  60

Gly Thr Glu Tyr Arg Val Glu Ile Arg Gly Val Lys Gly Gly Ser Trp
65                  70                  75                  80

Ser Ser Pro Leu Ser Ala Ile Phe Thr Thr
                85                  90

<210> SEQ ID NO 229
<211> LENGTH: 90
<212> TYPE: PRT
<213> ORGANISM: Artificial Sequence
<220> FEATURE:
<223> OTHER INFORMATION: synthetic sequence

<400> SEQUENCE: 229

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

Ser Ile His Tyr Asp Glu Asp Trp Arg Arg Gly Glu Ala Ile Val Leu
            35                  40                  45

Thr Val Pro Gly Ser Glu Arg Ser Tyr Asp Leu Thr Gly Leu Lys Pro
        50                  55                  60

Gly Thr Glu Tyr Leu Val Glu Ile Pro Gly Val Lys Gly Gly Lys Ala
65                  70                  75                  80

Ser Tyr Pro Leu Ser Ala Ile Phe Thr Thr
                85                  90

<210> SEQ ID NO 230
<211> LENGTH: 90
<212> TYPE: PRT
<213> ORGANISM: Artificial Sequence
<220> FEATURE:
<223> OTHER INFORMATION: synthetic sequence

<400> SEQUENCE: 230

```
Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Gln Ile Arg Tyr Pro Lys Arg Trp Ile Ser Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Glu Val Val Ile Arg Gly Val Lys Gly Gly Glu Tyr
65                  70                  75                  80

Ser Trp Pro Leu Ser Ala Ile Phe Thr Thr
                85                  90
```

<210> SEQ ID NO 231
<211> LENGTH: 90
<212> TYPE: PRT
<213> ORGANISM: Artificial Sequence
<220> FEATURE:
<223> OTHER INFORMATION: synthetic sequence

<400> SEQUENCE: 231

```
Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Glu Ile Pro Tyr Ile Glu Thr Val Ala Leu Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Tyr Val Glu Ile Tyr Gly Val Lys Gly Gly Ser Tyr
65                  70                  75                  80

Ser Tyr Pro Leu Ser Ala Ile Ser Thr Thr
                85                  90
```

<210> SEQ ID NO 232
<211> LENGTH: 90
<212> TYPE: PRT
<213> ORGANISM: Artificial Sequence
<220> FEATURE:
<223> OTHER INFORMATION: synthetic sequence

<400> SEQUENCE: 232

```
Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Thr Ile Ala Tyr Asp Glu Thr Leu Asn Leu Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Ile Val Gly Ile Phe Gly Val Lys Gly Gly Thr His
65                  70                  75                  80

Ser Trp Pro Leu Ser Ala Ile Phe Thr Thr
                85                  90
```

<210> SEQ ID NO 233
<211> LENGTH: 90
<212> TYPE: PRT
<213> ORGANISM: Artificial Sequence
<220> FEATURE:
<223> OTHER INFORMATION: synthetic sequence

<400> SEQUENCE: 233

```
Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Tyr Ile Val Tyr Ala Glu Pro Ile Pro Asn Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Ser Val Leu Ile His Gly Val Lys Gly Gly Arg Asn
65                  70                  75                  80

Ser Asp Pro Leu Ser Ala Ile Phe Thr Thr
                85                  90
```

<210> SEQ ID NO 234
<211> LENGTH: 90
<212> TYPE: PRT
<213> ORGANISM: Artificial Sequence
<220> FEATURE:
<223> OTHER INFORMATION: synthetic sequence

<400> SEQUENCE: 234

```
Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Tyr Ile Thr Tyr Trp Glu Thr Trp Asp Tyr Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Lys Val Pro Ile Thr Gly Val Lys Gly Gly Gly Pro
65                  70                  75                  80

Ser Val Pro Leu Ser Ala Ile Phe Thr Thr
                85                  90
```

<210> SEQ ID NO 235
<211> LENGTH: 90
<212> TYPE: PRT
<213> ORGANISM: Artificial Sequence
<220> FEATURE:
<223> OTHER INFORMATION: synthetic sequence

<400> SEQUENCE: 235

```
Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Ser Ile Asn Tyr Arg Glu Trp Trp Ser Asp Gly Glu Ala Ile Tyr Leu
        35                  40                  45

Pro Val Pro Gly Ser Glu Arg Ser Tyr Asp Leu Thr Gly Leu Lys Pro
    50                  55                  60

Gly Thr Glu Tyr Ala Val Tyr Ile Gln Gly Val Lys Gly Gly Ser Arg
```

65                  70                  75                  80

Ser Phe Pro Leu His Ala Trp Phe Thr Thr
                85                  90

<210> SEQ ID NO 236
<211> LENGTH: 90
<212> TYPE: PRT
<213> ORGANISM: Artificial Sequence
<220> FEATURE:
<223> OTHER INFORMATION: synthetic sequence

<400> SEQUENCE: 236

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Trp Ile Glu Tyr Tyr Glu Leu Gly Ser Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Arg Val Tyr Ile Tyr Gly Val Lys Gly Gly Tyr Pro
65                  70                  75                  80

Ser Ser Pro Leu Ser Ala Ile Phe Thr Thr
                85                  90

<210> SEQ ID NO 237
<211> LENGTH: 90
<212> TYPE: PRT
<213> ORGANISM: Artificial Sequence
<220> FEATURE:
<223> OTHER INFORMATION: synthetic sequence

<400> SEQUENCE: 237

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Thr Ile Leu Tyr Gly Glu Met Gly Thr Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Asp Val Phe Ile Glu Gly Val Lys Gly Gly Glu Leu
65                  70                  75                  80

Ser Trp Pro Leu Ser Ala Ile Phe Thr Thr
                85                  90

<210> SEQ ID NO 238
<211> LENGTH: 88
<212> TYPE: PRT
<213> ORGANISM: Artificial Sequence
<220> FEATURE:
<223> OTHER INFORMATION: synthetic sequence

<400> SEQUENCE: 238

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Lys Ile Phe Tyr Gln Glu Phe Gly Gly Glu Ala Ile Val Leu Thr Val
        35                  40                  45

Pro Gly Ser Glu Arg Ser Tyr Asp Leu Thr Gly Leu Lys Pro Gly Thr
            50                  55                  60

Glu Tyr Trp Val Asp Ile Tyr Gly Val Lys Gly Tyr Thr Ser Ser
 65                  70                  75                  80

Pro Leu Ser Ala Ile Phe Thr Thr
                85

<210> SEQ ID NO 239
<211> LENGTH: 90
<212> TYPE: PRT
<213> ORGANISM: Artificial Sequence
<220> FEATURE:
<223> OTHER INFORMATION: synthetic sequence

<400> SEQUENCE: 239

Met Leu Pro Ala Pro Lys Asn Leu Val Val Ser Arg Val Thr Glu Asp
  1               5                  10                  15

Ser Ala Arg Leu Ser Trp Thr Ala Pro Asp Ala Ala Phe Asp Ser Phe
                 20                  25                  30

Ala Ile Thr Tyr Tyr Glu Gly Arg Trp Arg Gly Glu Ala Ile Val Leu
             35                  40                  45

Thr Val Pro Gly Ser Glu Arg Ser Tyr Asp Leu Thr Gly Leu Lys Pro
         50                  55                  60

Gly Thr Glu Tyr Gly Val Pro Ile Arg Gly Val Lys Gly Gly Thr Gly
 65                  70                  75                  80

Ser Leu Pro Leu Ser Ala Ile Phe Thr Thr
                 85                  90

<210> SEQ ID NO 240
<211> LENGTH: 90
<212> TYPE: PRT
<213> ORGANISM: Artificial Sequence
<220> FEATURE:
<223> OTHER INFORMATION: synthetic sequence

<400> SEQUENCE: 240

Met Leu Pro Ala Pro Lys Asn Leu Val Val Ser Arg Val Thr Glu Asp
  1               5                  10                  15

Ser Ala Arg Leu Ser Trp Thr Ala Pro Asp Ala Ala Phe Asp Ser Phe
                 20                  25                  30

Arg Ile Lys Tyr Leu Glu Trp Trp Leu Gly Gly Glu Ala Ile Val Leu
             35                  40                  45

Thr Val Pro Gly Ser Glu Arg Ser Tyr Asp Leu Thr Gly Leu Lys Pro
         50                  55                  60

Gly Thr Glu Tyr Trp Val Asp Ile Gln Gly Val Lys Gly Gly Val Leu
 65                  70                  75                  80

Ser Trp Pro Leu Ser Ala Ile Phe Thr Thr
                 85                  90

<210> SEQ ID NO 241
<211> LENGTH: 90
<212> TYPE: PRT
<213> ORGANISM: Artificial Sequence
<220> FEATURE:
<223> OTHER INFORMATION: synthetic sequence

<400> SEQUENCE: 241

Met Leu Pro Ala Pro Lys Asn Leu Val Val Ser Arg Val Thr Glu Asp
  1               5                  10                  15

Ser Ala Arg Leu Ser Trp Thr Ala Pro Asp Ala Ala Phe Asp Ser Phe
            20                  25                  30

Asn Ile Tyr Tyr Tyr Glu Trp Phe Val Ser Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Phe Val Asp Ile Asp Gly Val Lys Gly Gly Tyr Arg
65                  70                  75                  80

Ser Arg Pro Leu Ser Ala Ile Phe Thr Thr
                85                  90

<210> SEQ ID NO 242
<211> LENGTH: 90
<212> TYPE: PRT
<213> ORGANISM: Artificial Sequence
<220> FEATURE:
<223> OTHER INFORMATION: synthetic sequence

<400> SEQUENCE: 242

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Pro Ile Lys Tyr Leu Glu Trp Trp Ser Trp Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Arg Val Pro Ile Ser Gly Val Lys Gly Gly Gly Met
65                  70                  75                  80

Ser Gly Pro Leu Ser Ala Ile Phe Thr Thr
                85                  90

<210> SEQ ID NO 243
<211> LENGTH: 90
<212> TYPE: PRT
<213> ORGANISM: Artificial Sequence
<220> FEATURE:
<223> OTHER INFORMATION: synthetic sequence

<400> SEQUENCE: 243

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Ala Ile Pro Tyr Tyr Glu Trp Val Asn His Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Pro Val Gly Ile Asp Gly Val Lys Gly Gly Gly Pro
65                  70                  75                  80

Ser Trp Pro Leu Ser Ala Ile Phe Thr Thr
                85                  90

<210> SEQ ID NO 244
<211> LENGTH: 89
<212> TYPE: PRT
<213> ORGANISM: Artificial Sequence
<220> FEATURE:
<223> OTHER INFORMATION: synthetic sequence -continued

<400> SEQUENCE: 244

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

His Ile Asp Tyr Ser Glu Phe His Leu Arg Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Leu Gly Ile Phe Gly Val Lys Gly Glu Gln Ser
65                  70                  75                  80

Gly Pro Leu Ser Ala Ile Phe Thr Thr
                85

<210> SEQ ID NO 245
<211> LENGTH: 90
<212> TYPE: PRT
<213> ORGANISM: Artificial Sequence
<220> FEATURE:
<223> OTHER INFORMATION: synthetic sequence

<400> SEQUENCE: 245

Met Leu Pro Ala Pro Lys Asn Leu Val Val Ser Arg Ile Thr Glu Asp
1               5                   10                  15

Ser Ala Arg Leu Ser Trp Thr Ala Pro Asp Ala Ala Phe Asp Ser Phe
            20                  25                  30

Gly Ile Ala Tyr Asn Glu Gly Asp His Tyr Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Ser Val Trp Ile Glu Gly Val Lys Gly Gly Asn Leu
65                  70                  75                  80

Ser Tyr Pro Leu Ser Ala Ile Phe Thr Thr
                85                  90

<210> SEQ ID NO 246
<211> LENGTH: 90
<212> TYPE: PRT
<213> ORGANISM: Artificial Sequence
<220> FEATURE:
<223> OTHER INFORMATION: synthetic sequence

<400> SEQUENCE: 246

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Thr Ile Ala Tyr Asn Glu Gln Asn His Tyr Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Gly Val Trp Ile Glu Gly Val Lys Gly Gly Thr Leu
65                  70                  75                  80

Ser Trp Pro Leu Ser Ala Ile Phe Thr Thr
                85                  90

<210> SEQ ID NO 247
<211> LENGTH: 87

```
<212> TYPE: PRT
<213> ORGANISM: Artificial Sequence
<220> FEATURE:
<223> OTHER INFORMATION: synthetic sequence

<400> SEQUENCE: 247

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Tyr Ile Glu Trp Thr Tyr Lys Gly Glu Ala Ile Val Leu Thr Val Pro
        35                  40                  45

Gly Ser Glu Arg Ser Tyr Asp Leu Thr Gly Leu Lys Pro Gly Thr Glu
50                  55                  60

Tyr Phe Val Gly Ile Pro Gly Val Lys Gly Gly Lys Ser Ser Tyr Pro
65                  70                  75                  80

Leu Ser Ala Ile Phe Thr Thr
                85

<210> SEQ ID NO 248
<211> LENGTH: 92
<212> TYPE: PRT
<213> ORGANISM: Artificial Sequence
<220> FEATURE:
<223> OTHER INFORMATION: synthetic sequence

<400> SEQUENCE: 248

Met Gly Ser Leu Pro Ala Pro Lys Asn Leu Val Val Ser Arg Val Thr
1               5                   10                  15

Glu Asp Ser Ala Arg Leu Ser Trp Thr Ala Pro Asp Ala Ala Phe Asp
            20                  25                  30

Ser Phe Ala Ile Pro Tyr Ala Glu Pro Ser Pro Thr Gly Glu Ala Ile
        35                  40                  45

Val Leu Thr Val Pro Gly Ser Glu Arg Ser Tyr Asp Leu Thr Gly Leu
50                  55                  60

Lys Pro Gly Thr Glu Tyr Pro Val Trp Ile Gln Gly Val Lys Gly Gly
65                  70                  75                  80

Ser Pro Ser Ala Pro Leu Ser Ala Glu Phe Thr Thr
                85                  90

<210> SEQ ID NO 249
<211> LENGTH: 90
<212> TYPE: PRT
<213> ORGANISM: Artificial Sequence
<220> FEATURE:
<223> OTHER INFORMATION: synthetic sequence

<400> SEQUENCE: 249

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Ser Ile Asp Tyr Phe Glu Ser Val Gly Phe Gly Glu Ala Ile Val Leu
        35                  40                  45

Thr Val Pro Gly Ser Glu Arg Ser Tyr Asp Leu Thr Gly Leu Lys Pro
50                  55                  60

Gly Thr Glu Tyr Asp Val Gln Ile Thr Gly Val Lys Gly Gly Pro His
65                  70                  75                  80

Ser Leu Pro Leu Ser Ala Ile Phe Thr Thr
                85                  90
```

```
                    85                  90

<210> SEQ ID NO 250
<211> LENGTH: 90
<212> TYPE: PRT
<213> ORGANISM: Artificial Sequence
<220> FEATURE:
<223> OTHER INFORMATION: synthetic sequence

<400> SEQUENCE: 250

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Phe Ile Gly Tyr Leu Glu Pro Tyr Pro Pro Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Ala Val Glu Ile Ala Gly Val Lys Gly Gly Leu Leu
65                  70                  75                  80

Ser Ser Pro Leu Ser Ala Ile Ser Thr Thr
                85                  90

<210> SEQ ID NO 251
<211> LENGTH: 90
<212> TYPE: PRT
<213> ORGANISM: Artificial Sequence
<220> FEATURE:
<223> OTHER INFORMATION: synthetic sequence

<400> SEQUENCE: 251

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Phe Ile Gly Tyr Leu Glu Pro Gln Pro Pro Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Asn Val Thr Ile Gln Gly Val Lys Gly Gly Phe Pro
65                  70                  75                  80

Ser Met Pro Leu Ser Ala Ile Val Thr Thr
                85                  90

<210> SEQ ID NO 252
<211> LENGTH: 90
<212> TYPE: PRT
<213> ORGANISM: Artificial Sequence
<220> FEATURE:
<223> OTHER INFORMATION: synthetic sequence

<400> SEQUENCE: 252

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Asp Ile Gly Tyr Thr Glu Tyr Gly Gly Tyr Gly Glu Ala Ile Val Leu
        35                  40                  45

Thr Val Pro Gly Ser Glu Arg Ser Tyr Asp Leu Thr Gly Leu Lys Pro
    50                  55                  60
```

Gly Thr Glu Tyr Trp Val Leu Ile Gln Gly Val Lys Gly Gly Ser
65                  70                  75                  80

Ser Val Pro Leu Ser Ala Ile Phe Thr Thr
                85                  90

<210> SEQ ID NO 253
<211> LENGTH: 90
<212> TYPE: PRT
<213> ORGANISM: Artificial Sequence
<220> FEATURE:
<223> OTHER INFORMATION: synthetic sequence

<400> SEQUENCE: 253

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Thr Ile Glu Tyr Trp Glu Thr Ile Gly Gly Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Tyr Val Gly Ile Tyr Gly Val Lys Gly Gly Trp Trp
65                  70                  75                  80

Ser Arg Pro Leu Ser Ala Ile Phe Thr Thr
                85                  90

<210> SEQ ID NO 254
<211> LENGTH: 90
<212> TYPE: PRT
<213> ORGANISM: Artificial Sequence
<220> FEATURE:
<223> OTHER INFORMATION: synthetic sequence

<400> SEQUENCE: 254

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Phe Ile Pro Tyr Ala Glu Pro Ser Pro Thr Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Ser Val Leu Ile His Gly Val Lys Gly Gly His Leu
65                  70                  75                  80

Ser Asp Pro Leu Ser Ala Ile Ser Thr Thr
                85                  90

<210> SEQ ID NO 255
<211> LENGTH: 90
<212> TYPE: PRT
<213> ORGANISM: Artificial Sequence
<220> FEATURE:
<223> OTHER INFORMATION: synthetic sequence

<400> SEQUENCE: 255

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Asp Ile Glu Tyr Tyr Glu Leu Ile Gly Arg Gly Glu Ala Ile Val Leu
            35                  40                  45

Thr Val Pro Gly Ser Glu Arg Ser Tyr Asp Leu Thr Gly Leu Lys Pro
 50                  55                  60

Gly Thr Glu Tyr Trp Val Gly Ile Tyr Gly Val Lys Gly Gly Trp Leu
 65                  70                  75                  80

Ser Arg Pro Leu Ser Ala Ile Phe Thr Thr
                85                  90

<210> SEQ ID NO 256
<211> LENGTH: 90
<212> TYPE: PRT
<213> ORGANISM: Artificial Sequence
<220> FEATURE:
<223> OTHER INFORMATION: synthetic sequence

<400> SEQUENCE: 256

Met Leu Pro Ala Pro Lys Asn Leu Val Val Ser Arg Val Thr Glu Asp
 1               5                  10                  15

Ser Ala Arg Leu Ser Trp Thr Ala Pro Asp Ala Ala Phe Asp Ser Phe
                20                  25                  30

His Ile Val Tyr His Glu Pro Arg Pro Ser Gly Glu Ala Ile Val Leu
            35                  40                  45

Thr Val Pro Gly Ser Glu Arg Ser Tyr Asp Leu Thr Gly Leu Lys Pro
 50                  55                  60

Gly Thr Glu Tyr Glu Val Gly Ile Val Gly Val Lys Gly Gly Asp Leu
 65                  70                  75                  80

Ser Val Pro Leu Ser Ala Ile Phe Thr Thr
                85                  90

<210> SEQ ID NO 257
<211> LENGTH: 90
<212> TYPE: PRT
<213> ORGANISM: Artificial Sequence
<220> FEATURE:
<223> OTHER INFORMATION: synthetic sequence

<400> SEQUENCE: 257

Met Leu Pro Ala Pro Lys Asn Leu Val Val Ser Arg Val Thr Glu Asp
 1               5                  10                  15

Ser Ala Arg Leu Ser Trp Thr Ala Pro Asp Ala Ala Phe Asp Ser Phe
                20                  25                  30

His Ile Val Tyr His Glu Pro Arg Pro Ser Gly Glu Ala Ile Val Leu
            35                  40                  45

Thr Val Pro Gly Ser Glu Arg Ser Tyr Asp Leu Thr Gly Leu Lys Pro
 50                  55                  60

Gly Thr Glu Tyr Glu Val Gly Ile Val Ser Val Lys Gly Gly Asp Leu
 65                  70                  75                  80

Ser Val Pro Leu Ser Ala Ile Phe Thr Thr
                85                  90

<210> SEQ ID NO 258
<211> LENGTH: 90
<212> TYPE: PRT
<213> ORGANISM: Artificial Sequence
<220> FEATURE:
<223> OTHER INFORMATION: synthetic sequence

<400> SEQUENCE: 258

Met Leu Pro Ala Pro Lys Asn Leu Val Val Ser Arg Val Thr Glu Asp

```
1               5                   10                  15
Ser Ala Arg Leu Ser Trp Thr Ala Pro Asp Ala Ala Phe Asp Ser Phe
                20                  25                  30

Phe Ile Pro Tyr Ala Glu Pro Ser Pro Thr Gly Glu Ala Ile Val Leu
                35                  40                  45

Thr Val Pro Gly Ser Glu Arg Ser Tyr Asp Leu Thr Gly Leu Lys Pro
                50                  55                  60

Gly Thr Glu Tyr Asp Val Trp Ile Glu Gly Val Lys Gly Gly Val Leu
65                  70                  75                  80

Ser Trp Pro Leu Ser Ala Ile Phe Thr Thr
                85                  90
```

<210> SEQ ID NO 259
<211> LENGTH: 90
<212> TYPE: PRT
<213> ORGANISM: Artificial Sequence
<220> FEATURE:
<223> OTHER INFORMATION: synthetic sequence

<400> SEQUENCE: 259

```
Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

Thr Ile Glu Tyr Phe Glu Phe Val Asp Ala Gly Glu Ala Ile Val Leu
                35                  40                  45

Thr Val Pro Gly Ser Glu Arg Ser Tyr Asp Leu Thr Gly Leu Lys Pro
                50                  55                  60

Gly Thr Glu Tyr Trp Val Glu Ile Trp Gly Val Lys Gly Gly Ser Trp
65                  70                  75                  80

Ser Lys Pro Leu Ser Ala Ile Phe Thr Thr
                85                  90
```

<210> SEQ ID NO 260
<211> LENGTH: 89
<212> TYPE: PRT
<213> ORGANISM: Artificial Sequence
<220> FEATURE:
<223> OTHER INFORMATION: synthetic sequence

<400> SEQUENCE: 260

```
Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

Asn Ile Ser Tyr Tyr Glu Tyr Phe Val His Gly Glu Ala Ile Val Leu
                35                  40                  45

Thr Val Pro Gly Ser Glu Arg Ser Tyr Asp Leu Thr Gly Leu Lys Pro
                50                  55                  60

Gly Thr Glu Tyr Tyr Val Ile Asp Gly Val Lys Gly Gly Asp Pro Ser
65                  70                  75                  80

Glu Pro Leu Ser Ala Ile Phe Thr Thr
                85
```

<210> SEQ ID NO 261
<211> LENGTH: 90
<212> TYPE: PRT
<213> ORGANISM: Artificial Sequence
<220> FEATURE:

<223> OTHER INFORMATION: synthetic sequence

<400> SEQUENCE: 261

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Thr Ile Val Tyr Gly Glu Trp Gly Val Pro Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Asp Val Trp Ile Glu Gly Val Lys Gly Gly Asp Leu
65                  70                  75                  80

Ser Trp Pro Leu Ser Ala Ile Val Thr Thr
                85                  90

<210> SEQ ID NO 262
<211> LENGTH: 90
<212> TYPE: PRT
<213> ORGANISM: Artificial Sequence
<220> FEATURE:
<223> OTHER INFORMATION: synthetic sequence

<400> SEQUENCE: 262

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Ala Ile Glu Tyr Phe Glu Tyr Thr Gly Glu Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Tyr Val Gly Ile Tyr Gly Val Lys Gly Gly Tyr Leu
65                  70                  75                  80

Ser Arg Pro Leu Ser Ala Ile Phe Thr Thr
                85                  90

<210> SEQ ID NO 263
<211> LENGTH: 90
<212> TYPE: PRT
<213> ORGANISM: Artificial Sequence
<220> FEATURE:
<223> OTHER INFORMATION: synthetic sequence

<400> SEQUENCE: 263

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Phe Ile Gly Tyr Leu Glu Pro Gln Pro Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Asn Val Thr Ile Gln Gly Val Lys Gly Gly Phe Pro
65                  70                  75                  80

Ser Met Pro Leu Ser Ala Ile Ser Thr Thr
                85                  90

```
<210> SEQ ID NO 264
<211> LENGTH: 90
<212> TYPE: PRT
<213> ORGANISM: Artificial Sequence
<220> FEATURE:
<223> OTHER INFORMATION: synthetic sequence

<400> SEQUENCE: 264

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Arg Ile Lys Tyr Gln Glu Trp Trp Val Glu Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Val Val Gln Ile Ala Gly Val Lys Gly Gly Leu Ser
65                  70                  75                  80

Ser Tyr Pro Leu Ser Ala Ile Phe Thr Thr
                85                  90

<210> SEQ ID NO 265
<211> LENGTH: 90
<212> TYPE: PRT
<213> ORGANISM: Artificial Sequence
<220> FEATURE:
<223> OTHER INFORMATION: synthetic sequence

<400> SEQUENCE: 265

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Trp Ile Tyr Tyr Ile Glu Thr Ser His Gln Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Phe Val Leu Ile Lys Gly Val Lys Gly Gly Tyr Asp
65                  70                  75                  80

Ser Val Pro Leu Ser Ala Ile Phe Thr Thr
                85                  90

<210> SEQ ID NO 266
<211> LENGTH: 90
<212> TYPE: PRT
<213> ORGANISM: Artificial Sequence
<220> FEATURE:
<223> OTHER INFORMATION: synthetic sequence

<400> SEQUENCE: 266

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Met Ile Arg Tyr Gln Glu Gly Thr Arg Trp Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Ile Val Met Ile Ala Gly Val Lys Gly Gly Gln Ile
65                  70                  75                  80
```

```
Ser Leu Pro Leu Ser Ala Ile Phe Thr Thr
                85                  90

<210> SEQ ID NO 267
<211> LENGTH: 90
<212> TYPE: PRT
<213> ORGANISM: Artificial Sequence
<220> FEATURE:
<223> OTHER INFORMATION: synthetic sequence

<400> SEQUENCE: 267

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

Pro Ile Val Tyr Ser Glu Ile His Val Ile Gly Glu Ala Ile Val Leu
            35                  40                  45

Thr Val Pro Gly Ser Glu Arg Ser Tyr Asp Leu Thr Gly Leu Lys Pro
        50                  55                  60

Gly Thr Glu Tyr Asp Val Trp Ile Glu Gly Val Lys Gly Gly His Leu
65                  70                  75                  80

Ser Glu Pro Leu Ser Ala Ile Phe Thr Thr
                85                  90

<210> SEQ ID NO 268
<211> LENGTH: 90
<212> TYPE: PRT
<213> ORGANISM: Artificial Sequence
<220> FEATURE:
<223> OTHER INFORMATION: synthetic sequence

<400> SEQUENCE: 268

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

Thr Ile Val Tyr Gly Glu Ala Gly Ala Phe Gly Glu Ala Ile Val Leu
            35                  40                  45

Thr Val Pro Gly Ser Glu Arg Ser Tyr Asp Leu Thr Gly Leu Lys Pro
        50                  55                  60

Gly Thr Glu Tyr Asp Val Leu Ile Glu Gly Val Lys Gly Gly Asn Leu
65                  70                  75                  80

Ser Trp Pro Leu Ser Ala Ile Phe Thr Thr
                85                  90

<210> SEQ ID NO 269
<211> LENGTH: 90
<212> TYPE: PRT
<213> ORGANISM: Artificial Sequence
<220> FEATURE:
<223> OTHER INFORMATION: synthetic sequence

<400> SEQUENCE: 269

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

His Ile Asn Tyr Ala Glu Val Tyr Thr Lys Gly Glu Ala Ile Leu Leu
            35                  40                  45
```

```
Thr Val Pro Gly Ser Glu Arg Ser Tyr Asp Leu Thr Gly Leu Lys Pro
    50                  55                  60

Gly Thr Glu Tyr Glu Val Tyr Ile Pro Gly Val Lys Gly Gly Pro Phe
65                  70                  75                  80

Ser Arg Pro Leu Asn Ala Gln Phe Thr Thr
                85                  90

<210> SEQ ID NO 270
<211> LENGTH: 90
<212> TYPE: PRT
<213> ORGANISM: Artificial Sequence
<220> FEATURE:
<223> OTHER INFORMATION: synthetic sequence

<400> SEQUENCE: 270

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

Leu Ile Arg Tyr Gln Glu Trp Gln Arg Trp Gly Glu Ala Ile Val Leu
            35                  40                  45

Thr Val Pro Gly Ser Glu Arg Ser Tyr Asp Leu Thr Gly Leu Lys Pro
    50                  55                  60

Gly Thr Glu Tyr Thr Val His Ile Ala Gly Val Lys Gly Gly Met Leu
65                  70                  75                  80

Ser Leu Pro Leu Ser Ala Ile Phe Thr Thr
                85                  90

<210> SEQ ID NO 271
<211> LENGTH: 90
<212> TYPE: PRT
<213> ORGANISM: Artificial Sequence
<220> FEATURE:
<223> OTHER INFORMATION: synthetic sequence

<400> SEQUENCE: 271

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

Tyr Ile Pro Tyr Ala Glu Thr Arg Asp Asp Gly Glu Ala Ile Val Leu
            35                  40                  45

Thr Val Pro Gly Ser Glu Arg Ser Tyr Asp Leu Thr Gly Leu Lys Pro
    50                  55                  60

Gly Thr Glu Tyr Ser Val Leu Ile His Gly Val Lys Gly Gly Asp Leu
65                  70                  75                  80

Ser Ser Pro Leu Ser Ala Ile Phe Thr Thr
                85                  90

<210> SEQ ID NO 272
<211> LENGTH: 90
<212> TYPE: PRT
<213> ORGANISM: Artificial Sequence
<220> FEATURE:
<223> OTHER INFORMATION: synthetic sequence

<400> SEQUENCE: 272

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
```

```
                    20                  25                  30

Gly Ile Pro Tyr Ala Glu Ser Thr Pro Thr Gly Glu Ala Ile Val Leu
                35                  40                  45

Thr Val Pro Gly Ser Glu Arg Ser Tyr Asp Leu Thr Gly Leu Lys Pro
         50                  55                  60

Gly Thr Glu Tyr Ser Val Leu Ile His Gly Val Lys Gly Gly His Leu
 65                  70                  75                  80

Ser Asp Pro Leu Ser Ala Ile Phe Thr Thr
                85                  90

<210> SEQ ID NO 273
<211> LENGTH: 85
<212> TYPE: PRT
<213> ORGANISM: Artificial Sequence
<220> FEATURE:
<223> OTHER INFORMATION: synthetic sequence

<400> SEQUENCE: 273

Met Leu Pro Ala Pro Lys Asn Leu Val Val Ser Arg Val Thr Glu Asp
 1               5                  10                  15

Ser Ala Arg Leu Ser Trp Thr Ala Pro Asp Ala Ala Phe Asp Ser Phe
                20                  25                  30

Thr Ile Phe Lys Asp Gly Glu Ala Ile Val Leu Thr Val Pro Gly Ser
                35                  40                  45

Glu Arg Ser Tyr Asp Leu Thr Gly Leu Lys Pro Gly Thr Glu Tyr Tyr
         50                  55                  60

Val Tyr Ile Tyr Gly Val Lys Gly Gly Tyr Pro Ser Lys Pro Leu Ser
 65                  70                  75                  80

Ala Ile Phe Thr Thr
                85

<210> SEQ ID NO 274
<211> LENGTH: 90
<212> TYPE: PRT
<213> ORGANISM: Artificial Sequence
<220> FEATURE:
<223> OTHER INFORMATION: synthetic sequence

<400> SEQUENCE: 274

Met Leu Pro Ala Pro Lys Asn Leu Val Val Ser Arg Val Thr Glu Asp
 1               5                  10                  15

Ser Val Arg Leu Ser Trp Thr Ala Pro Asp Ala Ala Phe Asp Ser Phe
                20                  25                  30

Ala Ile Ser Tyr Glu Glu Trp Trp Val His Gly Glu Ala Ile Val Leu
                35                  40                  45

Thr Val Pro Gly Ser Glu Arg Ser Tyr Asp Leu Thr Gly Leu Lys Pro
         50                  55                  60

Gly Thr Glu Tyr Ser Val Val Ile Pro Gly Val Lys Gly Gly Leu Tyr
 65                  70                  75                  80

Ser Trp Thr Leu Ser Ala Ile Ser Thr Thr
                85                  90

<210> SEQ ID NO 275
<211> LENGTH: 90
<212> TYPE: PRT
<213> ORGANISM: Artificial Sequence
<220> FEATURE:
<223> OTHER INFORMATION: synthetic sequence

<400> SEQUENCE: 275
```

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Leu Ile Ala Tyr Ala Glu Val Thr Leu His Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Ser Val Leu Ile His Gly Val Lys Gly Gly Arg Asn
65                  70                  75                  80

Ser Asp Pro Leu Ser Ala Ile Phe Thr Thr
                85                  90

<210> SEQ ID NO 276
<211> LENGTH: 90
<212> TYPE: PRT
<213> ORGANISM: Artificial Sequence
<220> FEATURE:
<223> OTHER INFORMATION: synthetic sequence

<400> SEQUENCE: 276

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Arg Ile Asp Tyr Leu Glu Leu Thr Ser Leu Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Pro Val Pro Ile Leu Gly Val Lys Gly Gly Leu Ser
65                  70                  75                  80

Ser Trp Pro Leu Ser Ala Ile Phe Thr Thr
                85                  90

<210> SEQ ID NO 277
<211> LENGTH: 90
<212> TYPE: PRT
<213> ORGANISM: Artificial Sequence
<220> FEATURE:
<223> OTHER INFORMATION: synthetic sequence

<400> SEQUENCE: 277

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Trp Ile Asn Tyr Tyr Glu Gly Ile Gly Glu Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Tyr Val Asp Ile Ser Gly Val Lys Gly Gly Ser Tyr
65                  70                  75                  80

Ser Leu Pro Leu Ser Ala Ile Phe Thr Thr
                85                  90

<210> SEQ ID NO 278
<211> LENGTH: 90
<212> TYPE: PRT

```
<213> ORGANISM: Artificial Sequence
<220> FEATURE:
<223> OTHER INFORMATION: synthetic sequence

<400> SEQUENCE: 278

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Pro Ile Ala Tyr Ala Glu Pro Arg Pro Asp Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Ser Val Leu Ile His Gly Val Lys Gly Gly His Leu
65                  70                  75                  80

Ser Asp Pro Leu Ser Ala Ile Phe Thr Thr
                85                  90

<210> SEQ ID NO 279
<211> LENGTH: 90
<212> TYPE: PRT
<213> ORGANISM: Artificial Sequence
<220> FEATURE:
<223> OTHER INFORMATION: synthetic sequence

<400> SEQUENCE: 279

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Ser Ile Glu Tyr Tyr Glu Ser Val Gly Leu Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Asp Val Ser Ile Tyr Gly Val Lys Gly Gly Tyr Leu
65                  70                  75                  80

Ser Arg Pro Leu Ser Ala Ile Phe Thr Thr
                85                  90

<210> SEQ ID NO 280
<211> LENGTH: 90
<212> TYPE: PRT
<213> ORGANISM: Artificial Sequence
<220> FEATURE:
<223> OTHER INFORMATION: synthetic sequence
<220> FEATURE:
<221> NAME/KEY: misc_feature
<222> LOCATION: (12)..(12)
<223> OTHER INFORMATION: Xaa can be any naturally occurring amino acid

<400> SEQUENCE: 280

Met Leu Pro Ala Pro Lys Asn Leu Val Val Arg Xaa Val Thr Glu Asp
1               5                   10                  15

Ser Ala Arg Leu Ser Trp Thr Ala Pro Asp Ala Ala Phe Asp Ser Phe
            20                  25                  30

Glu Ile Glu Tyr Asp Glu Pro Tyr Arg Gly Gly Glu Ala Ile Val Leu
        35                  40                  45

Thr Val Pro Gly Ser Glu Arg Ser Tyr Asp Leu Thr Ser Leu Lys Pro
    50                  55                  60

Gly Thr Glu Tyr Pro Val Ser Ile Gly Gly Val Lys Gly Gly Ile Thr
```

```
                65                  70                  75                  80
Ser Asp Pro Leu Ser Ala Ile Phe Thr Thr
                    85                  90

<210> SEQ ID NO 281
<211> LENGTH: 90
<212> TYPE: PRT
<213> ORGANISM: Artificial Sequence
<220> FEATURE:
<223> OTHER INFORMATION: synthetic sequence

<400> SEQUENCE: 281

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

Tyr Ile Asp Tyr Asp Glu Ile His Asp Trp Gly Glu Ala Ile Val Leu
            35                  40                  45

Thr Val Pro Gly Ser Glu Arg Ser Tyr Asp Leu Thr Gly Leu Lys Pro
        50                  55                  60

Gly Thr Glu Tyr Ala Val Gln Ile Gly Gly Val Lys Gly Gly Ser Phe
65                  70                  75                  80

Ser Trp Thr Leu Ser Ala Ile Phe Thr Thr
                85                  90

<210> SEQ ID NO 282
<211> LENGTH: 90
<212> TYPE: PRT
<213> ORGANISM: Artificial Sequence
<220> FEATURE:
<223> OTHER INFORMATION: synthetic sequence

<400> SEQUENCE: 282

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

Ala Ile Val Tyr His Glu Pro Arg Pro Asp Gly Glu Ala Ile Val Leu
            35                  40                  45

Thr Val Pro Gly Ser Glu Arg Ser Tyr Asp Leu Thr Gly Leu Lys Pro
        50                  55                  60

Gly Thr Glu Tyr Glu Val Val Ile Leu Gly Val Lys Gly Gly Val His
65                  70                  75                  80

Ser Tyr Pro Leu Ser Ala Ile Phe Thr Thr
                85                  90

<210> SEQ ID NO 283
<211> LENGTH: 90
<212> TYPE: PRT
<213> ORGANISM: Artificial Sequence
<220> FEATURE:
<223> OTHER INFORMATION: synthetic sequence

<400> SEQUENCE: 283

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

Pro Ile Ala Tyr Ala Glu Pro Arg Pro Asp Gly Glu Ala Ile Val Leu
            35                  40                  45
```

```
Thr Val Pro Gly Ser Glu Arg Ser Tyr Asp Leu Thr Gly Leu Lys Pro
         50                  55                  60

Gly Thr Glu Tyr Ser Val Leu Ile His Gly Val Lys Gly Gly Leu Leu
 65                  70                  75                  80

Ser Ser Pro Leu Ser Ala Ile Phe Thr Thr
                 85                  90

<210> SEQ ID NO 284
<211> LENGTH: 90
<212> TYPE: PRT
<213> ORGANISM: Artificial Sequence
<220> FEATURE:
<223> OTHER INFORMATION: synthetic sequence

<400> SEQUENCE: 284

Met Leu Pro Ala Pro Lys Asn Leu Val Val Ser Arg Val Thr Glu Asp
 1               5                  10                  15

Ser Ala Arg Leu Ser Trp Thr Ala Pro Asp Ala Ala Phe Asp Ser Phe
                 20                  25                  30

Phe Ile Gly Tyr Leu Glu Pro Gln Pro Pro Gly Glu Ala Ile Val Leu
             35                  40                  45

Thr Val Pro Gly Ser Glu Arg Ser Tyr Asp Leu Thr Gly Leu Lys Pro
         50                  55                  60

Gly Thr Glu Tyr Asn Val Thr Ile Gln Gly Val Lys Gly Gly Phe Pro
 65                  70                  75                  80

Ser Met Pro Leu Ser Ala Ile Phe Thr Thr
                 85                  90

<210> SEQ ID NO 285
<211> LENGTH: 90
<212> TYPE: PRT
<213> ORGANISM: Artificial Sequence
<220> FEATURE:
<223> OTHER INFORMATION: synthetic sequence

<400> SEQUENCE: 285

Met Leu Pro Ala Pro Lys Asn Leu Val Val Ser Arg Val Thr Glu Asp
 1               5                  10                  15

Ser Ala Arg Leu Ser Trp Thr Ala Pro Asp Ala Ala Phe Asp Ser Phe
                 20                  25                  30

Leu Ile Pro Tyr Ala Glu Thr Ser Pro Ser Gly Glu Ala Ile Val Leu
             35                  40                  45

Thr Val Pro Gly Ser Glu Arg Ser Tyr Asp Leu Thr Gly Leu Lys Pro
         50                  55                  60

Gly Thr Glu Tyr Ser Val Leu Ile His Gly Val Lys Gly Gly Asp Tyr
 65                  70                  75                  80

Ser Ser Pro Leu Ser Ala Ile Phe Thr Thr
                 85                  90

<210> SEQ ID NO 286
<211> LENGTH: 90
<212> TYPE: PRT
<213> ORGANISM: Artificial Sequence
<220> FEATURE:
<223> OTHER INFORMATION: synthetic sequence

<400> SEQUENCE: 286

Met Leu Pro Ala Pro Lys Asn Leu Val Val Ser Arg Val Thr Glu Asp
 1               5                  10                  15
```

```
Ser Ala Arg Leu Ser Trp Thr Ala Pro Asp Ala Ala Phe Asp Ser Phe
            20                  25                  30

Asn Ile Tyr Tyr Pro Glu Phe Pro Val Arg Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Val Val Ser Ile Trp Gly Val Lys Gly Gly Thr Gln
65                  70                  75                  80

Ser Trp Pro Leu Ser Ala Ile Phe Thr Thr
                85                  90

<210> SEQ ID NO 287
<211> LENGTH: 90
<212> TYPE: PRT
<213> ORGANISM: Artificial Sequence
<220> FEATURE:
<223> OTHER INFORMATION: synthetic sequence

<400> SEQUENCE: 287

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Thr Ile Glu Tyr His Glu Ser Gly Pro Val Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Met Val Trp Ile Phe Gly Val Lys Gly Gly Phe Val
65                  70                  75                  80

Ser Arg Pro Leu Ser Ala Ile Phe Thr Thr
                85                  90

<210> SEQ ID NO 288
<211> LENGTH: 90
<212> TYPE: PRT
<213> ORGANISM: Artificial Sequence
<220> FEATURE:
<223> OTHER INFORMATION: synthetic sequence

<400> SEQUENCE: 288

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Leu Ile Pro Tyr Ala Glu Thr Ser Pro Ser Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Ser Val Leu Ile His Gly Val Lys Gly Gly Asp Tyr
65                  70                  75                  80

Ser Ser Pro Leu Ser Ala Ile Ser Thr Thr
                85                  90

<210> SEQ ID NO 289
<211> LENGTH: 90
<212> TYPE: PRT
<213> ORGANISM: Artificial Sequence
<220> FEATURE:
<223> OTHER INFORMATION: synthetic sequence
```

```
<400> SEQUENCE: 289

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

Ala Ile Pro Tyr Tyr Glu Asp Thr Asn Asp Gly Glu Ala Ile Val Leu
            35                  40                  45

Thr Val Pro Gly Ser Glu Arg Ser Tyr Asp Leu Thr Gly Leu Lys Pro
        50                  55                  60

Gly Thr Glu Tyr Trp Val Ser Ile Gln Gly Val Lys Gly Gly Thr Val
65                  70                  75                  80

Ser Gly Pro Leu Ser Ala Ile Phe Thr Thr
                85                  90

<210> SEQ ID NO 290
<211> LENGTH: 88
<212> TYPE: PRT
<213> ORGANISM: Artificial Sequence
<220> FEATURE:
<223> OTHER INFORMATION: synthetic sequence

<400> SEQUENCE: 290

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

Phe Tyr Leu Glu Gln Ala Trp Gly Gly Glu Ala Ile Val Leu Thr Val
            35                  40                  45

Pro Gly Ser Glu Arg Ser Tyr Asp Leu Thr Gly Leu Lys Pro Gly Thr
        50                  55                  60

Glu Tyr Trp Val Glu Ile Thr Gly Val Lys Gly Gly Tyr Ala Ser Ser
65                  70                  75                  80

Pro Leu Ser Ala Ile Phe Thr Thr
                85

<210> SEQ ID NO 291
<211> LENGTH: 90
<212> TYPE: PRT
<213> ORGANISM: Artificial Sequence
<220> FEATURE:
<223> OTHER INFORMATION: synthetic sequence

<400> SEQUENCE: 291

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

His Ile Glu Tyr Glu Glu Pro Glu Thr Glu Gly Glu Ala Ile Tyr Leu
            35                  40                  45

His Val Pro Gly Ser Glu Arg Ser Tyr Asp Leu Thr Gly Leu Lys Pro
        50                  55                  60

Gly Thr Glu Tyr Lys Val Leu Ile Arg Gly Val Lys Gly Gly Ser Tyr
65                  70                  75                  80

Ser Ile Pro Leu Gln Ala Pro Phe Thr Thr
                85                  90

<210> SEQ ID NO 292
<211> LENGTH: 90
```

```
<212> TYPE: PRT
<213> ORGANISM: Artificial Sequence
<220> FEATURE:
<223> OTHER INFORMATION: synthetic sequence

<400> SEQUENCE: 292

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Asp Ile Ala Tyr Trp Glu Leu Thr Pro Ser Gly Glu Ala Ile Glu Leu
        35                  40                  45

Leu Val Pro Gly Ser Glu Arg Ser Tyr Asp Leu Thr Gly Leu Lys Pro
    50                  55                  60

Gly Thr Glu Tyr Arg Val Asp Ile Ile Gly Val Lys Gly Gly Phe Ile
65                  70                  75                  80

Ser Glu Pro Leu Gly Ala Thr Phe Thr Thr
                85                  90

<210> SEQ ID NO 293
<211> LENGTH: 90
<212> TYPE: PRT
<213> ORGANISM: Artificial Sequence
<220> FEATURE:
<223> OTHER INFORMATION: synthetic sequence

<400> SEQUENCE: 293

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Thr Ile Glu Tyr Trp Glu Phe Thr Gly Ser Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Asp Val Ser Ile Tyr Gly Val Lys Gly Gly Trp Leu
65                  70                  75                  80

Ser Tyr Pro Leu Ser Ala Ile Phe Thr Thr
                85                  90

<210> SEQ ID NO 294
<211> LENGTH: 90
<212> TYPE: PRT
<213> ORGANISM: Artificial Sequence
<220> FEATURE:
<223> OTHER INFORMATION: synthetic sequence

<400> SEQUENCE: 294

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Ser Ile Ile Tyr Ser Glu Trp Asn Val Thr Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Asp Val Trp Ile Glu Gly Val Lys Gly Gly Gly Met
65                  70                  75                  80

Ser Lys Pro Leu Ser Ala Ile Ser Thr Thr
```

```
                    85                  90

<210> SEQ ID NO 295
<211> LENGTH: 90
<212> TYPE: PRT
<213> ORGANISM: Artificial Sequence
<220> FEATURE:
<223> OTHER INFORMATION: synthetic sequence

<400> SEQUENCE: 295

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Phe Ile Gly Tyr Leu Glu Pro Ile Pro Ser Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Pro Val Val Ile Gln Gly Val Lys Gly Gly His Pro
65                  70                  75                  80

Ser Gln Pro Leu Ser Ala Ile Phe Thr Thr
                85                  90

<210> SEQ ID NO 296
<211> LENGTH: 90
<212> TYPE: PRT
<213> ORGANISM: Artificial Sequence
<220> FEATURE:
<223> OTHER INFORMATION: synthetic sequence

<400> SEQUENCE: 296

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Phe Ile Gly Tyr Leu Glu Pro Gln Pro Pro Gly Glu Ala Ile Ile Leu
        35                  40                  45

Thr Val Pro Gly Ser Glu Arg Ser Tyr Asp Leu Thr Gly Leu Lys Pro
    50                  55                  60

Gly Thr Glu Tyr Asn Val Thr Ile Gln Gly Val Lys Gly Gly Phe Pro
65                  70                  75                  80

Ser Met Pro Leu Ser Ala Ile Phe Thr Thr
                85                  90

<210> SEQ ID NO 297
<211> LENGTH: 90
<212> TYPE: PRT
<213> ORGANISM: Artificial Sequence
<220> FEATURE:
<223> OTHER INFORMATION: synthetic sequence

<400> SEQUENCE: 297

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Leu Ile Pro Tyr Ala Glu Thr Ser Pro Ser Gly Glu Ala Ile Thr Leu
        35                  40                  45

Phe Val Pro Gly Ser Glu Arg Ser Tyr Asp Leu Thr Gly Leu Lys Pro
    50                  55                  60
```

Gly Thr Glu Tyr Asn Val Val Ile Gln Gly Val Lys Gly Gly Arg Pro
65                  70                  75                  80

Ser Asn Pro Leu Val Ala Ala Ser Thr Thr
                85                  90

<210> SEQ ID NO 298
<211> LENGTH: 90
<212> TYPE: PRT
<213> ORGANISM: Artificial Sequence
<220> FEATURE:
<223> OTHER INFORMATION: synthetic sequence

<400> SEQUENCE: 298

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

Pro Ile Ala Tyr Ala Glu Pro Arg Pro Asp Gly Glu Ala Ile Val Leu
            35                  40                  45

Thr Val Pro Gly Ser Glu Arg Ser Tyr Asp Leu Thr Gly Leu Lys Pro
        50                  55                  60

Gly Thr Glu Tyr Ser Val Leu Ile His Gly Val Lys Gly Gly Leu Leu
65                  70                  75                  80

Ser Ser Pro Leu Ser Ala Ile Ser Thr Thr
                85                  90

<210> SEQ ID NO 299
<211> LENGTH: 90
<212> TYPE: PRT
<213> ORGANISM: Artificial Sequence
<220> FEATURE:
<223> OTHER INFORMATION: synthetic sequence

<400> SEQUENCE: 299

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

Leu Ile Glu Tyr Trp Glu Ser Val Gly Tyr Gly Glu Ala Ile Val Leu
            35                  40                  45

Thr Val Pro Gly Ser Glu Arg Ser Tyr Asp Leu Thr Gly Leu Lys Pro
        50                  55                  60

Gly Thr Glu Tyr Trp Val Gly Ile Tyr Gly Val Lys Gly Gly Tyr Tyr
65                  70                  75                  80

Ser Arg Pro Leu Ser Ala Ile Phe Thr Thr
                85                  90

<210> SEQ ID NO 300
<211> LENGTH: 90
<212> TYPE: PRT
<213> ORGANISM: Artificial Sequence
<220> FEATURE:
<223> OTHER INFORMATION: synthetic sequence

<400> SEQUENCE: 300

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
                20                  25                  30

```
Phe Ile Gly Tyr Leu Glu Pro Gln Pro Pro Gly Glu Ala Ile Val Leu
            35                  40                  45

Thr Val Pro Gly Ser Glu Arg Ser Tyr Asp Leu Thr Gly Leu Lys Pro
 50                  55                  60

Gly Thr Glu Tyr Asn Val Thr Ile His Gly Val Lys Gly Gly Thr Pro
 65                  70                  75                  80

Ser Met Pro Leu Ser Ala Ile Phe Thr Thr
                85                  90
```

<210> SEQ ID NO 301
<211> LENGTH: 90
<212> TYPE: PRT
<213> ORGANISM: Artificial Sequence
<220> FEATURE:
<223> OTHER INFORMATION: synthetic sequence

<400> SEQUENCE: 301

```
Met Leu Pro Ala Pro Lys Asn Leu Val Val Ser Arg Val Thr Glu Asp
 1               5                  10                  15

Ser Ala Arg Leu Ser Trp Thr Ala Pro Asp Ala Ala Phe Asp Ser Phe
                20                  25                  30

Glu Ile Glu Tyr Asp Glu Pro Tyr Arg Gly Glu Ala Ile Val Leu
            35                  40                  45

Thr Val Pro Gly Ser Glu Arg Ser Tyr Asp Leu Thr Ser Leu Lys Pro
 50                  55                  60

Gly Thr Glu Tyr Pro Val Ser Ile Gly Gly Val Lys Gly Gly Ile Thr
 65                  70                  75                  80

Ser Asp Pro Leu Ser Ala Ile Phe Thr Thr
                85                  90
```

<210> SEQ ID NO 302
<211> LENGTH: 90
<212> TYPE: PRT
<213> ORGANISM: Artificial Sequence
<220> FEATURE:
<223> OTHER INFORMATION: synthetic sequence

<400> SEQUENCE: 302

```
Met Leu Pro Ala Pro Lys Asn Leu Val Val Ser Arg Val Thr Glu Asp
 1               5                  10                  15

Ser Ala Arg Leu Ser Trp Thr Ala Pro Asp Ala Ala Phe Asp Ser Phe
                20                  25                  30

Asp Ile Tyr Tyr Pro Glu Tyr Tyr Asp Arg Gly Glu Ala Ile Val Leu
            35                  40                  45

Thr Val Pro Gly Ser Glu Arg Ser Tyr Asp Leu Thr Gly Leu Lys Pro
 50                  55                  60

Gly Thr Glu Tyr Thr Val Tyr Ile Asp Gly Val Lys Gly Gly Gly Gly
 65                  70                  75                  80

Ser Gly Pro Leu Ser Ala Ile Phe Thr Thr
                85                  90
```

<210> SEQ ID NO 303
<211> LENGTH: 90
<212> TYPE: PRT
<213> ORGANISM: Artificial Sequence
<220> FEATURE:
<223> OTHER INFORMATION: synthetic sequence

<400> SEQUENCE: 303

```
Met Leu Pro Ala Pro Lys Asn Leu Val Val Ser Arg Val Thr Glu Asp
```

-continued

```
  1               5                  10                 15
Ser Ala Arg Leu Ser Trp Thr Ala Pro Asp Ala Ala Phe Asp Ser Phe
                20                 25                 30

Phe Ile Ala Tyr Phe Glu Phe Ala Asn Pro Gly Glu Ala Ile Val Leu
                35                 40                 45

Thr Val Pro Gly Ser Glu Arg Ser Tyr Asp Leu Thr Gly Leu Lys Pro
                50                 55                 60

Gly Thr Glu Tyr Lys Val Val Ile Gln Gly Val Lys Gly Gly Thr Pro
 65                 70                 75                 80

Ser Glu Pro Leu Ser Ala Ile Phe Thr Thr
                85                 90

<210> SEQ ID NO 304
<211> LENGTH: 90
<212> TYPE: PRT
<213> ORGANISM: Artificial Sequence
<220> FEATURE:
<223> OTHER INFORMATION: synthetic sequence

<400> SEQUENCE: 304

Met Leu Pro Ala Pro Lys Asn Leu Val Val Ser Arg Val Thr Glu Asp
 1               5                  10                 15

Ser Ala Arg Leu Ser Trp Thr Ala Pro Asp Ala Ala Phe Asp Ser Phe
                20                 25                 30

Ile Ile Thr Tyr Trp Glu His Val Gly Asp Gly Glu Ala Ile Val Leu
                35                 40                 45

Thr Val Pro Gly Ser Glu Arg Ser Tyr Asp Leu Thr Gly Leu Lys Pro
                50                 55                 60

Gly Thr Glu Tyr Phe Val Glu Ile Tyr Gly Val Lys Gly Gly Tyr Leu
 65                 70                 75                 80

Ser Lys Pro Leu Ser Ala Ile Phe Thr Thr
                85                 90

<210> SEQ ID NO 305
<211> LENGTH: 90
<212> TYPE: PRT
<213> ORGANISM: Artificial Sequence
<220> FEATURE:
<223> OTHER INFORMATION: synthetic sequence

<400> SEQUENCE: 305

Met Leu Pro Ala Pro Lys Asn Leu Val Val Ser Arg Val Thr Glu Asp
 1               5                  10                 15

Ser Ala Arg Leu Ser Trp Thr Ala Pro Asp Ala Ala Phe Asp Ser Phe
                20                 25                 30

Glu Ile Asp Tyr Asp Glu Pro Phe Val Tyr Gly Glu Ala Ile Val Leu
                35                 40                 45

Thr Val Pro Gly Ser Glu Arg Ser Tyr Asp Leu Thr Gly Leu Lys Pro
                50                 55                 60

Gly Thr Glu Tyr Arg Val Phe Ile Phe Gly Val Lys Gly Gly Asn Gly
 65                 70                 75                 80

Ser Trp Pro Leu Ser Ala Ile Phe Thr Thr
                85                 90

<210> SEQ ID NO 306
<211> LENGTH: 90
<212> TYPE: PRT
<213> ORGANISM: Artificial Sequence
<220> FEATURE:
```

<223> OTHER INFORMATION: synthetic sequence

<400> SEQUENCE: 306

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Tyr Ile Glu Tyr Phe Glu Thr Gln Gly Tyr Gly Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Tyr Val Ala Ile Tyr Gly Val Lys Gly Gly Tyr Leu
65                  70                  75                  80

Ser Arg Pro Leu Ser Ala Ile Phe Thr Thr
            85                  90

<210> SEQ ID NO 307
<211> LENGTH: 90
<212> TYPE: PRT
<213> ORGANISM: Artificial Sequence
<220> FEATURE:
<223> OTHER INFORMATION: synthetic sequence

<400> SEQUENCE: 307

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Pro Ile Thr Tyr Ser Glu Pro Ala His Tyr Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr His Val Gly Ile Met Gly Val Lys Gly Gly Val Phe
65                  70                  75                  80

Ser Ser Pro Leu Ser Ala Ile Phe Thr Thr
            85                  90

<210> SEQ ID NO 308
<211> LENGTH: 90
<212> TYPE: PRT
<213> ORGANISM: Artificial Sequence
<220> FEATURE:
<223> OTHER INFORMATION: synthetic sequence

<400> SEQUENCE: 308

Met Leu Pro Ala Pro Lys Asn Leu Val Val Ser Glu Val Thr Glu Asp
1               5                   10                  15

Ser Ala Arg Leu Ser Trp Gln Gly Val Ala Arg Ala Phe Asp Ser Phe
            20                  25                  30

Leu Ile Thr Tyr Arg Glu Gln Ile Phe Ala Gly Glu Val Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Pro Val Trp Ile Gln Gly Val Lys Gly Gly Ser Pro
65                  70                  75                  80

Ser Ala Pro Leu Ser Ala Ile Ser Thr Thr
            85                  90

```
<210> SEQ ID NO 309
<211> LENGTH: 90
<212> TYPE: PRT
<213> ORGANISM: Artificial Sequence
<220> FEATURE:
<223> OTHER INFORMATION: synthetic sequence

<400> SEQUENCE: 309

Met Leu Pro Ala Pro Lys Asn Leu Val Val Ser Arg Val Thr Glu Asp
1               5                   10                  15

Ser Ala Arg Leu Ser Trp Thr Ala Pro Asp Ala Ala Phe Asp Ser Phe
            20                  25                  30

Ile Ile Asp Tyr Leu Glu Leu Asp Gln Glu Gly Glu Ala Ile Val Leu
        35                  40                  45

Thr Val Pro Gly Ser Glu Arg Ser Tyr Asp Leu Thr Gly Leu Lys Pro
    50                  55                  60

Gly Thr Glu Tyr Ala Val Tyr Ile Phe Gly Val Lys Gly Gly Tyr Pro
65                  70                  75                  80

Ser Thr Pro Leu Ser Ala Ile Phe Thr Thr
                85                  90
```